(12) United States Patent
Johns et al.

(10) Patent No.: US 10,112,899 B2
(45) Date of Patent: Oct. 30, 2018

(54) ISOINDOLINE DERIVATIVES FOR USE IN THE TREATMENT OF A VIRAL INFECTION

(71) Applicant: ViiV HEALTHCARE UK LIMITED, Brentford, Middlesex (GB)

(72) Inventors: Brian Alvin Johns, Research Triangle Park, NC (US); Emile Johann Velthuisen, Research Triangle Park, NC (US); Jason Gordon Weatherhead, Research Triangle Park, NC (US); Lita Suwandi, Research Triangle Park, NC (US); David Temelkoff, Research Triangle Park, NC (US)

(73) Assignee: ViiV HEALTHCARE UK LIMITED, Brentford, Middlesex (GB)

( * ) Notice: Subject to any disclaimer, the term of this patent is extended or adjusted under 35 U.S.C. 154(b) by 106 days.

(21) Appl. No.: 15/314,549

(22) PCT Filed: Jul. 6, 2015

(86) PCT No.: PCT/IB2015/055095
§ 371 (c)(1),
(2) Date: Nov. 29, 2016

(87) PCT Pub. No.: WO2016/005878
PCT Pub. Date: Jan. 14, 2016

(65) Prior Publication Data
US 2018/0244617 A1 Aug. 30, 2018

Related U.S. Application Data
(60) Provisional application No. 62/134,616, filed on Mar. 18, 2015, provisional application No. 62/064,615, filed on Oct. 16, 2014, provisional application No. 62/021,844, filed on Jul. 8, 2014.

(51) Int. Cl.
| | |
|---|---|
| C07D 209/44 | (2006.01) |
| A61P 31/18 | (2006.01) |
| C07D 401/06 | (2006.01) |
| C07D 405/06 | (2006.01) |
| C07D 403/06 | (2006.01) |
| C07D 413/06 | (2006.01) |
| C07D 498/08 | (2006.01) |
| C07D 487/04 | (2006.01) |
| C07D 487/08 | (2006.01) |
| C07D 405/14 | (2006.01) |
| C07D 409/14 | (2006.01) |
| C07D 409/06 | (2006.01) |
| C07D 413/14 | (2006.01) |
| C07F 5/02 | (2006.01) |
| C07D 417/06 | (2006.01) |
| C07D 403/12 | (2006.01) |
| C07D 491/06 | (2006.01) |
| C07D 413/04 | (2006.01) |
| C07D 405/04 | (2006.01) |

(52) U.S. Cl.
CPC ............ *C07D 209/44* (2013.01); *A61P 31/18* (2018.01); *C07D 401/06* (2013.01); *C07D 403/06* (2013.01); *C07D 403/12* (2013.01); *C07D 405/04* (2013.01); *C07D 405/06* (2013.01); *C07D 405/14* (2013.01); *C07D 409/06* (2013.01); *C07D 409/14* (2013.01); *C07D 413/04* (2013.01); *C07D 413/06* (2013.01); *C07D 413/14* (2013.01); *C07D 417/06* (2013.01); *C07D 487/04* (2013.01); *C07D 487/08* (2013.01); *C07D 491/06* (2013.01); *C07D 498/08* (2013.01); *C07F 5/025* (2013.01)

(58) Field of Classification Search
None
See application file for complete search history.

(56) References Cited

U.S. PATENT DOCUMENTS

| | | | | |
|---|---|---|---|---|
| 8,183,279 B2 * | 5/2012 | Eggenweiler | ........ | C07D 209/44 514/416 |
| 9,163,023 B2 * | 10/2015 | De La Rosa | ........ | C07D 471/04 |

FOREIGN PATENT DOCUMENTS

| | | |
|---|---|---|
| WO | WO 2008/155001 A1 | 12/2008 |
| WO | WO 2009/030316 A1 | 3/2009 |
| WO | WO 2013/012649 A1 | 1/2013 |
| WO | WO 2013/103738 A1 | 7/2013 |
| WO | WO 2013/134142 A1 | 9/2013 |
| WO | WO 2014/009794 A1 | 1/2014 |

* cited by examiner

*Primary Examiner* — Heidi Reese
(74) *Attorney, Agent, or Firm* — Robert H. Brink; Edward R. Gimmi; William R. Majarian

(57) ABSTRACT

Compounds of Formula I are disclosed and methods of treating viral infections with compositions comprising such compounds.

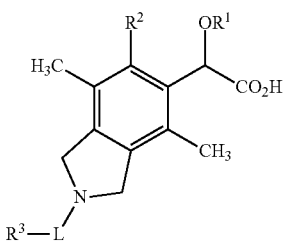

Formula I

13 Claims, No Drawings

ISOINDOLINE DERIVATIVES FOR USE IN THE TREATMENT OF A VIRAL INFECTION

This application is a § 371 of International Application No. PCT/IB2015/055095, filed 6 Jul. 2015, which claims the benefit of U.S. Provisional Application Nos. 62/134,616, filed 18 Mar. 2015, 62/064,615, filed 16 Oct. 2014, 62/021,844, filed 8 Jul. 2014, which are incorporated herein in their entireties.

FIELD OF THE INVENTION

The present invention relates to substituted isoindoline compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required because of undesirable drug-drug interactions; drug-food interactions; non-adherence to therapy; and drug resistance due to mutation of the enzyme target.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur. The emergence of multidrug-resistant HIV-1 isolates has serious clinical consequences and must be suppressed with a new drug regimen, known as salvage therapy.

Current guidelines recommend that salvage therapy includes at least two, and preferably three, fully active drugs. Typically, first-line therapies combine three to four drugs targeting the viral enzymes reverse transcriptase and protease. One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase inhibitors. However, resistance to all three new drug classes has already been reported both in the lab and in patients. Sustained successful treatment of HIV-1-infected patients with antiretroviral drugs will therefore require the continued development of new and improved drugs with new targets and mechanisms of action.

For example, over the last decade HIV inhibitors have been reported to target the protein-protein interaction between HIV-1 integrase and Lens Epithelium Derived Growth Factor/p75 ("LEDGF"). LEDGF is a cellular transcriptional cofactor of HIV-1 integrase that promotes viral integration of reverse transcribed viral cDNA into the host cell's genome by tethering the preintegration complex to the chromatin. Because of its crucial role in the early steps of HIV replication, the interaction between LEDGF and integrase represents another attractive target for HIV drug therapy.

SUMMARY OF THE INVENTION

Briefly, in one aspect, the present invention discloses compounds of Formula I:

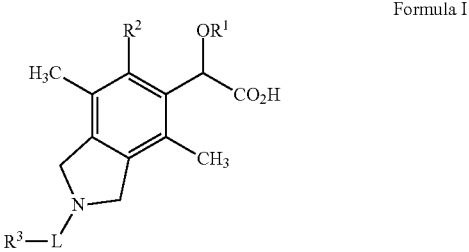

Formula I wherein:
$R^1$ is $C_{1-6}$alkyl;
$R^2$ is $C_{5-14}$aryl, $C_{3-7}$cycloalkyl, $C_{3-7}$cycloalkenyl, $C_{2-9}$heterocycle, or $C_{2-9}$heteroaryl, wherein each $R^2$ group is optionally substituted by one to four substituents selected from halo, $C_{1-6}$alkyl, $C_{1-6}$hetereoalkyl, or $C_{1-6}$alkylene or $C_{1-6}$hetereoalkylene wherein said $C_{1-6}$alkylene or $C_{1-6}$hetereoalklylene are bonded to adjacent carbon atoms on said $C_{5-14}$aryl, $C_{3-7}$cycloalkyl, $C_{3-7}$cycloalkenyl, $C_{3-9}$heterocycle, or $C_{5-9}$heteroaryl to form a fused ring;
L is a bond, —CH$_2$(CO)—, —C$_{1-3}$alkylene-, —SO$_2$—, —C(O)—, —C(S)—, —C(NH)—, —C(O)NH—, —C(O)NHCH$_2$—, —C(O)N—, —C(O)OCH$_2$—, —C(O)O—, —C(O)C(O)—, —SO$_2$—NH—, or —CH$_2$C(O)—;
$R^3$ is H, CN, $C_{1-6}$alkyl, $C_{5-14}$aryl, CH$_2$C$_{5-14}$aryl, CH$_2$C$_{3-7}$cycloalkyl, $C_{3-7}$cycloalkyl, $C_{3-7}$spirocycloalkyl, $C_{3-7}$cycloalkenyl, $C_{2-9}$heterocycle, or $C_{2-9}$heteroaryl, wherein each $R^3$ group is optionally substituted by one to four substituents selected from halo, $C_{1-6}$alkyl, $C_{2-8}$bridgedheterocycle, $C_{3-7}$cycloalkyl, $C_{1-3}$fluoroalkyl, —OC$_{1-6}$alkyl, —C(O)R$^4$, —C(O)NR$^4$, —C(O)NHR$^4$, $C_{5-14}$aryl, $C_{1-6}$hetereoalkyl, —B(OH)$_2$, $C_{2-9}$heterocycle, $C_{1-6}$heteroaryl, —C(O)OC$_{1-6}$alkyl, or two substituents bonded to adjacent atoms may bond together to form a fused ring and that fused ring may optionally be substituted with $R^4$;
$R^4$ is CN, halo, —OC$_{1-6}$alkyl, $C_{1-6}$alkyl, $C_{3-7}$cycloalkyl, $C_{2-9}$heterocycle, or $C_{5-14}$aryl; and wherein each heterocycle, heteroaryl, heteroalkyl, and heteroalkylene comprises one to three heteroatoms selected from S, N, B, or O.

In another aspect the present invention discloses pharmaceutically acceptable salts of the compounds of Formula I.

In another aspect, the present invention discloses pharmaceutical compositions comprising a compound of Formula I or a pharmaceutically acceptable salt thereof.

In another aspect, the present invention discloses a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

DETAILED DESCRIPTION OF THE INVENTION

Preferably $R^1$ is $C_{1-6}$alkyl. Most preferably, $R^1$ is t-butyl.

Preferably $R^2$ is optionally substituted phenyl. Most preferably, $R^2$ is phenyl substituted by one to four substituents selected from fluorine, methyl, —CH$_2$CH$_2$CH$_2$O— wherein said —CH$_2$CH$_2$CH$_2$O— is bonded to adjacent carbon atoms on said phenyl to form a bicyclic ring, or —NHCH$_2$CH$_2$O— wherein said —NHCH$_2$CH$_2$O— is bonded to adjacent carbon atoms on said phenyl to form a bicyclic ring.

Preferably $R^3$ is $C_{1-6}$alkyl, phenyl, naphthyl, cyclopentyl, cyclohexyl, pyridyl, or tetrahydropyranyl, each of which is optionally substituted by 1-3 substituents selected from halogen, $C_{1-6}$alkyl, —O$C_{1-6}$alky, $C_{1-3}$fluoroalkyl, or phenyl.

Preferably the stereochemistry on the carbon to which $OR^1$ is bound is as depicted below.

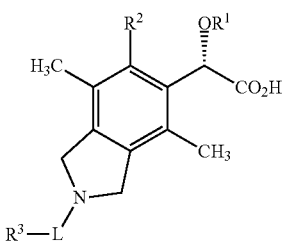

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

EXAMPLES

The compounds of this invention may be made by a variety of methods, including well-known standard synthetic methods. Illustrative general synthetic methods are set out below and then specific compounds of the invention are prepared in the working examples.

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

| | |
|---|---|
| aq. = | aqueous |
| µL = | microliters |
| µM = | micromolar |
| NMR = | nuclear magnetic resonance |
| boc = | tert-butoxycarbonyl |
| br = | broad |
| Cbz = | benzyloxycarbonyl |
| d = | doublet |
| δ = | chemical shift |
| oC = | degrees celcius |
| DCM = | dichloromethane |
| dd = | doublet of doublets |
| DMEM = | Dulbeco's Modified Eagle's Medium |
| DMF = | N,N-dimethylformamide |
| DMSO = | dimethylsulfoxide |
| EtOAc = | ethyl acetate |
| g = | gram |
| h or hr = | hours |
| HCV = | hepatitus C virus |
| HPLC = | high performance liquid chromatography |
| Hz = | hertz |
| IU = | International Units |
| IC$_{50}$ = | inhibitory concentration at 50% inhibition |
| J = | coupling constant (given in Hz unless otherwise indicated) |
| m = | multiplet |
| M = | molar |
| M + H$^+$ = | parent mass spectrum peak plus H+ |
| mg = | milligram |
| min = | minutes |
| mL = | milliliter |
| mM = | millimolar |
| mmol = | millimole |
| MS = | mass spectrum |
| nm = | nanomolar |
| Ppm = | parts per million |
| q.s. = | sufficient amount |
| s = | singlet |
| RT = | room temperature |
| sat. = | saturated |
| t = | triplet |
| TFA = | trifluoroacetic acid |
| Z = | benzyloxycarbonyl |

Scheme 1

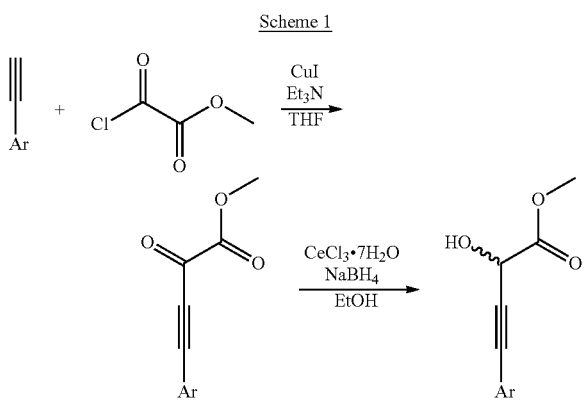

-continued

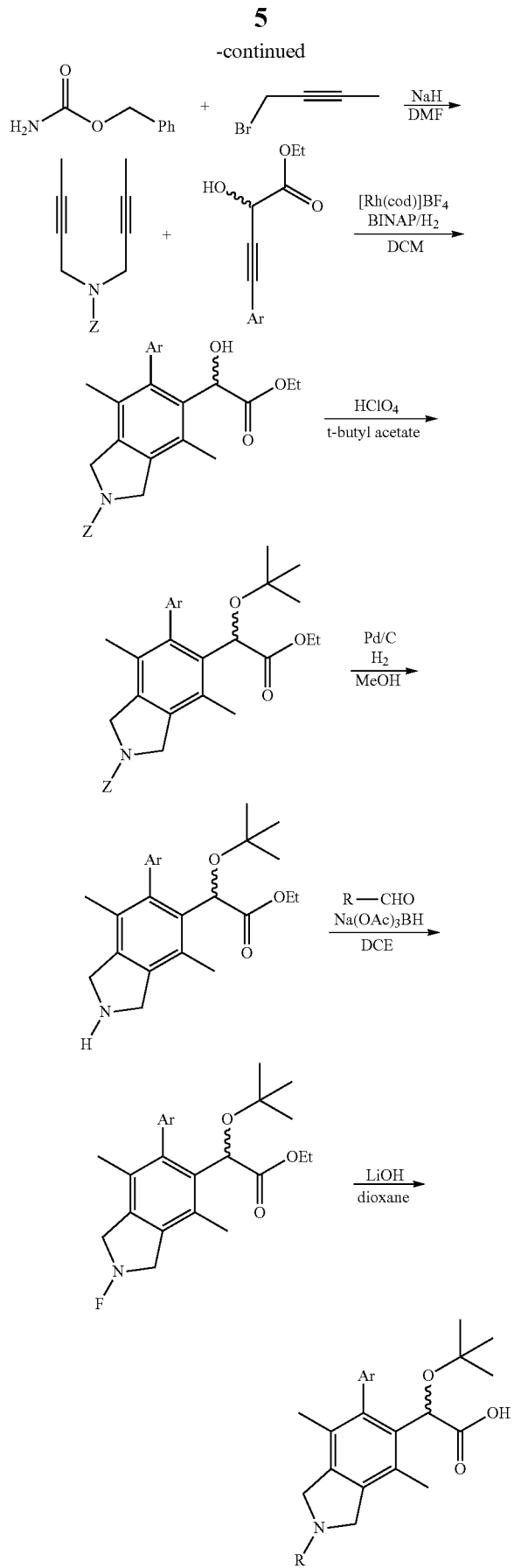

Example 1: 2-(tert-Butoxy)-2-(2-(4-fluorobenzyl)-4,7-dimethyl-6-(p-tolyl)isoindolin-5-yl)acetic acid

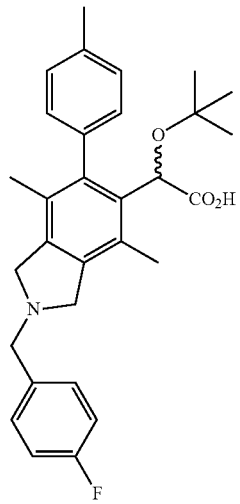 [SMILES: Cc1ccc(-c2c(C)c3c(c(C)c2C(OC(C)(C)C)C(=O)O)CN(Cc2ccc(F)cc2)C3)cc1]

Step 1: Methyl 2-oxo-4-(p-tolyl)but-3-ynoate

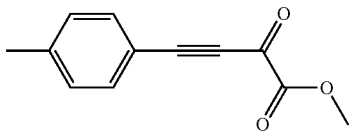

A suspension of CuI (0.1 eq, 1.722 mmol, 0.328 g) in THF (40 mL) was treated with Et$_3$N (3 eq, 51.7 mmol, 7.20 mL) and stirred until a colorless solution formed. Then, 1-ethynyl-4-methylbenzene (1.0 eq, 17.22 mmol, 2.183 mL) and methyl-2-chloro-2-oxoacetate (2.0 eq, 34.4 mmol, 3.17 mL) were added and the yellow reaction mixture stirred at ambient temperature. After 18 h, the reaction mixture was quenched with sat. aq. NaHCO$_3$. The aqueous layer was extracted with ethyl acetate (×3). The combined organic layers were washed with brine, dried over Na$_2$SO$_4$ and concentrated in vacuo to a brown solid. The crude material was purified via silica gel column chromatography (0-100% EtOAc-hexanes) to afford the title compound as an orange solid (2.32 g, 67% yield). $^1$H NMR (400 MHz, CDCl$_3$) δ 7.58-7.56 (m, 2H), 7.23-7.21 (m, 2H), 3.95 (s, 3H), 2.40 (s, 3H). LCMS (ES+) (m/z): 203.15 (M+H).

Step 2: Ethyl 2-hydroxy-4-(p-tolyl)but-3-ynoate

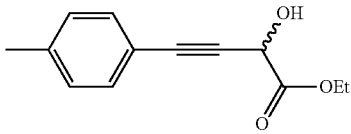 [SMILES: CCOC(=O)C(O)C#Cc1ccc(C)cc1]

A solution of methyl-2-oxo-4-(p-tolyl)but-3-ynoate (1.0 eq, 200 mg, 0.989 mmol) in ethanol (5 mL) was treated with CeCl$_3$.7H$_2$O (1.25 eq, 0.461 g, 1.23 mmol) and then NaBH$_4$ (0.5 eq, 0.47945 mmol, 19 mg) was added portion wise. After 15 min, the reaction mixture was concentrated in vacuo the residue was quenched with dilute HCl and extracted with DCM (×3). The combined organic layers were washed with brine, dried over Na$_2$SO$_4$ and concentrated. The crude material was purified via column chromatography (0-100% EtOAc-hexanes) to afford an orange oil.

(122 mg, 57% yield). $^1$H NMR (400 MHz, CDCl$_3$) δ 7.34-7.32 (m, 2H), 7.12-7.10 (m, 2H), 5.03 (d, 1H), 4.34 (q, 2H), 3.07 (d, 1H), 2.34 (s, 3H), 1.32 (t, 3H). LCMS (ES+) (m/z): 219.81 (M+H).

Step 3: Benzyl di(but-2-yn-1-yl)carbamate

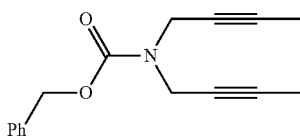 [SMILES: CC#CCN(CC#CC)C(=O)OCc1ccccc1]

To a suspension of NaH (27.8 mmol, 1.11 g, 60% dispersion) in DMF (100 mL) was added 1-bromobut-2-yne (27.1 mmol, 2.375 mL). The reaction mixture was cooled in an ice bath and a solution of benzyl carbamate (13.23 mmol, 2.0 g) in DMF (10 mL) was added dropwise over 25 min. The ice bath was removed and the reaction mixture stirred at ambient temperature. After 15 min, the reaction mixture was poured slowly over ice. The mixture was extracted with ether (3×100 mL) and the combined organic layers were washed with H$_2$O (4×100 mL), brine, dried over Na$_2$SO$_4$ and concentrated in vacuo. The crude material was purified via silica gel chromatography (0-100% EtOAc-hexanes) to afford the title compound as a yellow oil (1.94 g, 58% yield). $^1$H NMR (400 MHz, CDCl$_3$) δ 7.39-7.30 (m, 4H), 5.17 (s, 2H), 4.18 (s, 4H), 1.81 (s, 6H). LCMS (ES+) (m/z): 256.8 (M+H).

Step 4: Benzyl 5-(2-ethoxy-1-hydroxy-2-oxoethyl)-4,7-dimethyl-6-(p-tolyl)isoindoline-2-carboxylate

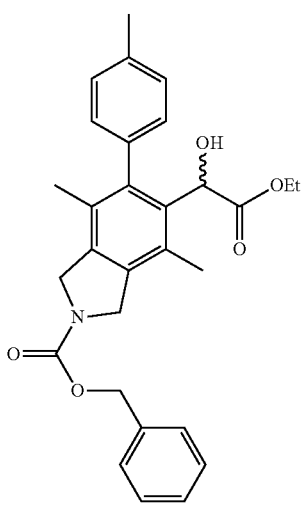 [SMILES: CCOC(=O)C(O)c1c(C)c2c(c(C)c1-c1ccc(C)cc1)CN(C(=O)OCc1ccccc1)C2]

To an oven dried flask under N$_2$ was added racemic BINAP (342 mg, 0.550 mmol) and Rh[(COD)$_2$]BF$_4$ (223 mg, 0.550 mmol) in dry DCM (5 mL) and the reaction mixture stirred for 5 minutes at RT. H$_2$ gas was bubbled through the solution and the reaction mixture stirred under an atmosphere of H$_2$. After 1 h, a solution of ethyl 2-hydroxy-4-(p-tolyl)but-3-ynoate (400 mg, 1.833 mmol) in DCM (1 mL) was added, followed by the dropwise addition of a solution of benzyl di(but-2-yn-1-yl)carbamate (515 mg, 2.016 mmol) in DCM (3 mL) and the reaction mixture was heated to reflux. After 18 h, the reaction mixture was cooled to ambient temperature and concentrated in vacuo. The residue was purified by silica gel chromatography (0-100% EtOAc-hexanes) to afford the title compound (555 mg, 64% yield) as a yellow oil. $^1$H NMR (400 MHz, CDCl$_3$) δ 7.41-7.32 (m, 5H), 7.23-7.19 (m, 2H), 7.07-7.05 (m, 2H), 5.22 (s, 2H), 5.04 (s, 1H), 4.76-4.70 (m, 4H), 4.25-4.08 (m, 2H), 3.04-3.03 (d, 1H), 2.39 (s, 3H), 2.175 (d, 3H), 1.85 (d, 3H), 1.27-1.18 (m, 3H). LCMS (ES+) (m/z): 474.21 (M+H).

Step 5: Benzyl 5-(1-(tert-butoxy)-2-ethoxy-2-oxoethyl)-4,7-dimethyl-6-(p-tolyl)isoindoline-2-carboxylate

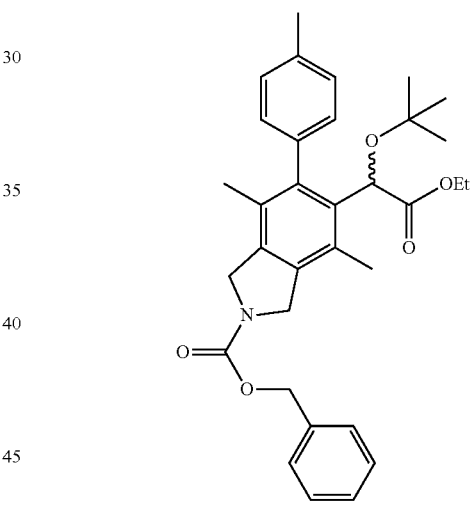

To a solution of benzyl 5-(1-(tert-butoxy)-2-ethoxy-2-oxoethyl)-4,7-dimethyl-6-(p-tolyl)isoindoline-2-carboxylate (76 mg, 0.1603 mmol) in tert-butyl acetate (40 mL) was added perchloric acid (0.4809 mL, 70%). After 45 min, the reaction mixture was cooled to 0° C. and the pH adjusted to 8 with 1N NaOH. The aqueous layer was extracted with ethyl acetate (×3) and the combined organic layers were washed with brine, dried over Na$_2$SO$_4$ and concentrated in vacuo. The crude material was purified by flash column chromatography (H:EA) to afford a clear oil (50 mg, 59% yield). $^1$H NMR (400 MHz, CDCl$_3$) δ 7.42-7.34 (m, 5H), 7.22-7.21 (m, 3H), 7.06-7.05 (m, 1H), 5.24 (s, 2H), 4.89 (s, 1H), 4.77-4.70 (m, 4H), 4.22-4.08 (m, 2H), 2.42 (s, 3H), 2.315 (d, 3H), 1.3545 (d, 3H), 1.23 (t, 3H), 0.96 (s, 9H). LCMS (ES+) (m/z): 530.18 (M+1).

Step 6: Ethyl 2-(tert-butoxy)-2-(4,7-dimethyl-6-(p-tolyl)isoindolin-5-yl)acetate

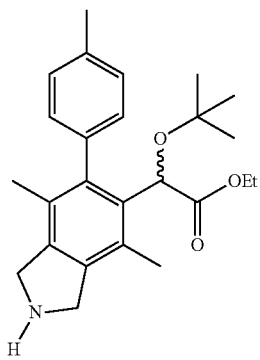 [SMILES: CCOC(=O)C(OC(C)(C)C)c1c(C)c2c(c(C)c1-c1ccc(C)cc1)CNC2]

A solution of benzyl 5-(1-(tert-butoxy)-2-ethoxy-2-oxoethyl)-4,7-dimethyl-6-(p-tolyl)isoindoline-2-carboxylate (352 mg, 0.665 mmol) in MeOH (15 mL) was degassed with N₂ for 15 min and treated with Pd/C (70 mg). A balloon of H₂ was bubbled through the reaction mixture at which time LCMS indicated complete consumption of the starting material. The reaction mixture was then bubbled with N₂ for 15 min and filtered through a pad of Celite, rinsing with MeOH and DCM. The filtrate was concentrated in vacuo to afford the title compound as a purple solid (277 mg, 100%). ¹H NMR (400 MHz, CDCl₃) δ 7.22-7.19 (m, 3H), 7.08-7.06 (m, 1H), 4.98 (s, 1H), 4.26-4.24 (m, 4H), 4.20-4.05 (m, 2H), 2.42 (s, 3H), 2.32 (s, 3H), 1.84 (s, 3H), 1.23 (t, 3H), 0.96 (s, 9H). LCMS (ES+) (m/z): 396.35 (M+1).

Step 7: Ethyl 2-(tert-butoxy)-2-(2-(4-fluorobenzyl)-4,7-dimethyl-6-(p-tolyl)isoindolin-5-yl)acetate

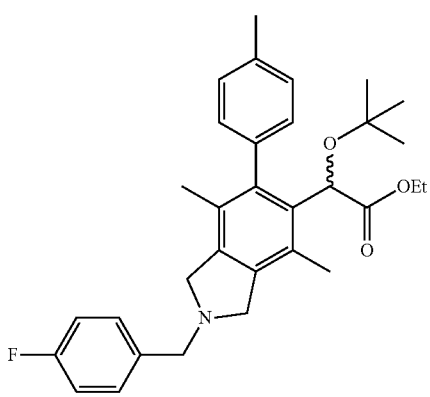 [SMILES: CCOC(=O)C(OC(C)(C)C)c1c(C)c2c(c(C)c1-c1ccc(C)cc1)CN(Cc1ccc(F)cc1)C2]

To a solution of ethyl 2-(tert-butoxy)-2-(4,7-dimethyl-6-(p-tolyl)isoindolin-5-yl)acetate (427 mg, 1.080 mmol) in DCE (10 mL) was added 4-fluorobenzaldehyde (1.5 eq, 1.619 mmol, 0.171 mL). The reaction mixture stirred for a few minutes at ambient temperature and sodium triacetoxyborohydride (1.5 eq, 1.619 mmol, 343 mg) was added. After 30 minutes, the RM was quenched with aq. sat. sodium bicarbonate and extracted with DCM (×3). The combined organic layers were washed with brine, dried over Na₂SO₄ and concentrated in vacuo. The crude material was purified via flash column chromatography (H:EA) to yield a purple oil (377 mg, 70% yield). ¹H NMR (400 MHz, CDCl3) δ 7.42-7.38 (m, 2H), 7.23-7.18 (m, 3H), 7.07-7.03 (m, 3H), 4.95 (s, 1H), 4.21-4.00 (m, 2H), 3.96 (s, 2H), 3.93-3.92 (m, 4H), 2.42 (s, 3H), 2.27 (s, 3H), 1.80 (s, 3H), 1.23 (t, 3H), 0.95 (s, 9H). LCMS (ES+) (m/z): 504.38 (M+1).

Step 8: 2-(tert-Butoxy)-2-(2-(4-fluorobenzyl)-4,7-dimethyl-6-(p-tolyl)isoindolin-5-yl)acetic acid

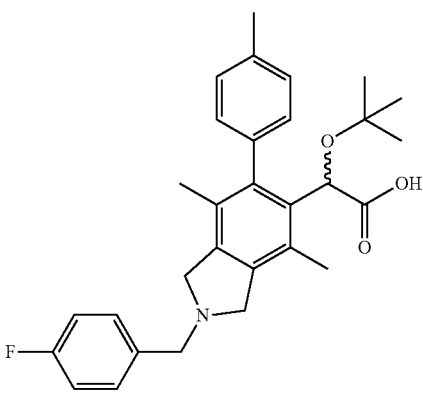 [SMILES: Cc1ccc(-c2c(C)c3c(c(C)c2C(OC(C)(C)C)C(=O)O)CN(Cc2ccc(F)cc2)C3)cc1]

To a solution of ethyl 2-(tert-butoxy)-2-(2-(4-fluorobenzyl)-4,7-dimethyl-6-(p-tolyl)isoindolin-5-yl)acetate (15 mg, 0.030 mmol) in 1,4-dioxane (3 mL) was added LiOH (0.596 mL, 0.596 mmol, 1 M) and the reaction mixture stirred at reflux. After 18 h, the reaction mixture was cooled to ambient temperature and concentrated in vacuo. The white residue was dissolved in a minimal amount of water, acidified using 1 N HCl, and extracted with ethyl acetate. The combined organic layers were washed with brine, dried over Na₂SO₄ and concentrated in vacuo. The residue was purified by reverse phase HPLC to yield a white solid (8 mg, 57% yield). ¹H NMR (400 MHz, CDCl₃ δ 7.51-7.48 (m, 2H), 7.33-7.32 (m, 2H), 7.19-7.15 (m, 3H), 7.08-7.06 (m, 1H), 5.14 (s, 1H), 4.95 (t, 2H), 4.46 (s, 2H), 4.28 (t, 2H), 2.42 (s, 3H), 2.22 (s, 3H), 1.87 (s, 3H), 0.96 (s, 9H). LCMS (ES+) (m/z): 476.04 (M+1).

Example 2: (S)-2-(tert-Butoxy)-2-(2-(4-fluorobenzyl)-4,7-dimethyl-6-(p-tolyl)isoindolin-5-yl)acetic acid

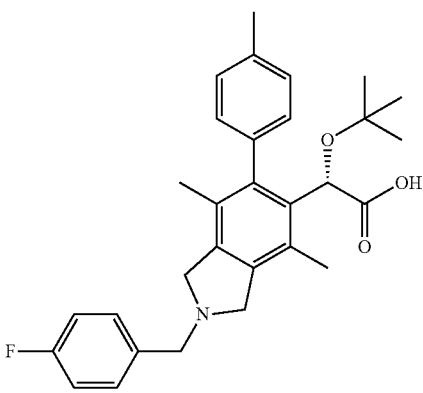 [SMILES: Cc1ccc(-c2c(C)c3c(c(C)c2[C@H](OC(C)(C)C)C(=O)O)CN(Cc2ccc(F)cc2)C3)cc1]

A sample of 2-(tert-Butoxy)-2-(2-(4-fluorobenzyl)-4,7-dimethyl-6-(p-tolyl)isoindolin-5-yl)acetic acid was purified using a CC4 (250×30 mm i.d., 5 μm; ES Industries, West Berlin, N.J.) under supercritical conditions maintained at 40° C., 140 bar, with methanol/diethylamine modified $CO_2$ (10% MeOH+0.1% DEA, 90% $CO_2$) delivered at a combined flow rate of 90 ml/min on a PIC prep SFC system (PIC Solution; Avignon, France). Triggered collections were made using a Knauer selectable wavelength UV-Vis detector at 220 nm.

Chiral purity was determined by chiral analytical HPLC on a CC4 column (250×4.6 mm i.d., 5 μm; ES Industries, West Berlin, N.J.) under supercritical conditions maintained at 40° C., 140 bar, with methanol/diethylamine modified $CO_2$ (10% MeOH+0.1% DEA, 90% $CO_2$) delivered at a combined flow rate of 2 ml/min on an Aurora Fusion A5 Evolution SFC system (Agilent Technologies, Santa Clara, Calif.) equipped with a DAD detector and monitored at 220 nm. Retention time of the title compound under these conditions was 8.6 min.

Example 3: (S)-2-(tert-butoxy)-2-(2-(2,3-difluorobenzyl)-4,7-dimethyl-6-(p-tolyl)isoindolin-5-yl)acetic acid

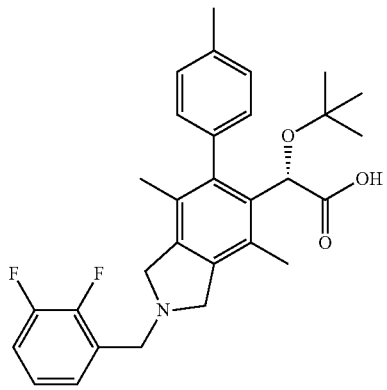 [SMILES: Cc1ccc(-c2c(C)c3c(c(C)c2[C@H](OC(C)(C)C)C(=O)O)CN(Cc2cccc(F)c2F)C3)cc1]

The title compound was prepared according to the procedure described in Example 1 except the intermediate from Step 5 was purified by chiral HPLC using the following conditions:

Benzyl 5-(1-(tert-Butoxy)-2-ethoxy-2-oxoethyl)-4,7-dimethyl-6-(p-tolyl)isoindoline-2-carboxylate was purified using a RegisCell column (250×30 mm i.d., 10 μm; Regis Technologies, Morton Grove, Ill.) under supercritical conditions maintained at 40° C., 140 bar, with methanol modified $CO_2$ (15% MeOH, 85% $CO_2$) delivered at a combined flow rate of 90 ml/min on a PIC prep SFC system (PIC Solution; Avignon, France). Triggered collections were made using a Knauer selectable wavelength UV-Vis detector at 220 nm.

Chiral purity was determined by chiral analytical SFC on a RegisCell column (250×4.6 mm i.d., 5 μm; RegisTechnologies, Morton Grove, Ill.) under supercritical conditions maintained at 40° C., 140 bar, with methanol modified $CO_2$ (15% MeOH, 85% $CO_2$) delivered at a combined flow rate of 2 ml/min on PIC Solution Analytical SFC system (Avignon, France) equipped with a DAD detector and monitored at 220 nm. Retention time of the title compound under these conditions was 6.17 minutes.

$^1$H NMR (400 MHz, $CDCl_3$) δ 7.45-7.42 (m, 1H), 7.34-7.30 (m, 2H), 7.27-7.21 (m, 3H), 7.05-7.03 (m, 1H), 5.12 (s, 1H), 4.96 (s, 2H), 4.60 (s, 2H), 4.36 (s, 2H), 2.42 (s, 3H), 2.24 (s, 3H), 1.87 (s, 3H), 0.97 (s, 9H). LCMS (ES+) (m/z): 494.57 (M+1).

Example 4: (S)-2-(tert-Butoxy)-2-(2-(cyclohexylcarbamoyl)-4,7-dimethyl-6-(p-tolyl)isoindolin-5-yl) acetic acid

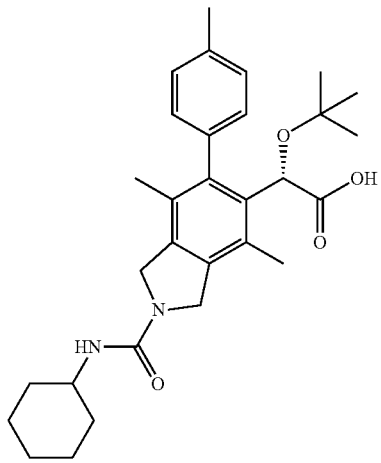 [SMILES: Cc1ccc(-c2c(C)c3c(c(C)c2[C@H](OC(C)(C)C)C(=O)O)CN(C(=O)NC2CCCCC2)C3)cc1]

Step 1: (S)-Ethyl 2-(tert-butoxy)-2-(2-(cyclohexylcarbamoyl)-4,7-dimethyl-6-(p-tolyl)isoindolin-5-yl) acetate

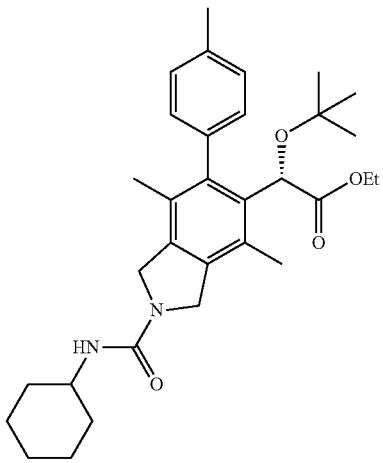 [SMILES: CCOC(=O)[C@@H](OC(C)(C)C)c1c(C)c2c(c(C)c1-c1ccc(C)cc1)CN(C(=O)NC1CCCCC1)C2]

A solution of (S)-Ethyl 2-(tert-butoxy)-2-(4,7-dimethyl-6-(p-tolyl)isoindolin-5-yl)acetate (13 mg, 0.033 mmol) in DCM (1 mL) was added $Et_3N$ (0.013 mL, 0.099 mmol) and cyclohexylisocyanate (0.008 mL, 0.493 mmol). After 5 min, sat. aq. $NaHCO_3$ was added and the layers partitioned. The aqueous layer was extracted with DCM (3×) and the combined extracts washed with brine, dried ($Na_2SO_4$), filtered, and concentrated in vacuo. The residue was purified by silica gel chromatography (0-100% EtOAc-hexanes) to afford the title compound (13.3 mg, 79%). $^1$H NMR (400 Mz, $CDCl_3$) δ 7.22-7.21 (m, 3H), 7.07-7.00 (m, 1H), 4.98 (s, 1H), 4.65 (s, 4H), 4.20-4.09 (m, 2H), 2.42 (s, 3H), 2.33 (s, 3H), 2.05-2.01 (m, 2H), 1.86 (s, 3H), 1.75-1.72 (m, 2H), 1.66-1.62 (m, 1H), 1.46-1.36 (m, 2H), 1.23 (t, 3H), 1.19-1.12 (m, 4H), 0.96 (s, 9H). LCMS (ES+) (m/z): 521.48 (M+1).

Step 2: (S)-2-(tert-Butoxy)-2-(2-(cyclohexylcarbamoyl)-4,7-dimethyl-6-(p-tolyl)isoindolin-5-yl)acetic acid

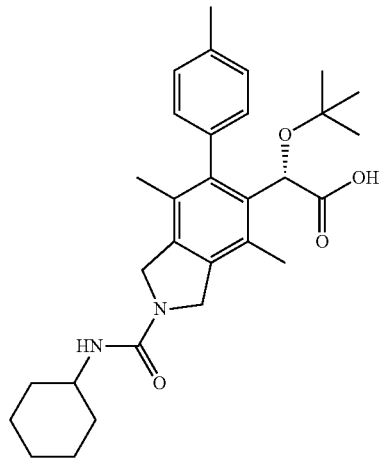 [SMILES: Cc1ccc(-c2c(C)c3c(c(C)c2[C@H](OC(C)(C)C)C(=O)O)CN(C(=O)NC2CCCCC2)C3)cc1]

To a solution of (S)-Ethyl 2-(tert-butoxy)-2-(2-(cyclohexylcarbamoyl)-4,7-dimethyl-6-(p-tolyl)isoindolin-5-yl)acetate (13.3 mg, 0.026 mmol) in 1,4-dioxane (3 mL) was added LiOH (0.511 mL, 0.511 mmol, 1 M) and the reaction mixture stirred at reflux. After 18 h, the reaction mixture was cooled to ambient temperature and concentrated in vacuo. The white residue was dissolved in a minimal amount of water, acidified using 1 N HCl, and extracted with ethyl acetate. The combined organic layers were washed with brine, dried over $Na_2SO_4$ and concentrated in vacuo. The residue was purified by reverse phase HPLC to yield a white solid (5 mg, 40% yield). $^1$H NMR (400 MHz, $CDCl_3$) δ 7.37-7.36 (m, 1H), 7.25-7.24 (m, 2H), 7.08-7.06 (m, 1H), 5.16 (s, 1H), 4.72-4.60 (m, 4H), 3.74-3.71 (m, 1H), 2.41 (s, 3H), 2.26 (s, 3H), 2.03-2.01 (m, 3H), 1.90 (s, 3H), 1.76-1.63 (m, 3H), 1.46-1.36 (m, 2H), 1.21-1.12 (m, 3H), 0.99 (s, 9H). LCMS (ES+) (m/z): 493.42 (M+1).

Example 5: 2-(tert-Butoxy)-2-(4,7-dimethyl-2-(naphthalen-1-ylsulfonyl)-6-(p-tolyl)isoindolin-5-yl) acetic acid

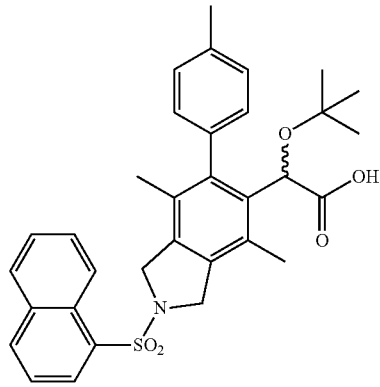 [SMILES: Cc1ccc(-c2c(C)c3c(c(C)c2C(OC(C)(C)C)C(=O)O)CN(S(=O)(=O)c2cccc4ccccc24)C3)cc1]

Step 1: Ethyl 2-(tert-butoxy)-2-(4,7-dimethyl-2-(naphthalen-1-ylsulfonyl)-6-(p-tolyl)isoindolin-5-yl) acetate

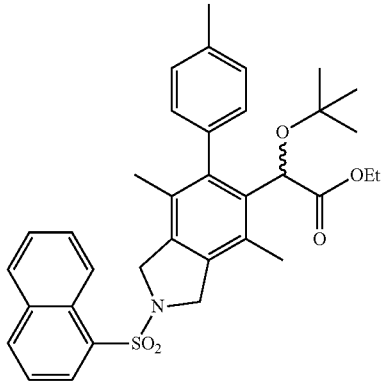 [SMILES: CCOC(=O)C(OC(C)(C)C)c1c(C)c2c(c(C)c1-c1ccc(C)cc1)CN(S(=O)(=O)c1cccc3ccccc13)C2]

A solution of Ethyl 2-(tert-butoxy)-2-(4,7-dimethyl-6-(p-tolyl)isoindolin-5-yl)acetate (40 mg, 0.101 mmol) in DCM (3 mL) was added $Et_3N$ (0.042 mL, 0.30 mmol) and naphthalene-1-sulfonyl chloride (34 mg, 0.152 mmol). After 5 min, sat. aq. $NaHCO_3$ was added and the layers partitioned. The aqueous layer was extracted with DCM (3×) and the combined extracts washed with brine, dried ($Na_2SO_4$), filtered, and concentrated in vacuo. The residue was purified by silica gel chromatography (0-100% EtOAc-hexanes) to afford the title compound (40 mg, 68%) as a brown oil. $^1$H NMR (400 MHz, $CDCl_3$) δ 8.92-8.90 (m, 1H), 8.28-8.26 (m, 1H), 8.08-8.06 (m, 1H), 7.93-7.91 (m, 1H), 7.93-7.91 (m, 1H), 7.67-7.61 (m, 1H), 7.59-7.56 (m, 2H), 7.20-7.11 (m, 3H), 6.98-6.96 (m, 1H), 4.90 (s, 1H), 4.71 (s, 4H), 4.15-4.02 (m, 2H), 2.39 (s, 3H), 2.23 (s, 3H), 1.76 (s, 3H), 1.19 (t, 3H), 0.91 (s, 9H). LCMS (ES+) (m/z): 586.40 (M+1).

Step 2: (2-(tert-Butoxy)-2-(4,7-dimethyl-2-(naphthalen-1-ylsulfonyl)-6-(p-tolyl)isoindolin-5-yl)acetic acid

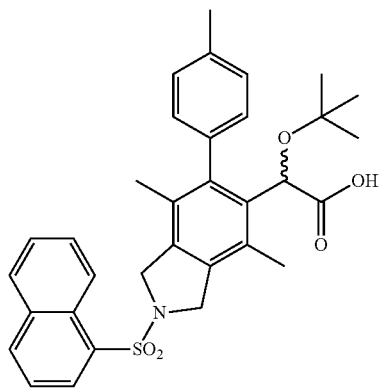 [SMILES: Cc1ccc(-c2c(C)c3c(c(C)c2C(OC(C)(C)C)C(=O)O)CN(S(=O)(=O)c2cccc4ccccc24)C3)cc1]

To a solution of Ethyl 2-(tert-butoxy)-2-(4,7-dimethyl-2-(naphthalen-1-ylsulfonyl)-6-(p-tolyl)isoindolin-5-yl)acetate (40 mg, 0.068 mmol) in 1,4-dioxane (3 mL) was added LiOH (0.511 mL, 0.511 mmol, 1 M) and the reaction mixture stirred at reflux. After 2 h, the reaction mixture was cooled to ambient temperature and concentrated in vacuo.

The white residue was dissolved in a minimal amount of water, acidified using 1 N HCl, and extracted with ethyl acetate. The combined organic layers were washed with brine, dried over Na$_2$SO$_4$ and concentrated in vacuo. The residue was purified by reverse phase HPLC to yield a white solid (27 mg, 71% yield). $^1$H NMR (400 MHz, CDCl$_3$) δ 8.92-8.90 (m, 1H), 8.28-8.26 (m, 1H), 8.10-8.08 (m, 1H), 7.95-7.93 (m, 1H), 7.69-7.67 (m, 1H), 7.62-7.60 (m, 2H), 7.23-7.21 (m, 3H), 7.03-7.01 (m, 1H), 5.11 (s, 1H), 4.84-4.79 (m, 2H), 4.70-4.63 (m, 2H), 2.40 (s, 3H), 2.17 (s, 3H), 1.81 (s, 3H), 0.96 (s, 9H). LCMS (ES+) (m/z): 558.32 (M+1).

Example 6: 2-(tert-Butoxy)-2-(4,7-dimethyl-2,6-di-p-tolylisoindolin-5-yl)acetic acid

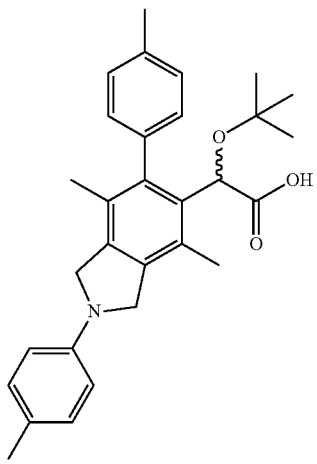 [SMILES: Cc1ccc(-c2c(C)c3c(c(C)c2C(OC(C)(C)C)C(=O)O)CN(c2ccc(C)cc2)C3)cc1]

Step 1: Ethyl 2-(tert-butoxy)-2-(4,7-dimethyl-2,6-di-p-tolylisoindolin-5-yl)acetate

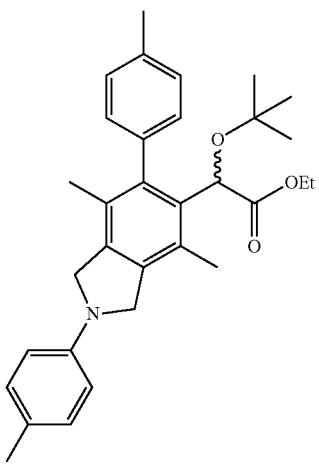 [SMILES: CCOC(=O)C(OC(C)(C)C)c1c(C)c2c(c(C)c1-c1ccc(C)cc1)CN(c1ccc(C)cc1)C2]

To a solution of ethyl 2-(tert-butoxy)-2-(4,7-dimethyl-6-(p-tolyl)isoindolin-5-yl)acetate (25 mg, 0.063 mmol) in THF (2 mL) was added 4-iodotoluene (41 mg, 0.19 mmol), ruphos palladacycle (5.2 mg, 6.3 mol) and finally LiHMDS (0.158 mL, 0.158 mmol) dropwise. After 15 min, the reaction mixture was cooled to 0° C. and quenched with sat. aq. NH$_4$Cl (aq), extracted with EtOAc, and the combined extracts dried over Na$_2$SO$_4$, filtered and concentrated in vacuo. The residue was purified by silica gel chromatography (0-100% EtOAc-hexanes) to afford the title compound (7.3 mg, 24%) as an orange oil. LCMS (ES+) (m/z): 486.42 (M+1).

Step 2: 2-(tert-Butoxy)-2-(4,7-dimethyl-2,6-di-p-tolylisoindolin-5-yl)acetic acid

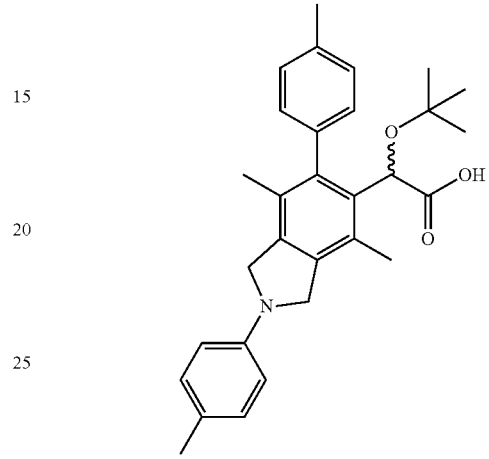

To a solution of ethyl 2-(tert-butoxy)-2-(4,7-dimethyl-2,6-di-p-tolylisoindolin-5-yl)acetate (7.3 mg, 0.015 mmol) in 1,4-dioxane (3 mL) was added LiOH (0.30 mL, 0.30 mmol, 1 M) and the reaction mixture was irradiated in the microwave at 120° C. for 20 min. The reaction mixture was concentrated in vacuo to afford a white residue that was dissolved in a minimal amount of water, acidified using 1 N HCl, and extracted with ethyl acetate. The combined organic layers were washed with brine, dried over Na$_2$SO$_4$ and concentrated in vacuo. The residue was purified by reverse phase HPLC to yield a white solid (1.1 mg, 16% yield). $^1$H NMR (400 MHz, CDCl$_3$) δ 7.39-7.38 (m, 1H), 7.12-7.08 (m, 4H), 6.64-6.62 (m, 3H), 5.18 (s, 1H), 4.66-4.52 (m, 4H), 2.41 (s, 3H), 2.31 (s, 3H), 2.28 (s, 3H), 1.95 (s, 3H). LCMS (ES+) (m/z): 458.14 (M+1).

Example 7: (S)-2-(tert-butoxy)-2-(4,7-dimethyl-2-(piperidine-1-carbonyl)-6-(p-tolyl)isoindolin-5-yl)acetic acid

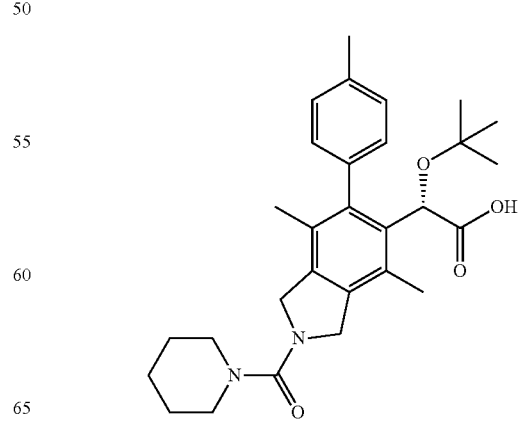

Step 1: Ethyl 2-(tert-butoxy)-2-(4,7-dimethyl-2,6-di-p-tolylisoindolin-5-yl)acetate

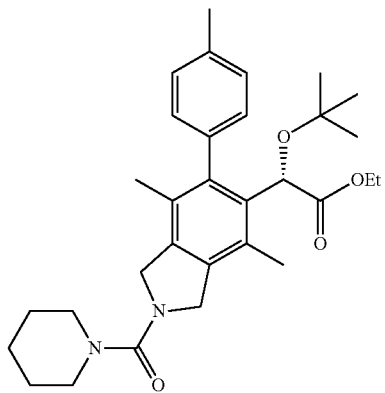 [SMILES: CCOC(=O)[C@@H](OC(C)(C)C)c1c(C)c2c(c(C)c1-c1ccc(C)cc1)CN(C(=O)N1CCCCC1)C2]

An ice cold solution of phosgene (0.1516 mmol, 0.08 mL, 20% in toluene) was treated dropwise with a solution of ethyl 2-(tert-butoxy)-2-(4,7-dimethyl-6-(p-tolyl)isoindolin-5-yl)acetate (25 mg, 0.0632 mmol) in THF (1.25 mL). After 10 min, the reaction mixture was concentrated in vacuo and the residue dissolved in THF (1.25 mL) and cooled to 0° C. Pyridine (1.05 eq, 0.0663 mmol) was added dropwise, followed by the dropwise addition of piperidine (1.05 eq, 0.0663 mmol). After 10 min, the reaction mixture was partitioned between EtOAc and water. The organic layer was washed with 1M HCl, water, brine, dried ($Na_2SO_4$), filtered and concentrated in vacuo. The residue was purified by ISCO (0-100% EtOAc-hexanes) to afford the title compound (19 mg, 61%) as a brown oil. $^1$H NMR (400 MHz, $CDCl_3$) δ7.24-7.20 (m, 3H), 7.06-7.04 (m, 1H), 4.97 (s, 1H), 4.75 (s, 4H), 4.19-4.07 (m, 2H), 3.29 (br.s., 4H), 2.42 (s, 3H), 2.32 (s, 3H), 1.85 (s, 3H), 1.63 (s, 6H), 1.23 (t, 3H), 0.96 (s, 9H). LCMS (ES+) (m/z): 507.55 (M+1).

Step 2: (S)-2-(tert-Butoxy)-2-(4,7-dimethyl-2-(piperidine-1-carbonyl)-6-(p-tolyl)isoindolin-5-yl)acetic acid

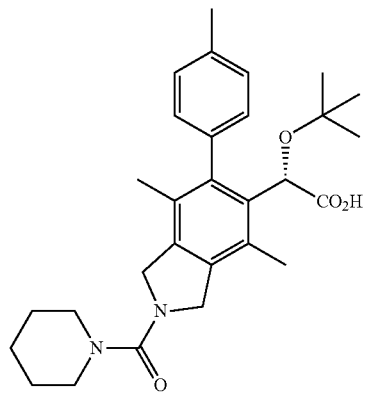 [SMILES: Cc1ccc(-c2c(C)c3c(c(C)c2[C@H](OC(C)(C)C)C(=O)O)CN(C(=O)N2CCCCC2)C3)cc1]

To a solution of ethyl 2-(tert-butoxy)-2-(4,7-dimethyl-2,6-di-p-tolylisoindolin-5-yl)acetate (19 mg, 0.037 mmol) in 1,4-dioxane (3 mL) was added LiOH (0.76 mL, 0.76 mmol, 1 M) and the reaction mixture was heated to reflux. After 18 h, the reaction mixture was concentrated in vacuo to afford a white residue that was dissolved in a minimal amount of water, acidified using 1 N HCl, and extracted with ethyl acetate. The combined organic layers were washed with brine, dried over $Na_2SO_4$ and concentrated in vacuo. The residue was purified by reverse phase HPLC to yield a white solid (11.1 mg, 61% yield). $^1$H NMR (400 MHz, $CDCl_3$) δ 7.37-7.36 (m, 1H), 7.24-7.21 (m, 2H), 7.07-7.05 (m, 1H), 5.15 (s, 1H), 4.86-4.80 (m, 2H), 4.72-4.65 (m, 2H), 3.30 (br.s., 4H), 2.41 (s, 3H), 2.25 (s, 3H), 1.89 (s, 3H), 1.64 (s, 6H), 0.98 (s, 9H). LCMS (ES+) (m/z): 479.5 (M+1).

Scheme 2

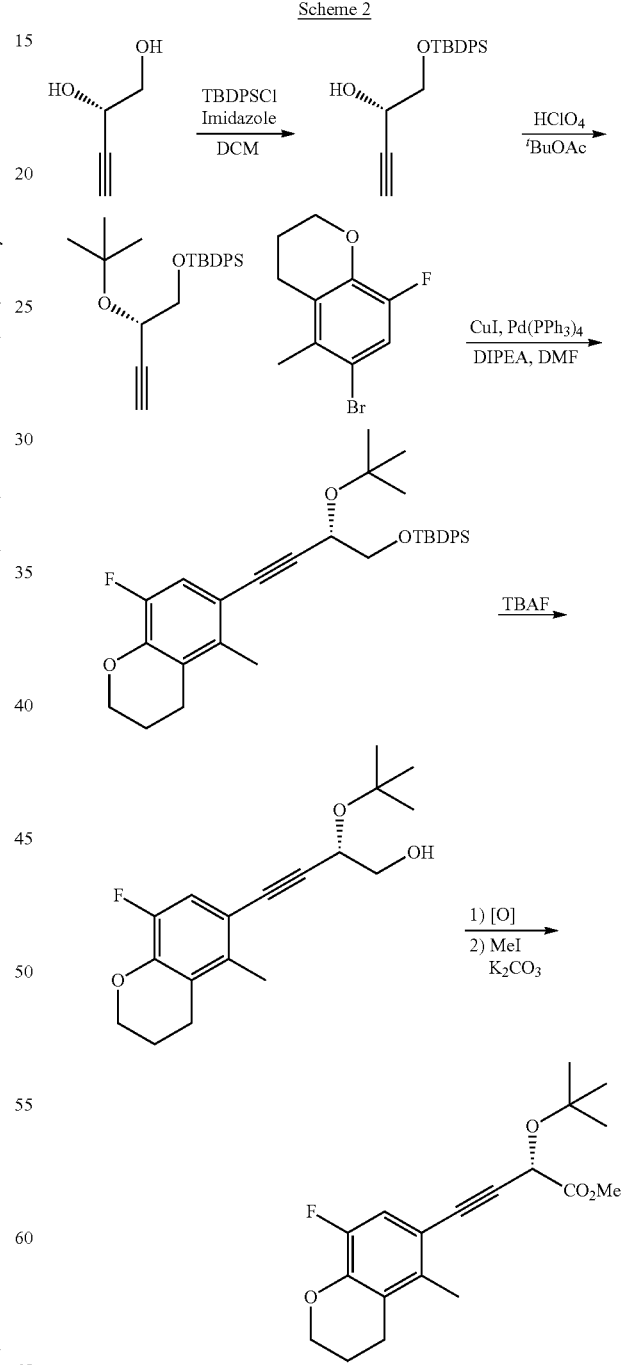

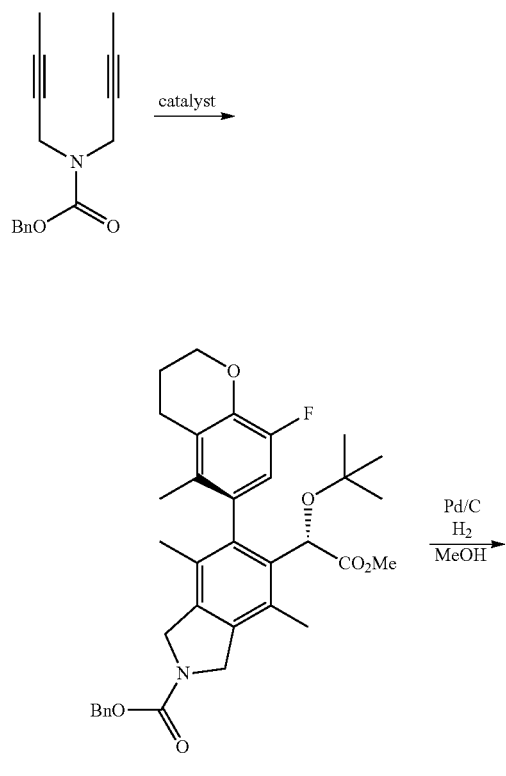
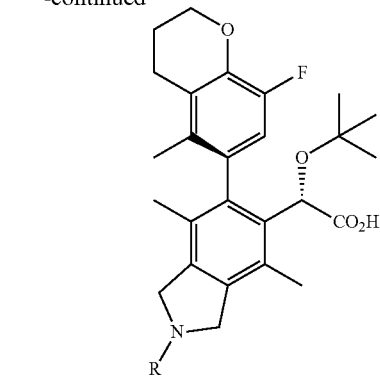
Example 8: (2S)(M)-2-(tert-Butoxy)-2-(-6-(8-fluoro-5-methylchroman-6-yl)-2-(3-fluorobenzyl)-4,7-dimethylisoindolin-5-yl)acetic acid
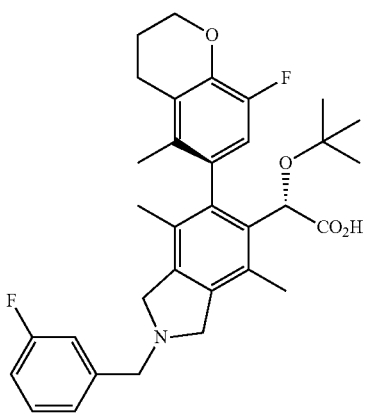
(S)-But-3-yne-1,2-diol
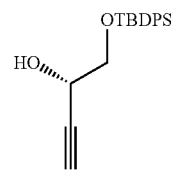
The title compound was prepared from the known procedure as described in WO2010/130034.
Step 1: (S)-1-((tert-Butyldiphenylsilyl)oxy)but-3-yn-2-ol
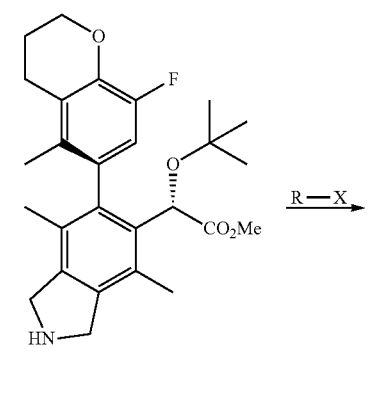
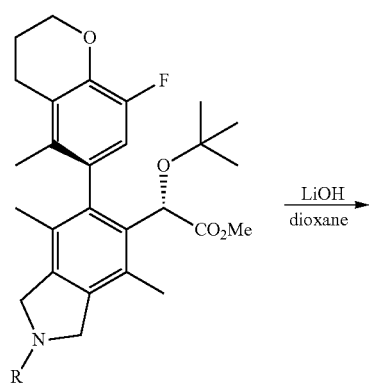

An ice cold solution of (S)-But-3-yne-1,2-diol (220 mg, 2.56 mmol) in DCM (10 mL) was treated with imidazole (209 mg, 3.067 mmol) and TBDPSCl (0.730 mL, 2.812 mmol). After 18 h, the reaction mixture was poured into sat. aq. NaHCO₃ and the layers partitioned. The organic layer was washed with brine, dried (MgSO₄), filtered and concentrated in vacuo. The residue was purified by silica gel chromatography (0-100% EtOAc-hexanes) to afford the title compound (425 mg, 51%) as a colorless oil. 1H NMR (400 MHz, CHLOROFORM-d): δ 1.07 (s, 9H), 2.41 (d, 1H), 2.64 (d, 1H), 3.73 (dd, 1H), 3.80 (dd, 1H), 4.45 (m, 1H), 7.41 (m, 6H), 7.67 (m, 4H). LCMS (m/z ES+): 347 (M+23).

Step 2: (S)-((2-(tert-Butoxy)but-3-yn-1-yl)oxy)(tert-butyl)diphenylsilane

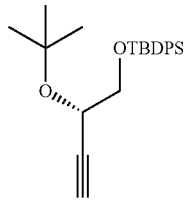

A solution of (S)-1-((tert-Butyldiphenylsilyl)oxy)but-3-yn-2-ol (425 mg, 1.311 mmol) in tert-butyl acetate (70 mL) was treated with HClO₄ (3.93 mL, 1.311 mmol). After 10 min, the reaction mixture was cooled to 0 C and treated with 1N NaOH until the pH was =7. The reaction mixture was diluted with EtOAc and the layers partitioned. The organic phase was washed with brine, dried (Na₂SO₄), filtered and concentrated in vacuo. The residue was purified by silica gel chromatography (0-100% EtOAc-hexanes) to afford the title compound (470 mg, 95%) as a colorless oil. ¹H NMR (400 MHz, CHLOROFORM-d): δ 1.04 (s, 9H), 1.24 (s, 9H), 2.31 (d, 1H), 3.70 (m, 2H), 4.24 (m, 1H), 7.37 (m, 6H), 7.70 (m, 4H). LCMS (m/z ES+): 403 (M+23).

6-Bromo-8-fluoro-5-methylchroman

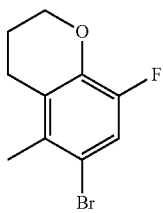

The title compound was prepared from the known procedure as described in WO2010/130842

Step 3: (S)-((2-(tert-Butoxy)-4-(8-fluoro-5-methyl-chroman-6-yl)but-3-yn-1-yl)oxy)(tert-butyl)diphenylsilane

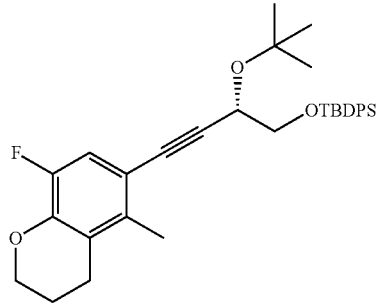

A solution of 6-Bromo-8-fluoro-5-methylchroman (409 mg, 1.68 mmol), (S)-((2-(tert-Butoxy)but-3-yn-1-yl)oxy)(tert-butyl)diphenylsilane (956 mg, 2.516 mmol) and diisopropyl amine (3.59 mL, 252 mmol) in DMF (10 mL) was degassed with N₂ for 10 min and treated with CuI (64 mg, 0.336 mmol) and Pd(PPh₃)₄ (388 mg, 0.336 mmol) and then heated to 80° C. After 18 h, the reaction mixture was diluted with EtOAc. Saturated aqueous NH₄Cl was added and the layers partitioned. The organic phase was washed with water, brine, dried (MgSO₄) filtered and concentrated in vacuo. The residue was purified by silica gel chromatography (0-100% EtOAc-hexanes) to afford the title compound (762 mg, 83%) as a red oil. ¹H NMR (400 MHz, CHLOROFORM-d): δ 1.07 (s, 9H), 1.29 (s, 9H), 2.05 (m, 2H), 2.23 (s, 3H), 2.63 (t, 2H), 3.78 (m, 2H), 4.20 (m, 2H), 4.51 (dd, 1H), 6.95 (d, 1H), 7.39 (m, 6H), 7.73 (m, 4H). LCMS (m/z ES+): 567 (M+23).

Step 4: (S)-2-(tert-Butoxy)-4-(8-fluoro-5-methyl-chroman-6-yl)but-3-yn-1-ol

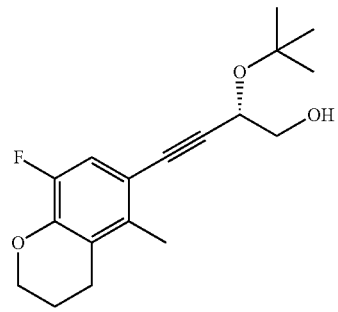 [SMILES: Cc1c(C#C[C@@H](CO)OC(C)(C)C)cc(F)c2c1CCCO2]

A solution of (S)-((2-(tert-Butoxy)-4-(8-fluoro-5-methyl-chroman-6-yl)but-3-yn-1-yl)oxy)(tert-butyl)diphenylsilane (760 mg, 1.4 mmol) in THF (2 mL) was treated with TBAF (14 mL, 14 mmol, 1.0 M in THF). After 15 min, the reaction mixture was concentrated in vacuo and purified by silica gel chromatography (0-100% EtOAc-hexanes) to afford the title compound (402 mg, 94%) as a colorless oil. ¹H NMR (400 MHz, CHLOROFORM-d): δ 1.34 (s, 9H), 2.06 (m, 2H), 2.26 (s, 3H), 2.65 (t, 2H), 3.70 (m, 2H), 4.21 (m, 2H), 4.48 (dd, 1H), 6.97 (d, 1H). LCMS (m/z ES+): 329 (M+23).

Step 5: (S)-2-(tert-Butoxy)-4-(8-fluoro-5-methyl-chroman-6-yl)but-3-ynoic acid

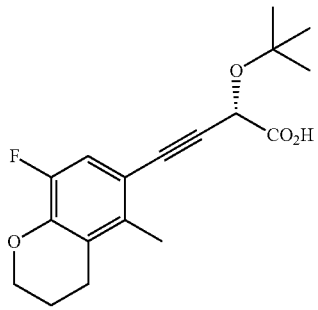 [SMILES: Cc1c(C#C[C@H](OC(C)(C)C)C(=O)O)cc(F)c2c1CCCO2]

A suspension of (S)-((2-(tert-Butoxy)-4-(8-fluoro-5-methylchroman-6-yl)but-3-yn-1-yl)oxy)(tert-butyl)diphenylsilane (108 mg, 0.353 mmol) in DCM (5 mL) was treated with Dess Martin periodinane (300 mg, 0.706 mmol). After 18 h, the reaction mixture was quenched with sat. aq. $Na_2S_2O_3$ and the layers partitioned. The organic layer was washed with brine, dried ($Na_2SO_4$), filtered and concentrated in vacuo to afford the title compound as a yellow oil (312 mg) that was used immediately without further purification. LCMS (m/z ES+): 343 (M+23).

Step 6: (S)-methyl 2-(tert-butoxy)-4-(8-fluoro-5-methylchroman-6-yl)but-3-ynoate

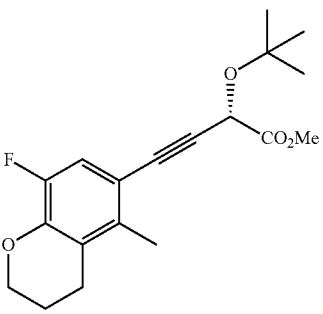 [SMILES: COC(=O)[C@H](C#Cc1cc(F)c2c(c1C)CCCO2)OC(C)(C)C]

A solution of (S)-2-(tert-Butoxy)-4-(8-fluoro-5-methylchroman-6-yl)but-3-ynoic acid (312 mg) and $Cs_2CO_3$ (171 mg, 0.525 mmol) was treated with MeI (0.110 mL, 1.75 mmol). After 2 h, the reaction mixture was diluted with EtOAc and water. The layers were partitioned and the organic layer was washed with water, brine, dried (MgSO₄), filtered and concentrated in vacuo.

The residue was purified by silica gel chromatography (0-100% EtOAc-hexanes) to afford the title compound (40 mg, 32% of 2 steps) as a colorless oil. $^1$H NMR (400 MHz, CHLOROFORM-d): δ 1.32 (s, 9H), 2.06 (m, 2H), 2.26 (s, 3H), 2.63 (t, 2H), 3.83 (s, 3H), 4.20 (m, 2H), 4.99 (s, 1H), 7.00 (d, 1H). LCMS (m/z ES+): 335 (M+1)

Step 7: (2S)(M)(Benzyl 5-(-1-(tert-butoxy)-2-methoxy-2-oxoethyl)-6-(8-fluoro-5-methylchroman-6-yl)-4,7-dimethylisoindoline-2-carboxylate

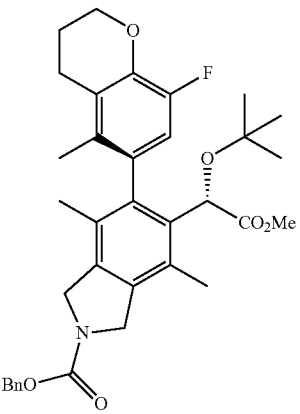

An oven dried flask was charged with (R)-BINAP (12.2 mg, 0.020 mmol) and [Rh(cod)₂]BF₄ (8 mg, 0.020 mmol) in DCM (1 mL). After 5 min, the reaction mixture was saturated with H₂ and placed under an atmosphere of H₂. After 1 h, a solution of (S)-methyl 2-(tert-butoxy)-4-(8-fluoro-5-methylchroman-6-yl)but-3-ynoate (22 mg, 0.066 mmol) in DCM (0.5 mL) and benzyl di(but-2-yn-1-yl)carbamate (51 mg, 0.197 mmol) in DCM (1.5 mL). After 18 h, the reaction mixture was concentrated in vacuo to afford an 8:1 mixture of diastereomers that were purified by silica gel chromatography (0-100% EtOAc-hex) to afford the title compound (24 mg, 62%). $^1$H NMR (400 MHz, CHLOROFORM-d): δ 1.09 (s, 9H), 1.74 (d, 3H), 1.78 (s, 3H), 2.14 (m, 2H), 2.37 (d, 3H), 2.71 (m, 2H), 3.57 (d, 3H), 4.28 (m, 2H), 4.73 (m, 4H), 4.97 (s, 1H), 5.24 (s, 2H), 6.64 (d, 1H), 7.41 (m, 5H). LCMS (m/z ES+): 590 (M+1).

Step 8: (2S)(M)-Methyl 2-(tert-butoxy)-2-(-6-(8-fluoro-5-methylchroman-6-yl)-4,7-dimethylisoindolin-5-yl)acetate

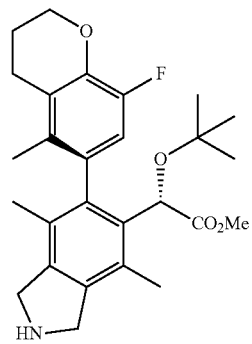

A solution of (2S)(M)(Benzyl 5-(-1-(tert-butoxy)-2-methoxy-2-oxoethyl)-6-(8-fluoro-5-methylchroman-6-yl)-4,7-dimethylisoindoline-2-carboxylate (14 mg, 0.024 mmol) in MeOH (2 mL) was degassed with N₂ and treated with Pd/C (7.5 mg). The reaction mixture was saturated with H₂ and then placed under an atmosphere of H₂. After 10 min, the reaction mixture was filtered through a pad of celite and the filtrated concentrated in vacuo to afford the title compound (12 mg, 100%) as a red oil. LCMS (ES+) (m/z): 456 (M+1).

Step 9: (2S)(M)-Methyl 2-(tert-butoxy)-2-(-6-(8-fluoro-5-methylchroman-6-yl)-2-(3-fluorobenzyl)-4,7-dimethylisoindolin-5-yl)acetate

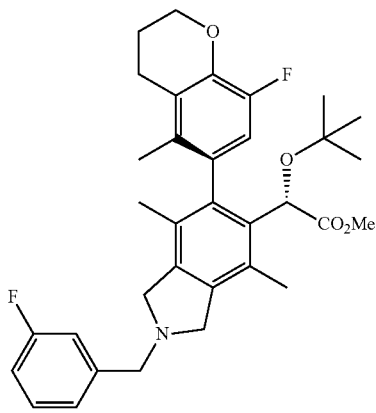

A solution of (2S)(M)-Methyl 2-(tert-butoxy)-2-(-6-(8-fluoro-5-methylchroman-6-yl)-4,7-dimethylisoindolin-5-yl)acetate (12 mg, 0.026 mmol) in DCE (1.5 mL) was treated with added 3-fluorobenzaldehyde (0.004 mL 0.036 mmol) and Na(OAc₃)BH (7.5 mg, 0.036 mmol). After 15 min, the reaction mixture was diluted with DCM and poured into sat. aq. NaHCO₃. The layers were partitioned and the organic phase washed with water, brine, dried (Na₂SO₄), filtered and concentrated in vacuo. The residue was purified by reverse phase HPLC to afford the title compound (4 mg, 30%) as a colorless oil. ¹H NMR (400 MHz, CHLOROFORM-d): δ 1.12 (s, 9H), 1.76 (s, 3H), 1.77 (s, 3H), 2.18 (m, 2H), 2.38 (s, 3H), 2.73 (m, 2H), 3.61 (s, 3H), 4.31 (m, 4H), 4.49 (s, 2H), 4.99 (m, 3H), 6.62 (d, 1H), 7.23 (m, 2H), 7.34 (d, 1H), 7.50 (m, 1H). LCMS (ES+) (m/z): 564 (M+1).

Step 10: (2S) (M)-2-(tert-Butoxy)-2-(-6-(8-fluoro-5-methylchroman-6-yl)-2-(3-fluorobenzyl)-4,7-dimethylisoindolin-5-yl)acetic acid

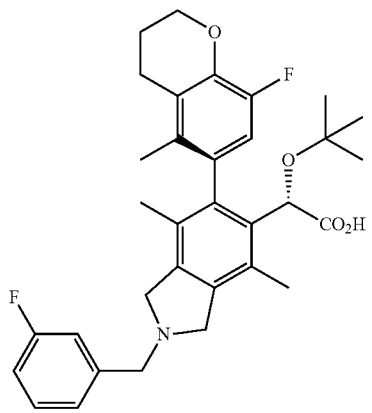

A solution of (2S)(M)-Methyl 2-(tert-butoxy)-2-(-6-(8-fluoro-5-methylchroman-6-yl)-2-(3-fluorobenzyl)-4,7-dimethylisoindolin-5-yl)acetate (4 mg, 0.007 mmol) in 1,4-dioxane (2 mL) was treated with LiOH (0.142 mL, 0.142 mmol, 1.0 M) and heated to 105° C. After 18 h, the reaction mixture was concentrated in vacuo and the residue was partitioned between EtOAc and water. The organic phase was washed with water, dried (MgSO₄), filtered and concentrated in vacuo. The residue was purified by reverse phase HPLC to afford the title compound (1.3 mg, 33%) as a colorless oil. ¹H NMR (400 MHz, METHANOL-d4): δ 1.05 (s, 9H), 1.76 (m, 6H), 2.07 (m, 2H), 2.38 (s, 3H), 2.69 (t, 2H), 4.20 (t, 2H), 4.65 (s, 2H), 4.71 (m, 4H), 4.95 (s, 1H), 6.53 (d, 1H), 7.25 (m, 1H), 7.39 (m, 2H), 7.53 (m, 1H). LCMS (m/z ES+): 550 (M+1);

The following compounds were prepared in a manner similar to the procedures described above for Examples 1-8.

Example 9: 2-(2-Benzyl-4,7-dimethyl-6-(p-tolyl)isoindolin-5-yl)-2-(tert-butoxy)acetic acid

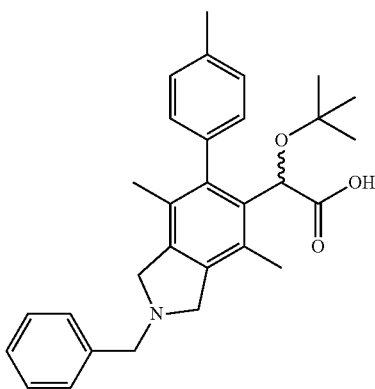 [SMILES: Cc1ccc(-c2c(C)c3c(c(C)c2C(OC(C)(C)C)C(=O)O)CN(Cc2ccccc2)C3)cc1]

¹H NMR (400 MHz, CDCl₃) δ 7.54-7.47 (m, 5H), 7.32-7.30 (m, 3H), 7.06-7.04 (m, 1H), 5.12 (s, 1H), 4.93 (t, 2H), 4.45 (s, 2H), 4.26 (t, 2H), 2.40 (s, 3H), 2.20 (s, 3H), 1.84 (s, 3H), 0.94, (s, 9H). LCMS (ES+) (m/z): 458.31 (M+1)

Example 10: 2-(tert-butoxy)-2-(2-(cyclohexylmethyl)-4,7-dimethyl-6-(p-tolyl)isoindolin-5-yl)acetic acid

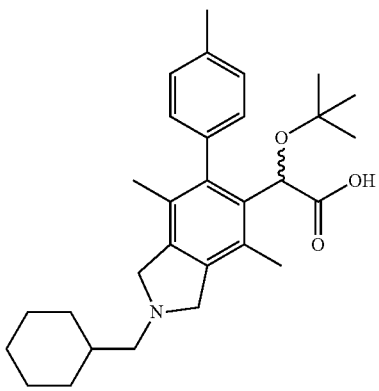 [SMILES: Cc1ccc(-c2c(C)c3c(c(C)c2C(OC(C)(C)C)C(=O)O)CN(CC2CCCCC2)C3)cc1]

¹H NMR (400 MHz, CDCl₃) δ 7.34-7.32 (m, 1H), 7.27-7.25 (m, 2H), 7.09-7.07 (m, 1H), 5.20-5.10 (m, 2H), 5.13 (s, 1H), 4.21-4.10 (m, 2H), 3.175 (d, 2H), 2.42 (s, 3H), 2.24 (s,

3H), 1.90 (s, 3H), 1.82-1.70 (m, 4H), 1.33-1.06 (m, 7H), 0.97 (s, 9H). LCMS (ES+) (m/z): 464.45 (M+1).

Example 11: (S)-2-(tert-butoxy)-2-(4,7-dimethyl-2-(pyridin-4-ylmethyl)-6-(p-tolyl)isoindolin-5-yl)acetic acid

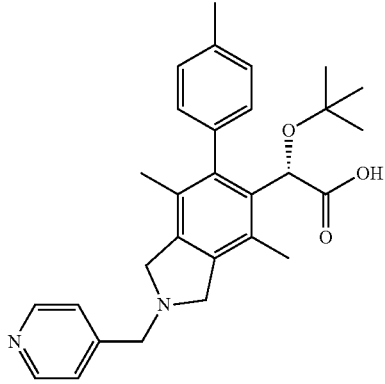 [SMILES: Cc1ccc(-c2c(C)c3c(c(C)c2[C@H](OC(C)(C)C)C(=O)O)CN(Cc2ccncc2)C3)cc1]

¹H NMR (400 MHz, CDCl₃) δ 8.87-8.86 (m, 2H), 7.83-7.82 (m, 2H), 7.32-7.28 (m, 3H), 7.06-7.00 (m, 1H), 5.15 (s, 1H), 4.86-4.79 (m, 2H), 4.60 (s, 2H), 4.42-4.34 (m, 2H), 2.42 (s, 3H), 2.24 (s, 3H), 1.87 (s, 3H), 0.98 (s, 9H). LCMS (ES+) (m/z): 459.40 (M+1).

Example 12: (S)-2-(tert-butoxy)-2-(4,7-dimethyl-2-((tetrahydro-2H-pyran-4-yl)methyl)-6-(p-tolyl)isoindolin-5-yl)acetic acid

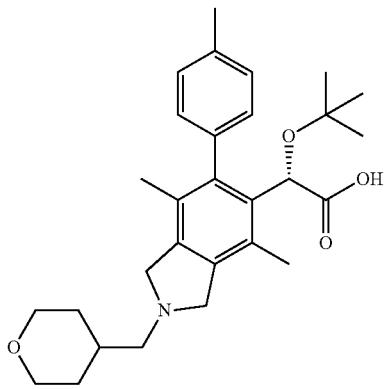 [SMILES: Cc1ccc(-c2c(C)c3c(c(C)c2[C@H](OC(C)(C)C)C(=O)O)CN(CC2CCOCC2)C3)cc1]

¹H NMR (400 MHz, CDCl₃) δ 7.22-7.18 (m, 3H), 7.05-7.00 (m, 1H), 4.95 (s, 1H), 4.20-4.14 (m, 2H), 4.03-3.98 (m, 4H), 3.95-3.93 (m, 4H), 3.44 (t, 1H), 2.64 (d, 2H), 2.41 (s, 3H), 2.30 (s, 3H), 1.82 (s, 3H), 1.79-1.76 (m, 2H), 1.42-1.28 (m, 2H), 1.22 (t, 3H), 0.95 (s, 9H). LCMS (ES+) (m/z): 494.14 (M+1).

Example 13: (S)-2-(tert-Butoxy)-2-(4,7-dimethyl-2-(naphthalen-1-ylmethyl)-6-(p-tolyl)isoindolin-5-yl)acetic acid

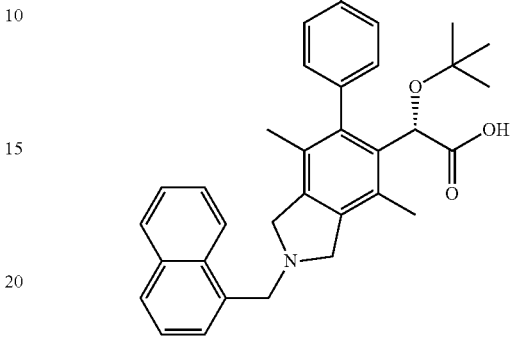

¹H NMR (400 MHz, CDCl₃) δ 8.02-7.95 (m, 3H), 7.74-7.72 (m, 1H), 7.36-7.34 (m, 1H), 7.29-7.258 (m, 2H), 7.08-7.06 (m, 1H), 4.60-4.52 (m, 3H), 5.15 (s, 1H), 4.98-4.88 (m, 2H), 4.95 (s, 2H), 4.47-4.40 (m, 2H), 2.42 (s, 3H), 2.17 (s, 3H), 1.84 (s, 3H), 0.96 (s, 9H). LCMS (ES+) (m/z): 508.09 (M+1).

Example 14: (S)-2-(tert-Butoxy)-2-(4,7-dimethyl-2-(naphthalen-1-ylmethyl)-6-(p-tolyl)isoindolin-5-yl)acetic acid

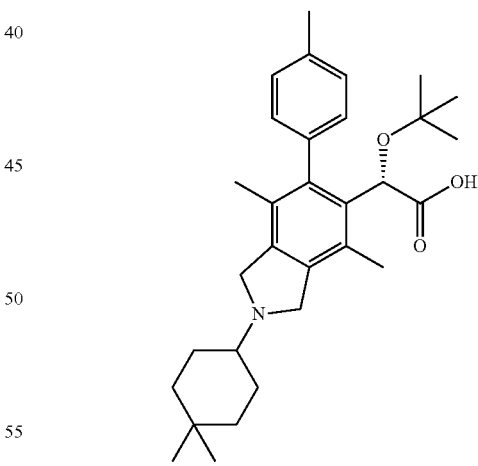

(S)-2-(tert-Butoxy)-2-(2-(4,4-dimethylcyclohexyl)-4,7-dimethyl-6-(p-tolyl)isoindolin-5-yl)acetic acid. ¹H NMR (400 MHz, CDCl₃) δ 7.34-7.32 (m, 1H), 7.26-7.25 (m, 2H), 7.11-7.09 (m, 1H), 5.13 (s, 1H), 5.11-5.06 (m, 2H), 4.27-4.20 (m, 2H), 2.42 (s, 3H), 2.25 (s, 3H), 2.03-1.97 (m, 2H), 1.93-1.87 (m, 2H), 1.90 (s, 3H), 1.63-1.60 (m, 2H), 1.33-1.24 (m, 3H), 0.98 (s, 6H), 0.95 (s, 9H). LCMS (ES+) (m/z): 478.16 (M+1),

Example 15: 2-(tert-Butoxy)-2-(4,7-dimethyl-2-(methylsulfonyl)-6-(p-tolyl)isoindolin-5-yl)acetic acid

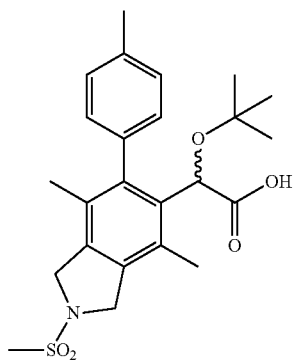 [SMILES: Cc1ccc(-c2c(C)c3c(c(C)c2C(OC(C)(C)C)C(=O)O)CN(S(C)(=O)=O)C3)cc1]

$^1$H NMR (400 MHz, CDCl$_3$) δ 7.35-7.33 (m, 1H), 7.27-7.22 (m, 2H), 7.07-7.05 (m, 1H), 5.16 (s, 1H), 4.78-4.73 (m, 2H), 4.68-4.60 (m, 2H), 2.92 (s, 3H), 2.42 (s, 3H), 2.24 (s, 3H), 1.88 (s, 3H), 0.99 (s, 9H). LCMS (ES+) (m/z): 446.22 (M+1).

Example 16: 2-(tert-Butoxy)-2-(4,7-dimethyl-2-(naphthalen-1-ylsulfonyl)-6-(p-tolyl)isoindolin-5-yl)acetic acid

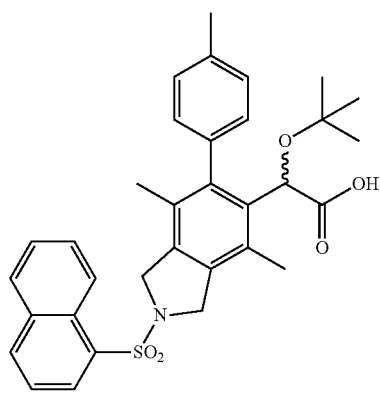 [SMILES: Cc1ccc(-c2c(C)c3c(c(C)c2C(OC(C)(C)C)C(=O)O)CN(S(=O)(=O)c2cccc4ccccc24)C3)cc1]

8.92-8.90 (m, 1H), 8.28-8.26 (m, 1H), 8.10-8.08 (m, 1H), 7.95-7.93 (m, 1H), 7.69-7.67 (m, 1H), 7.62-7.60 (m, 2H), 7.23-7.21 (m, 3H), 7.03-7.01 (m, 1H), 5.11 (s, 1H), 4.84-4.79 (m, 2H), 4.70-4.63 (m, 2H), 2.40 (s, 3H), 2.17 (s, 3H), 1.81 (s, 3H), 0.96 (s, 9H). LCMS (ES+) (m/z): 558.32 (M+1).

Example 17: 2-(2-((Benzyloxy)carbonyl)-4,7-dimethyl-6-(p-tolyl)isoindolin-5-yl)-2-(tert-butoxy)acetic acid

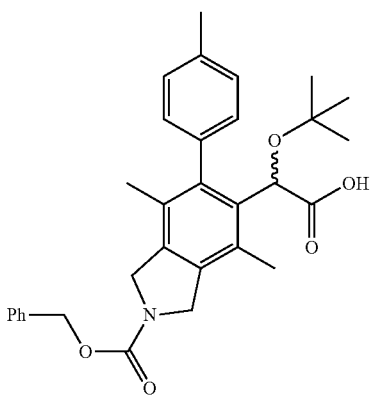 [SMILES: Cc1ccc(-c2c(C)c3c(c(C)c2C(OC(C)(C)C)C(=O)O)CN(C(=O)OCc2ccccc2)C3)cc1]

$^1$H NMR (400 MHz, CDCl$_3$) δ 7.41-7.33 (m, 5H), 7.24-7.21 (m, 1H), 5.25-5.20 (m, 2H), 5.16 (s, 1H), 4.82-4.65 (m, 4H), 2.41 (s, 3H), 2.245 (d, 3H), 1.875 (d, 3H), 0.98 (s, 9H). LCMS (ES+) (m/z): 502.24 (M+1).

Example 18: (S)-2-(tert-butoxy)-2-(2-(4-chlorobenzyl)-4,7-dimethyl-6-(p-tolyl)isoindolin-5-yl)acetic acid

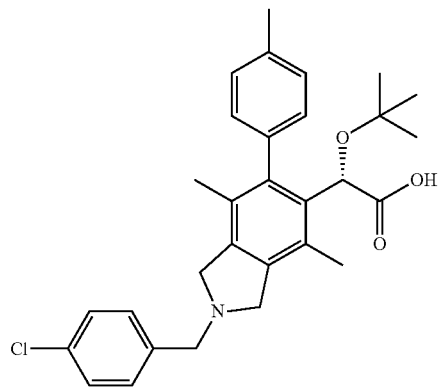 [SMILES: Cc1ccc(-c2c(C)c3c(c(C)c2[C@H](OC(C)(C)C)C(=O)O)CN(Cc2ccc(Cl)cc2)C3)cc1]

$^1$H NMR (400 MHz, CDCl$_3$) δ 7.49-7.45 (m, 4H), 7.34-7.32 (m, 1H), 7.28-7.24 (m, 2H), 7.06-7.05 (m, 1H), 5.14 (s, 1H), 4.98-4.89 (m, 2H), 4.42 (s, 2H), 4.24-4.19 (m, 2H), 2.42 (s, 3H), 2.22 (s, 3H), 1.85 (s, 3H), 0.97 (s, 9H). LCMS (ES+) (m/z): 492.45 (M+1).

Example 19: (S)-2-(tert-butoxy)-2-(2-(4-methoxybenzyl)-4,7-dimethyl-6-(p-tolyl)isoindolin-5-yl)acetic acid

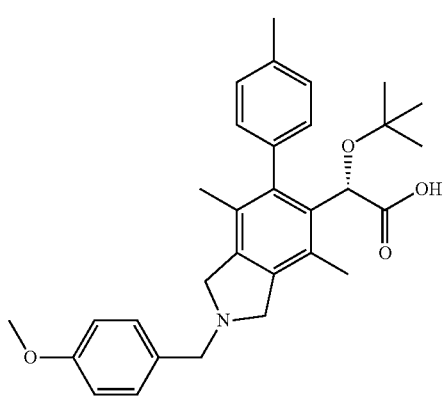 [SMILES: COc1ccc(CN2Cc3c(C)c(-c4ccc(C)cc4)c([C@H](OC(C)(C)C)C(=O)O)c(C)c3C2)cc1]

¹H NMR (400 MHz, CDCl₃) δ 7.40-7.38 (m, 2H), 7.32-7.30 (m, 1H), 7.25-7.22 (m, 2H), 7.05-7.04 (m, 1H), 6.96-6.94 (m, 2H), 5.11 (s, 1H), 4.93-4.85 (m, 2H), 4.37 (s, 2H), 4.28-4.21 (m, 2H), 3.83 (s, 3H), 2.40 (s, 3H), 2.19 (s, 3H), 1.84 (s, 3H), 0.94 (s, 9H). LCMS (ES+) (m/z): 488.50 (M+1).

Example 20: (S)-2-(tert-butoxy)-2-(4,7-dimethyl-2-(4-methylbenzyl)-6-(p-tolyl)isoindolin-5-yl)acetic acid

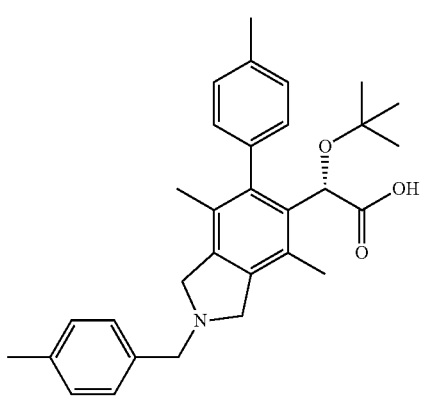 [SMILES: Cc1ccc(CN2Cc3c(C)c(-c4ccc(C)cc4)c([C@H](OC(C)(C)C)C(=O)O)c(C)c3C2)cc1]

¹H NMR (400 MHz, CDCl₃) δ 7.36-7.32 (m, 4H), 7.28-7.24 (m, 3H), 7.08-7.06 (m, 1H), 5.13 (s, 1H), 4.97-4.89 (m, 2H), 4.42 (s, 2H), 4.32-4.25 (m, 2H), 2.42 (s, 3H), 2.40 (s, 3H), 2.21 (s, 3H), 1.86 (s, 3H), 0.96 (s, 9H). LCMS (ES+) (m/z): 472.16 (M+1).

Example 21: (S)-2-(tert-butoxy)-2-(2-(2-fluorobenzyl)-4,7-dimethyl-6-(p-tolyl)isoindolin-5-yl)acetic acid

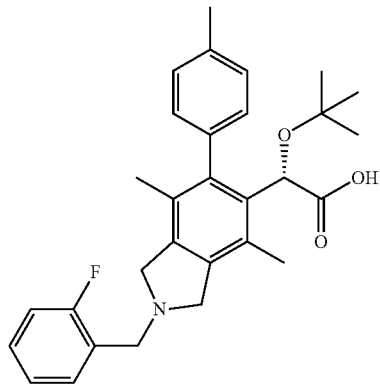 [SMILES: Cc1ccc(-c2c(C)c3c(c(C)c2[C@H](OC(C)(C)C)C(=O)O)CN(Cc2ccccc2F)C3)cc1]

¹H NMR (400 MHz, CDCl₃) δ 7.61-7.58 (m, 2H), 7.50-7.45 (m, 2H), 7.31-7.27 (m, 2H), 7.20-7.15 (m, 1H), 7.06-7.04 (m, 1H), 5.11 (s, 1H), 5.02-4.94 (m, 2H), 4.56 (s, 2H), 4.38-4.30 (m, 2H), 2.40 (s, 3H), 2.21 (s, 3H), 1.85 (s, 3H), 0.94 (s, 9H). LCMS (ES+) (m/z): 476.79 (M+1).

Example 22: (S)-2-(tert-butoxy)-2-(2-(3-fluorobenzyl)-4,7-dimethyl-6-(p-tolyl)isoindolin-5-yl)acetic acid

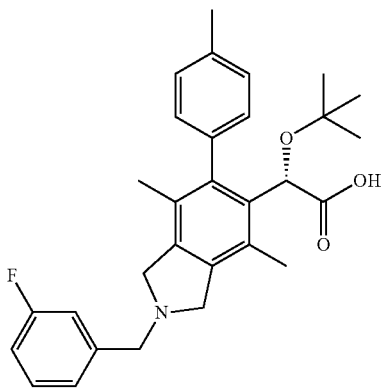

¹H NMR (400 MHz, CDCl₃) δ 7.49-7.44 (m, 1H), 7.33-7.31 (m, 3H), 7.24-7.17 (m, 3H), 7.06-7.04 (m, 1H), 5.13 (s, 1H), 5.01-4.92 (m, 2H), 4.46 (s, 2H), 4.31-4.23 (m, 2H), 2.42 (s, 3H), 2.23 (s, 3H), 1.86 (s, 3H), 0.97 (s, 9H). LCMS (ES+) (m/z): 476.48 (M+1).

Example 23: (S)-2-(tert-butoxy)-2-(4,7-dimethyl-2-((4-methyl-1H-imidazol-2-yl)methyl)-6-(p-tolyl)isoindolin-5-yl)acetic acid

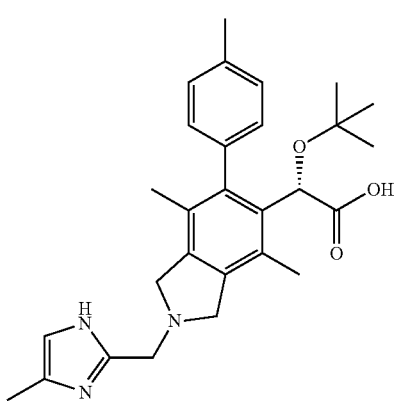 [SMILES: Cc1ccc(-c2c(C)c3c(c(C)c2[C@H](OC(C)(C)C)C(=O)O)CN(Cc2nc(C)c[nH]2)C3)cc1]

$^1$H NMR (400 MHz, CDCl$_3$) δ 7.36-7.34 (m, 1H), 7.28-7.24 (m, 2H), 7.14 (s, 1H), 7.07-7.05 (m, 1H), 5.29-5.28 (m, 2H), 5.13 (s, 1H), 4.74-4.63 (m, 4H), 2.46 (s, 3H), 2.42 (s, 3H), 2.24 (s, 3H), 1.87 (s, 3H), 0.98 (s, 9H). LCMS (ES+) (m/z): 462.44 (M+1).

Example 24: (S)-2-(tert-butoxy)-2-(2-(3-methoxybenzyl)-4,7-dimethyl-6-(p-tolyl)isoindolin-5-yl)acetic acid

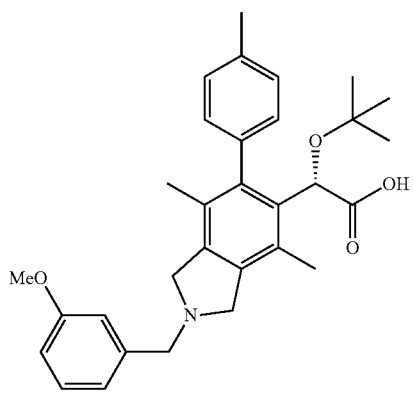 [SMILES: COc1cccc(CN2Cc3c(C)c(-c4ccc(C)cc4)c([C@H](OC(C)(C)C)C(=O)O)c(C)c3C2)c1]

$^1$H NMR (400 MHz, CDCl$_3$) δ7.38-7.32 (m, 2H), 7.28-7.24 (m, 2H), 7.12 (s, 1H), 7.08-7.00 (m, 3H), 5.14 (s, 1H), 5.00-4.91 (m, 2H), 4.42 (s, 2H), 4.32-4.24 (m, 2H), 3.83 (s, 3H), 2.42 (s, 3H), 2.22 (s, 3H), 1.86 (s, 3H), 0.96 (s, 9H). LCMS (ES+) (m/z): 488.50 (M+1).

Example 25: (S)-2-(tert-butoxy)-2-(2-isobutyl-4,7-dimethyl-6-(p-tolyl)isoindolin-5-yl)acetic acid

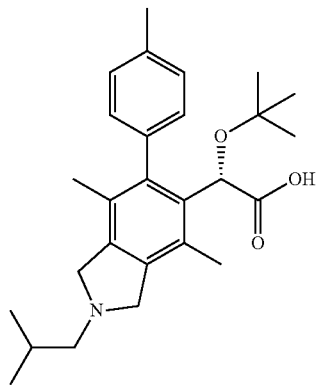 [SMILES: Cc1ccc(-c2c(C)c3c(c(C)c2[C@H](OC(C)(C)C)C(=O)O)CN(CC(C)C)C3)cc1]

$^1$H NMR (400 MHz, CDCl$_3$) δ7.34-7.32 (m, 1H), 7.27-7.25 (m, 2H), 7.09-7.08 (m, 1H), 5.22-5.14 (m, 3H), 4.24-4.17 (m, 2H), 3.20 (d, 2H), 2.42 (s, 3H), 2.25 (s, 3H), 2.22-2.1 (m, 1H), 1.90 (s, 3H), 1.15 (s, 3H), 1.13 (s, 3H), 0.96 (s, 9H). LCMS (ES+) (m/z): 423.58 (M+1).

Example 26: (S)-2-(tert-butoxy)-2-(2-(3,4-dichlorobenzyl)-4,7-dimethyl-6-(p-tolyl)isoindolin-5-yl)acetic acid

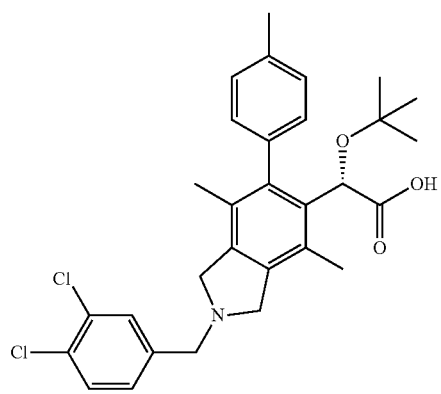 [SMILES: Cc1ccc(-c2c(C)c3c(c(C)c2[C@H](OC(C)(C)C)C(=O)O)CN(Cc2ccc(Cl)c(Cl)c2)C3)cc1]

$^1$H NMR (400 MHz, CDCl$_3$) 7.56 (s, 1H), 7.44-7.42 (m, 1H), 7.37-7.35 (m, 1H), 7.28-7.25 (m, 2H), 7.23-7.19 (m, 1H), 7.05-7.03 (m, 1H), 5.15 (s, 1H), 4.10-4.04 (m, 2H), 3.95-3.79 (m, 4H), 2.40 (s, 3H), 2.21 (s, 3H), 1.83 (s, 3H), 0.97 (s, 9H). LCMS (ES+) (m/z): 526.42 (M+1).

Example 27: (S)-2-(tert-butoxy)-2-(4,7-dimethyl-6-(p-tolyl)-2-(4-(trifluoromethyl)benzyl)isoindolin-5-yl)acetic acid

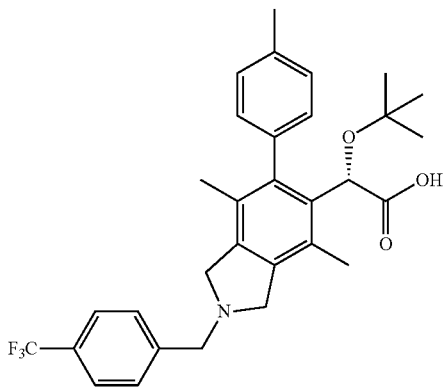

¹H NMR (400 MHz, CDCl₃) δ 7.76-7.74 (m, 2H), 7.69-7.67 (m, 2H), 7.34-7.32 (m, 1H), 7.28-7.24 (m, 2H), 7.06-7.04 (m, 2H), 5.14 (s, 1H), 4.52 (s, 2H), 2.42 (s, 3H), 2.23 (s, 3H), 1.86 (s, 3H), 0.98 (s, 9H). LCMS (ES+) (m/z): 526.48 (M+1).

Example 28: (S)-2-(tert-butoxy)-2-(4,7-dimethyl-6-(p-tolyl)-2-(3-(trifluoromethyl)benzyl)isoindolin-5-yl)acetic acid

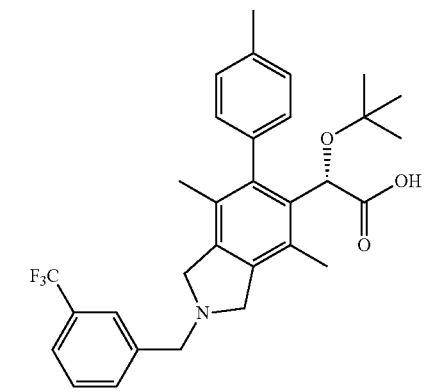 [SMILES: Cc1ccc(-c2c(C)c3c(c(C)c2[C@H](OC(C)(C)C)C(=O)O)CN(Cc2cccc(C(F)(F)F)c2)C3)cc1]

¹H NMR (400 MHz, CDCl₃) δ 7.72 (s, 1H), 7.63-7.47 (m, 3H), 7.73-7.35 (m, 1H), 7.24-7.19 (m, 2H), 7.05-7.03 (m, 1H), 5.13 (s, 1H), 4.15-3.85 (m, 6H), 2.40 (s, 3H), 2.22 (s, 3H), 1.83 (s, 3H), 0.97 (s, 9H). LCMS (ES+) (m/z): 526.03 (M+1).

Example 29: (S)-2-(2-([1,1'-biphenyl]-3-ylmethyl)-4,7-dimethyl-6-(p-tolyl)isoindolin-5-yl)-2-(tert-butoxy)acetic acid

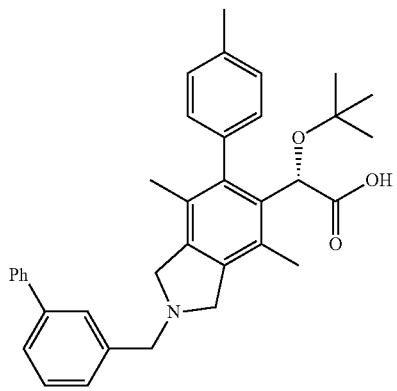 [SMILES: Cc1ccc(-c2c(C)c3c(c(C)c2[C@H](OC(C)(C)C)C(=O)O)CN(Cc2cccc(-c4ccccc4)c2)C3)cc1]

¹H NMR (400 MHz, CDCl₃) δ 7.75-7.71 (m, 2H), 7.61-7.59 (m, 2H), 7.57-7.53 (m, 1H), 7.49-7.37 (m, 4H), 7.34-7.32 (m, 1H), 7.28-7.32 (m, 1H), 7.08-7.07 (m, 1H), 5.14 (s, 1H), 5.05-4.97 (m, 2H), 4.55 (s, 2H), 4.39-4.31 (m, 2H), 2.42 (s, 3H), 2.23 (s, 3H), 1.87 (s, 3H), 0.96 (s, 9H). LCMS (ES+) (m/z): 534.4 (M+1).

Example 30: (S)-2-(tert-butoxy)-2-(2-(cyclohexylmethyl)-4,7-dimethyl-6-(p-tolyl)isoindolin-5-yl)acetic acid

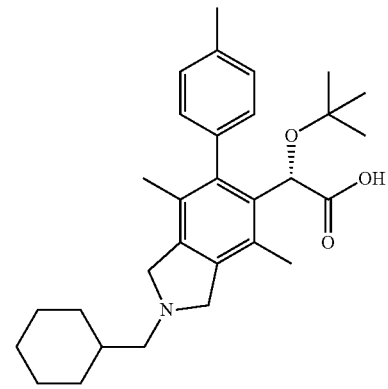 [SMILES: Cc1ccc(-c2c(C)c3c(c(C)c2[C@H](OC(C)(C)C)C(=O)O)CN(CC2CCCCC2)C3)cc1]

¹H NMR (400 MHz, CDCl₃) δ 7.34-7.32 (m, 1H), 7.27-7.25 (m, 2H), 7.09-7.07 (m, 1H), 5.20-5.10 (m, 2H), 5.13 (s, 1H), 4.21-4.10 (m, 2H), 3.175 (d, 2H), 2.42 (s, 3H), 2.24 (s, 3H), 1.90 (s, 3H), 1.82-1.70 (m, 4H), 1.33-1.06 (m, 7H), 0.97 (s, 9H). LCMS (ES+) (m/z): 464.16 (M+1).

Example 31: (2S)-2-(tert-butoxy)-2-(4,7-dimethyl-2-(3-phenylcyclohexyl)-6-(p-tolyl)isoindolin-5-yl)acetic acid

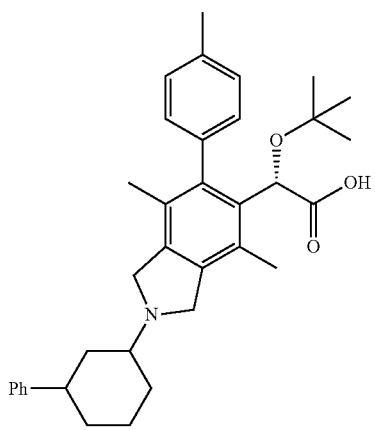 [SMILES: Cc1ccc(-c2c(C)c3c(c(C)c2[C@H](OC(C)(C)C)C(=O)O)CN(C2CCCC(c4ccccc4)C2)C3)cc1]

¹H NMR (400 MHz, CDCl₃) δ 7.37-7.30 (m, 5H), 7.24-7.22 (m, 3H), 7.10-7.08 (m, 1H), 5.34-5.16 (m, 2H), 5.13 (s, 1H), 4.20-4.10 (m, 2H), 3.46-3.40 (m, 2H), 2.41 (s, 3H), 2.33-2.30 (m, 2H), 2.25 (s, 3H), 2.04-1.95 (m, 6H), 1.91 (s, 3H), 0.96 (s, 9H). LCMS (ES+) (m/z): 526.47 (M+1).

Example 32: (2S)-2-(tert-butoxy)-2-(4,7-dimethyl-2-((3R)-3-methylcyclohexyl)-6-(p-tolyl)isoindolin-5-yl)acetic acid

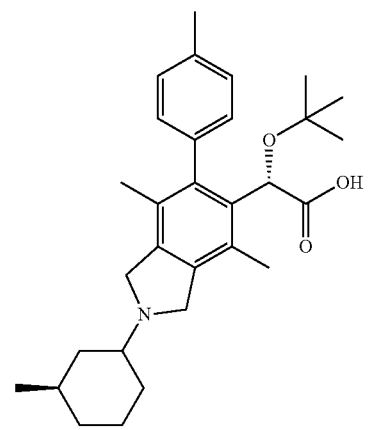 [SMILES: Cc1ccc(-c2c(C)c3c(c(C)c2[C@H](OC(C)(C)C)C(=O)O)CN(C2CCC[C@@H](C)C2)C3)cc1]

¹H NMR (400 MHz, CDCl₃) δ 7.34-7.32 (m, 1H), 7.26-7.25 (m, 2H), 7.10-7.08 (m, 1H), 5.15-5.06 (m, 2H), 5.13 (s, 1H), 4.29-4.10 (m, 2H), 3.44 (br.s., 1H), 2.42 (s, 3H), 2.25 (s, 3H), 2.11-2.08 (m, 1H), 1.95-1.83 (m, 3H), 1.90 (s, 3H), 1.80-1.17 (m, 2H), 1.65-1.61 (m, 2H), 1.43-1.42 (m, 1H), 1.02 (d, 3H), 0.95 (s, 9H). LCMS (ES+) (m/z): 464.49 (M+1).

Example 33: (S)-2-(tert-butoxy)-2-(4,7-dimethyl-2-(((1r,4S)-4-methylcyclohexyl)carbamoyl)-6-(p-tolyl)isoindolin-5-yl)acetic acid

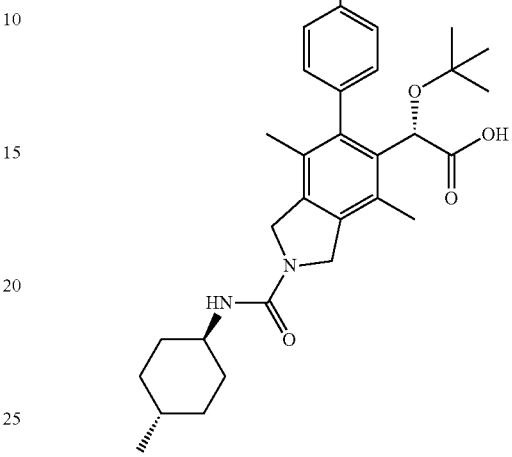

¹H NMR (400 MHz, CDCl₃) δ 7.37-7.35 (m, 1H), 7.24-7.22 (m, 2H), 7.08-7.06 (m, 1H), 5.16 (s, 1H), 4.72-4.59 (m, 4H), 3.70-3.65 (m, 1H), 2.41 (s, 3H), 2.26 (s, 3H), 2.07-2.04 (m, 2H), 1.89 (s, 3H), 1.75-1.72 (m, 2H), 1.35-1.28 (m, 1H), 1.22-1.07 (m, 4H), 0.98 (s, 9H), 0.91 (d, 3H). LCMS (ES+) (m/z): 507.52 (M+1).

Example 34: (S)-2-(2-(benzylcarbamoyl)-4,7-dimethyl-6-(p-tolyl)isoindolin-5-yl)-2-(tert-butoxy)acetic acid

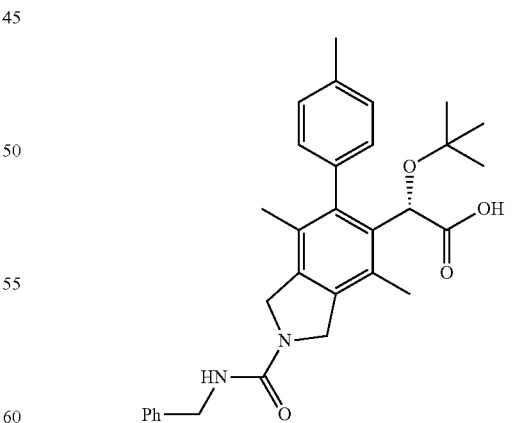

¹H NMR (400 MHz, CDCl₃) δ 7.33-7.29 (m, 5H), 7.23-7.15 (m, 3H), 7.01-7.00 (m, 1H), 5.09 (s, 1H), 4.65-4.61 (m, 5H), 4.48 (s, 2H), 2.35 (s, 3H), 2.19 (s, 3H), 1.81 (s, 3H), 0.92 (s, 9H). LCMS (ES+) (m/z): 501.49 (M+1).

Example 35: (S)-2-(tert-butoxy)-2-(4,7-dimethyl-2-(pyrrolidine-1-carbonyl)-6-(p-tolyl)isoindolin-5-yl)acetic acid

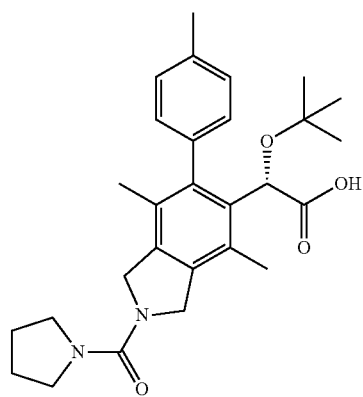 [SMILES: Cc1ccc(-c2c(C)c3c(c(C)c2[C@H](OC(C)(C)C)C(=O)O)CN(C(=O)N2CCCC2)C3)cc1]

$^1$H NMR (400 MHz, CDCl$_3$) δ 7.38-7.36 (m, 1H), 7.24-7.21 (m, 2H), 7.08-7.06 (m, 1H), 5.16 (s, 1H), 4.87-4.70 (m, 4H), 3.52-3.49 (m, 4H), 2.41 (s, 3H), 2.25 (s, 3H), 1.93-1.90 (m, 4H), 1.89 (s, 3H), 0.98 (s, 9H). LCMS (ES+) (m/z): 465.43 (M+1).

Example 36: (S)-2-(tert-butoxy)-2-(2-(cyclohexylsulfonyl)-4,7-dimethyl-6-(p-tolyl)isoindolin-5-yl)acetic acid

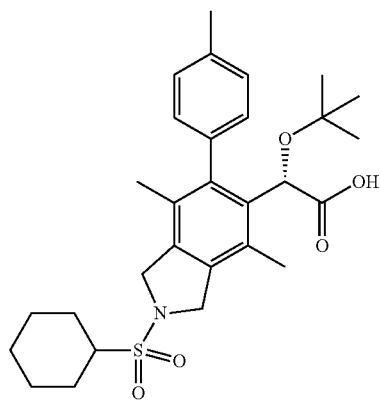 [SMILES: Cc1ccc(-c2c(C)c3c(c(C)c2[C@H](OC(C)(C)C)C(=O)O)CN(S(=O)(=O)C2CCCCC2)C3)cc1]

1H NMR (400 MHz, CDCl$_3$) δ 7.36-7.34 (m, 1H), 7.24-7.22 (m, 2H), 7.07-7.06 (m, 1H), 5.15 (s, 1H), 4.86-4.81 (m, 2H), 4.73-4.66 (m, 2H), 3.13-3.07 (m, 1H), 2.41 (s, 3H), 2.22 (s, 3H), 2.20 (s, 2H), 1.93-1.90 (m, 2H), 1.86 (s, 3H), 1.73-1.59 (m, 3H), 1.35-1.20 (m, 3H), 0.99 (s, 9H). LCMS (ES+) (m/z): 514.43 (M+1).

Example 37: (2S)-2-(tert-butoxy)-2-{4,7-dimethyl-2-[(1R,3R)-3-methylcyclohexyl]-6-(4-methylphenyl)-2,3-dihydro-1H-isoindol-5-yl}acetic acid

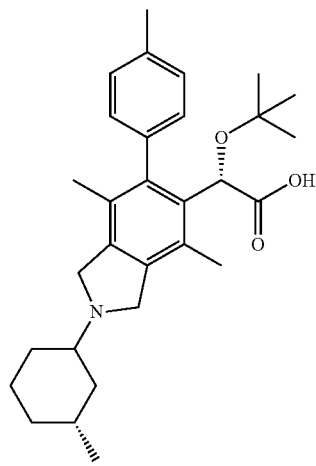 [SMILES: Cc1ccc(-c2c(C)c3c(c(C)c2[C@H](OC(C)(C)C)C(=O)O)CN(C2CCC[C@@H](C)C2)C3)cc1]

$^1$H NMR (400 MHz, CDCl$_3$) δ 7.34-7.32 (m, 1H), 7.26-7.25 (m, 2H), 7.10-7.08 (m, 1H), 5.15-5.06 (m, 2H), 5.13 (s, 1H), 4.29-4.10 (m, 2H), 3.44 (br.s., 1H), 2.42 (s, 3H), 2.25 (s, 3H), 2.11-2.08 (m, 1H), 1.95-1.83 (m, 3H), 1.90 (s, 3H), 1.80-1.17 (m, 2H), 1.65-1.61 (m, 2H), 1.43-1.42 (m, 1H), 1.02 (d, 3H), 0.95 (s, 9H). LCMS (ES+) (m/z): 464.49 (M+1).

Example 38: (2S)-2-(tert-butoxy)-2-{2-[3-(3-fluorophenyl)propyl]-4,7-dimethyl-6-(4-methylphenyl)-2,3-dihydro-1H-isoindol-5-yl}acetic acid

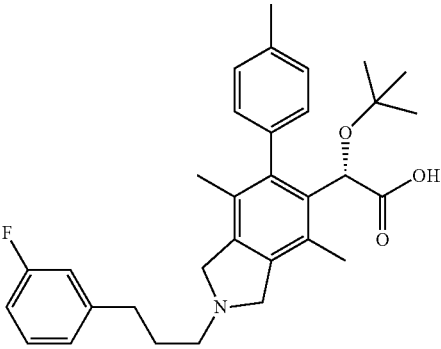 [SMILES: Cc1ccc(-c2c(C)c3c(c(C)c2[C@H](OC(C)(C)C)C(=O)O)CN(CCCc2cccc(F)c2)C3)cc1]

$^1$H NMR (400 MHz, CDCl$_3$) δ 7.32-7.25 (m, 4H), 7.08-7.06 (m, 1H), 6.99-6.89 (m, 3H), 5.15-5.07 (m, 3H), 4.22-4.10 (m, 2H), 3.32-3.28 (m, 2H), 2.78-2.75 (m, 2H), 2.41 (s, 3H), 2.28-2.18 (m, 2H), 2.23 (s, 3H), 1.87 (s, 3H), 0.97 (s, 9H). LCMS (ES+) (m/z): 504.11 (M+1).

Example 39: (2S)-2-(tert-butoxy)-2-[4,7-dimethyl-6-(4-methylphenyl)-2-(2-phenylethyl)-2,3-dihydro-1H-isoindol-5-yl]acetic acid

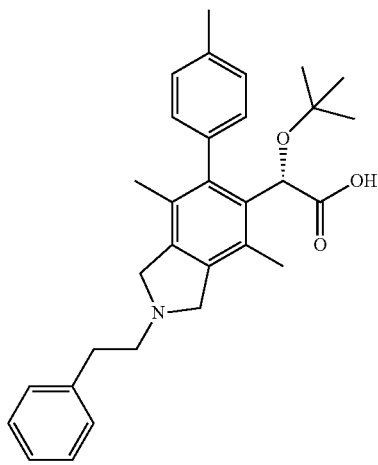 [SMILES: Cc1ccc(-c2c(C)c3c(c(C)c2[C@H](OC(C)(C)C)C(=O)O)CN(CCc2ccccc2)C3)cc1]

¹H NMR (400 MHz, METHANOL-d₄) δ ppm 0.86 (s, 9H) 1.85 (s, 3H) 2.31 (s, 3H) 2.37 (s, 3H) 3.02 (t, J=7.81 Hz, 2H) 3.28-3.34 (m, 2H) 4.17-4.41 (m, 4H) 4.90 (s, 1H) 7.03 (d, J=7.62 Hz, 1H) 7.15-7.35 (m, 7H) 7.45 (d, J=7.62 Hz, 1H). LCMS (ES+) (m/z): 472.47 (M+1)

Example 40: (2S)-2-(tert-butoxy)-2-[2-({1-[(tert-butoxy)carbonyl]pyrrolidin-2-yl}methyl)-4,7-dimethyl-6-(4-methylphenyl)-2,3-dihydro-1H-isoindol-5-yl]acetic acid

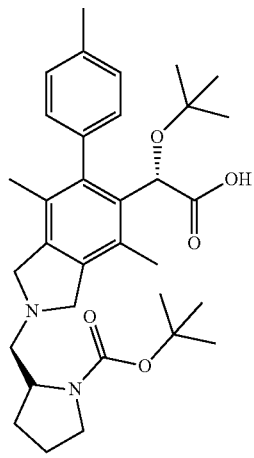

¹H NMR (400 MHz, METHANOL-d₄) δ ppm 0.90 (s, 9H) 1.48 (s, 9H) 1.86-1.98 (m, 5H) 2.34 (br. s., 3H) 2.40 (s, 3H) 3.23-3.68 (m, 11H) 4.99-5.06 (m, 1H) 7.06 (d, J=7.42 Hz, 1H) 7.19-7.34 (m, 3H). LCMS (ES+) (m/z): 551.55 (M+1).

Example 41: (2S)-2-(tert-butoxy)-2-[4,7-dimethyl-6-(4-methylphenyl)-2-(pyridin-3-ylmethyl)-2,3-dihydro-1H-isoindol-5-yl]acetic acid

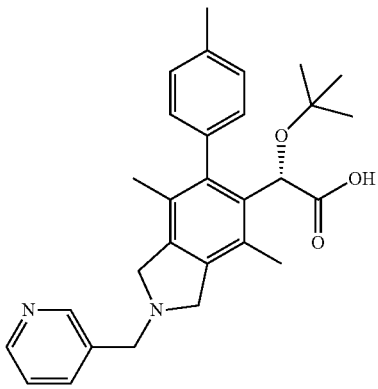 [SMILES: Cc1ccc(-c2c(C)c3c(c(C)c2[C@H](OC(C)(C)C)C(=O)O)CN(Cc2cccnc2)C3)cc1]

¹H NMR (400 MHz, CDCl₃) δ 8.83-8.77 (m, 2H), 8.34-8.32 (m, 1H), 7.68-7.65 (m, 1H), 7.33-7.24 (m, 3H), 7.06-7.04 (m, 1H), 5.13 (s, 1H), 4.82-4.73 (m, 2H), 4.58 (s, 2H), 4.49-4.42 (m, 2H), 2.42 (s, 3H), 2.23 (s, 3H), 1.87 (s, 3H), 0.98 (s, 9H). LCMS (ES+) (m/z): 459.42 (M+1).

Example 42: (2S)-2-(tert-butoxy)-2-{2-[(3,5-difluorophenyl)methyl]-4,7-dimethyl-6-(4-methylphenyl)-2,3-dihydro-1H-isoindol-5-yl}acetic acid

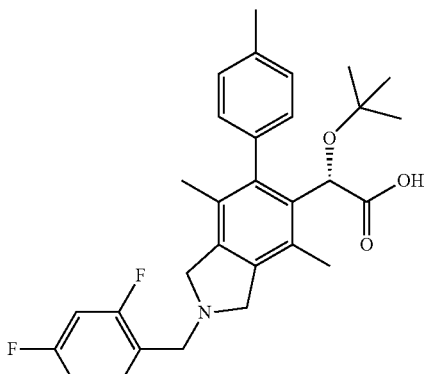

¹H NMR (400 MHz, METHANOL-d₄) δ 7.28-7.02 (m, 7H), 5.00 (s, 1H), 4.73-4.71 (m, 4H), 4.65 (s, 2H), 2.39 (s, 3H), 2.30 (s, 3H), 1.86 (s, 3H), 0.89 (s, 9H). LCMS (ES+) (m/z): 494.14 (M+1).

Example 43: (2S)-2-(tert-butoxy)-2-(4,7-dimethyl-2-{[3-(methylcarbamoyl)phenyl]methyl}-6-(4-methylphenyl)-2,3-dihydro-1H-isoindol-5-yl)acetic acid

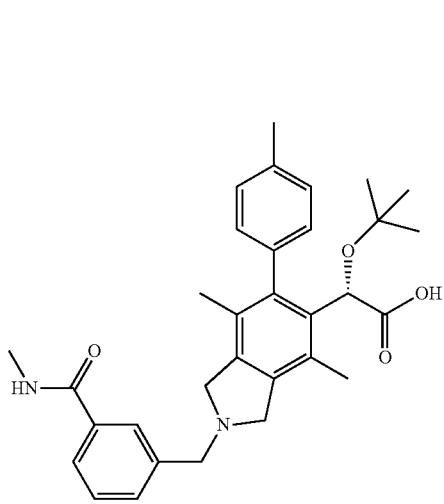 [SMILES: CNC(=O)c1cccc(CN2Cc3c(C)c(-c4ccc(C)cc4)c([C@H](OC(C)(C)C)C(=O)O)c(C)c3C2)c1]

¹H NMR (400 MHz, CHLOROFORM-d) δ ppm 0.89-1.08 (m, 9H) 1.86 (s, 3H) 2.22 (br. s., 3H) 2.42 (s, 3H) 3.01 (d, J=2.54 Hz, 3H) 3.71 (s, 1H) 4.17-4.34 (m, 2H) 4.47 (s., 1H) 4.91-4.99 (m, 2H) 5.14 (s, 1H) 7.05 (d, J=6.05 Hz, 2H) 7.18-7.39 (m, 3H) 7.42-7.64 (m, 2H) 8.02 (d, J=7.62 Hz, 1H) 8.15 (s, 1H); LCMS (ES+) (m/z): 515.50 (M+1).

Example 44: (2S)-2-(tert-butoxy)-2-[4,7-dimethyl-6-(4-methylphenyl)-2-{[3-(piperidine-1-carbonyl)phenyl]methyl}-2,3-dihydro-1H-isoindol-5-yl]acetic acid

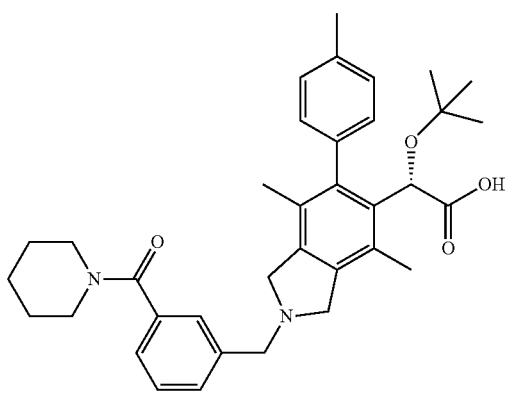 [SMILES: Cc1ccc(-c2c(C)c3c(c(C)c2[C@H](OC(C)(C)C)C(=O)O)CN(Cc2cccc(C(=O)N4CCCCC4)c2)C3)cc1]

¹H NMR (400 MHz, METHANOL-d₄) δ ppm 0.83-0.94 (m, 9H) 1.69 (br. s., 6H) 1.86 (s, 3H) 2.30 (s, 3H) 2.39 (s, 3H) 3.37 (br. s., 2H) 3.71 (br. s., 2H) 4.68 (s, 6H) 5.01 (s, 1H) 6.94-7.40 (m, 4H) 7.48-7.76 (m, 4H). LCMS (ES−) (m/z): 569.49 (M+1).

Example 45: (2S)-2-(tert-butoxy)-2-{2-[(3-chlorophenyl)methyl]-4,7-dimethyl-6-(4-methylphenyl)-2,3-dihydro-1H-isoindol-5-yl}acetic acid

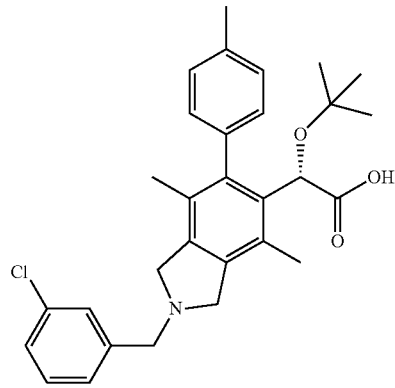 [SMILES: Cc1ccc(-c2c(C)c3c(c(C)c2[C@H](OC(C)(C)C)C(=O)O)CN(Cc2cccc(Cl)c2)C3)cc1]

¹H NMR (400 MHz, CHLOROFORM-d) δ ppm 0.97 (s., 9H), 1.87 (s, 3H), 2.23 (bs., 3H), 2.42 (s, 3H), 4.27 (br. s., 2H), 4.45 (s, 2H), 4.96 (br. s., 2H), 5.13 (s, 1H), 7.06 (br. s., 1H), 7.19-7.37 (m, 4H), 7.40-7.57 (m, 4H). LCMS (ES+) (m/z): 492.42 (M+1).

Example 46: (2S)-2-(tert-butoxy)-2-[4,7-dimethyl-6-(4-methylphenyl)-2-{[3-(morpholin-4-yl)phenyl]methyl}-2,3-dihydro-1H-isoindol-5-yl]acetic acid

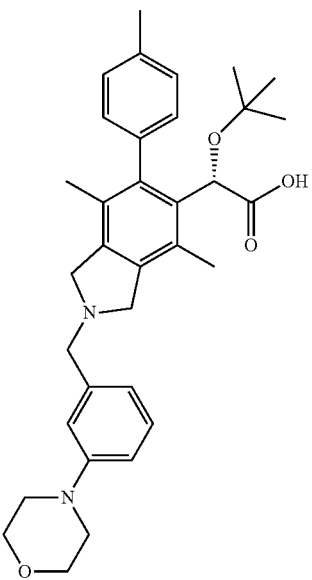 [SMILES: Cc1ccc(-c2c(C)c3c(c(C)c2[C@H](OC(C)(C)C)C(=O)O)CN(Cc2cccc(N4CCOCC4)c2)C3)cc1]

¹H NMR (400 MHz, CHLOROFORM-d) δ ppm 0.91-0.99 (m, 9H) 1.83 (s, 3H) 2.18 (s, 3H) 2.4 (s, 3H) 3.30 (d, J=3.66 Hz, 4H) 3.87 (d, J=3.48 Hz, 4H) 4.16-4.30 (m, 2H) 4.36 (br. s., 2H) 4.95 (d, J=14.47 Hz, 2H) 5.11 (s, 1H) 6.85-7.09 (m, 3H) 7.29 (d, J=7.14 Hz, 4H) 7.66 (br. s., 1H). LCMS (ES+) (m/z): 543.44 (M+1).

Example 47: (2S)-2-(tert-butoxy)-2-{2-[(3-fluoro-2-methylphenyl)methyl]-4,7-dimethyl-6-(4-methylphenyl)-2,3-dihydro-1H-isoindol-5-yl}acetic acid

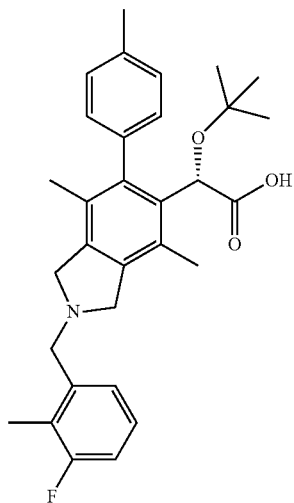 [SMILES: Cc1ccc(-c2c(C)c3c(c(C)c2[C@H](OC(C)(C)C)C(=O)O)CN(Cc2cccc(F)c2C)C3)cc1]

¹H NMR (400 MHz, CHLOROFORM-d) δ ppm 0.97 (s, 8H), 1.88 (s, 3H), 2.17-2.35 (m, 6H), 2.42 (s, 3H), 4.14-4.40 (m, 2H), 4.50 (s, 2H), 4.84-5.08 (m, 2H), 5.14 (s, 1H), 7.02-7.19 (m, 2H), 7.22-7.41 (m, 5H). LCMS (ES+) (m/z): 490.49 (M+1).

Example 48: (2S)-2-(tert-butoxy)-2-[2-(methoxycarbonyl)-4,7-dimethyl-6-(4-methylphenyl)-2,3-dihydro-1H-isoindol-5-yl]acetic acid

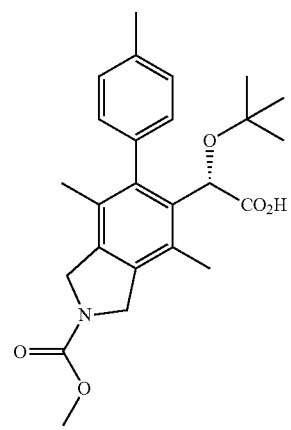 [SMILES: COC(=O)N1Cc2c(C)c(-c3ccc(C)cc3)c([C@H](OC(C)(C)C)C(=O)O)c(C)c2C1]

Step 1: (S)-methyl 5-(1-(tert-butoxy)-2-ethoxy-2-oxoethyl)-4,7-dimethyl-6-(p-tolyl)isoindoline-2-carboxylate

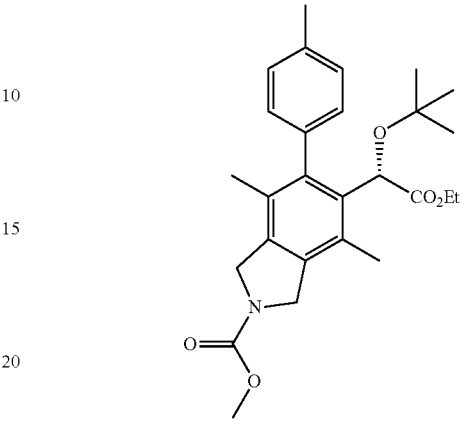

An ice cold solution of (2S)-ethyl 2-(tert-butoxy)-2-(4,7-dimethyl-6-(p-tolyl)isoindolin-5-yl)acetate (30 mg, 0.076 mmol) in dichloromethane and triethylamine (1.5 eq, 0.114 mmol, 0.015 mL) was treated dropwise with methyl chloroformate (1.1 eq, 0.083 mmol, 0.01 mL added) and allowed to warm to ambient temperature. After 10 min, the reaction mixture was diluted with water and the phases separated. The aqueous layer was extracted with DCM (×3), and the combined organics were washed with brine, dried, filtered, and concentrated in vacuo. The crude material was purified by silica gel chromatography (0-100% EtOAc-hexanes) to afford the title compound (24 mg, 70%) as a light red oil. ¹H NMR (400 MHz, CHLOROFORM-d) δ ppm 0.95 (s, 9H), 1.19-1.24 (m, 3H), 1.84 (d, J=5.86 Hz, 3H), 2.31 (d, J=5.67 Hz, 3H), 2.41 (s, 3H), 3.79 (d, J=2.54 Hz, 3H), 4.02-4.23 (m, 2H), 4.60-4.76 (m, 4H), 4.97 (s, 1H), 7.04 (d, J=7.82 Hz, 1H), 7.16-7.24 (m, 3H). LCMS (ES+) (m/z): 454.39 (M+1).

Step 2: (2S)-2-(tert-butoxy)-2-[2-(methoxycarbonyl)-4,7-dimethyl-6-(4-methylphenyl)-2,3-dihydro-1H-isoindol-5-yl]acetic acid

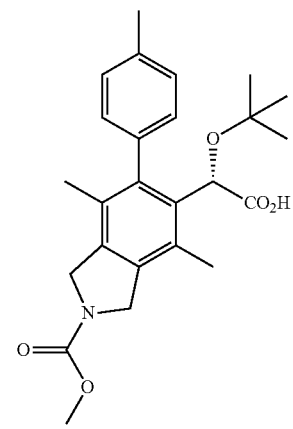 [SMILES: COC(=O)N1Cc2c(C)c(-c3ccc(C)cc3)c([C@H](OC(C)(C)C)C(=O)O)c(C)c2C1]

A solution of (2S)-methyl 5-(1-(tert-butoxy)-2-ethoxy-2-oxoethyl)-4,7-dimethyl-6-(p-tolyl)isoindoline-2-carboxylate (24 mg, 0.053 mmol) in 1,4-dioxane (3 mL) was treated with 1M LiOH (20 eq, 1.058 mmol, 1.058 mL) and heated to 90° C. After 18 h, the reaction mixture was cooled to ambient temperature and concentrated in vacuo. The white residue was dissolved in water, acidified with 1N HCl and extracted with ethyl acetate (×3). The combined organics were washed with brine, dried ($Na_2SO_4$), filtered, and concentrated in vacuo. The crude material was purified by reverse phase HPLC to afford the title compound as a white solid (13 mg, 57.7% yield). $^1$H NMR (400 MHz, CHLOROFORM-d) δ ppm 0.99 (s, 9H), 1.89 (d, J=6.84 Hz, 3H), 2.25 (d, J=7.42 Hz, 3H), 2.42 (s, 3H), 3.81 (d, J=2.54 Hz, 3H), 4.57-4.87 (m, 4H), 5.16 (s, 1H), 7.07 (d, J=6.83 Hz, 1H), 7.19-7.26 (m, 2H), 7.36 (d, J=6.44 Hz, 1H). LCMS (ES+) (m/z): 426.31 (M+1).

Example 49: (2S)-2-(tert-butoxy)-2-[2-(4-fluorobenzenesulfonyl)-4,7-dimethyl-6-(4-methylphenyl)-2,3-dihydro-1H-isoindol-5-yl]acetic acid

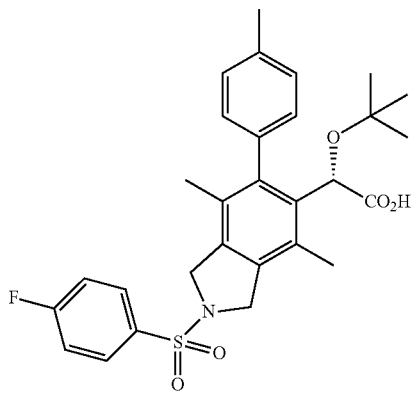 [SMILES: Cc1ccc(-c2c(C)c3c(c(C)c2[C@H](OC(C)(C)C)C(=O)O)CN(S(=O)(=O)c2ccc(F)cc2)C3)cc1]

$^1$H NMR (400 Mz, CDCl3) δ 7.95-7.91 (m, 2H), 7.30-7.20 (m, 5H), 7.03-7.01 (m, 1H), 5.11 (s, 1H), 4.74-4.69 (m, 2H), 4.55-4.48 (m, 2H), 2.40 (s, 3H), 2.19 (s, 3H), 1.82 (s, 3H), 0.97 (s, 9H). LCMS (ES+) (m/z): 526.34 (M+1).

Example 50: (2S)-2-(tert-butoxy)-2-[4,7-dimethyl-6-(4-methylphenyl)-2-(piperidine-1-sulfonyl)-2,3-dihydro-1H-isoindol-5-yl]acetic acid

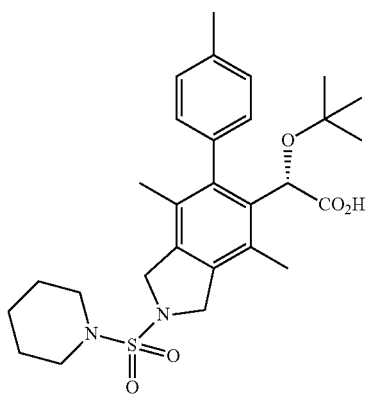 [SMILES: Cc1ccc(-c2c(C)c3c(c(C)c2[C@H](OC(C)(C)C)C(=O)O)CN(S(=O)(=O)N2CCCCC2)C3)cc1]

Step 1: (2S)-ethyl 2-(tert-butoxy)-2-(4,7-dimethyl-2-(piperidin-1-ylsulfonyl)-6-(p-tolyl)isoindolin-5-yl)acetate

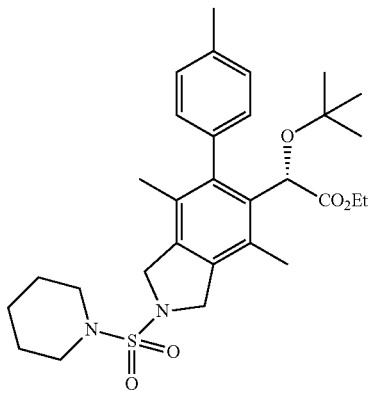 [SMILES: CCOC(=O)[C@@H](OC(C)(C)C)c1c(C)c2c(c(C)c1-c1ccc(C)cc1)CN(S(=O)(=O)N1CCCCC1)C2]

A solution of (S)-ethyl 2-(tert-butoxy)-2-(4,7-dimethyl-6-(p-tolyl)isoindolin-5-yl)acetate (45 mg, 0.114 mmol) and triethylamine (1.5 eq, 0.341 mmol, 0.048 mL) was treated dropwise with piperidine-1-sulfonyl chloride (1.5 eq, 0.171 mmol, 0.024 mL added). After 1 h, the reaction mixture was diluted with sat. aq. $NaHCO_3$ and the phases separated. The aqueous layer was extracted with DCM (×3), and the combined organics were washed with brine, dried, filtered, and concentrated in vacuo. The crude material was purified by silica gel chromatography (0-100% EtOAc-hexanes) to afford the title compound (24 mg, 51%) as a light red oil. $^1$H NMR (400 MHz, $CDCl_3$) δ 7.26-7.18 (m, 3H), 7.05-7.03 (m, 1H), 4.97 (s, 1H), 4.66 (s, 4H), 4.20-4.07 (m, 2H), 3.29-3.27 (m, 4H), 2.42 (s, 3H), 2.29 (s, 3H), 1.82 (s, 3H), 1.66-1.56 (m, 6H), 1.23 (t, 3H), 0.96 (s, 9H). LCMS (ES+) (m/z): 543.42 (M+1).

Step 2: (2S)-2-(tert-butoxy)-2-[4,7-dimethyl-6-(4-methylphenyl)-2-(piperidine-1-sulfonyl)-2,3-dihydro-1H-isoindol-5-yl]acetic acid

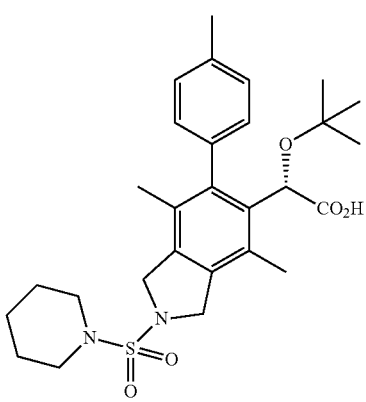 [SMILES: Cc1ccc(-c2c(C)c3c(c(C)c2[C@H](OC(C)(C)C)C(=O)O)CN(S(=O)(=O)N2CCCCC2)C3)cc1]

A solution of (2S)-ethyl 2-(tert-butoxy)-2-(4,7-dimethyl-2-(piperidin-1-ylsulfonyl)-6-(p-tolyl)isoindolin-5-yl)acetate (24 mg, 0.044 mmol) in MeOH (3 mL) was treated with 1M LiOH (20 eq, 1.058 mmol, 1.058 mL) and heated to 80° C. After 6 h, the reaction mixture was cooled to ambient temperature and concentrated in vacuo. The white residue was dissolved in water, acidified with 1N HCl and extracted with ethyl acetate (×3). The combined organics were washed with brine, dried, filtered, and concentrated in vacuo to afford the title compound (21 mg, 93% yield) as a tan oil. $^1$H NMR (400 MHz, CDCl$_3$) δ 7.36-7.34 (m, 1H), 7.24-7.22 (m, 2H), 7.07-7.05 (m, 1H), 5.15 (s, 1H), 4.75-4.59 (m, 4H), 3.29-3.27 (m, 4H), 2.41 (s, 3H), 2.23 (s, 3H), 1.86 (s, 3H), 1.66-1.56 (m, 6H), 0.99 (s, 9H). LCMS (ES+) (m/z): 515.43 (M+1).

Example 51: (2S)-2-(tert-butoxy)-2-[4,7-dimethyl-6-(4-methylphenyl)-2-[(propan-2-yl)sulfamoyl]-2,3-dihydro-1H-isoindol-5-yl]acetic acid The title compound was made in a manner similar to Example 50.

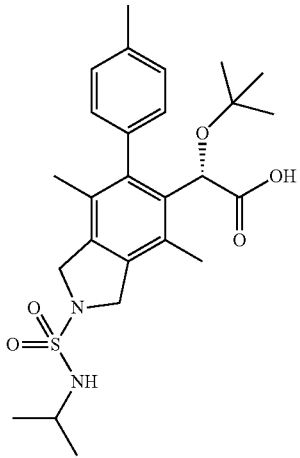 [SMILES: Cc1ccc(-c2c(C)c3c(c(C)c2[C@H](OC(C)(C)C)C(=O)O)CN(S(=O)(=O)NC(C)C)C3)cc1]

$^1$H NMR (400 MHz, CHLOROFORM-d) δ ppm 0.99 (s, 9H) 1.19-1.31 (m, 6H) 1.87 (s, 3H) 2.24 (s, 3H) 2.42 (s, 3H) 3.54-3.74 (m, 1H) 4.08-4.25 (m, 1H) 4.57-4.76 (m, 4H) 5.15 (s, 1H) 7.07 (d, J=7.03 Hz, 1H) 7.16-7.28 (m, 2H) 7.35 (d, J=7.23 Hz, 1H). LCMS (ES+) (m/z): 489.40 (M+1).

Example 52: (2S)-2-(tert-butoxy)-2-[4,7-dimethyl-6-(4-methylphenyl)-2-(morpholine-4-sulfonyl)-2,3-dihydro-1H-isoindol-5-yl]acetic acid The title compound was made in a manner similar to Example 50.

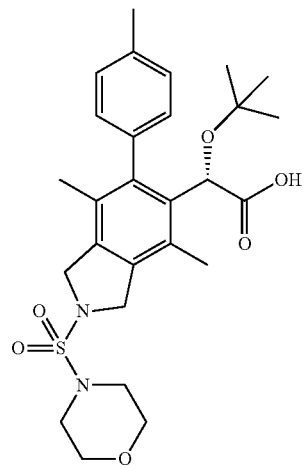 [SMILES: Cc1ccc(-c2c(C)c3c(c(C)c2[C@H](OC(C)(C)C)C(=O)O)CN(S(=O)(=O)N2CCOCC2)C3)cc1]

$^1$H NMR (400 MHz, CHLOROFORM-d) δ ppm 0.98 (s, 9H) 1.85 (s, 3H) 2.22 (s, 3H) 2.40 (s, 3H) 3.24-3.32 (m, 4H) 3.72-3.80 (m, 4H) 4.56-4.79 (m, 4H) 5.14 (s, 1H) 7.05 (d, J=7.04 Hz, 1H) 7.22 (d, J=8.40 Hz, 2H) 7.33 (d, J=7.23 Hz, 1H). LCMS (ES+) (m/z): 517.41 (M+1).

Example 53: (2S)-2-(tert-butoxy)-2-{2-[(3,4-difluorophenyl)methyl]-4,7-dimethyl-6-(4-methylphenyl)-2,3-dihydro-1H-isoindol-5-yl}acetic acid

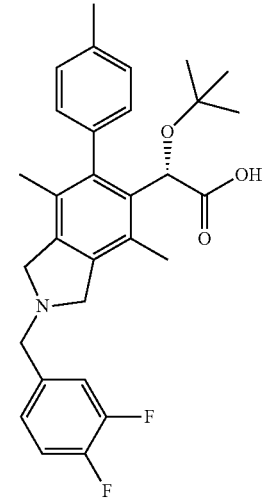 [SMILES: Cc1ccc(-c2c(C)c3c(c(C)c2[C@H](OC(C)(C)C)C(=O)O)CN(Cc2ccc(F)c(F)c2)C3)cc1]

$^1$H NMR (400 MHz, Methanol-d4) δ 7.58-7.54 (m, 1H), 7.42-7.39 (m, 2H), 7.28-7.21 (m, 3H), 7.04-7.02 (m, 1H), 5.00 (s, 1H), 4.71-4.69 (m, 4H), 4.62 (s, 2H), 2.39 (s, 3H), 2.30 (s, 3H), 1.86 (s, 3H), 0.89 (s, 9H). LCMS (ES+) (m/z): 494.43 (M+1).

Example 54: (2S)-2-(tert-butoxy)-2-[4,7-dimethyl-6-(4-methylphenyl)-2-{[(1r,4r)-4-methylcyclohexyl]carbamoyl}-2,3-dihydro-1H-isoindol-5-yl]acetic acid

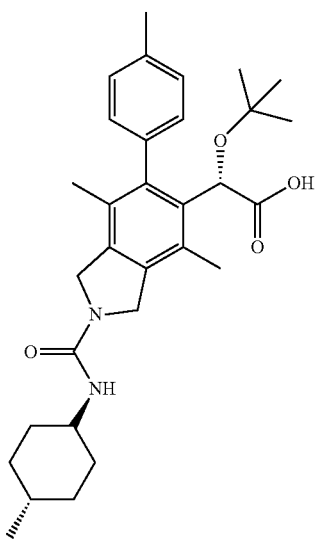

¹H NMR (400 MHz, CDCl₃) δ7.37-7.35 (m, 1H), 7.24-7.22 (m, 2H), 7.08-7.06 (m, 1H), 5.16 (s, 1H), 4.72-4.59 (m, 4H), 3.70-3.65 (m, 1H), 2.41 (s, 3H), 2.26 (s, 3H), 2.07-2.04 (m, 2H), 1.89 (s, 3H), 1.75-1.72 (m, 2H), 1.35-1.28 (m, 1H), 1.22-1.07 (m, 4H), 0.98 (s, 9H), 0.91 (d, 3H). LCMS (ES+) (m/z): 507.52 (M+1).

Example 55: (2S)-2-[2-(benzylcarbamoyl)-4,7-dimethyl-6-(4-methylphenyl)-2,3-dihydro-1H-isoindol-5-yl]-2-(tert-butoxy)acetic acid

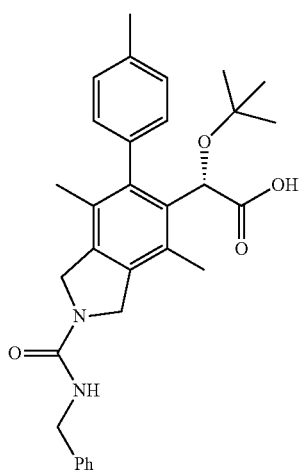 [SMILES: Cc1ccc(-c2c(C)c3c(c(C)c2[C@H](OC(C)(C)C)C(=O)O)CN(C(=O)NCc2ccccc2)C3)cc1]

¹H NMR (400 MHz, CDCl₃) δ 7.33-7.29 (m, 5H), 7.23-7.15 (m, 3H), 7.01-7.00 (m, 1H), 5.09 (s, 1H), 4.65-4.61 (m, 5H), 4.48 (s, 2H), 2.35 (s, 3H), 2.19 (s, 3H), 1.81 (s, 3H), 0.92 (s, 9H). LCMS (ES+) (m/z): 501.49 (M+1).

Example 56: (2S)-2-(tert-butoxy)-2-[4,7-dimethyl-6-(4-methylphenyl)-2-(pyrrolidine-1-carbonyl)-2,3-dihydro-1H-isoindol-5-yl]acetic acid

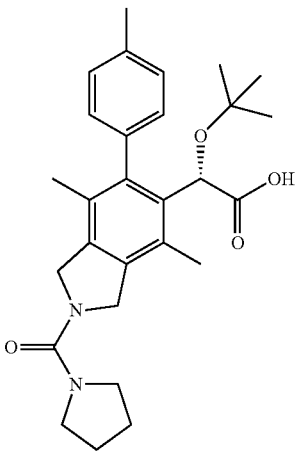 [SMILES: Cc1ccc(-c2c(C)c3c(c(C)c2[C@H](OC(C)(C)C)C(=O)O)CN(C(=O)N2CCCC2)C3)cc1]

¹H NMR (400 MHz, CDCl₃) δ 7.38-7.36 (m, 1H), 7.24-7.21 (m, 2H), 7.08-7.06 (m, 1H), 5.16 (s, 1H), 4.87-4.70 (m, 4H), 3.52-3.49 (m, 4H), 2.41 (s, 3H), 2.25 (s, 3H), 1.93-1.90 (m, 4H), 1.89 (s, 3H), 0.98 (s, 9H). LCMS (ES+) (m/z): 465.43 (M+1).

Example 57: (2S)-2-(tert-butoxy)-2-[4,7-dimethyl-6-(4-methylphenyl)-2-(morpholine-4-carbonyl)-2,3-dihydro-1H-isoindol-5-yl]acetic acid

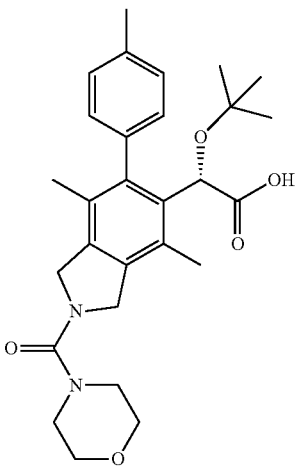 [SMILES: Cc1ccc(-c2c(C)c3c(c(C)c2[C@H](OC(C)(C)C)C(=O)O)CN(C(=O)N2CCOCC2)C3)cc1]

¹H NMR (400 MHz, CHLOROFORM-d) δ ppm 0.98 (s, 9H) 1.89 (s, 3H) 2.26 (s, 3H) 2.41 (s, 3H) 3.32-3.44 (m, 4H) 3.73-3.83 (m, 4H) 4.63-4.76 (m, 2H) 4.79-4.89 (m, 2H) 5.15 (s, 1H) 7.06 (d, J=7.03 Hz, 1H) 7.18-7.25 (m, 2H) 7.36 (d, J=7.23 Hz, 1H). LCMS (ES+) (m/z): 481.44 (M+1).

Example 58: (2S)-2-(tert-butoxy)-2-{2-[(cyclohexylmethyl)carbamoyl]-4,7-dimethyl-6-(4-methylphenyl)-2,3-dihydro-1H-isoindol-5-yl}acetic acid

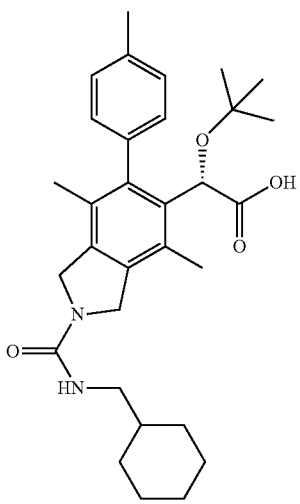 [SMILES: Cc1ccc(-c2c(C)c3c(c(C)c2[C@H](OC(C)(C)C)C(=O)O)CN(C(=O)NCC2CCCCC2)C3)cc1]

¹H NMR (400 MHz, CHLOROFORM-d) δ ppm 0.99 (s, 9H) 1.09-1.33 (m, 4H) 1.46-1.83 (m, 7H) 1.90 (s, 3H) 2.26 (s, 3H) 2.41 (s, 3H) 3.17 (t, J=6.35 Hz, 2H) 4.41 (t, J=5.66 Hz, 1H) 4.59-4.76 (m, 4H) 5.16 (s, 1H) 7.07 (d, J=7.23 Hz, 1H) 7.19-7.26 (m, 2H) 7.36 (d, J=7.03 Hz, 1H). LCMS (ES+) (m/z): 507.44 (M+1).

Example 59: (2S)-2-(tert-butoxy)-2-[2-(dimethylcarbamoyl)-4,7-dimethyl-6-(4-methylphenyl)-2,3-dihydro-1H-isoindol-5-yl]acetic acid

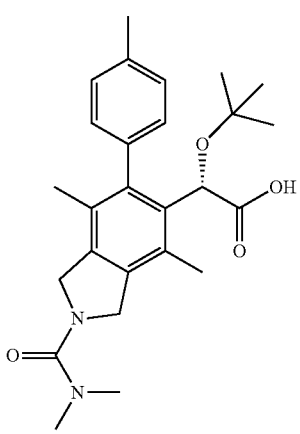 [SMILES: Cc1ccc(-c2c(C)c3c(c(C)c2[C@H](OC(C)(C)C)C(=O)O)CN(C(=O)N(C)C)C3)cc1]

¹H NMR (400 MHz, CHLOROFORM-d) δ ppm 0.98 (s, 9H) 1.88 (s, 3H) 2.26 (s, 3H) 2.41 (s, 3H) 2.94 (s, 6H) 4.65-4.88 (m, 4H) 5.15 (s, 1H) 7.06 (d, J=7.03 Hz, 1H) 7.18-7.26 (m, 2H) 7.36 (d, J=7.03 Hz, 1H). LCMS (ES+) (m/z): 439.42 (M+1).

Example 60: (2S)-2-[2-(azepane-1-carbonyl)-4,7-dimethyl-6-(4-methylphenyl)-2,3-dihydro-1H-isoindol-5-yl]-2-(tert-butoxy)acetic acid

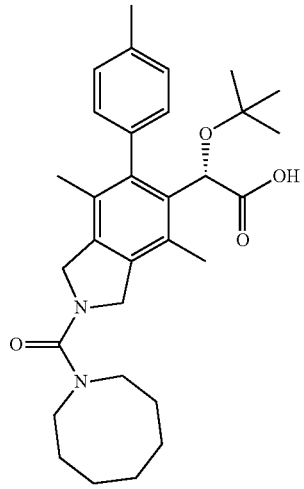 [SMILES: Cc1ccc(-c2c(C)c3c(c(C)c2[C@H](OC(C)(C)C)C(=O)O)CN(C(=O)N2CCCCCCC2)C3)cc1]

¹H NMR (400 MHz, CHLOROFORM-d) δ ppm 0.98 (m, 9H) 1.63 (d, J=2.73 Hz, 4H) 1.81 (br. s., 4H) 1.88 (s, 3H) 2.25 (s, 3H) 2.41 (s, 3H) 3.40-3.53 (m, 4H) 4.62-4.88 (m, 4H) 5.15 (s, 1H) 7.06 (d, J=7.23 Hz, 1H) 7.16-7.30 (m, 2H) 7.36 (d, J=7.23 Hz, 1H). LCMS (ES+) (m/z): 493.53 (M+1).

Example 61: (2S)-2-[2-(azetidine-1-carbonyl)-4,7-dimethyl-6-(4-methylphenyl)-2,3-dihydro-1H-isoindol-5-yl]-2-(tert-butoxy)acetic acid

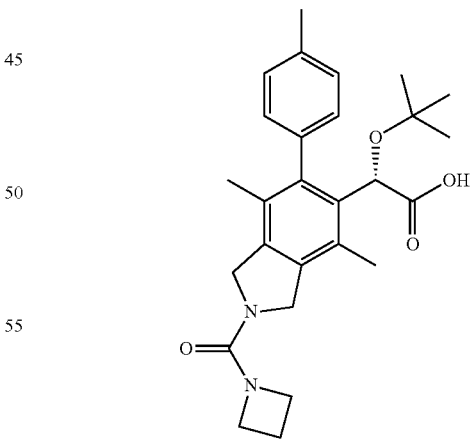

¹H NMR (400 MHz, CHLOROFORM-d) δ ppm 0.98 (s, 9H) 1.88 (s, 3H) 2.20-2.34 (m, 5H) 2.41 (s, 3H) 4.13 (t, 4H) 4.59-4.79 (m, 4H) 5.15 (s, 1H) 7.00-7.12 (m, 1H) 7.19-7.28 (m, 2H) 7.35 (d, J=7.23 Hz, 1H). LCMS (ES+) (m/z): 451.43 (M+1).

Example 62: (2S)-2-(tert-butoxy)-2-{2-[(2-methoxy-ethyl)(methyl)carbamoyl]-4,7-dimethyl-6-(4-methyl-phenyl)-2,3-dihydro-1H-isoindol-5-yl}acetic acid

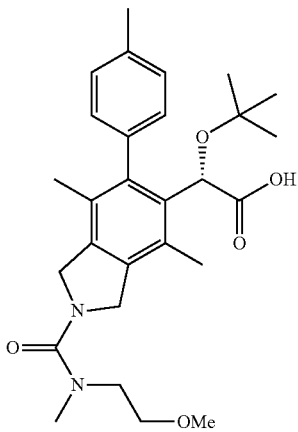 [SMILES: COCCN(C)C(=O)N1Cc2c(C)c(-c3ccc(C)cc3)c([C@H](OC(C)(C)C)C(=O)O)c(C)c2C1]

¹H NMR (400 MHz, CHLOROFORM-d) δ ppm 0.97 (s, 9H) 1.87 (s, 3H) 2.24 (s, 3H) 2.40 (s, 3H) 3.02 (s, 3H) 3.37 (s, 3H) 3.43 (t, 2H) 3.60 (t, 2H) 4.60-4.88 (m, 4H) 5.14 (s, 1H) 6.98-7.12 (m, 1H) 7.15-7.24 (m, 2H) 7.35 (d, J=7.04 Hz, 1H). LCMS (ES+) (m/z): 483.55 (M+1).

Example 63: (2S)-2-(tert-butoxy)-2-{2-[(2-methoxy-ethyl)(methyl)carbamoyl]-4,7-dimethyl-6-(4-methyl-phenyl)-2,3-dihydro-1H-isoindol-5-yl}acetic acid

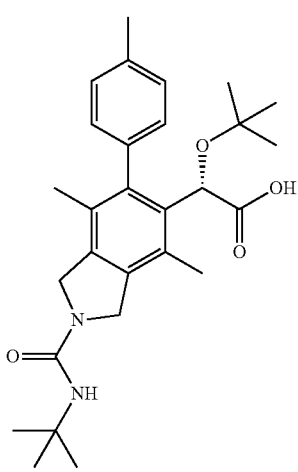 [SMILES: Cc1ccc(-c2c(C)c3c(c(C)c2[C@H](OC(C)(C)C)C(=O)O)CN(C(=O)NC(C)(C)C)C3)cc1]

¹H NMR (400 MHz, CHLOROFORM-d) δ ppm 0.98 (s, 9H) 1.43 (s, 9H) 1.89 (s, 3H) 2.26 (s, 3H) 2.41 (s, 3H) 4.22 (s, 1H) 4.55-4.72 (m, 4H) 5.16 (s, 1H) 7.07 (d, J=7.23 Hz, 1H) 7.19-7.26 (m, 2H) 7.36 (d, J=7.23 Hz, 1H). LCMS (ES+) (m/z): 467.46 (M+1).

Example 64: (2S)-2-(tert-butoxy)-2-[2-(1,1-dioxo-1λ⁶,4-thiomorpholine-4-carbonyl)-4,7-dimethyl-6-(4-methylphenyl)-2,3-dihydro-1H-isoindol-5-yl]acetic acid

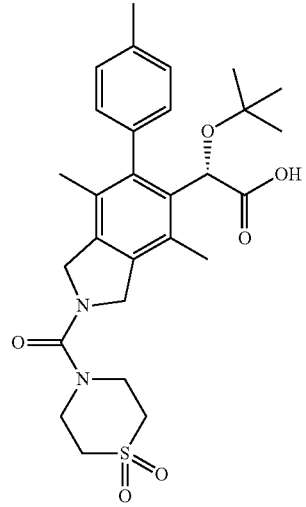 [SMILES: Cc1ccc(-c2c(C)c3c(c(C)c2[C@H](OC(C)(C)C)C(=O)O)CN(C(=O)N2CCS(=O)(=O)CC2)C3)cc1]

¹H NMR (400 MHz, CHLOROFORM-d) δ ppm 0.89-1.02 (m, 9H) 1.88 (s, 3H) 2.25 (s, 3H) 2.40 (s, 3H) 3.15 (br. s., 4H) 3.86 (br. s., 4H) 4.64-4.90 (m, 4H) 5.14 (s, 1H) 7.04 (d, J=7.04 Hz, 1H) 7.16-7.29 (m, 2H) 7.34 (d, J=7.23 Hz, 1H). LCMS (ES+) (m/z): 529.40 (M+1).

Example 65: (2S)-2-[2-(azocane-1-carbonyl)-4,7-dimethyl-6-(4-methylphenyl)-2,3-dihydro-1H-isoindol-5-yl]-2-(tert-butoxy)acetic acid

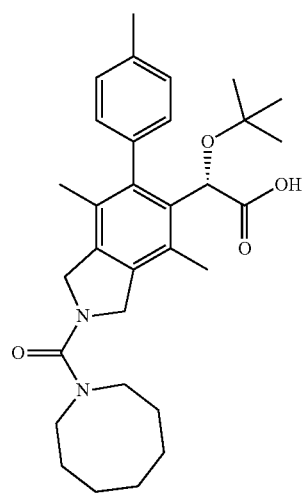 [SMILES: Cc1ccc(-c2c(C)c3c(c(C)c2[C@H](OC(C)(C)C)C(=O)O)CN(C(=O)N2CCCCCCC2)C3)cc1]

¹H NMR (400 MHz, CHLOROFORM-d) δ ppm 0.97 (s, 9H) 1.62 (d, J=7.82 Hz, 6H) 1.75 (d, J=3.32 Hz, 4H) 1.87 (s, 3H) 2.24 (s, 3H) 2.40 (s, 3H) 3.46 (d, J=5.08 Hz, 4H) 4.61-4.91 (m, 4H) 5.13 (s, 1H) 6.97-7.10 (m, 1H) 7.17-7.25 (m, 2H) 7.35 (d, J=6.84 Hz, 1H). LCMS (ES+) (m/z): 507.50 (M+1)

Example 66: (2S)-2-(tert-butoxy)-2-[2-(3,3-difluoropiperidine-1-carbonyl)-4,7-dimethyl-6-(4-methylphenyl)-2,3-dihydro-1H-isoindol-5-yl]acetic acid

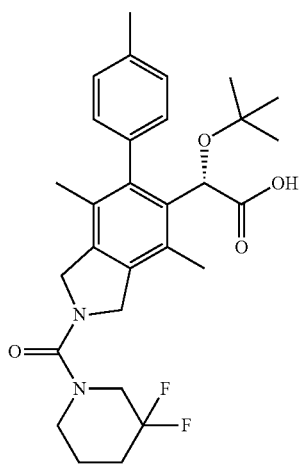 [SMILES: Cc1ccc(-c2c(C)c3c(c(C)c2[C@H](OC(C)(C)C)C(=O)O)CN(C(=O)N2CCCC(F)(F)C2)C3)cc1]

¹H NMR (400 MHz, CHLOROFORM-d) δ ppm 0.98 (s, 9H) 1.89 (s, 3H) 1.98-2.12 (m, 4H) 2.26 (s, 3H) 2.42 (s, 3H) 3.22-3.39 (m, 2H) 3.53 (t, J=11.33 Hz, 2H) 4.61-4.93 (m, 4H) 5.15 (s, 1H) 7.06 (d, J=7.03 Hz, 1H) 7.19-7.26 (m, 2H) 7.36 (d, J=7.03 Hz, 1H). LCMS (ES+) (m/z): 515.48 (M+1).

Example 67: (2S)-2-(tert-butoxy)-2-{2-[cyclohexyl(methyl)carbamoyl]-4,7-dimethyl-6-(4-methylphenyl)-2,3-dihydro-1H-isoindol-5-yl}acetic acid

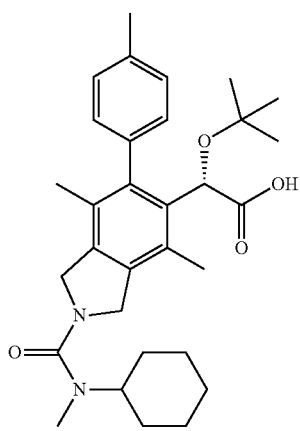 [SMILES: Cc1ccc(-c2c(C)c3c(c(C)c2[C@H](OC(C)(C)C)C(=O)O)CN(C(=O)N(C)C2CCCCC2)C3)cc1]

¹H NMR (400 MHz, METHANOL-d₄) δ ppm 0.87 (s, 9H) 1.06-1.27 (m, 2H) 1.30-1.46 (m, 2H) 1.50-1.69 (m, 2H) 1.73-1.89 (m, 4H) 1.84 (s, 3H) 2.30 (s, 3H) 2.37 (s, 3H) 2.84 (s, 3H) 3.65-3.75 (m, 1H) 4.63-4.78 (m, 4H) 4.92 (s, 1H) 6.99-7.09 (m, 1H) 7.21 (t, J=7.42 Hz, 2H) 7.43 (d, J=7.23 Hz, 1H). LCMS (ES+) (m/z): 507.48 (M+1).

Example 68: (2S)-2-(tert-butoxy)-2-[2-(3,3-difluoropyrrolidine-1-carbonyl)-4,7-dimethyl-6-(4-methylphenyl)-2,3-dihydro-1H-isoindol-5-yl]acetic acid

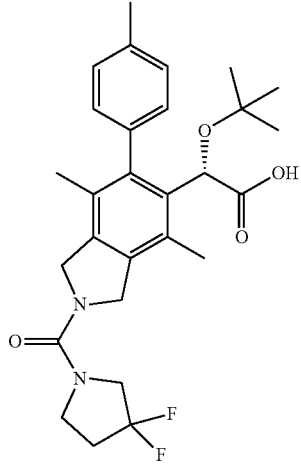 [SMILES: Cc1ccc(-c2c(C)c3c(c(C)c2[C@H](OC(C)(C)C)C(=O)O)CN(C(=O)N2CCC(F)(F)C2)C3)cc1]

¹H NMR (400 MHz, CHLOROFORM-d) δ ppm 0.99 (s, 9H) 1.89 (s, 3H) 2.26 (s, 3H) 2.32-2.41 (m, 2H) 2.42 (s, 3H) 3.75 (t, J=7.32 Hz, 2H) 3.84 (t, J=13.08 Hz, 2H) 4.64-4.87 (m, 4H) 5.16 (s, 1H) 6.98-7.12 (m, 1H) 7.20-7.26 (m, 2H) 7.36 (d, J=7.42 Hz, 1H). LCMS (ES+) (m/z): 501.43 (M+1).

Example 69: (2S)-2-(tert-butoxy)-2-[4,7-dimethyl-6-(4-methylphenyl)-2-[(2R)-2-methylpiperidine-1-carbonyl]-2,3-dihydro-1H-isoindol-5-yl]acetic acid

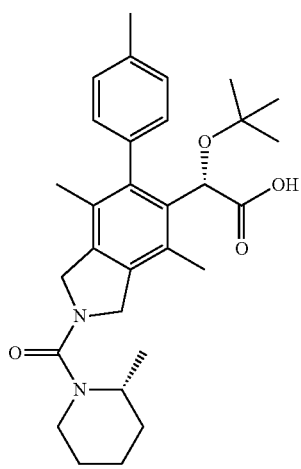 [SMILES: Cc1ccc(-c2c(C)c3c(c(C)c2[C@H](OC(C)(C)C)C(=O)O)CN(C(=O)N2CCCC[C@H]2C)C3)cc1]

¹H NMR (400 MHz, METHANOL-d₄) δ ppm 0.88 (s, 9H) 1.27 (d, J=6.64 Hz, 3H) 1.49-1.79 (m, 6H) 1.85 (s, 3H) 2.29 (s, 3H) 2.38 (s, 3H) 3.06-3.18 (m, 1H) 3.52 (d, J=13.67 Hz, 1H) 4.08 (br. s., 1H) 4.62-4.78 (m, 4H) 4.96 (s, 1H) 7.06 (d, J=7.62 Hz, 1H) 7.22 (t, J=7.42 Hz, 2H) 7.37 (d, J=7.03 Hz, 1H). LCMS (ES+) (m/z): 493.51 (M+1).

Example 70: (2S)-2-(tert-butoxy)-2-[2-(cyclobutyl-carbamoy)-4,7-dimethyl-6-(4-methylphenyl)-2,3-dihydro-1H-isoindol-5-yl]acetic acid

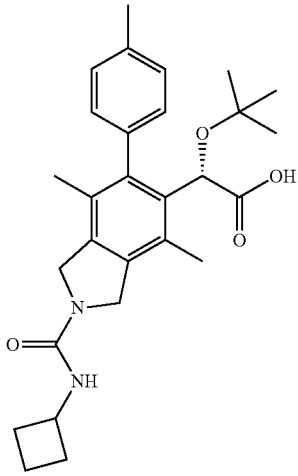 [SMILES: Cc1ccc(-c2c(C)c3c(c(C)c2[C@H](OC(C)(C)C)C(=O)O)CN(C(=O)NC2CCC2)C3)cc1]

$^1$H NMR (400 MHz, CHLOROFORM-d) δ ppm 0.95-1.02 (m, 9H) 1.63-1.77 (m, 2H) 1.80-1.95 (m, 2H) 1.89 (s, 3H) 2.26 (s, 3H) 2.38-2.42 (m, 2H) 2.42 (s, 3H) 4.33-4.53 (m, 1H) 4.57-4.76 (m, 4H) 5.16 (s, 1H) 7.07 (d, J=7.23 Hz, 1H) 7.17-7.27 (m, 3H) 7.36 (d, J=7.62 Hz, 1H). LCMS (ES+) (m/z): 465.40 (M+1).

Example 71: (2S)-2-(tert-butoxy)-2-[4,7-dimethyl-6-(4-methylphenyl)-2-(4-methylpiperazine-1-carbonyl)-2,3-dihydro-1H-isoindol-5-yl]acetic acid

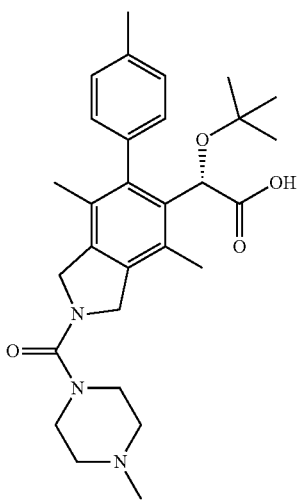 [SMILES: Cc1ccc(-c2c(C)c3c(c(C)c2[C@H](OC(C)(C)C)C(=O)O)CN(C(=O)N2CCN(C)CC2)C3)cc1]

$^1$H NMR (400 MHz, CHLOROFORM-d) δ ppm 0.97 (s, 9H) 1.87 (s, 3H) 2.24 (s, 3H) 2.40 (s, 3H) 2.84 (s, 3H) 2.93-3.01 (m, 2H) 3.50-3.65 (m, 4H) 3.93 (d, J=14.47 Hz, 2H) 4.60-4.74 (m, 2H) 4.76-4.89 (m, 2H) 5.14 (s, 1H) 7.04 (d, J=6.78 Hz, 1H) 7.22 (d, J=8.61 Hz, 2H) 7.32 (br. s., 1H). LCMS (ES+) (m/z): 494.33 (M+1).

Example 72: (2S)-2-(tert-butoxy)-2-{4,7-dimethyl-2-[(3R)-3-methylmorpholine-4-carbonyl]-6-(4-methylphenyl)-2,3-dihydro-1H-isoindol-5-yl}acetic acid

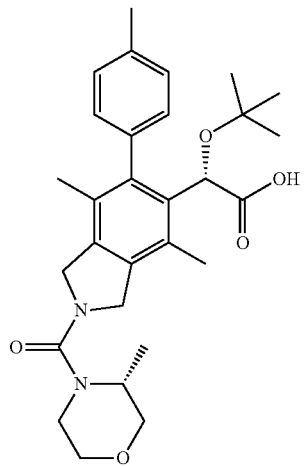 [SMILES: Cc1ccc(-c2c(C)c3c(c(C)c2[C@H](OC(C)(C)C)C(=O)O)CN(C(=O)N2CCOC[C@H]2C)C3)cc1]

$^1$H NMR (400 MHz, CHLOROFORM-d) δ ppm 0.96 (s, 9H) 1.34 (d, J=6.59 Hz, 3H) 1.88 (s, 3H) 2.24 (s, 3H) 2.40 (s, 3H) 3.37 (d, J=4.94 Hz, 2H) 3.56-3.92 (m, 5H) 4.55-4.80 (m, 3H) 4.87 (d, J=14.28 Hz, 1H) 5.14 (s, 1H) 7.05 (d, J=6.78 Hz, 1H) 7.17-7.24 (m, 2H) 7.35 (d, J=6.59 Hz, 1H). LCMS (ES+) (m/z): 495.52 (M+1).

Example 73: (2S)-2-(tert-butoxy)-2-{2-[(2S,6S)-2,6-dimethylmorpholine-4-carbonyl]-4,7-dimethyl-6-(4-methylphenyl)-2,3-dihydro-1H-isoindol-5-yl}acetic acid

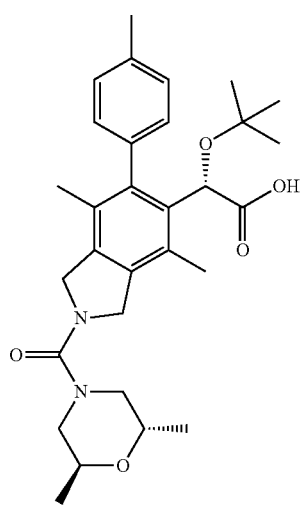 [SMILES: Cc1ccc(-c2c(C)c3c(c(C)c2[C@H](OC(C)(C)C)C(=O)O)CN(C(=O)N2C[C@H](C)O[C@@H](C)C2)C3)cc1]

$^1$H NMR (400 MHz, CHLOROFORM-d) δ ppm 0.97 (s, 9H) 1.26 (s, 3H) 1.28 (s, 3H) 1.87 (s, 3H) 2.24 (s, 3H) 2.40 (s, 3H) 3.09 (dd, J=12.82, 6.23 Hz, 2H) 3.43 (dd, J=12.82, 2.93 Hz, 2H) 4.04-4.14 (m, 2H) 4.62-4.89 (m, 4H) 5.14 (s, 1H) 7.05 (d, J=6.96 Hz, 1H) 7.18-7.24 (m, 2H) 7.35 (d, J=6.78 Hz, 1H). LCMS (ES+) (m/z): 509.50 (M+1).

Example 74: (2S)-2-(tert-butoxy)-2-{2-[(2,2-dimethylpropyl)carbamoyl]-4,7-dimethyl-6-(4-methylphenyl)-2,3-dihydro-1H-isoindol-5-yl}acetic acid

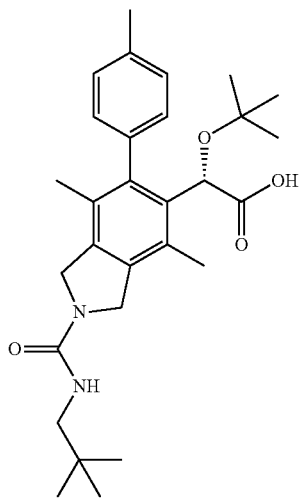 [SMILES: Cc1ccc(-c2c(C)c3c(c(C)c2[C@H](OC(C)(C)C)C(=O)O)CN(C(=O)NCC(C)(C)C)C3)cc1]

¹H NMR (400 MHz, CHLOROFORM-d) δ ppm 0.96 (s, 9H) 0.99 (s, 9H) 1.90 (s, 3H) 2.27 (s, 3H) 2.42 (s, 3H) 3.16 (d, J=6.05 Hz, 2H) 4.42 (t, J=6.15 Hz, 1H) 4.59-4.78 (m, 4H) 5.16 (s, 1H) 7.08 (d, J=7.23 Hz, 1H) 7.20-7.26 (m, 2H) 7.37 (d, J=7.23 Hz, 1H). LCMS (ES+) (m/z): 481.41 (M+1), Example 75: (2S)-2-(tert-butoxy)-2-[4,7-dimethyl-6-(4-methylphenyl)-2-{8-oxa-3-azabicyclo[3.2.1]octane-3-carbonyl}-2,3-dihydro-1H-isoindol-5-yl]acetic acid

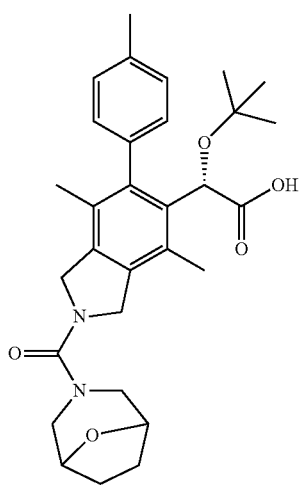 [SMILES: Cc1ccc(-c2c(C)c3c(c(C)c2[C@H](OC(C)(C)C)C(=O)O)CN(C(=O)N2CC4CCC(C2)O4)C3)cc1]

¹H NMR (400 MHz, CHLOROFORM-d) δ ppm 0.98 (s, 9H) 1.88 (s, 3H) 1.97 (br. s., 4H) 2.25 (s, 3H) 2.41 (s, 3H) 3.29 (d, J=11.72 Hz, 2H) 3.59 (d, J=12.50 Hz, 2H) 4.37 (br. s., 2H) 4.61-4.87 (m, 5H) 5.15 (s, 1H) 7.06 (d, J=6.83 Hz, 1H) 7.18-7.26 (m, 2H) 7.36 (d, J=6.44 Hz, 1H). LCMS (ES+) (m/z): 507.44 (M+1).

Example 76: (2S)-2-(tert-butoxy)-2-[4,7-dimethyl-6-(4-methylphenyl)-2-(1,4-oxazepane-4-carbonyl)-2,3-dihydro-1H-isoindol-5-yl]acetic acid

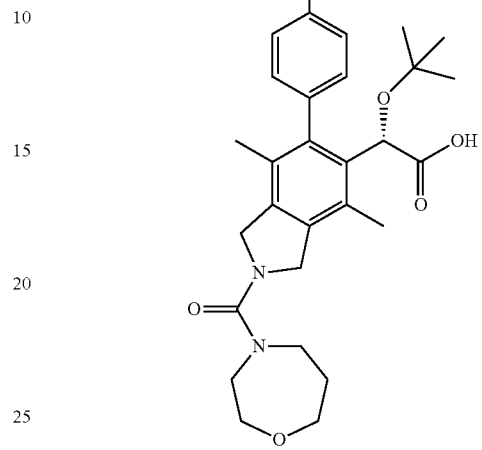

¹H NMR (400 MHz, CHLOROFORM-d) δ ppm 0.98 (s, 9H) 1.89 (s, 3H) 1.99-2.07 (m, 2H) 2.25 (s, 3H) 2.42 (s, 3H) 3.53-3.65 (m, 4H) 3.80-3.89 (m, 4H) 4.63-4.90 (m, 4H) 5.15 (s, 1H) 7.07 (d, J=7.03 Hz, 1H) 7.19-7.26 (m, 2H) 7.36 (d, J=7.03 Hz, 1H). LCMS (ES+) (m/z): 495.49 (M+1).

Example 77: (2S)-2-(tert-butoxy)-2-{2-[(3S)-3-hydroxypyrrolidine-1-carbonyl]-4,7-dimethyl-6-(4-methylphenyl)-2,3-dihydro-1H-isoindol-5-yl}acetic acid

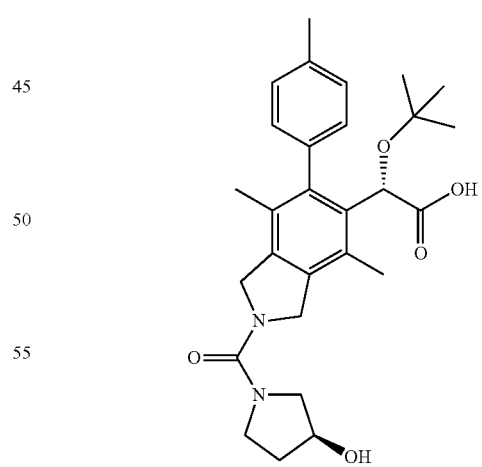

¹H NMR (400 MHz, CHLOROFORM-d) δ ppm 0.97 (s, 9H) 1.88 (s, 3H) 1.95-2.07 (m, 3H) 2.24 (s, 3H) 2.40 (s, 3H) 3.46 (d, J=11.35 Hz, 1H) 3.53-3.63 (m, 1H) 3.67-3.78 (m, 2H) 4.48-4.96 (m, 5H) 5.14 (s, 1H) 7.06 (d, J=7.14 Hz, 1H) 7.18-7.24 (m, 2H) 7.35 (d, J=7.33 Hz, 1H). LCMS (ES+) (m/z): 481.37 (M+1).

Example 78: (2S)-2-(tert-butoxy)-2-{2-[(cyclohexylmethyl)(methyl)carbamoyl]-4,7-dimethyl-6-(4-methylphenyl)-2,3-dihydro-1H-isoindol-5-yl}acetic acid

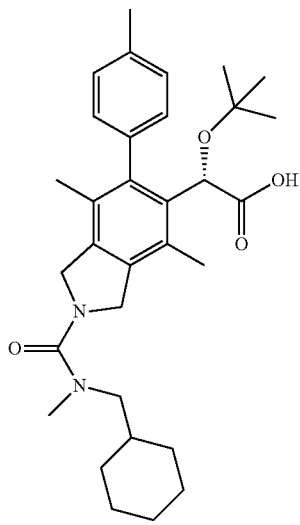 [SMILES: Cc1ccc(-c2c(C)c3c(c(C)c2[C@H](OC(C)(C)C)C(=O)O)CN(C(=O)N(C)CC2CCCCC2)C3)cc1]

¹H NMR (400 MHz, CHLOROFORM-d) δ ppm 0.94 (br. s., 1H) 0.99 (s, 9H) 1.11-1.30 (m, 4H) 1.60-1.78 (m, 6H) 1.89 (s, 3H) 2.26 (s, 3H) 2.42 (s, 3H) 2.96 (s, 3H) 3.11-3.21 (m, 2H) 4.63-4.88 (m, 4H) 5.16 (s, 1H) 7.07 (d, J=7.03 Hz, 1H) 7.18-7.26 (m, 2H) 7.37 (d, J=6.83 Hz, 1H). LCMS (ES+) (m/z): 521.49 (M+1)

Example 79: (2S)-2-(2-{[2-(benzyloxy)ethyl]carbamoyl}-4,7-dimethyl-6-(4-methylphenyl)-2,3-dihydro-1H-isoindol-5-yl)-2-(tert-butoxy)acetic acid

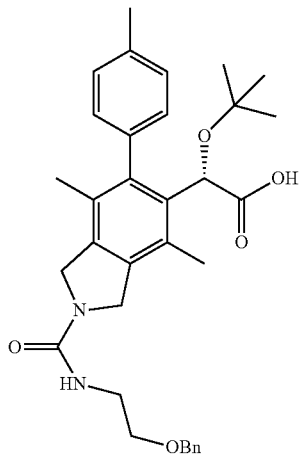 [SMILES: Cc1ccc(-c2c(C)c3c(c(C)c2[C@H](OC(C)(C)C)C(=O)O)CN(C(=O)NCCOCc2ccccc2)C3)cc1]

¹H NMR (400 MHz, CHLOROFORM-d) δ ppm 0.97 (s, 9H) 1.87 (s, 3H) 2.25 (s., 3H) 2.40 (s, 3H) 3.42-3.73 (m, 4H) 4.55 (s, 2H) 4.60-4.86 (m, 4H) 5.14 (s, 1H) 7.06 (d, J=6.78 Hz, 1H) 7.17-7.40 (m, 8H). LCMS (ES+) (m/z): 545.43 (M+1).

Example 80: (2S)-2-{2-[(8aR)-octahydropyrrolo[1,2-a]piperazine-2-carbonyl]-4,7-dimethyl-6-(4-methylphenyl)-2,3-dihydro-1H-isoindol-5-yl}-2-(tert-butoxy)acetic acid

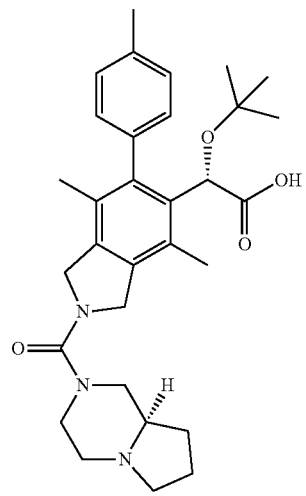 [SMILES: Cc1ccc(-c2c(C)c3c(c(C)c2[C@H](OC(C)(C)C)C(=O)O)CN(C(=O)N2CCN4CCC[C@@H]4C2)C3)cc1]

¹H NMR (400 MHz, METHANOL-d₄) δ ppm 0.87 (s, 9H) 1.27-1.52 (m, 2H) 1.85-1.90 (m, 5H) 2.27-2.34 (m, 5H) 2.35-2.40 (m, 4H) 2.78 (dd, J=12.69, 10.35 Hz, 1H) 3.03-3.16 (m, 3H) 3.79-3.99 (m, 2H) 4.66-4.80 (m, 4H) 4.92 (s, 1H) 7.05 (d, J=7.81 Hz, 1H) 7.21 (t, J=8.20 Hz, 2H) 7.43 (d, J=7.81 Hz, 1H). LCMS (ES+) (m/z): 520.48 (M+1).

Example 81: (S)-2-(tert-butoxy)-2-(4,7-dimethyl-2-(4-methylpiperidine-1-carbonyl)-6-(p-tolyl)isoindolin-5-yl)acetic acid

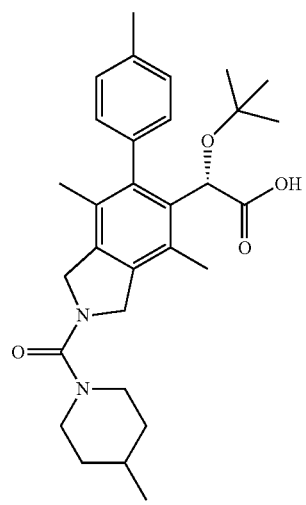 [SMILES: Cc1ccc(-c2c(C)c3c(c(C)c2[C@H](OC(C)(C)C)C(=O)O)CN(C(=O)N2CCC(C)CC2)C3)cc1]

¹H NMR (400 MHz, CDCl₃) δ 0.87-1.08 (m, 12H), 1.29 (m, 1H), 1.72 (d, J=12.30 Hz, 3H), 1.91 (s, 3H), 2.28 (s, 3H), 2.44 (s, 3H), 2.86 (t, J=12.05 Hz, 2H), 3.83 (d, J=13.05 Hz, 2H), 4.63-4.78 (m, 2H), 4.78-4.92 (m, 2H), 5.17 (s, 1H), 7.09 (d, J=7.28 Hz, 1H), 7.21-7.27 (m, 2H) 7.39 (d, J=7.03 Hz, 1H). LCMS (ES+) (m/z): 493.47 (M+1).

Example 82: (2S)-2-(tert-butoxy)-2-(4,7-dimethyl-2-(octahydrocyclopenta[c]pyrrole-2-carbonyl)-6-(p-tolyl)isoindolin-5-yl)acetic acid

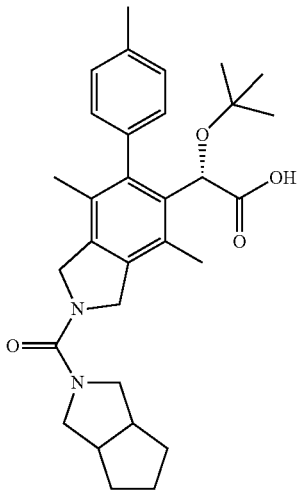 [SMILES: Cc1ccc(-c2c(C)c3c(c(C)c2[C@H](OC(C)(C)C)C(=O)O)CN(C(=O)N2CC4CCCC4C2)C3)cc1]

¹H NMR (400 MHz, CDCl₃) δ 1.01 (s, 9H), 1.48-1.60 (m, 2H), 1.60-1.71 (m, 1H), 1.77-1.89 (m, 3H), 1.91 (s, 3H), 2.28 (s, 3H), 2.44 (s, 3H), 2.64-2.74 (m, 2H), 3.29 (dd, J=10.67, 4.14 Hz, 2H), 3.72 (dd, J=10.67, 7.91 Hz, 2H), 4.68-4.80 (m, 2H), 4.80-4.91 (m, 2H), 5.18 (s, 1H), 7.09 (d, J=7.53 Hz, 1H), 7.22-7.28 (m, 2H), 7.39 (d, J=7.53 Hz, 1H). LCMS (ES+) (m/z): 505.54 (M+1).

Example 83: (S)-2-(2-((1R,4R)-7-azabicyclo[2.2.1]heptane-7-carbonyl)-4,7-dimethyl-6-(p-tolyl)isoindolin-5-yl)-2-(tert-butoxy)acetic acid

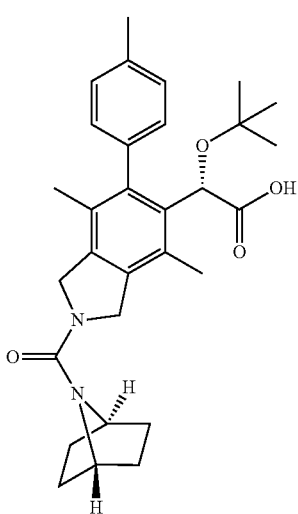 [SMILES: Cc1ccc(-c2c(C)c3c(c(C)c2[C@H](OC(C)(C)C)C(=O)O)CN(C(=O)N2[C@H]4CC[C@@H]2CC4)C3)cc1]

¹H NMR (400 MHz, CDCl₃) δ 0.98 (s, 9H), 1.45 (d, J=6.78 Hz, 3H), 1.80-1.95 (m, 8H), 2.26 (s, 3H), 2.41 (s, 3H), 4.24 (br. s., 2H), 4.66-4.80 (m, 2H), 4.80-4.92 (m, 2H), 5.15 (s, 1H), 7.07 (d, J=7.03 Hz, 1H), 7.19-7.29 (m, 2H), 7.37 (d, J=7.28 Hz, 1H). LCMS (ES+) (m/z): 491.44 (M+1), δ 13.31 (M+23), 981.90 (2M+1).

Example 84: (S)-2-(tert-butoxy)-2-(2-(4,4-dimethylpiperidine-1-carbonyl)-4,7-dimethyl-6-(p-tolyl)isoindolin-5-yl)acetic acid

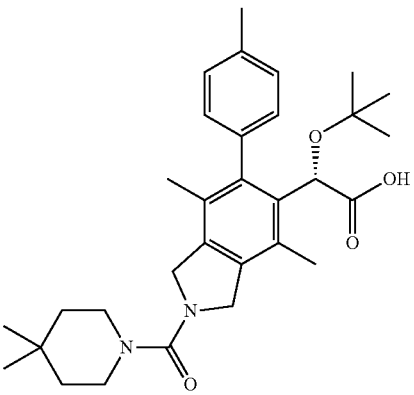 [SMILES: Cc1ccc(-c2c(C)c3c(c(C)c2[C@H](OC(C)(C)C)C(=O)O)CN(C(=O)N2CCC(C)(C)CC2)C3)cc1]

¹H NMR (400 MHz, CDCl₃) δ 7.36-7.04 (m, 4H) (under CHCl₃), 5.14 (s, 1H), 4.73 (m, 4H), 3.30 (m, 4H), 2.40 (s, 3H), 2.25 (s, 3H), 1.87 (s, 3H), 1.41 (m, 4H), 1.01-0.94 (m, 15H). LCMS (ES+) (m/z): 507.55 (M+1); 1113.97 (2M+1).

Example 85: (S)-2-(2-(4-acetylpiperazine-1-carbonyl)-4,7-dimethyl-6-(p-tolyl)isoindolin-5-yl)-2-(tert-butoxy)acetic acid

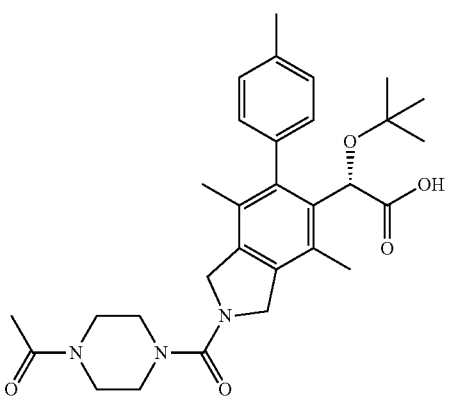 [SMILES: CC(=O)N1CCN(C(=O)N2Cc3c(C)c(-c4ccc(C)cc4)c([C@H](OC(C)(C)C)C(=O)O)c(C)c3C2)CC1]

¹H NMR (400 MHz, CDCl₃) δ 7.34 (m, 1H), 7.25-7.18 (m, 2H), 7.04 (m, 1H), 5.14 (s, 1H) 4.77 (m, 4H), 3.72 (m, 2H), 3.58 (m, 2H), 3.41 (m, 4H), 2.40 (s, 3H), 2.25 (s, 3H), 2.18 (s, 3H), 1.87 (s, 3H), 0.97 (s, 9H). LCMS (ES+) (m/z): 522.54 (M+1); 1043.95 (2M+1).

Example 86: (S)-2-(tert-butoxy)-2-(4,7-dimethyl-2-(piperazine-1-carbonyl)-6-(p-tolyl)isoindolin-5-yl)acetic acid

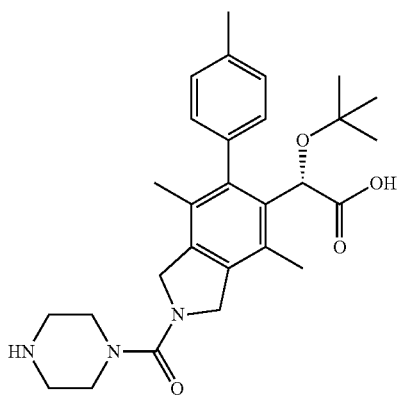 [SMILES: Cc1ccc(-c2c(C)c3c(c(C)c2[C@H](OC(C)(C)C)C(=O)O)CN(C(=O)N2CCNCC2)C3)cc1]

$^1$H NMR (400 MHz, CDCl$_3$) δ 7.32 (m, 1H), 7.24-7.17 (m, 2H), 7.04 (m, 1H), 5.13 (s, 1H) 4.76 (m, 4H), 3.63 (m, 4H), 3.29 (m, 4H), 2.40 (s, 3H), 2.24 (s, 3H), 1.88 (s, 3H), 0.97 (s, 9H). LCMS (ES+) (m/z): 480.5 (M+1); 959.98 (2M+1).

Example 87: (S)-2-(tert-butoxy)-2-(4,7-dimethyl-2-((S)-2-methylpyrrolidine-1-carbonyl)-6-(p-tolyl)isoindolin-5-yl)acetic acid

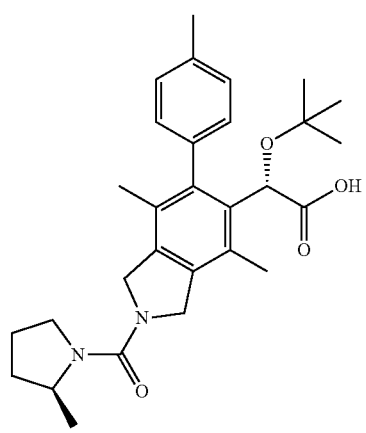 [SMILES: Cc1ccc(-c2c(C)c3c(c(C)c2[C@H](OC(C)(C)C)C(=O)O)CN(C(=O)N2CCC[C@@H]2C)C3)cc1]

$^1$H NMR (400 MHz, CDCl$_3$) δ 7.36 (m, 1H), 7.25-7.20 (m, 2H), 7.07 (m, 1H), 5.16 (s, 1H), 5.09-4.88 (m, 2H), 4.63-4.45 (m, 2H), 4.10 (m, 1H), 3.60-3.40 (m, 2H), 2.41 (s, 3H), 2.25 (s, 3H), 2.13 (m, 1H), 1.91 (m, 1H), 1.89 (s, 3H), 1.80 (m, 1H), 1.52 (m, 1H), 0.99 (s, 9H). LCMS (ES+) (m/z): 479.51 (M+1); 1041.91 (2M+1).

Example 88: (S)-2-(tert-butoxy)-2-(2-((2S,5R)-2,5-dimethylmorpholine-4-carbonyl)-4,7-dimethyl-6-(p-tolyl)isoindolin-5-yl)acetic acid

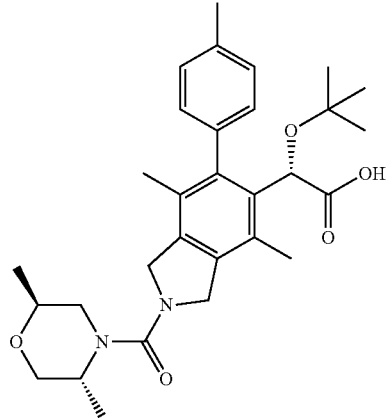 [SMILES: Cc1ccc(-c2c(C)c3c(c(C)c2[C@H](OC(C)(C)C)C(=O)O)CN(C(=O)N2C[C@H](C)OC[C@H]2C)C3)cc1]

$^1$H NMR (400 MHz, CDCl$_3$) 7.36 (m, 1H), 7.23 (m, 2H), 7.06 (m, 1H), 5.16 (s, 1H), 4.91-4.58 (m, 4H), 4.0-3.4 (m, 5H), 2.98 (m, 1H), 2.42 (s, 3H), 2.25 (s, 3H), 1.89 (s, 3H), 1.38 (m, 3H), 1.22 (m, 3H), 0.98 (s, 9H). LCMS (ES+) (m/z): 509.46 (M+1); 1017.92 (2M+1).

Example 89: (S)-2-(tert-butoxy)-2-(2-(4-fluoropiperidine-1-carbonyl)-4,7-dimethyl-6-(p-tolyl)isoindolin-5-yl)acetic acid

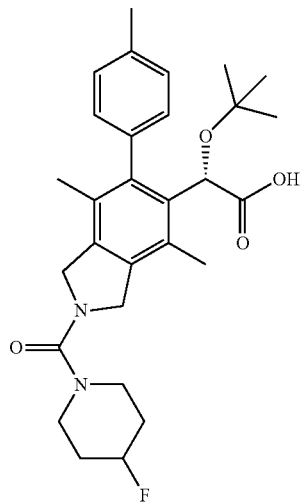 [SMILES: Cc1ccc(-c2c(C)c3c(c(C)c2[C@H](OC(C)(C)C)C(=O)O)CN(C(=O)N2CCC(F)CC2)C3)cc1]

$^1$H NMR (400 MHz, CDCl$_3$) δ 1.01 (s, 9H), 1.87-2.00 (m, 5H) 2.00-2.10 (m, 3H), 2.28 (s, 3H), 2.44 (s, 3H), 3.32-3.43 (m, 2H), 3.48-3.59 (m, 2H), 4.66-4.79 (m, 2H), 4.79-4.91 (m, 3H), 5.18 (s, 1H) 7.09 (d, J=7.28 Hz, 1H), 7.22-7.29 (m, 2H), 7.39 (d, J=7.03 Hz, 1H). LCMS (ES+) (m/z): 497.52 (M+1), 519.49 (M+23), 993.94 (2M+1).

Example 90: (S)-2-(tert-butoxy)-2-(4,7-dimethyl-2-(4-methyl-3-oxopiperazine-1-carbonyl)-6-(p-tolyl)isoindolin-5-yl)acetic acid

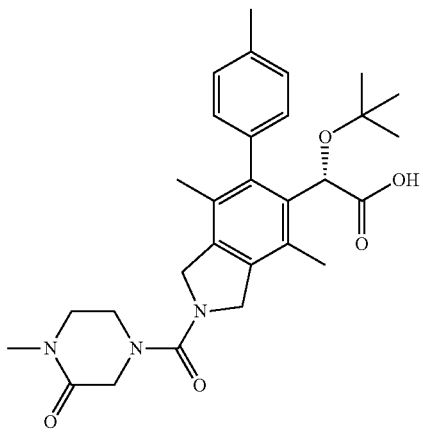 [SMILES: Cc1ccc(-c2c(C)c3c(c(C)c2[C@H](OC(C)(C)C)C(=O)O)CN(C(=O)N2CCN(C)C(=O)C2)C3)cc1]

¹H NMR (400 MHz, CDCl₃) δ 7.35 (m, 1H), 7.21 (m, 2H), 7.05 (m, 1H), 5.13 (s, 1H), 4.75 (m, 4H), 4.12 (s, 2H), 3.61 (m, 2H), 3.47 (m, 2H), 3.02 (s, 3H), 2.39 (s, 3H), 2.25 (s, 3H), 1.85 (s, 3H), 0.96 (s, 9H). LCMS (ES+) (m/z): 508.44 (M+1); 1015.81 (2M+1).

Example 91: (S)-2-(tert-butoxy)-2-(4,7-dimethyl-2-((S)-3-methylmorpholine-4-carbonyl)-6-(p-tolyl)isoindolin-5-yl)acetic acid

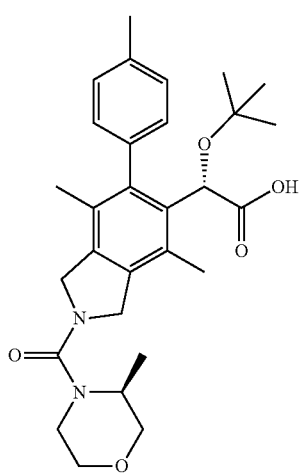 [SMILES: Cc1ccc(-c2c(C)c3c(c(C)c2[C@H](OC(C)(C)C)C(=O)O)CN(C(=O)N2CCOC[C@@H]2C)C3)cc1]

¹H NMR (400 MHz, CDCl₃) δ 1.01 (s, 9H), 1.39 (d, J=6.78 Hz, 3H), 1.92 (s, 3H), 2.28 (s, 3H), 2.44 (s, 3H), 3.36-3.49 (m, 2H), 3.58-3.73 (m, 2H), 3.73-3.82 (m, 1H), 3.84-3.97 (m, 2H), 4.66 (d, J=14.56 Hz, 1H), 4.80 (br. s., 2H), 4.89 (d, J=14.56 Hz, 1H), 5.18 (s, 1H), 7.09 (d, J=7.53 Hz, 1H), 7.21-7.32 (m, 2H), 7.38 (br. s., 1H). LCMS (ES+) (m/z): 495.53 (M+1), 517.47 (M+23), 989.77 (2M+1).

Example 92: (S)-2-(tert-butoxy)-2-(2-(4,4-difluoropiperidine-1-carbonyl)-4,7-dimethyl-6-(p-tolyl)isoindolin-5-yl)acetic acid

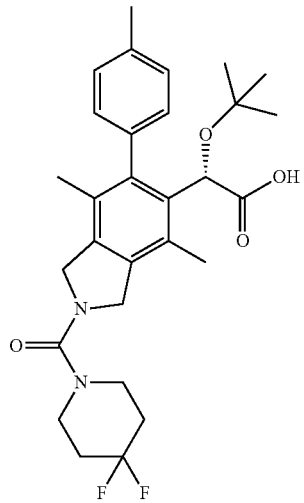 [SMILES: Cc1ccc(-c2c(C)c3c(c(C)c2[C@H](OC(C)(C)C)C(=O)O)CN(C(=O)N2CCC(F)(F)CC2)C3)cc1]

¹H NMR (400 MHz, CDCl₃) δ 0.98 (s, 9H), 1.89 (s, 3H), 1.98-2.15 (m, 4H), 2.25 (s, 3H), 2.41 (s, 4H), 3.48 (t, J=5.52 Hz, 5H), 4.63-4.77 (m, 2H), 4.77-4.89 (m, 2H), 5.15 (s, 1H), 7.07 (br. s., 1H), 7.17-7.29 (m, 2H), 7.35 (br. s., 1H). LCMS (ES+) (m/z): 515.51 (M+1), 537.43 (M+23).

Example 93: (S)-2-(tert-butoxy)-2-(2-(3,3-dimethylpiperidine-1-carbonyl)-4,7-dimethyl-6-(p-tolyl)isoindolin-5-yl)acetic acid

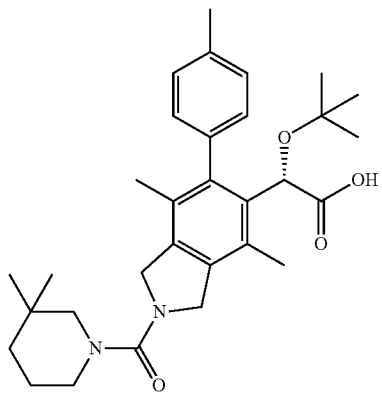 [SMILES: Cc1ccc(-c2c(C)c3c(c(C)c2[C@H](OC(C)(C)C)C(=O)O)CN(C(=O)N2CCCC(C)(C)C2)C3)cc1]

¹H NMR (400 MHz, CDCl₃) δ 7.43-7.01 (m, 4H), 5.14 (s, 1H), 4.77 (m, 4H), 3.23 (m, 2H), 3.0 (s, 2H), 2.39 (s, 3H), 2.24 (s, 3H), 1.87 (s, 3H), 1.39 (m, 2H), 0.96 (m, 17H). LCMS (ES+) (m/z): 507.52 (M+1); 1013.91 (2M+1).

Example 94: (S)-2-(tert-butoxy)-2-(4,7-dimethyl-6-(p-tolyl)-2-((2,2,2-trifluoroethyl)carbamoyl)isoindolin-5-yl)acetic acid

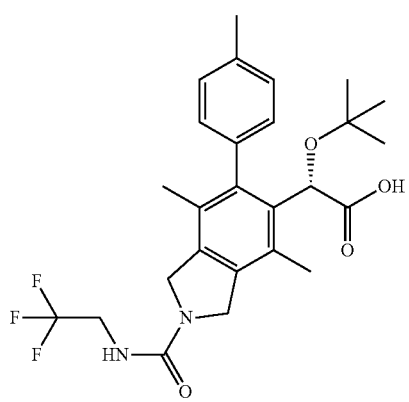 [SMILES: Cc1ccc(-c2c(C)c3c(c(C)c2[C@H](OC(C)(C)C)C(=O)O)CN(C(=O)NCC(F)(F)F)C3)cc1]

¹H NMR (400 MHz, CDCl₃) δ 7.35 (m, 1H), 7.22 (m, 2H), 7.06 (m, 1H), 5.16 (s, 1H), 4.70 (m, 4H), 2.40 (s, 3H), 2.25 (s, 3H), 1.89 (s, 3H), 1.58 (m, 2H), 0.97 (s, 9H). LCMS (ES+) (m/z): 493.41 (M+1); 985.68 (2M+1).

Example 95: (S)-2-(2-(4-benzylpiperidine-1-carbonyl)-4,7-dimethyl-6-(p-tolyl)isoindolin-5-yl)-2-(tert-butoxy)acetic acid

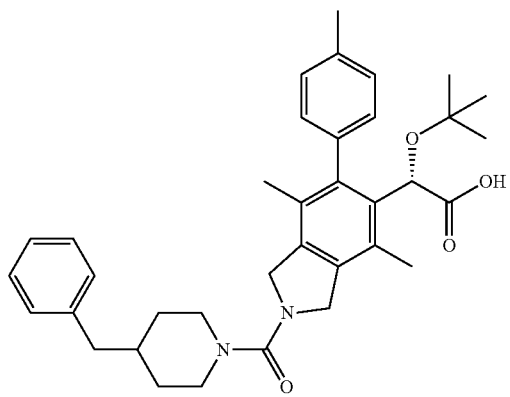 [SMILES: Cc1ccc(-c2c(C)c3c(c(C)c2[C@H](OC(C)(C)C)C(=O)O)CN(C(=O)N2CCC(Cc4ccccc4)CC2)C3)cc1]

¹H NMR (400 MHz, CDCl₃) δ 7.35 (m, 1H), 7.32-7.11 (m, 7H), 7.04 (m, 1H), 5.13 (s, 1H) 4.86-4.59 (m, 4H), 3.79 (m, 2H), 2.77 (m, 2H), 2.57 (m, 2H), 2.40 (s, 3H), 2.25 (s, 3H), 1.87 (s, 3H), 1.70 (m, 2H), 1.28 (m, 2H), 0.96 (s, 9H), 0.85 (m, 1H). LCMS (ES+) (m/z): 569.50 (M+1); 1137.87 (2M+1).

Example 96: (S)-2-(tert-butoxy)-2-(2-((R)-3-fluoropyrrolidine-1-carbon yl)-4,7-dimethyl-6-(p-tolyl)isoindolin-5-yl)acetic acid

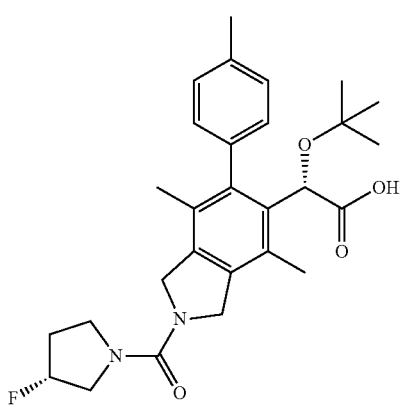 [SMILES: Cc1ccc(-c2c(C)c3c(c(C)c2[C@H](OC(C)(C)C)C(=O)O)CN(C(=O)N2CC[C@@H](F)C2)C3)cc1]

¹H NMR (400 MHz, CDCl₃) δ 7.36 (m, 1H), 7.22 (m, 2H), 7.06 (m, 1H), 5.38-5.19 (m, 1H), 5.14 (s, 1H), 5.04-4.80 (m, 2H), 4.65 (m, 2H), 3.91-3.60 (m, 4H), 2.40 (s, 3H), 2.25 (s, 3H), 1.87 (s, 3H), 0.98 (s, 9H), 0.85 (m, 2H). LCMS (ES+) (m/z): 483.43 (M+1); 965.75 (2M+1).

Example 97: (S)-2-(tert-butoxy)-2-(4,7-dimethyl-2-((2-phenylpropan-2-yl)carbamoyl)-6-(p-tolyl)isoindolin-5-yl)acetic acid

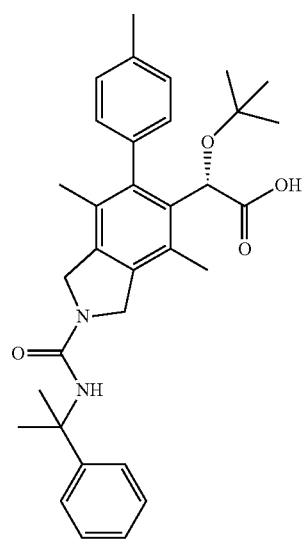 [SMILES: Cc1ccc(-c2c(C)c3c(c(C)c2[C@H](OC(C)(C)C)C(=O)O)CN(C(=O)NC(C)(C)c2ccccc2)C3)cc1]

¹H NMR (400 MHz, CDCl₃) δ 0.98 (s, 9H), 1.78 (s, 6H), 1.88 (s, 3H), 2.25 (s, 3H), 2.41 (s, 3H), 4.60-4.75 (m, 5H), 5.16 (s, 1H), 7.07 (d, J=7.03 Hz, 1H), 7.19-7.28 (m, 2H), 7.34 (t, J=7.65 Hz, 4H), 7.46 (d, J=7.78 Hz, 2H). LCMS (ES+) (m/z): 529.53 (M+1), 1079.95 (2M+23).

Example 98: (S)-2-(tert-butoxy)-2-(4,7-dimethyl-2-(4-morpholinopiperidine-1-carbonyl)-6-(p-tolyl)isoindolin-5-yl)acetic acid

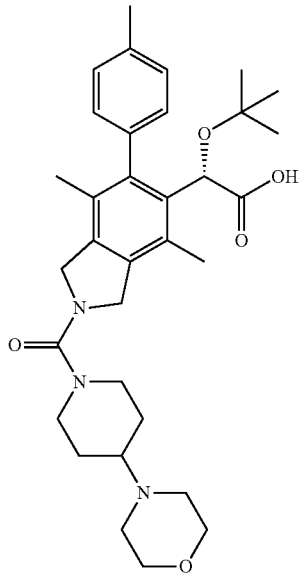 [SMILES: Cc1ccc(-c2c(C)c3c(c(C)c2[C@H](OC(C)(C)C)C(=O)O)CN(C(=O)N2CCC(N4CCOCC4)CC2)C3)cc1]

$^1$H NMR (400 MHz, CDCl$_3$) δ 1.01 (s, 9H) 1.22-1.36 (m, 3H) 1.83-1.97 (m, 5H) 2.14 (d, J=11.04 Hz, 3H) 2.28 (s, 3H) 2.44 (s, 3H) 2.94 (t, J=12.67 Hz, 2H) 3.04 (d, J=9.03 Hz, 2H) 3.52 (d, J=11.54 Hz, 2H) 3.97-4.12 (m, 6H) 4.67-4.78 (m, 2H) 4.78-4.90 (m, 2H) 5.18 (s, 1H) 7.08 (d, J=7.78 Hz, 1H) 7.20-7.31 (m, 2H) 7.37 (d, J=7.28 Hz, 1H).

Example 99: (S)-2-(tert-butoxy)-2-(2-(((S)-1-cyclohexylethyl)carbamoyl)-4,7-dimethyl-6-(p-tolyl)isoindolin-5-yl)acetic acid

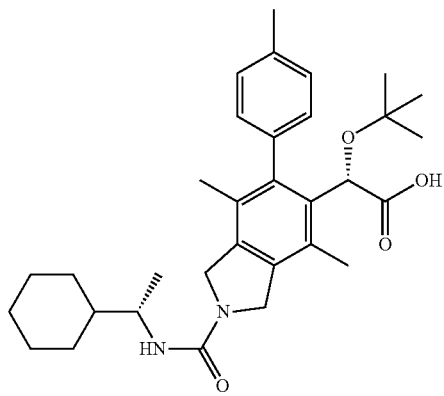 [SMILES: Cc1ccc(-c2c(C)c3c(c(C)c2[C@H](OC(C)(C)C)C(=O)O)CN(C(=O)N[C@@H](C)C2CCCCC2)C3)cc1]

$^1$H NMR (400 MHz, CDCl$_3$) δ 7.35 (m, 1H), 7.21 (m, 2H), 7.06 (m, 1H), 5.14 (s, 1H), 4.66 (m, 4H), 4.12 (m, 1H), 3.85 (m, 1H), 2.40 (s, 3H), 2.25 (s, 3H), 1.88 (s, 3H), 1.83-1.62 (m, 3H), 1.61-1.30 (m, 2H), 1.28-1.09 (m, 5H), 1.08-0.93 (m, 12H). LCMS (ES+) (m/z): 521.50 (M+1); 1041.91 (2M+1).

Example 100: (2S)-2-(tert-Butoxy)-2-(2-(3,3-difluoropyrrolidine-1-carbonyl)-6-(M)-(8-fluoro-5-methylchroman-6-yl)-4,7-dimethylisoindolin-5-yl)acetic acid

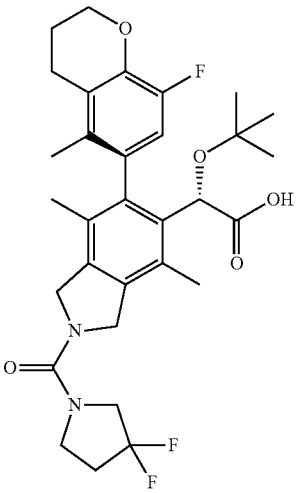

Step 1: (2S)-Methyl 2-(tert-butoxy)-2-((M)-2-(3,3-difluoropyrrolidine-1-carbonyl)-6-(8-fluoro-5-methylchroman-6-yl)-4,7-dimethylisoindolin-5-yl)acetate

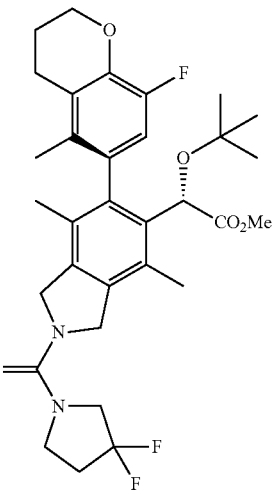

An ice cold solution of phosgene (0.129 mL, 0.243 mmol, 20% in PhMe) in THF (1 mL) was treated dropwise with a solution of (S)-methyl 2-(tert-butoxy)-2-((M)-6-(8-fluoro-5-methylchroman-6-yl)-4,7-dimethylisoindolin-5-yl)acetate (45.7 mg, 0.10 mmol) in THF (2.0 mL). After 40 min, the reaction mixture was concentrated in vacuo and dissolved in THF (2.0 mL) and cooled to 0° C. The reaction mixture was treated with pyridine (0.01 mL, 0.124 mmol), triethylamine (0.04 mL, 0.287 mmol) and 3,3-difluoropyrrolidine, HCl (22 mg, 0.15 mmol). After 18 h, the reaction mixture was poured into sat. aq. NaHCO$_3$ and extracted with EtOAc. The organics were dried over Na2SO4, filtered and concentrated in vacuo. The residue was purified by silica gel chromatography (0-100% EtOAc-hexanes) to afford the title compound (29 mg, 49%). LCMS (ES+) (m/z): 589.49 (M+1).

Step 2: (2S)-2-(tert-Butoxy)-2-(2-(3,3-difluoropyrrolidine-1-carbonyl)-6-(M)-(8-fluoro-5-methylchroman-6-yl)-4,7-dimethylisoindolin-5-yl)acetic acid A solution of (2S)-methyl 2-(tert-butoxy)-2-((M)-2-(3,3-difluoropyrrolidine-1-carbonyl)-6-(8-fluoro-5-methylchroman-6-yl)-4,7-dimethylisoindolin-5-yl)acetate (29 mg, 0.049 mmol) in EtOH (3 mL) and 1,4-dioxane (3 mL) was treated with LiOH (1.0 mL, 1.0 mmol) and heated to 70° C. After 18 h, the reaction mixture was concentrated in vacuo and diluted with water. The pH was adjusted to 3 with 1N HCl and then extracted with EtOAc. The organics were washed with Na2SO4, filtered and concentrated. The residue was purified by reverse phase HPLC to afford the title compound (15 mg, 53%) as a white solid. $^1$H NMR (400 MHz, CDCl$_3$) δ 6.67 (m, 1H), 5.05 (s, 1H), 4.77 (m, 4H), 4.26 (m, 2H), 3.87-3.71 (m, 4H), 2.68 (m, 2H), 2.37 (m, 2H), 2.27 (s, 3H), 2.11 (m, 2H), 1.85 (s, 3H), 1.77 (s, 3H), 1.11 (s, 9H). LCMS (ES+) (m/z): 575.45 (M+1).

Example 101: (2S)-2-(tert-butoxy)-2-(6-(M)-(8-fluoro-5-methylchroman-6-yl)-4,7-dimethyl-2-(piperidine-1-carbonyl)isoindolin-5-yl)acetic acid The title compound was made in a similar manner to example 100.

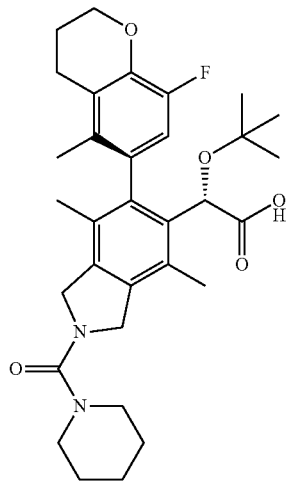

$^1$H NMR (400 MHz, CDCl$_3$) δ 6.69 (d, J=11.3 Hz, 1H), 5.06 (s, 1H), 4.77 (m, 4H), 4.27 (m, 2H), 3.31 (br. s., 4H), 2.68 (m, 2H), 2.28 (s, 3H), 2.12 (m, 2H), 1.86 (s, 3H), 1.77 (s, 3H), 1.64 (br.s., 6H), 1.13 (s, 9H). LCMS (ES+) (m/z): 553.49 (M+1).

Example 102: (S)-2-(tert-butoxy)-2-((R)-2-(3,3-difluoropiperidine-1-carbonyl)-6-(8-fluoro-5-methylchroman-6-yl)-4,7-dimethylisoindolin-5-yl)acetic acid The title compound was made in a similar manner to example 100.

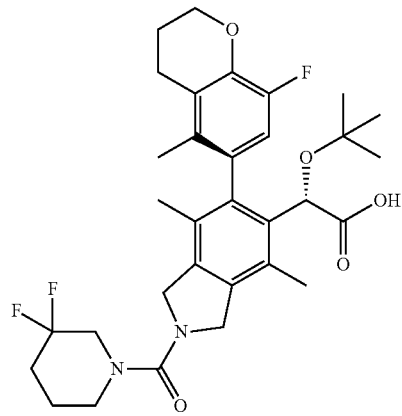

$^1$H NMR (400 MHz, CDCl$_3$) δ 6.68 (m, 1H), 5.06 (br.s, 1H), 4.78 (m, 4H), 4.25 (m, 2H), 3.52 (m, 2H), 3.31 (m, 2H), 2.68 (m, 2H), 2.27 (s, 3H), 2.14-1.98 (m, 4H), 1.90-1.82 (m, 5H), 1.76 (s, 3H), 1.12 (s, 9H). LCMS (ES+) (m/z): 589.49 (M+1).

Example 103: (2S)-2-(tert-butoxy)-2-((M)6-(8-fluoro-5-methylchroman-6-yl)-2-(3-fluorobenzoyl)-4,7-dimethylisoindolin-5-yl)acetic acid

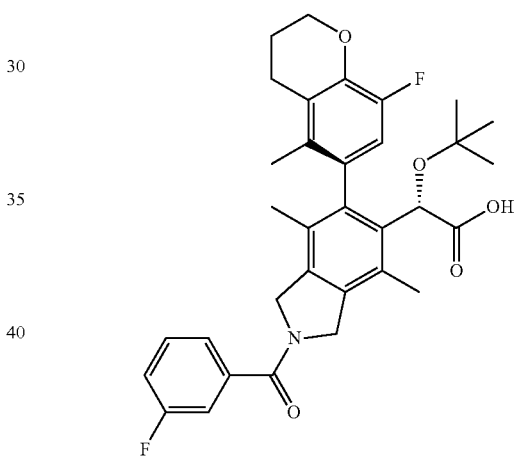

Step 1. (S)-Methyl 2-(tert-butoxy)-2-((M)-6-(8-fluoro-5-methylchroman-6-yl)-2-(3-fluorobenzoyl)-4,7-dimethylisoindolin-5-yl)acetate

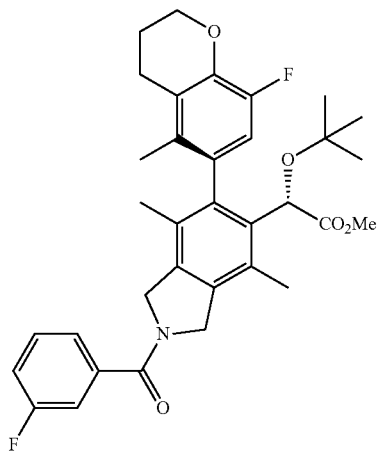

A solution of (S)-methyl 2-(tert-butoxy)-2-((M)-6-(8-fluoro-5-methylchroman-6-yl)-4,7-dimethylisoindolin-5-yl)acetate (70 mg, 0.154 mmol) and 3-fluorobenzoic acid (43 mg, 0.307 mmol) in EtOAc (3 mL) was treated with Et$_3$N (0.064 mL, 0.461 mmol) and T3P (0.23 mL, 0.387 mmol, 50% in EtOAc). After 3 h, the reaction mixture was poured into sat. aq. NaHCO3 and extracted with EtOAc. The organics were dried (Na$_2$SO$_4$), filtered and concentrated in vacuo, The residue was purified by silica gel chromatography (0-100% EtOAc-hexanes) to afford the title compound (39 mg, 44%) as a white solid. LCMS (ES+) (m/z): 578.35 (M+1).

Step 2. (2S)-2-(tert-butoxy)-2-((M)-6-(8-fluoro-5-methylchroman-6-yl)-2-(3-fluorobenzoyl)-4,7-dimethylisoindolin-5-yl)acetic acid A solution of (S)-Methyl 2-(tert-butoxy)-2-((M)-6-(8-fluoro-5-methylchroman-6-yl)-2-(3-fluorobenzoyl)-4,7-dimethylisoindolin-5-yl)acetate (39 mg, 0.068 mmol) in 1,4-dioxane (5 mL) was treated with 1M LiOH (1 mL, 1.00 mmol) and heated to 70° C. After 8 h, the reaction mixture was warmed to ambient temperature and stirring continued for an additional 12 h. The reaction mixture was concentrated in vacuo, dissolved in water and acidified using 6N HCl. The aqueous layer was then extracted with EtOAc and the organic layer concentrated in vacuo, and purified by reverse phase HPLC to afford the title compound (21 mg, 24%) as a white solid. $^1$H NMR (400 MHz, CDCl$_3$) δ 7.48-7.26 (m, 3H), 7.17 (m, 1H), 6.66 (m, 1H), 5.06 (br.s., 1H), 4.99 (m, 2H), 4.72 (m, 2H), 4.25 (m, 2H), 2.67 (m, 2H), 2.42-2.01 (m, 5H), 1.91-1.60 (m, 6H), 1.12 (m, 9H). LCMS (ES+) (m/z): 564.41 (M+1).

Example 104: (S)-2-(tert-butoxy)-2-((M)-2-(3,3-dimethylbutanoyl)-6-(8-fluoro-5-methylchroman-6-yl)-4,7-dimethylisoindolin-5-yl)acetic acid The title compound was made in a similar manner to example 103.

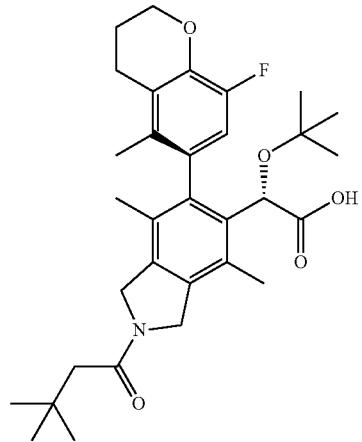

$^1$H NMR (400 MHz, CDCl$_3$) δ 6.68 (m, 1H), 5.08 (br.s., 1H), 4.80 (m, 4H), 4.26 (m, 2H), 2.69 (m, 2H), 2.36-2.24 (m, 5H), 2.11 (m, 2H), 1.85 (m, 3H), 1.77 (s, 3H), 1.16-1.08 (m, 18H). LCMS (ES+) (m/z): 540.58 (M+1).

Example 105: (S)-2-(tert-butoxy)-2-(2-(2,3-dihydrobenzo[b][1,4]dioxine-5-carbonyl)-4,7-dimethyl-6-(p-tolyl)isoindolin-5-yl)acetic acid

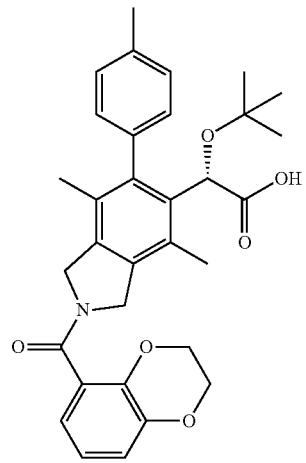 [SMILES: Cc1ccc(-c2c(C)c3c(c(C)c2[C@H](OC(C)(C)C)C(=O)O)CN(C(=O)c2cccc4c2OCCO4)C3)cc1]

Step 1: (S)-methyl 2-(tert-butoxy)-2-(2-(2,3-dihydrobenzo[b][1,4]dioxine-5-carbonyl)-4,7-dimethyl-6-(p-tolyl)isoindolin-5-yl)acetate

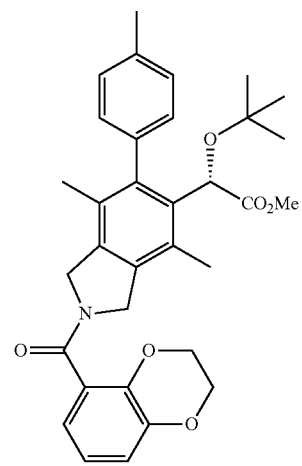 [SMILES: COC(=O)[C@@H](OC(C)(C)C)c1c(C)c2c(c(C)c1-c1ccc(C)cc1)CN(C(=O)c1cccc3c1OCCO3)C2]

A solution of (S)-methyl 2-(tert-butoxy)-2-(4,7-dimethyl-6-(p-tolyl)isoindolin-5-yl)acetate (40 mg, 0.105 mmol) in ethyl acetate (2 mL) was treated with 2,3-dihydrobenzo[b][1,4]dioxine-5-carboxylic acid (37.8 mg, 0.210 mmol), Et$_3$N (0.044 mL, 0.315 mmol), and Propylphosphonic anhydride (~50 wt % in EtOAc) (0.156 mL, 0.262 mmol) at ambient temperature. After 1 h, the reaction mixture was diluted with sat. NaHCO$_3$ and the layers partitioned. The organic layer was washed with brine, dried (Na2SO4), filtered and concentrated in vacuo to afford the title compound (55 mg, 97%) as a purple solid. LCMS (m/z) ES$^+$=544 (M+1).

Step 2: (S)-2-(tert-butoxy)-2-(2-(2,3-dihydrobenzo[b][1,4]dioxine-5-carbonyl)-4,7-dimethyl-6-(p-tolyl)isoindolin-5-yl)acetic acid A solution of (S)-methyl 2-(tert-butoxy)-2-(2-(2,3-dihydrobenzo[b][1,4]dioxine-5-carbonyl)-4,7-dimethyl-6-(p-tolyl)isoindolin-5-yl)acetate (55.3 mg, 0.102 mmol) in tetrahydrofuran (3 mL) and Methanol (3 mL) was treated with 2M LiOH (0.524 mL, 1.048 mmol) and stirred at 70° C. After 10 h, the reaction mixture was cooled to ambient temperature and concentrated in vacuo. The residue was purified by reverse phase HPLC to afford the title compound (27.2 mg, 0.049 mmol, 46.5% yield) as white solid. $^1$H NMR (400 MHz, CHLOROFORM-d) δ ppm 7.35 (d, J=7.0 Hz, 1H), 7.30-7.17 (m, 2H), 7.12-7.00 (m, 1H), 6.99-6.85 (m, 3H), 5.16 (s, 1H), 5.07-4.89 (m, 2H), 4.72-4.55 (m, 2H), 4.36-4.24 (m, 4H), 2.42 (d, J=5.5 Hz, 3H), 2.35-2.07 (m, 3H), 2.00-1.72 (m, 3H), 0.99 (d, J=8.0 Hz, 9H); LCMS (m/z) ES$^+$=530 (M+1).

Examples 106-123 were made in a similar manner as Example 105.

Example 106: (S)-2-(tert-butoxy)-2-(4,7-dimethyl-2-(2-(piperidin-1-yl)acetyl)-6-(p-tolyl)isoindolin-5-yl)acetic acid

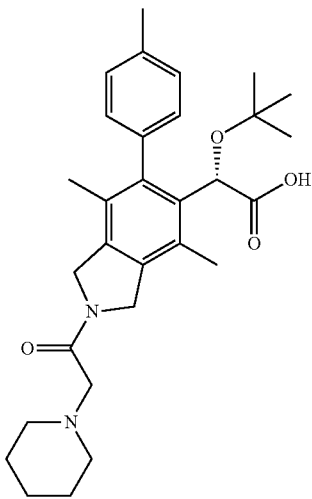 [SMILES: Cc1ccc(-c2c(C)c3c(c(C)c2[C@H](OC(C)(C)C)C(=O)O)CN(C(=O)CN2CCCCC2)C3)cc1]

$^1$H NMR (400 MHz, CDCl$_3$) δ 7.37-7.30 (m, 1H), 7.29-7.18 (m, 2H), 7.07 (d, J=7.3 Hz, 1H), 5.16 (d, J=4.7 Hz, 1H), 4.92-4.59 (m, 4H), 4.37-4.19 (m, 1H), 4.01 (d, J=15.5 Hz, 1H), 3.84-3.56 (m, 2H), 3.37 (br. s., 2H), 2.42 (s, 3H), 2.26 (d, J=9.7 Hz, 3H), 2.12-1.91 (m, 5H), 1.88 (d, J=7.4 Hz, 3H), 1.52 (br. s., 1H), 0.99 (d, J=1.8 Hz, 9H). LCMS (ES+) (m/z): 493 (M+1).

Example 107: (S)-2-(tert-butoxy)-2-(2-(cyclohexanecarbonyl)-4,7-dimethyl-6-(p-tolyl)isoindolin-5-yl)acetic acid

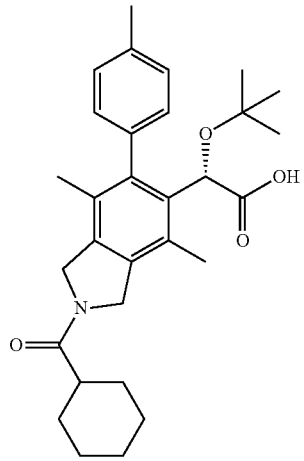 [SMILES: Cc1ccc(-c2c(C)c3c(c(C)c2[C@H](OC(C)(C)C)C(=O)O)CN(C(=O)C2CCCCC2)C3)cc1]

$^1$H NMR (400 MHz, METHANOL-d$_4$) δ 7.36-7.22 (m, 3H), 7.09 (d, J=7.6 Hz, 1H), 5.05 (d, J=1.3 Hz, 1H), 4.94 (br. s., 2H), 4.72 (br. s., 2H), 2.76-2.59 (m, 1H), 2.42 (s, 3H), 2.33 (d, J=10.1 Hz, 3H), 1.94-1.80 (m, 7H), 1.75 (d, J=12.1 Hz, 1H), 1.61-1.22 (m, 5H), 0.93 (d, J=1.2 Hz, 9H). LCMS (ES+) (m/z): 478 (M+1).

Example 108: (S)-2-(tert-butoxy)-2-(2-(3-fluorobenzoyl)-4,7-dimethyl-6-(p-tolyl)isoindolin-5-yl)acetic acid $^1$H NMR (400 MHz, METHANOL-d$_4$) δ 7.61-7.49 (m, 1H), 7.49-7.44 (m, 1H), 7.40 (d, J=9.1 Hz, 1H), 7.32-7.20 (m, 4H), 7.08 (dd, J=8.0, 14.7 Hz, 1H), 5.05 (d, J=4.1 Hz, 1H), 4.96 (br. s., 2H), 4.81 (d, J=3.2 Hz, 2H), 2.42 (d, J=6.8 Hz, 3H), 2.38-2.11 (m, 3H), 1.99-1.68 (m, 3H), 0.93 (d, J=7.6 Hz, 9H). LCMS (ES+) (m/z): 490 (M+1).

Example 109: (S)-2-(tert-butoxy)-2-(4,7-dimethyl-2-pivaloyl-6-(p-tolyl)isoindolin-5-yl)acetic acid Example 111: (S)-2-(tert-butoxy)-2-(2-(4,4-difluorocyclohexanecarbonyl)-4,7-dimethyl-6-(p-tolyl)isoindolin-5-yl)acetic acid

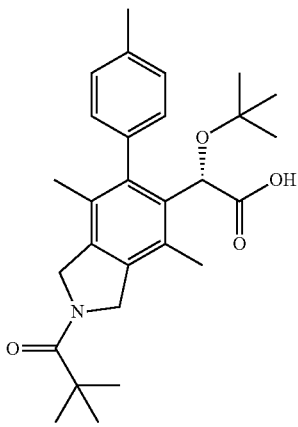 [SMILES: Cc1ccc(-c2c(C)c3c(c(C)c2[C@H](OC(C)(C)C)C(=O)O)CN(C(=O)C(C)(C)C)C3)cc1]

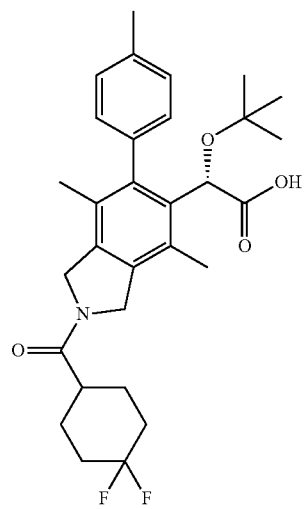

¹H NMR (400 MHz, CDCl₃) δ 7.36 (d, J=7.0 Hz, 1H), 7.30-7.19 (m, 2H), 7.08 (d, J=7.3 Hz, 1H), 5.17 (s, 1H), 5.10-4.70 (m, 4H), 2.42 (s, 3H), 2.28 (s, 3H), 1.91 (s, 3H), 1.38 (s, 9H), 1.00 (s, 9H). LCMS (ES+) (m/z): 452 (M+1).

¹H NMR (400 MHz, CDCl₃) δ 7.43-7.31 (m, 1H), 7.31-7.20 (m, 2H), 7.07 (d, J=7.2 Hz, 1H), 5.17 (d, J=5.3 Hz, 1H), 4.95-4.69 (m, 4H), 2.68-2.53 (m, 1H), 2.42 (s, 3H), 2.35-2.19 (m, 5H), 2.11-1.70 (m, 9H), 1.00 (s, 9H). LCMS (ES+) (m/z): 514 (M+1).

Example 110: (S)-2-(tert-butoxy)-2-(2-(3,3-dimethylbutanoyl)-4,7-dimethyl-6-(p-tolyl)isoindolin-5-yl)acetic acid Example 112: (S)-2-(tert-butoxy)-2-(2-(cyclopentanecarbonyl)-4,7-dimethyl-6-(p-tolyl)isoindolin-5-yl)acetic acid

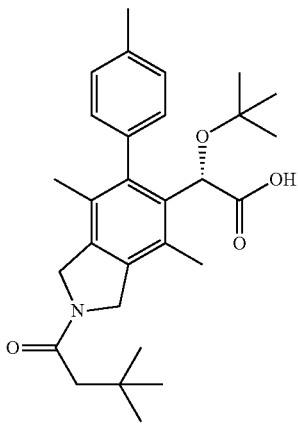 [SMILES: Cc1ccc(-c2c(C)c3c(c(C)c2[C@H](OC(C)(C)C)C(=O)O)CN(C(=O)CC(C)(C)C)C3)cc1]

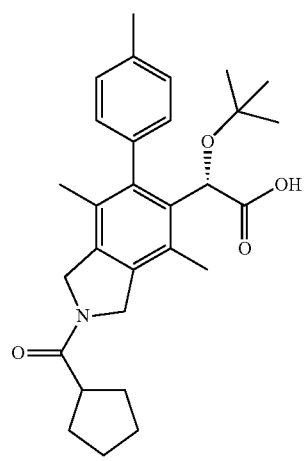 [SMILES: Cc1ccc(-c2c(C)c3c(c(C)c2[C@H](OC(C)(C)C)C(=O)O)CN(C(=O)C2CCCC2)C3)cc1]

¹H NMR (400 MHz, CDCl₃) δ 7.35 (d, J=6.9 Hz, 1H), 7.31-7.17 (m, 2H), 7.08 (d, J=6.8 Hz, 1H), 5.17 (d, J=5.1 Hz, 1H), 4.93-4.65 (m, 4H), 2.42 (s, 3H), 2.35 (dd, J=2.3, 5.4 Hz, 2H), 2.27 (s, 3H), 1.91 (s, 3H), 1.14 (d, J=3.3 Hz, 9H), 1.00 (s, 9H). LCMS (ES+) (m/z): 466 (M+1).

¹H NMR (400 MHz, CDCl₃) δ 0.99 (s, 9H), 1.63 (d, J=5.52 Hz, 2H), 1.82 (d, J=7.03 Hz, 2H), 1.90 (s, 7H), 2.27 (br. s., 3H), 2.41 (s, 3H), 2.93 (d, J=8.03 Hz, 1H), 4.70-4.91 (m, 4H), 5.16 (d, J=4.52 Hz, 1H), 7.08 (br. s., 1H), 7.19-7.31 (m, 2H), 7.36 (br. s., 1H). LCMS (ES+) (m/z): 464.49 (M+1), 486.40 (M+23), 927.84 (2M+1).

Example 113: (2S)-2-(tert-butoxy)-2-(2-(3,3-difluorocyclopentanecarbonyl)-4,7-dimethyl-6-(p-tolyl)isoindolin-5-yl)acetic acid

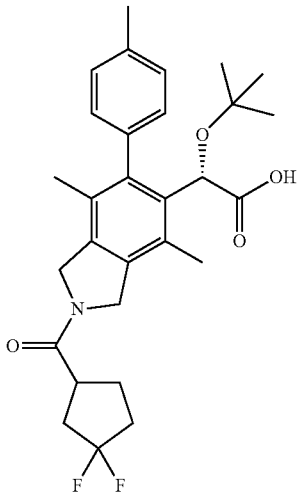 [SMILES: Cc1ccc(-c2c(C)c3c(c(C)c2[C@H](OC(C)(C)C)C(=O)O)CN(C(=O)C2CCC(F)(F)C2)C3)cc1]

$^1$H NMR (400 MHz, CDCl$_3$) δ 0.99 (s, 9H), 1.90 (s, 3H), 2.12 (d, J=8.03 Hz, 4H), 2.27 (s, 3H), 2.34 (br. s., 2H), 2.39-2.46 (m, 3H), 2.56 (d, J=12.55 Hz, 1H), 3.22 (d, J=8.53 Hz, 1H), 4.71-4.91 (m, 4H), 5.16 (d, J=3.26 Hz, 1H), 7.07 (br. s., 1H), 7.19-7.30 (m, 2H), 7.30-7.41 (m, 1H). LCMS (ES+) (m/z): 500.49 (M+1), 522.42 (M+23), 1021.78 (2M+23).

Example 114: (S)-2-(tert-butoxy)-2-(2-(3-methoxybenzoyl)-4,7-dimethyl-6-(p-tolyl)isoindolin-5-yl) acetic acid

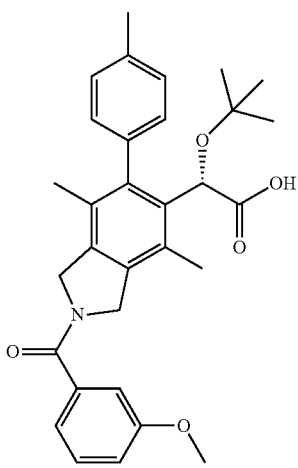 [SMILES: COc1cccc(C(=O)N2Cc3c(C)c(-c4ccc(C)cc4)c([C@H](OC(C)(C)C)C(=O)O)c(C)c3C2)c1]

$^1$H NMR (400 MHz, CDCl$_3$) δ 0.98 (d, J=8.03 Hz, 9H), 1.78 (br. s., 1.5H), 1.86-2.00 (m, 1.5H), 2.14 (br. s., 1.5H), 2.22-2.36 (m, 1.5H), 2.41 (br. s., 3H), 3.86 (br. s., 3H), 4.73 (d, J=12.55 Hz, 3H), 4.88-5.10 (m, 2H), 5.15 (br. s., 1H), 7.01 (br. s., 2H), 7.05-7.18 (m, 3H), 7.26 (br. s., 3H), 7.36 (br. s., 2H). LCMS (ES+) (m/z): 502.37 (M+1, 524.36 (M+23), 1003.69 (2M+1), 1025.53 (2M+23).

Example 115: (S)-2-(tert-butoxy)-2-(2-(3-fluoro-4-methylbenzoyl)-4,7-dimethyl-6-(p-tolyl)isoindolin-5-yl)acetic acid

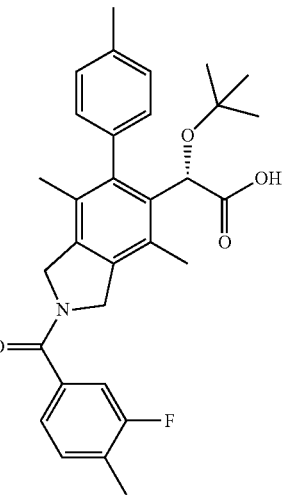

$^1$H NMR (400 MHz, CDCl$_3$) δ 0.98 (d, J=8.53 Hz, 9H), 1.79 (s, 1.5H), 1.94 (s, 1.5H), 2.15 (s, 1.5H), 2.31 (s, 1.5H), 2.33-2.38 (m, 4H), 2.41 (d, J=5.27 Hz, 3H), 4.74 (d, J=13.80 Hz, 2H), 4.88-5.09 (m, 2H), 5.15 (s, 1H), 7.19-7.30 (m, 9H), 7.35 (d, J=7.28 Hz, 1H). LCMS (ES+) (m/z): 504.38 (M+1), 1007.78 (2M+1), 1029.73 (2M+23).

Example 116: (S)-2-(tert-butoxy)-2-(2-(4-methoxycyclohexanecarbonyl)-4,7-dimethyl-6-(p-tolyl)isoindolin-5-yl)acetic acid

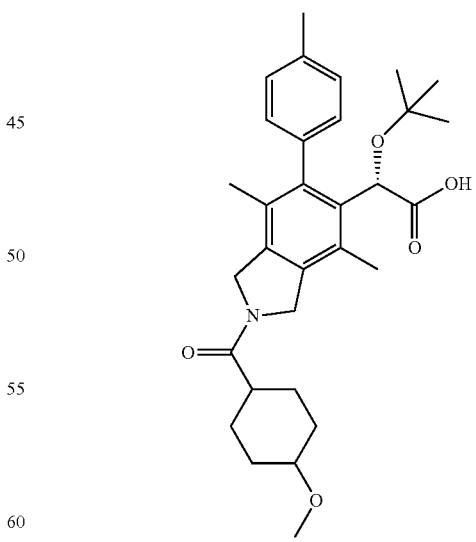

$^1$H NMR (400 MHz, CDCl$_3$) δ 1.02 (s, 9H) 1.23-1.42 (m, 2H) 1.72 (d, J=11.29 Hz, 2H) 1.94 (d, J=8.03 Hz, 6H) 2.24 (d, J=12.55 Hz, 2H) 2.30 (d, J=7.03 Hz, 3H) 2.44 (s, 3H) 2.47-2.59 (m, 1H) 3.24 (br. s., 1H) 3.42 (d, J=3.01 Hz, 3H) 4.71-4.94 (m, 4H) 5.19 (d, J=4.52 Hz, 1H) 7.09 (d, J=6.53

Hz, 1H) 7.22-7.34 (m, 2H) 7.38 (d, J=5.77 Hz, 1H). LCMS (ES+) (m/z): 508.54 (M+1), 1015.78 (2M+1), 1037.62 (2M+23).

Example 117: (S)-2-(tert-butoxy)-2-(2-(2-cyclohexylacetyl)-4,7-dimethyl-6-(p-tolyl)isoindolin-5-yl)acetic acid

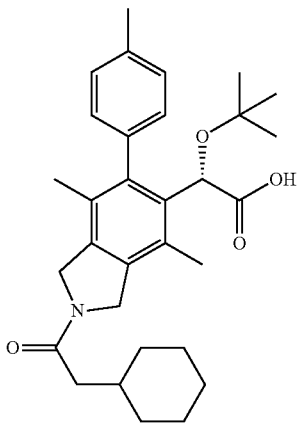 [SMILES: Cc1ccc(-c2c(C)c3c(c(C)c2[C@H](OC(C)(C)C)C(=O)O)CN(C(=O)CC2CCCCC2)C3)cc1]

$^1$H NMR (400 MHz, CDCl$_3$) δ 7.42-7.31 (m, 1H), 7.30-7.18 (m, 2H), 7.07 (d, J=7.1 Hz, 1H), 5.17 (d, J=5.0 Hz, 1H), 4.90-4.69 (m, 4H), 2.42 (s, 3H), 2.35-2.21 (m, 5H), 2.04-1.93 (m, 1H), 1.91 (s, 3H), 1.83 (d, J=12.5 Hz, 2H), 1.76-1.62 (m, 3H), 1.42-1.25 (m, 2H), 1.24-1.09 (m, 1H), 1.09-0.91 (m, 11H). LCMS (ES+) (m/z): 492 (M+1).

Example 118: (S)-2-(tert-butoxy)-2-(4,7-dimethyl-2-(spiro[3.3]heptane-2-carbonyl)-6-(p-tolyl)isoindolin-5-yl)acetic acid

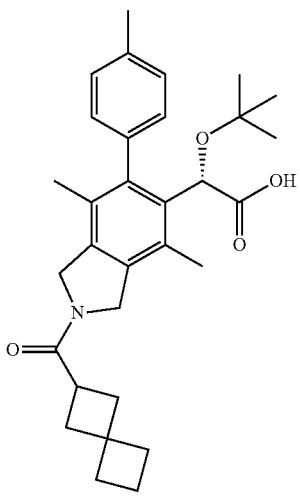 [SMILES: Cc1ccc(-c2c(C)c3c(c(C)c2[C@H](OC(C)(C)C)C(=O)O)CN(C(=O)C2CC4(CCC4)C2)C3)cc1]

$^1$H NMR (400 MHz, CDCl$_3$) δ 7.47-7.31 (m, 1H), 7.29-7.17 (m, 2H), 7.15-6.97 (m, 1H), 5.17 (d, J=4.8 Hz, 1H), 4.89-4.57 (m, 4H), 3.25-3.08 (m, 1H), 2.47-2.32 (m, 5H), 2.31-2.18 (m, 5H), 2.11 (q, J=6.8 Hz, 2H), 2.00-1.92 (m, 2H), 1.92-1.78 (m, 5H), 1.00 (s, 9H). LCMS (ES+) (m/z): 490.51 (M+1).

Example 119: (S)-2-(tert-butoxy)-2-(2-(3,5-difluorobenzoyl)-4,7-dimethyl-6-(p-tolyl)isoindolin-5-yl)acetic acid

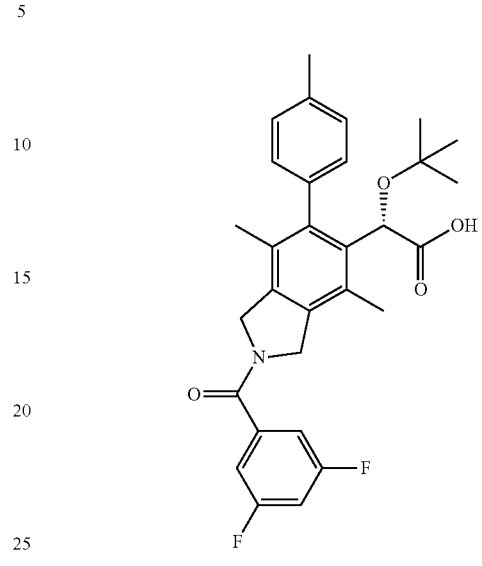

$^1$H NMR (400 MHz, CDCl$_3$) δ 7.36 (d, J=7.2 Hz, 1H), 7.30-7.18 (m, 2H), 7.15-7.00 (m, 3H), 6.94 (tdt, J=2.3, 6.5, 8.8 Hz, 1H), 5.16 (s, 1H), 5.10-4.87 (m, 2H), 4.81-4.63 (m, 2H), 2.42 (d, J=4.9 Hz, 3H), 2.36-2.12 (m, 3H), 2.00-1.76 (m, 3H), 0.99 (d, J=7.6 Hz, 9H). LCMS (ES+) (m/z): 508 (M+1).

Example 120: (S)-2-(tert-butoxy)-2-(2-(2,3-difluorobenzoyl)-4,7-dimethyl-6-(p-tolyl)isoindolin-5-yl)acetic acid

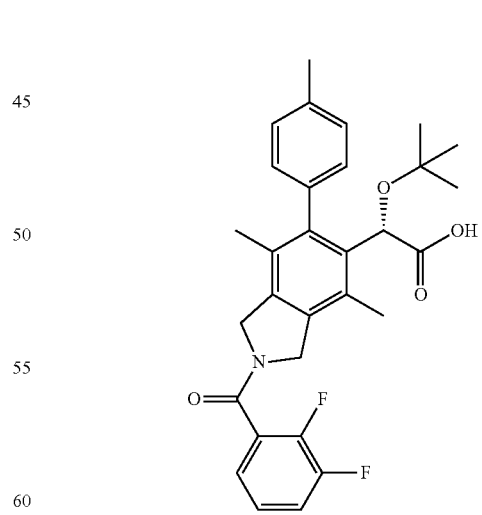

$^1$H NMR (400 MHz, METHANOL-d$_4$) δ 7.52-7.38 (m, 1H), 7.37-7.20 (m, 5H), 7.09 (dd, J=8.0, 14.8 Hz, 1H), 5.05 (d, J=4.2 Hz, 1H), 5.01-4.90 (m, 2H), 4.75-4.65 (m, 2H), 2.42 (d, J=7.4 Hz, 3H), 2.39-2.13 (m, 3H), 1.99-1.71 (m, 3H), 0.93 (d, J=8.3 Hz, 9H). LCMS (ES+) (m/z): 508 (M+1).

Example 121: (S)-2-(tert-butoxy)-2-(2-(5-fluoro-2-methylbenzoyl)-4,7-dimethyl-6-(p-tolyl)isoindolin-5-yl)acetic acid

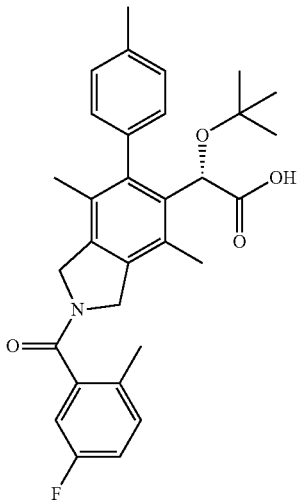 [SMILES: Cc1ccc(-c2c(C)c3c(c(C)c2[C@H](OC(C)(C)C)C(=O)O)CN(C(=O)c2cc(F)ccc2C)C3)cc1]

¹H NMR (400 MHz, METHANOL-d$_4$) δ 7.36 (td, J=5.7, 8.4 Hz, 1H), 7.31-7.21 (m, 3H), 7.19-7.03 (m, 3H), 5.04 (d, J=4.8 Hz, 1H), 4.98-4.91 (m, 2H), 4.55 (d, J=3.2 Hz, 2H), 2.41 (d, J=8.2 Hz, 3H), 2.37 (s, 1.5H), 2.32 (s, 3H), 2.16 (s, 1.5H), 1.97-1.69 (m, 3H), 0.93 (d, J=8.9 Hz, 9H). LCMS (ES+) (m/z): 504 (M+1).

Example 122: (S)-2-(tert-butoxy)-2-(2-(3-fluoro-5-methoxybenzoyl)-4,7-dimethyl-6-(p-tolyl)isoindolin-5-yl)acetic acid

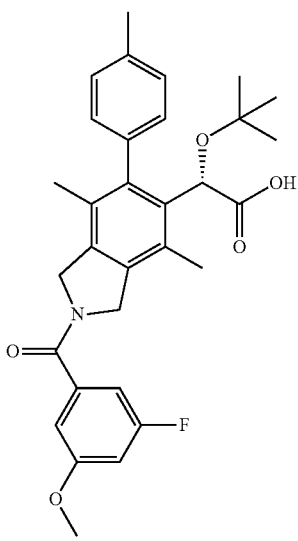 [SMILES: COc1cc(F)cc(C(=O)N2Cc3c(C)c(-c4ccc(C)cc4)c([C@H](OC(C)(C)C)C(=O)O)c(C)c3C2)c1]

¹H NMR (400 MHz, METHANOL-d$_4$) δ 7.32-7.21 (m, 3H), 7.08 (dd, J=8.0, 13.4 Hz, 1H), 7.02-6.92 (m, 2H), 6.90-6.81 (m, 1H), 5.04 (d, J=3.9 Hz, 1H), 4.98-4.91 (m, 2H), 4.80 (d, J=4.1 Hz, 2H), 3.86 (d, J=5.7 Hz, 3H), 2.42 (d, J=6.3 Hz, 3H), 2.38-2.17 (m, 3H), 1.96-1.75 (m, 3H), 0.93 (d, J=6.9 Hz, 9H). LCMS (ES+) (m/z): 520 (M+1).

Example 123: (S)-2-(tert-butoxy)-2-(2-(3-fluoro-5-methylbenzoyl)-4,7-dimethyl-6-(p-tolyl)isoindolin-5-yl)acetic acid

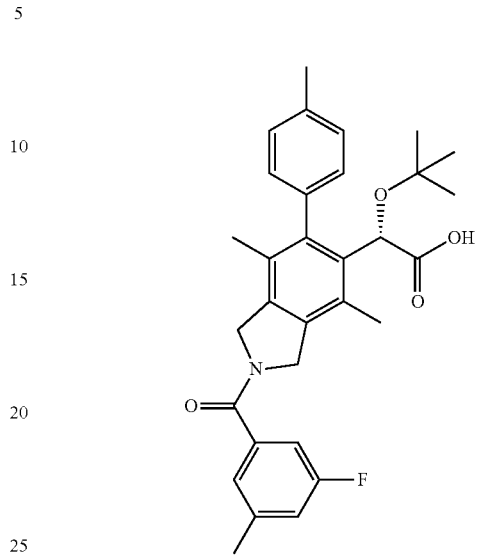

¹H NMR (400 MHz, METHANOL-d$_4$) δ 7.32-7.23 (m, 4H), 7.21-7.02 (m, 3H), 5.04 (d, J=4.0 Hz, 1H), 4.98-4.91 (m, 2H), 4.80 (d, J=3.6 Hz, 2H), 2.48-2.39 (m, 6H), 2.38-2.16 (m, 3H), 1.97-1.74 (m, 3H), 0.93 (d, J=7.3 Hz, 9H). LCMS (ES+) (m/z): 504 (M+1).

Example 124: (S)-2-(tert-butoxy)-2-(4,7-dimethyl-6-(p-tolyl)isoindolin-5-yl)acetic acid The title compound was made in a similar manner to Example 1.

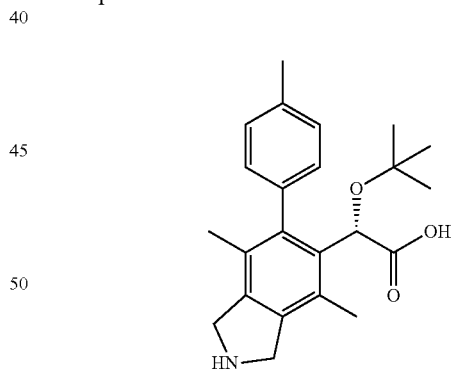

¹H NMR (400 MHz, METHANOL-d$_4$) δ 7.41-7.24 (m, 3H), 7.11 (d, J=7.5 Hz, 1H), 5.07 (s, 1H), 4.66 (d, J=5.0 Hz, 4H), 2.45 (s, 3H), 2.39 (s, 3H), 1.95 (s, 3H), 0.95 (s, 9H). LCMS (ES+) (m/z): 368 (M+1).

Example 125: (S)-2-(tert-butoxy)-2-(2-((2,3-dihydrobenzo[b][1,4]dioxin-5-yl)methyl)-4,7-dimethyl-6-(p-tolyl)isoindolin-5-yl)acetic acid The title compound was made in a similar manner to Example 1.

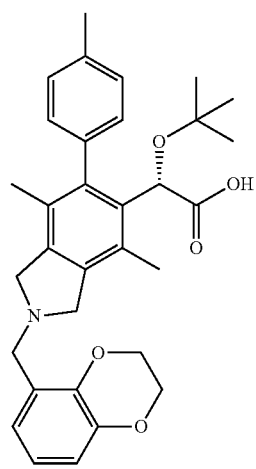 [SMILES: Cc1ccc(-c2c(C)c3c(c(C)c2[C@H](OC(C)(C)C)C(=O)O)CN(Cc2cccc4c2OCCO4)C3)cc1]

¹H NMR (400 MHz, CDCl₃) δ 7.37-7.30 (m, 1H), 7.27 (s, 2H), 7.08 (d, J=7.7 Hz, 1H), 7.03-6.84 (m, 3H), 5.14 (s, 1H), 5.00 (t, J=14.0 Hz, 2H), 4.48-4.19 (m, 8H), 2.42 (s, 3H), 2.22 (s, 3H), 1.87 (s, 3H), 0.97 (s, 9H). LCMS (ES+) (m/z): 516 (M+1).

Example 126: (S)-2-(tert-butoxy)-2-(2-(tert-butoxycarbonyl)-4,7-dimethyl-6-(p-tolyl)isoindolin-5-yl)acetic acid The title compound was made in a similar manner to Example 48.

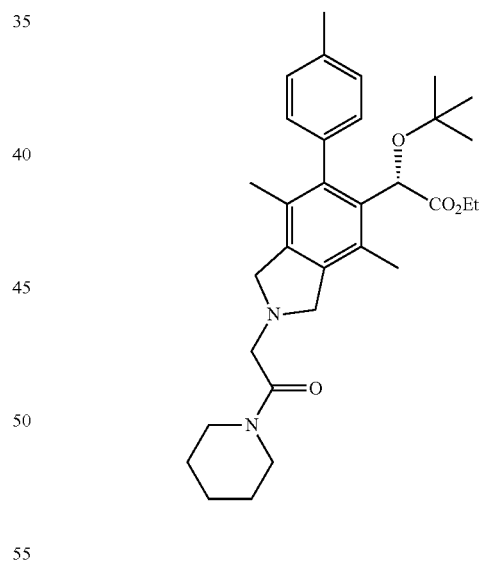

¹H NMR (400 MHz, CDCl₃) δ 7.36 (br. s., 1H), 7.29-7.19 (m, 2H), 7.07 (d, J=7.4 Hz, 1H), 5.16 (d, J=2.2 Hz, 1H), 4.79-4.49 (m, 4H), 2.42 (s, 3H), 2.26 (s, 3H), 1.89 (s, 3H), 1.54 (d, J=3.1 Hz, 9H), 0.99 (s, 9H). LCMS (ES−) (m/z): 466 (M−1).

Example 127: (S)-2-(tert-butoxy)-2-(4,7-dimethyl-2-(2-oxo-2-(piperidin-1-yl)ethyl)-6-(p-tolyl)isoindolin-5-yl)acetic acid

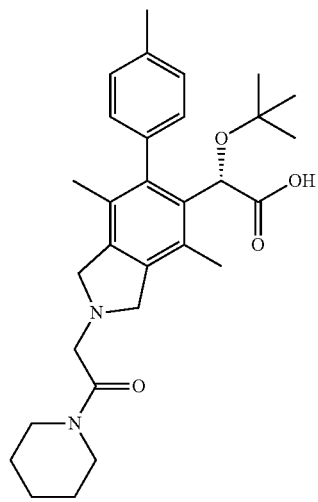 [SMILES: Cc1ccc(-c2c(C)c3c(c(C)c2[C@H](OC(C)(C)C)C(=O)O)CN(CC(=O)N2CCCCC2)C3)cc1]

Step 1: (S)-Methyl 2-(tert-butoxy)-2-(4,7-dimethyl-2-(2-oxo-2-(piperidin-1-yl)ethyl)-6-(p-tolyl)isoindolin-5-yl)acetate An ice cold suspension of (S)-Ethyl 2-(tert-butoxy)-2-(4,7-dimethyl-6-(p-tolyl)isoindolin-5-yl)acetate (20 mg, 0.051 mmol) in DCM (0.5 mL) was treated with 2-chloro-1-(piperidin-1-yl)ethanone (9.81 mg, 0.061 mmol), and Et₃N (10.57 μl, 0.076 mmol). After 18 h. the reaction mixture was diluted with sat. NaHCO₃ and the layers partitioned. The organic phase was washed with water, brine, dried over Na₂SO₄, filtered, and concentrated in vacuo to afford the title compound (31.5 mg, 120% yield) as a brown oil. LCMS (ES+) (m/z): 521.56 (M+1).

Step 2: (S)-2-(tert-butoxy)-2-(4,7-dimethyl-2-(2-oxo-2-(piperidin-1-yl)ethyl)-6-(D-tolyl)isoindolin-5-yl)acetic acid An ice cold solution of crude (S)-ethyl 2-(tert-butoxy)-2-(4,7-dimethyl-2-(2-oxo-2-(piperidin-1-yl)acetyl)-6-(p-tolyl)isoindolin-5-yl)acetate (44.3 mg, 0.083 mmol) in THF (3 mL) and ethanol (3 mL) was treated with 2M LiOH (0.208 mL, 0.415 mmol) and stirred at 70° C. After 18 h, the reaction mixture was cooled to ambient temperature and concentrated in vacuo. The residue was purified by reverse phase HPLC to afford the title compound (15 mg, 34.6% yield) as beige solid. $^1$H NMR (400 MHz, CHLOROFORM-d) δ ppm 7.35 (d, J=7.3 Hz, 1H), 7.30-7.18 (m, 2H), 7.08 (br. s., 1H), 5.17 (s, 1H), 5.02-4.68 (m, 4H), 3.72-3.59 (m, 2H), 3.52-3.35 (m, 2H), 2.42 (s, 3H), 2.34-2.16 (m, 3H), 1.97-1.82 (m, 3H), 1.79-1.54 (m, 6H), 1.00 (d, J=3.1 Hz, 9H); LCMS (m/z) ES$^-$=505 (M−1).

Example 128: (S)-2-(tert-butoxy)-2-(2-(imino(piperidin-1-yl)methyl)-4,7-dimethyl-6-(p-tolyl)isoindolin-5-yl)acetic acid

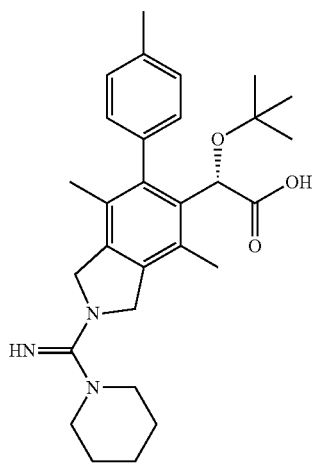

Step 1: (S)-Ethyl 2-(tert-butoxy)-2-(2-cyano-4,7-dimethyl-6-(p-tolyl)isoindolin-5-yl)acetate

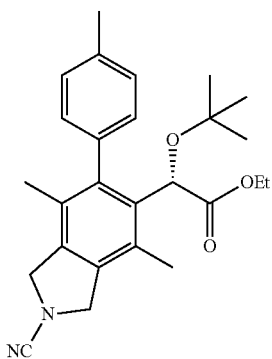 [SMILES: CCOC(=O)[C@@H](OC(C)(C)C)c1c(C)c2c(c(C)c1-c1ccc(C)cc1)CN(C#N)C2]

A solution of (S)-Ethyl 2-(tert-butoxy)-2-(4,7-dimethyl-6-(p-tolyl)isoindolin-5-yl)acetate (30 mg, 0.076 mmol) and Et$_3$N (0.014 mL, 0.099 mmol) in THF (0.5 mL) was treated with a solution of cyanogen bromide (9.24 mg, 0.087 mmol) in THF (0.5 mL) and stirred at ambient temperature. After 18 h, the mixture was filtered through acrodisc ptfe filter and partitioned between EtOAc and sat. NaHCO$_3$. The organics were washed with brine, dried (Na$_2$SO$_4$), filtered and concentrated in vacuo to afford the title compound (36.9 mg, 115% yield) as a brown oil. LCMS (m/z) ES+=443 (M+Na).

Step 2: (S)-Ethyl 2-(tert-butoxy)-2-(2-(imino(piperidin-1-yl)methyl)-4,7-dimethyl-6-(p-tolyl)isoindolin-5-yl)acetate

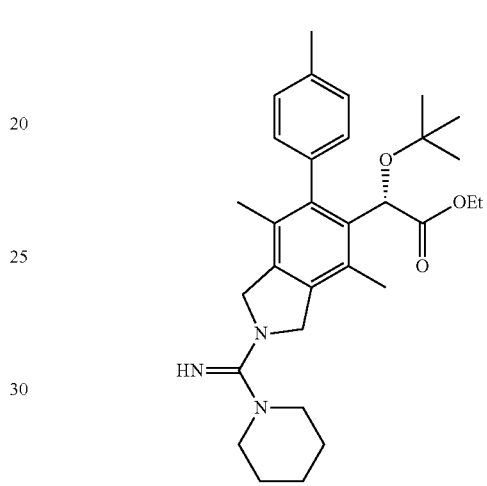

A solution of (S)-Ethyl 2-(tert-butoxy)-2-(2-cyano-4,7-dimethyl-6-(p-tolyl)isoindolin-5-yl)acetate (17.3 mg, 0.041 mmol) in DCM (0.5 mL) was treated with piperidine (0.3 mL) and heated at 60° C. After 18 h, additional piperidine (400 uL) and pyridine (20 uL) was added and stirring continued for an additional 6 h. Additional piperidine (400 uL) and Et$_3$N (0.014 mL, 0.099 mmol), was added and the temperature of the reaction mixture was raised to 70° C. After 18 h, the reaction mixture was diluted with water and the laters partitioned. The organic layer was washed with 1N HCl, brine, dried over Na$_2$SO$_4$, filtered, and concentrated in vacuo to afford the title compound. LCMS (m/z) ES$^+$=506 (M+1).

Step 3: (S)-2-(tert-butoxy)-2-(2-(imino(piperidin-1-yl)methyl)-4,7-dimethyl-6-(p-tolyl)isoindolin-5-yl)acetic acid A solution of (20 mg, 0.041 mmol) in THF (0.5 mL) and EtOH (0.5 mL) was treated with 2M LiOH (205 uL) and stirred at 70° C. After 18 h, the reaction mixture was concentrated in vacuo and the residue purified by reverse phase HPLC to afford the title compound (1.1 mg, 2.073 μmol, 3.91% yield). $^1$H NMR (400 MHz, CHLOROFORM-d) δ ppm 7.39-7.32 (m, 1H), 7.31-7.21 (m, 2H), 7.07 (d, J=8.4 Hz, 1H), 5.16 (s, 1H), 4.98-4.87 (m, 2H), 4.80 (t, J=14.7 Hz, 2H), 3.43 (br. s., 4H), 2.43 (s, 3H), 2.27 (s, 3H), 1.91 (s, 3H), 1.77 (br. s., 6H), 0.99 (s, 9H); LCMS (m/z) ES$^+$=478 (M+1).

Example 129: (S)-2-(tert-butoxy)-2-(2-(imino(piperidin-1-yl)methyl)-4,7-dimethyl-6-(p-tolyl)isoindolin-5-yl)acetic acid

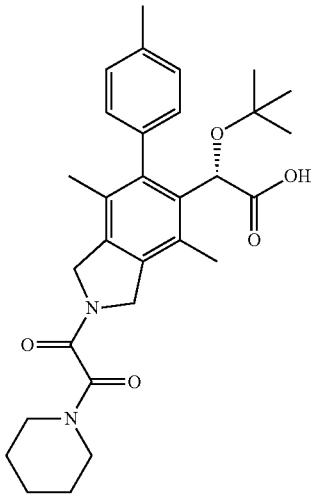 [SMILES: Cc1ccc(-c2c(C)c3c(c(C)c2[C@H](OC(C)(C)C)C(=O)O)CN(C(=O)C(=O)N2CCCCC2)C3)cc1]

2-oxo-2-(piperidin-1-yl)acetyl chloride

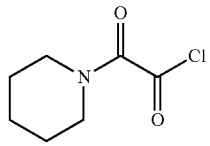 [SMILES: O=C(Cl)C(=O)N1CCCCC1]

An ice cold solution of 2-oxo-2-(piperidin-1-yl)acetic acid (70 mg, 0.445 mmol) in DCM (1.8 mL) was treated with oxalyl chloride (0.058 mL, 0.668 mmol) and DMF (2 drops). After 1 h, the reaction mixture was concentrated in vacuo to afford the title compound (100.3 mg, 0.571 mmol, 128% yield) as a yellow oil. $^1$H NMR (400 MHz, CHLOROFORM-d) δ ppm 3.64-3.52 (m, 2H), 3.46-3.31 (m, 2H), 1.81-1.60 (m, 6H); LCMS (m/z) ES+=172 (M+1, methyl ester).

Step 1: (S)-Ethyl 2-(tert-butoxy)-2-(4,7-dimethyl-2-(2-oxo-2-(piperidin-1-yl)acetyl)-6-(p-tolyl)isoindolin-5-yl)acetate

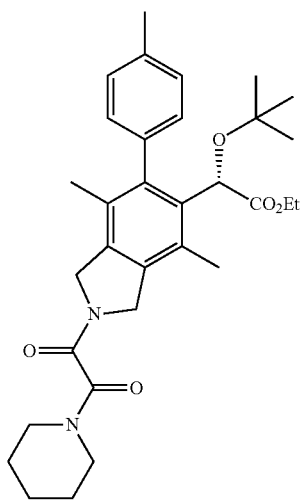 [SMILES: CCOC(=O)[C@@H](OC(C)(C)C)c1c(C)c2c(c(C)c1-c1ccc(C)cc1)CN(C(=O)C(=O)N1CCCCC1)C2]

An ice cold suspension of 2-oxo-2-(piperidin-1-yl)acetyl chloride (17.76 mg, 0.101 mmol) in DCM (0.5 mL) was treated dropwise with a solution of (S)-Ethyl 2-(tert-butoxy)-2-(4,7-dimethyl-6-(p-tolyl)isoindolin-5-yl)acetate (40 mg, 0.101 mmol) in DCM (0.5 mL), Et$_3$N (0.014 mL, 0.101 mmol) and was then warmed to ambient temperature. After 18 h, the reaction mixture was diluted with sat. aq. NaHCO3, extracted with DCM, washed with water, brine, dried over Na$_2$SO$_4$, filtered, and concentrated in vacuo. The residue was purified by silica gel chromatography (0-100% EtOAc/Hexane) to afford the title compound (44.3 mg, 0.083 mmol, 82% yield) as brown oil. LCMS (m/z) ES$^+$=1070 (2M+1).

Step 2: (S)-2-(tert-butoxy)-2-(2-(imino(piperidin-1-yl)methyl)-4,7-dimethyl-6-(p-tolyl)isoindolin-5-yl) acetic acid An ice cold solution of (S)-ethyl 2-(tert-butoxy)-2-(4,7-dimethyl-2-(2-oxo-2-(piperidin-1-yl)acetyl)-6-(p-tolyl)isoindolin-5-yl)acetate (44.3 mg, 0.083 mmol) in THF (3 mL) and Ethanol (3 mL) was treated with 2M LiOH (0.208 mL, 0.415 mmol) and stirred at 70° C. After 18 h, the reaction mixture was cooled to ambient temperature and concentrated in vacuo. The residue was purified by reverse phase HPLC to afford the title compound (15 mg, 34.6% yield) as beige solid. $^1$H NMR (400 MHz, CHLOROFORM-d) δ ppm 7.35 (d, J=7.3 Hz, 1H), 7.30-7.18 (m, 2H), 7.08 (br. s., 1H), 5.17 (s, 1H), 5.02-4.68 (m, 4H), 3.72-3.59 (m, 2H), 3.52-3.35 (m, 2H), 2.42 (s, 3H), 2.34-2.16 (m, 3H), 1.97-1.82 (m, 3H), 1.79-1.54 (m, 6H), 1.00 (d, J=3.1 Hz, 9H); LCMS (m/z) ES$^-$=505 (M−1).

Example 130: (S)-2-(tert-butoxy)-2-(4,7-dimethyl-2-(2-((R)-3-methylmorpholino)-2-oxoacetyl)-6-(p-tolyl)isoindolin-5-yl)acetic acid The title compound was made in a similar manner as Example 129.

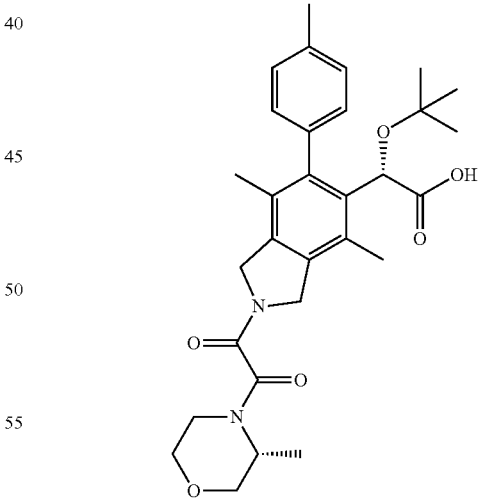

$^1$H NMR (400 MHz, METHANOL-d$_4$) δ 7.34-7.23 (m, 3H), 7.15-7.05 (m, 1H), 5.08-5.02 (m, 1H), 4.97-4.75 (m, 4H), 4.52 (dt, J=2.8, 6.8 Hz, 0.5H), 4.25-4.15 (m, 0.5H), 4.03-3.94 (m, 0.5H), 3.92-3.81 (m, 1H), 3.81-3.74 (m, 0.5H), 3.73-3.48 (m, 3H), 3.45 (d, J=12.0 Hz, 0.5H), 3.28-3.18 (m, 0.5H), 2.42 (s, 3H), 2.32 (d, J=18.1 Hz, 3H), 1.94-1.83 (m, 3H), 1.49-1.34 (m, 3H), 1.00-0.86 (m, 9H). LCMS (ES−) (m/z): 521 (M−1).

Example 131: (S)-2-(tert-butoxy)-2-(4,7-dimethyl-2-(piperidine-1-carbonothioyl)-6-(p-tolyl)isoindolin-5-yl)acetic acid

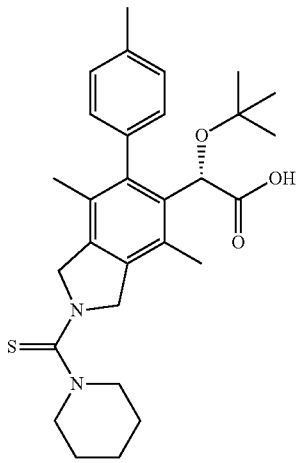 [SMILES: Cc1ccc(-c2c(C)c3c(c(C)c2[C@H](OC(C)(C)C)C(=O)O)CN(C(=S)N2CCCCC2)C3)cc1]

Step 1. (S)-Ethyl 2-(tert-butoxy)-2-(4,7-dimethyl-2-(piperidine-1-carbonothioyl)-6-(p-tolyl)isoindolin-5-yl)acetate

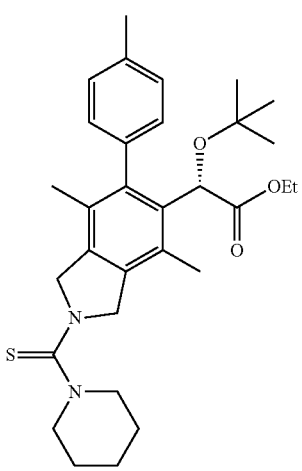 [SMILES: CCOC(=O)[C@@H](OC(C)(C)C)c1c(C)c2c(c(C)c1-c1ccc(C)cc1)CN(C(=S)N1CCCCC1)C2]

An ice cold suspension of 1,1'-thiocarbonyldiimidazole (18.92 mg, 0.106 mmol) in DCM (1 mL) was treated dropwise with a solution of (S)-Ethyl 2-(tert-butoxy)-2-(4,7-dimethyl-6-(p-tolyl)isoindolin-5-yl)acetate (40 mg, 0.101 mmol) in DCM (1 mL). After 25 min, the reaction mixture was treated with piperidine (0.011 mL, 0.111 mmol) and stirring continued at 0° C. After 1 h, additional piperidine (9 uL) and pyridine (9 uL, 0.111 mmol) was added and stirring continued at 0° C. After 1 h, the reaction mixture was warmed to 40° C. After 18 h, the reaction mixture was warmed to 60° C. After 18 h, additional DCM (0.5 mL) and piperidine (200 uL) was added and the reaction mixture warmed to 80° C. After 18 h, the reaction mixture was cooled to ambient temperature, diluted with water, extracted with DCM, and washed with 1N HCl, brine, dried over Na$_2$SO$_4$, filtered, and concentrated in vacuo to afford the title compound (38.7 mg, 0.074 mmol, 73.2% yield) as brown foam. LCMS (m/z) ES$^+$=523 (M+1).

Step 2. (S)-2-(tert-butoxy)-2-(4,7-dimethyl-2-(piperidine-1-carbonothioyl)-6-(D-tolyl)isoindolin-5-yl) acetic acid A solution of crude (S)-Ethyl 2-(tert-butoxy)-2-(4,7-dimethyl-2-(piperidine-1-carbonothioyl)-6-(p-tolyl)isoindolin-5-yl)acetate (38.7 mg, 0.074 mmol) in THF (1.5 mL) and Ethanol (1.5 mL) was treated with 2M LiOH (0.37 mL, 0.74 mmol) was warmed to 65° C. After 18 h, the reaction was cooled to ambient temperature and concentrated in vacuo. The residue was purified by reverse phase HPLC to afford the title compound (16.6 mg, 0.032 mmol, 31.9% yield) as pinkish beige solid. $^1$H NMR (400 MHz, METHANOL-d$_4$) δ ppm 7.33-7.22 (m, 3H), 7.09 (d, J=8.2 Hz, 1H), 5.11-4.92 (m, 5H), 3.47 (br. s., 4H), 2.42 (s, 3H), 2.32 (s, 3H), 1.89 (s, 3H), 1.71 (br. s., 6H), 0.94 (s, 9H); LCMS (m/z) ES$^+$=495 (M+1).

Example 132: (S)-2-(tert-butoxy)-2-(6-(4-chlorophenyl)-4,7-dimethyl-2-(piperidine-1-carbonyl)isoindolin-5-yl)acetic acid

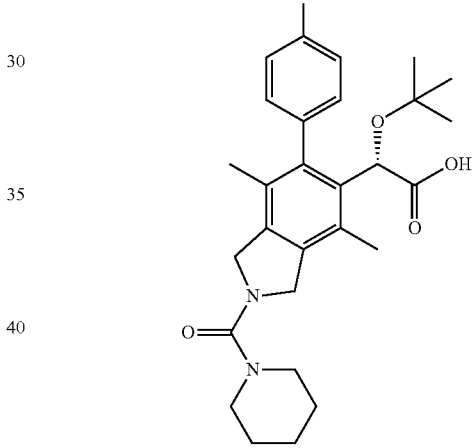

(S)-methyl 2-(tert-butoxy)-4-(4-chlorophenyl)but-3-ynoate

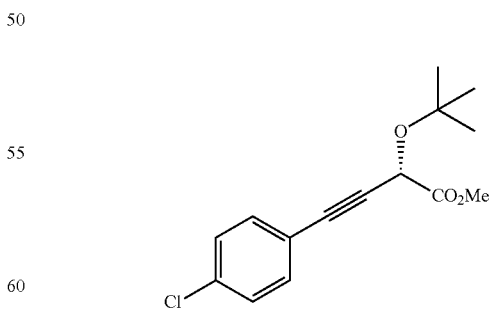

The title compound was made in a manner similar to Step 6 in Example 8 except using 1-chloro-4-iodobenzene in Step 3. $^1$H NMR (400 MHz, CHLOROFORM-d) δ=7.42-7.38 (m, 2H), 7.30 (d, J=8.3 Hz, 2H), 4.98 (s, 1H), 3.85 (s, 3H), 1.34 (s, 9H).

Step 1: (S)-benzyl 5-(1-(tert-butoxy)-2-methoxy-2-oxoethyl)-6-(4-chlorophenyl)-4,7-dimethylisoindoline-2-carboxylate

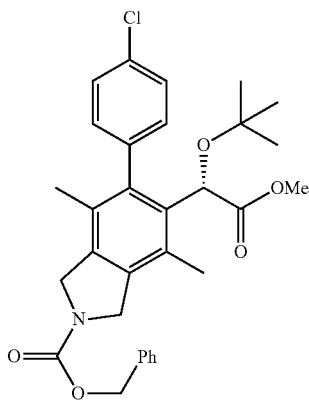 [SMILES: COC(=O)[C@@H](OC(C)(C)C)c1c(C)c2c(c(C)c1-c1ccc(Cl)cc1)CN(C(=O)OCc1ccccc1)C2]

To an oven dried flask under $N_2$ was added racemic BINAP (18 mg, 0.029 mmol) and [Rh(cod)$_2$]BF$_4$ (11.5 mg, 0.029 mmol) in dry DCM (5 mL) After 5 min, $H_2$ gas was bubbled through the solution and the reaction mixture stirred under an atmosphere of $H_2$. After 1 h, a solution of (S)-methyl 2-(tert-butoxy)-4-(4-chlorophenyl)but-3-ynoate (80 mg, 0.285 mmol) in DCM (1 mL) was added, followed by the dropwise addition of a solution of benzyl di(but-2-yn-1-yl)carbamate (109 mg, 0.427 mmol) in DCM (1 mL) and the reaction mixture was heated to reflux. After 3 h, the reaction mixture was charged with additional benzyl di(but-2-yn-1-yl)carbamate (109 mg, 0.427 mmol) in DCM (1 mL) and stirring continued. After 1 h, the reaction mixture was cooled to ambient temperature and concentrated in vacuo. The residue was purified by silica gel chromatography (0-40% EtOAc-hexanes) to afford the title compound (85 mg, 0.159 mmol, 55.6% yield). $^1$H NMR (400 MHz, CHLOROFORM-d) δ=7.50-7.27 (m, 8H), 7.14 (ddd, J=2.1, 3.7, 8.0 Hz, 1H), 5.26 (d, J=2.8 Hz, 2H), 4.95 (s, 1H), 4.76 (dd, J=10.0, 14.6 Hz, 4H), 3.70 (d, J=2.0 Hz, 3H), 2.33 (d, J=11.3 Hz, 2H), 1.86 (d, J=11.8 Hz, 2H), 1.00 (d, J=1.5 Hz, 9H). LCMS (ES+) (m/z): 558.4 (M+Na).

Step 2: (S)-Methyl 2-(tert-butoxy)-2-(6-(4-chlorophenyl)-4,7-dimethylisoindolin-5-yl)acetate

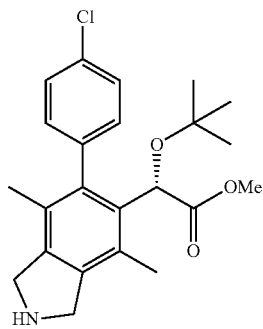 [SMILES: COC(=O)[C@@H](OC(C)(C)C)c1c(C)c2c(c(C)c1-c1ccc(Cl)cc1)CNC2]

A solution of (S)-benzyl 5-(1-(tert-butoxy)-2-methoxy-2-oxoethyl)-6-(4-chlorophenyl)-4,7-dimethylisoindoline-2-carboxylate (70 mg, 0.131 mmol) in MeOH (1.5 mL) was treated with Pd/C (14.0 mg, 0.131 mmol) and then placed under an atmosphere of $H_2$. After 1 h, the reaction mixture was filtered through a pad of Celite and the filtrate concentrated in vacuo to afford the title compound (64 mg, 56%). $^1$H NMR (400 MHz, CHLOROFORM-d) δ=7.48-7.38 (m, 2H), 7.29-7.21 (m, 1H), 7.10 (dd, J=2.0, 8.0 Hz, 1H), 4.91 (s, 1H), 4.62-4.47 (m, 4H), 3.68 (s, 3H), 2.36-2.26 (m, 3H), 1.88-1.78 (m, 3H), 1.02-0.92 (m, 9H). LCMS (ES+) (m/z): 402.9 (M+H).

Step 3: (S)-Methyl 2-(tert-butoxy)-2-(6-(4-chlorophenyl)-4,7-dimethyl-2-(piperidine-1-carbonyl)isoindolin-5-yl)acetate

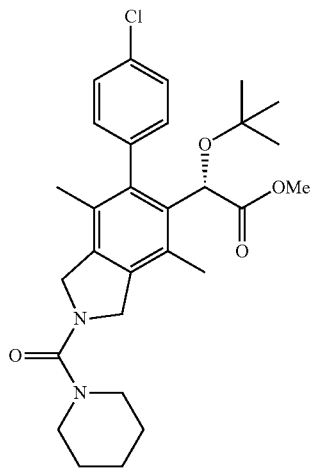 [SMILES: COC(=O)[C@@H](OC(C)(C)C)c1c(C)c2c(c(C)c1-c1ccc(Cl)cc1)CN(C(=O)N1CCCCC1)C2]

An ice cold solution of phosgene (20% in toluene) (0.079 mL, 0.149 mmol) was treated dropwise with a solution of (S)-Methyl 2-(tert-butoxy)-2-(6-(4-chlorophenyl)-4,7-dimethylisoindolin-5-yl)acetate (20 mg, 0.050 mmol) in THF (1.25 mL). After 30 min, the reaction mixture was concentrated in vacuo and redissolved in THF (1.2 mL). The reaction mixture was cooled to 0° C. and pyridine (4.23 μl, 0.052 mmol) was added, followed by piperidine (5.16 μl, 0.052 mmol). After 30 min, the reaction mixture was wanted to ambient temperature. After 1 h, the reaction mixture was diluted with $H_2O$ and extracted with EtOAc. The organics were washed with 1M HCl, $H_2O$, brine, dried ($Na_2SO_4$), filtered and concentrated in vacuo. The residue was purified by silica gel chromatography (0-100% EtOAc-Hexanes) to afford the title compound (20 mg, 0.039 mmol, 78% yield). LCMS (ES+) (m/z): 513.44 (M+H).

Step 4: (S)-Methyl 2-(tert-butoxy)-2-(6-(4-chlorophenyl)-4,7-dimethyl-2-(piperidine-1-carbonyl)isoindolin-5-yl)acetate A solution of (S)-Methyl 2-(tert-butoxy)-2-(6-(4-chlorophenyl)-4,7-dimethyl-2-(piperidine-1-carbonyl)isoindolin-5-yl)acetate (20 mg, 0.039 mmol) in 1,4-dioxane (1.2 mL) was treated with 2M LiOH (0.373 mL, 0.746 mmol) and warmed to 70° C. After 72 h, the reaction mixture was cooled to ambient temperature and concentrated in vacuo. The residue was purified by reverse phase HPLC to afford the title compound (6.0 mg, 24%). 1H NMR (400 MHz, CHLOROFORM-d) δ ppm 0.99 (s, 10H) 1.64 (br. s., 6H) 1.87 (s, 3H) 2.26 (s, 3H) 3.30 (br. s., 4H) 4.69 (t, J=14.38 Hz, 2H) 4.75-4.88 (m, 2H) 5.04 (br. s., 1H) 7.12 (d, J=7.50 Hz, 1H) 7.38-7.50 (m, 3H). LCMS (ES+) (m/z): 499.44 (M+H).

Example 133: (S)-2-(tert-butoxy)-2-(6-(4-chlorophenyl)-2-(3-fluorobenzoyl)-4,7-dimethylisoindolin-5-yl)acetic acid

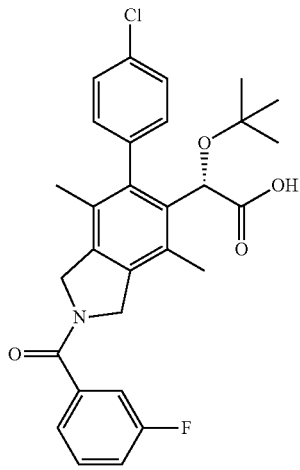 [SMILES: Cc1c2c(c(C)c([C@H](OC(C)(C)C)C(=O)O)c1-c1ccc(Cl)cc1)CN(C(=O)c1cccc(F)c1)C2]

Step 1: (S)-Methyl 2-(tert-butoxy)-2-(6-(4-chlorophenyl)-2-(3-fluorobenzoyl)-4,7-dimethylisoindolin-5-yl)acetate

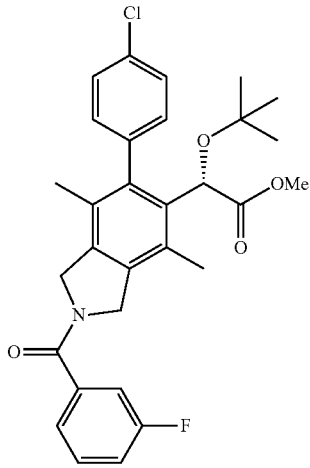 [SMILES: COC(=O)[C@@H](OC(C)(C)C)c1c(C)c2c(c(C)c1-c1ccc(Cl)cc1)CN(C(=O)c1cccc(F)c1)C2]

To a solution of (S)-methyl 2-(tert-butoxy)-2-(6-(4-chlorophenyl)-4,7-dimethylisoindolin-5-yl)acetate (19.5 mg, 0.049 mmol) in EtOAc (0.5 mL) was added 3-fluorobenzoic acid (13.60 mg, 0.097 mmol), triethylamine (0.020 mL, 0.146 mmol), and T3P (50% weight) (0.072 mL, 0.121 mmol). After 1.5 h, the reaction mixture was poured into sat. aq. NaHCO₃ and extracted with EtOAc. The organic layer was washed with brine, dried over Na₂SO₄, and concentrated in vacuo. The residue was purified by silica chromotography (0-40% EtOAc-Hexanes) to afford the title compound (13 mg, 0.025 mmol, 51.1% yield). LCMS (ES+) (m/z): 524.42 (M+H).

Step 2: (S)-2-(tert-butoxy)-2-(6-(4-chlorophenyl)-2-(3-fluorobenzoyl)-4,7-dimethylisoindolin-5-yl)acetic acid A solution of (S)-methyl 2-(tert-butoxy)-2-(6-(4-chlorophenyl)-2-(3-fluorobenzoyl)-4,7-dimethylisoindolin-5-yl)acetate (13 mg, 0.025 mmol) in 1,4-dioxane (0.5 mL) was treated with 2 M LiOH (0.125 mL, 0.25 mmol) and heated to 70° C. After 16 h, the reaction mixture was cooled to ambient temperature and concentrated in vacuo. The residue was dissolved in DCM and washed with 1 M HCl. The organic layer was dried (Na₂SO₄), filtered and concentrated in vacuo. The residue was purified by reverse phase HPLC to afford the title compound (7.5 mg, 0.015 mmol, 30.3% yield). ¹H NMR (400 MHz, CDCl₃) δ ppm 7.53-7.29 (m, 5H), 7.23-6.98 (m, 3H), 5.05 (br. s., 1H), 5.05-4.64 (m, 4H), 2.36-2.13 (d, 3H), 1.94-1.74 (d, 3H), 1.00 (d, 9H). LCMS (ES+) (m/z): 510.41/512.39 (M+1).

Example 134: (S)-2-(tert-butoxy)-2-(6-(4-chlorophenyl)-2-(cyclohexanecarbonyl)-4,7-dimethylisoindolin-5-yl)acetic acid The title compound was made in a similar manner as Example 133.

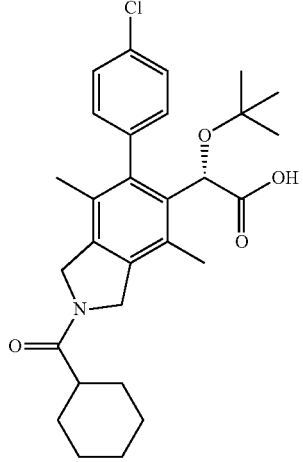 [SMILES: Cc1c2c(c(C)c([C@H](OC(C)(C)C)C(=O)O)c1-c1ccc(Cl)cc1)CN(C(=O)C1CCCCC1)C2]

¹H NMR (400 MHz, CDCl3) δ ppm 7.47-7.38 (m, 3H), 7.13 (d, 1H), 5.06 (br. s., 1H), 4.89-4.71 (m, 4H), 2.56-2.43 (m, 1H), 2.28 (d, 3H), 1.89 (d, 3H), 1.82 (d, 4H), 1.76-1.29 (m, 6H), 1.01 (s, 9H). LCMS (ES+) (m/z): 498.48/500.51 (M+1).

Example 135: (S)-2-(tert-butoxy)-2-(6-(4-chlorophenyl)-2-(3,3-dimethylbutanol)-4,7-dimethylisoindolin-5-yl)acetic acid The title compound was made in a similar manner as Example 133.

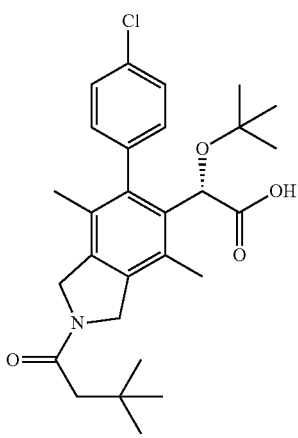 [SMILES: Cc1c2c(c(C)c([C@H](OC(C)(C)C)C(=O)O)c1-c1ccc(Cl)cc1)CN(C(=O)CC(C)(C)C)C2]

¹H NMR (400 MHz, CDCl3) δ ppm 7.49-7.39 (m, 3H), 7.13 (br. s., 1H), 5.06 (br. s., 1H), 4.88-4.72 (m, 4H), 2.36-2.30 (m, 2H), 2.27 (s, 3H), 1.88 (s, 3H), 1.13 (d, 9H), 1.01 (s, 9H). LCMS (ES+) (m/z): 486.46/488.39 (M+1).

Example 136: (S)-2-(tert-butoxy)-2-((R)-2-(5-fluoro-2-methylbenzoyl)-6-(8-fluoro-5-methylchroman-6-yl)-4,7-dimethylisoindolin-5-yl)acetic acid The title compound was made in a similar manner as Example 103.

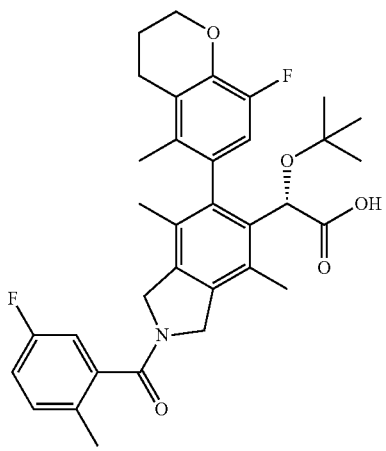 [SMILES: Cc1ccc(F)cc1C(=O)N1Cc2c(C)c(-c3cc(F)c4c(c3C)CCCO4)c([C@H](OC(C)(C)C)C(=O)O)c(C)c2C1]

¹H NMR (400 MHz, CDCl3) δ 7.26 (m, 1H) (under CHCl₃), 7.09-6.97 (m, 2H), 6.68 (m, 1H), 5.13-4.95 (m, 3H), 4.50 (m, 2H), 4.27 (m, 2H), 2.69 (m, 2H), 2.35 (m, 4H), 2.19-2.16 (m, 3H), 1.90-1.80 (m, 5H), 1.68-1.51 (m, 2H), 1.14 (m, 9H). LCMS (ES+) (m/z): 578.47 (M+1)

Examples 137-162 were made in a similar manner as Example 103.

Example 137: (S)-2-(tert-butoxy)-2-((M)-2-(cyclohexanecarbonyl)-6-(8-fluoro-5-methylchroman-6-yl)-4,7-dimethylisoindolin-5-yl)acetic acid

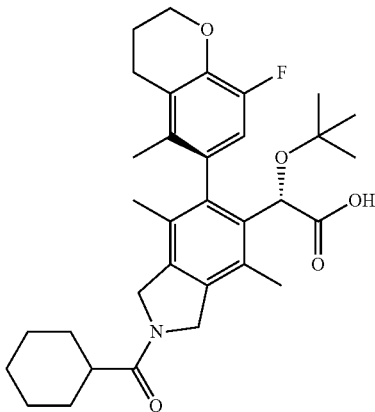

1H NMR (400 MHz, CDCl3) δ (mixture of rotamers) 6.69 (m, 1H), 5.08 (s, 1H), 4.82 (m, 4H), 4.27 (m, 2H), 2.70 (m, 2H), 2.50 (m, 1H), 2.30 (m, 3H), 2.13 (m, 2H), 1.90-1.54 (m, 13H), 1.33 (m, 3H), 1.14 (m, 9H); LCMS (ES+) (m/z): 552.62 (M+1)

Example 138: (S)-2-((M)-2-(benzo[d][1,3]dioxole-4-carbonyl)-6-(8-fluoro-5-methylchroman-6-yl)-4,7-dimethylisoindolin-5-yl)-2-(tert-butoxy)acetic acid

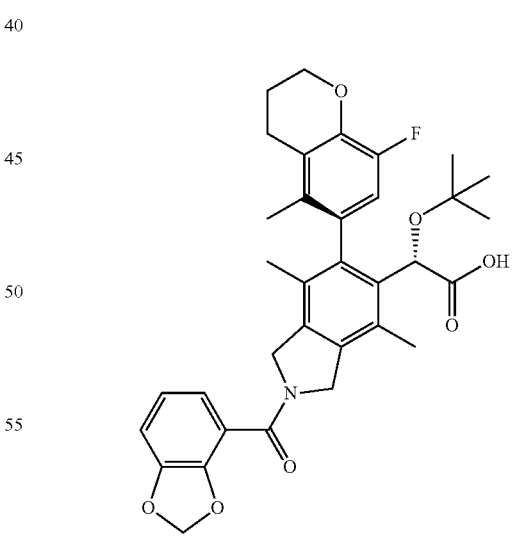

¹H NMR (400 MHz, CHLOROFORM-d) δ (mixture of rotamers) 7.04-6.87 (m, 3H), 6.67 (m, 1H) 6.04 (m, 2H), 5.09-4.95 (m, 3H), 4.85-4.71 (m, 2H), 4.26 (m, 2H), 2.69 (m, 2H), 2.36-2.14 (m, 3H), 2.10 (m, 2H), 1.89-1.64 (m, 6H), 1.11 (m, 9H); ES+MS: 590.47 (M+1)

Example 139: (S)-2-(tert-butoxy)-2-((M)-6-(8-fluoro-5-methylchroman-6-yl)-2-(3-methoxy-2-methylbenzoyl)-4,7-dimethylisoindolin-5-yl)acetic acid

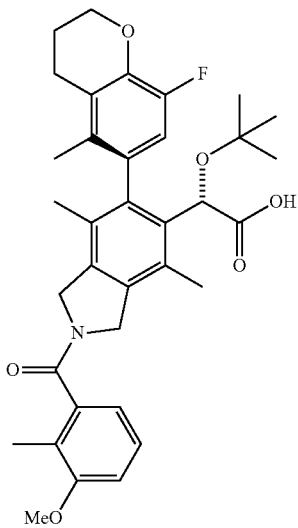

$^1$H NMR (400 MHz, CDCl$_3$) δ mixture of rotamers: 7.25 (m, 1H), 6.90 (m, 2H), 6.67 (m, 1H), 5.06-4.99 (m, 3H), 4.48 (m, 2H), 4.27 (m, 2H), 3.88 (m, 3H), 2.70 (m, 2H), 2.35-2.14 (m, 8H), 1.87-1.63 (m, 6H), 1.13 (m, 9H). LCMS (ES+) (m/z): 590.57 (M+1).

Example 140: (S)-2-(tert-butoxy)-2-((M)-2-(3-fluoro-5-methoxybenzoyl)-6-(8-fluoro-5-methyl-chroman-6-yl)-4,7-dimethylisoindolin-5-yl)acetic acid

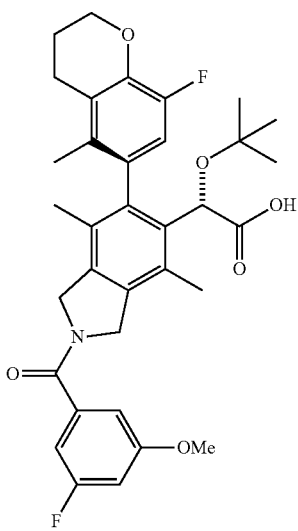

$^1$H NMR (400 MHz, CDCl$_3$) δ mixture of rotamers: 6.88 (m, 2H), 6.71 (m, 2H), 5.06-4.98 (m, 3H), 4.74 (m, 2H), 4.27 (m, 2H), 3.86 (m, 3H), 2.89 (m, 2H), 2.35-2.20 (m, 3H), 2.13 (m, 2H), 1.86-1.69 (m, 6H), 1.13 (m, 9H). LCMS (ES+) (m/z): 594.55 (M+1).

Example 141: (S)-2-(tert-butoxy)-2-((M)-2-(3-fluoro-2-methylbenzoyl)-6-(8-fluoro-5-methylchroman-6-yl)-4,7-dimethylisoindolin-5-yl)acetic acid

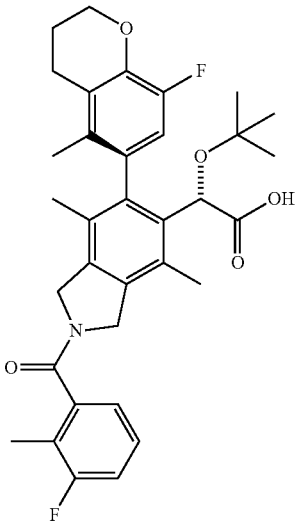

$^1$H NMR (400 MHz, CDCl$_3$) δ mixture of rotamers: 7.28 (m, 1H), 7.10 (m, 2H), 6.67 (m, 1H), 5.06-4.99 (m, 3H), 4.49 (m, 2H), 4.28 (m, 2H), 2.69 (m, 2H), 2.36-2.12 (m, 8H), 1.87-1.65 (m, 6H), 1.13 (m, 9H). LCMS (ES+) (m/z): 578.55 (M+1).

Example 142: (S)-2-(tert-butoxy)-2-((M)-6-(8-fluoro-5-methylchroman-6-yl)-4,7-dimethyl-2-(2-methylnicotinoyl)isoindolin-5-yl)acetic acid

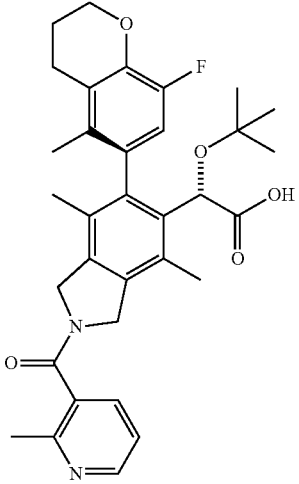

$^1$H NMR (400 MHz, CDCl$_3$) δ mixture of rotamers: 8.91 (s, 1H), 8.16 (m, 1H), 7.74 (m, 1H), 6.65 (m, 1H), 5.06 (m, 3H), 4.54 (m, 2H), 4.28 (m, 2H), 2.85 (m, 3H), 2.70 (m, 2H), 2.27 (m, 5H), 1.76 (m, 6H), 1.13 (m, 9H). LCMS (ES+) (m/z): 561.55 (M+1).

Example 143: (S)-2-(tert-butoxy)-2-((M)-6-(8-fluoro-5-methylchroman-6-yl)-2-(5-methoxynicotinoyl)-4,7-dimethylisoindolin-5-yl)acetic acid

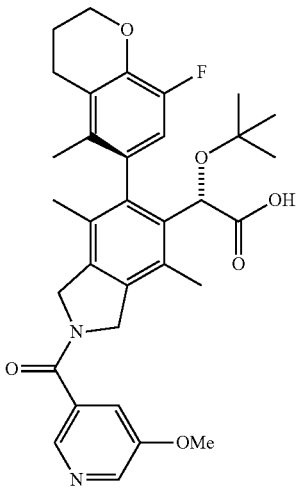

¹H NMR (400 MHz, CDCl₃) δ mixture of rotamers: 8.51 (m, 2H), 7.54 (bs, 1H), 6.68 (m, 1H), 5.07-4.99 (m, 3H), 4.86-4.74 (m, 2H), 4.27 (m, 2H), 3.95 (m, 3H), 2.69 (m, 2H), 2.37-2.21 (m, 3H), 2.13 (m, 2H), 1.85-1.69 (m, 6H), 1.13 (m, 9H). LCMS (ES+) (m/z): 577.56 (M+1).

Example 144: (S)-2-(tert-butoxy)-2-((M)-2-(3-fluoro-4-methylbenzoyl)-6-(8-fluoro-5-methylchroman-6-yl)-4,7-dimethylisoindolin-5-yl)acetic acid

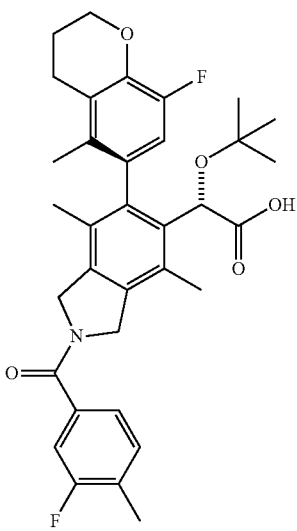

¹H NMR (400 MHz, CDCl₃) δ mixture of rotamers: 7.32-7.23 (m, 3H), 6.67 (m, 1H), 5.06-4.99 (m, 3H), 4.76 (m, 2H), 4.27 (m, 2H), 2.69 (m, 2H), 2.35-2.19 (m, 6H), 2.13 (m, 2H), 1.86-1.69 (m, 6H), 1.13 (m, 9H). LCMS (ES+) (m/z): 578.51 (M+1).

Example 145: (S)-2-(tert-butoxy)-2-((M)-2-(4-fluoro-3-methylbenzoyl)-6-(8-fluoro-5-methylchroman-6-yl)-4,7-dimethylisoindolin-5-yl)acetic acid

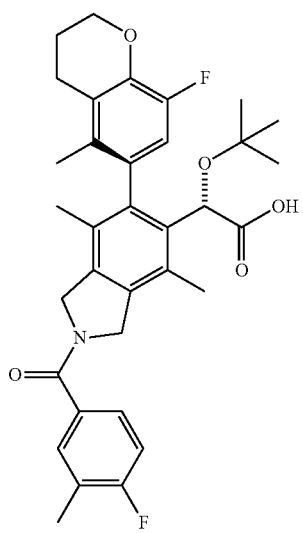

¹H NMR (400 MHz, CDCl₃) δ mixture of rotamers: 7.45-7.39 (m, 2H), 7.08 (m, 1H), 6.67 (m, 1H), 5.06-4.99 (m, 3H), 4.76 (m, 2H), 4.27 (m, 2H), 2.69 (m, 2H), 2.35-2.12 (m, 8H), 1.86-1.69 (m, 6H), 1.13 (m, 9H). LCMS (ES+) (m/z): 578.50 (M+1).

Example 146: (S)-2-(tert-butoxy)-2-((M)-6-(8-fluoro-5-methylchroman-6-yl)-4,7-dimethyl-2-(2-methylbenzoyl)isoindolin-5-yl)acetic acid

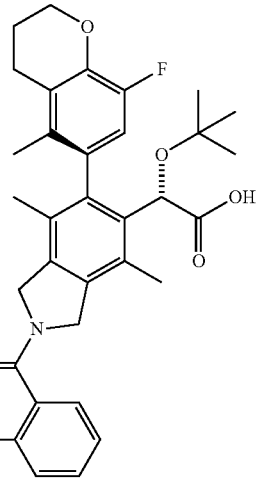

¹H NMR (400 MHz, CDCl₃) δ mixture of rotamers: 7.36-7.27 (m, 4H), 6.67 (m, 1H), 5.06-5.00 (m, 3H), 4.49 (m, 2H), 4.28 (m, 2H), 2.69 (m, 2H), 2.39-2.12 (m, 8H), 1.87-1.63 (m, 6H), 1.13 (m, 9H). LCMS (ES+) (m/z): 560.53 (M+1).

Example 147: (S)-2-(tert-butoxy)-2-((M)-2-(3-chlorobenzoyl)-6-(8-fluoro-5-methylchroman-6-yl)-4,7-dimethylisoindolin-5-yl)acetic acid

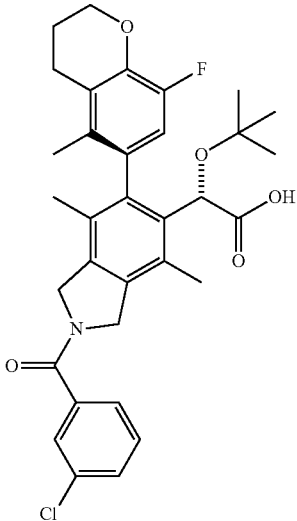

¹H NMR (400 MHz, CDCl₃) δ mixture of rotamers: 7.57 (s, 1H), 7.46-7.41 (m, 3H), 6.68 (m, 1H), 5.06-4.99 (m, 3H), 4.73 (m, 2H), 4.27 (m, 2H), 2.69 (m, 2H), 2.35-2.12 (m, 5H), 1.86-1.69 (m, 6H), 1.13 (m, 9H). LCMS (ES+) (m/z): 580.48 (M+1).

Example 148: (S)-2-(tert-butoxy)-2-((M)-2-(2-fluoro-3-methoxybenzoyl)-6-(8-fluoro-5-methylchroman-6-yl)-4,7-dimethylisoindolin-5-yl)acetic acid

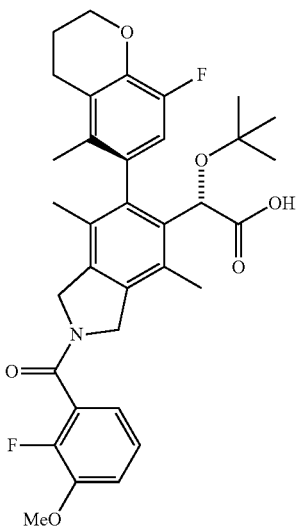

¹H NMR (400 MHz, CDCl₃) δ mixture of rotamers: 7.20-6.99 (m, 3H), 6.67 (m, 1H), 5.06-4.99 (m, 3H), 4.67 (m, 2H), 4.27 (m, 2H), 3.95 (m, 3H), 2.69 (m, 2H), 2.35-2.12 (m, 5H), 1.88-1.66 (m, 6H), 1.13 (m, 9H). LCMS (ES+) (m/z): 594.55 (M+1).

Example 149: (S)-2-(tert-butoxy)-2-((M)-6-(8-fluoro-5-methylchroman-6-yl)-4,7-dimethyl-2-(3-methylbenzoyl)isoindolin-5-yl)acetic acid

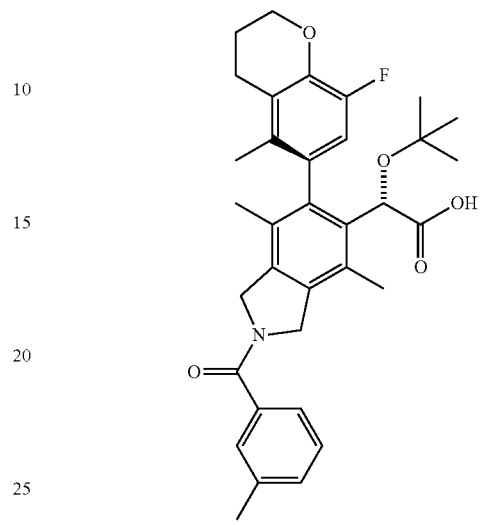

¹H NMR (400 MHz, CDCl₃) δ mixture of rotamers: 7.39-7.27 (m, 4H), 6.68 (m, 1H), 5.07-5.00 (m, 3H), 4.75 (m, 2H), 4.28 (m, 2H), 2.70 (m, 2H), 2.42 (m, 3H), 2.35-2.11 (m, 5H), 1.87-1.68 (m, 6H), 1.14 (m, 9H). LCMS (ES+) (m/z): 560.55 (M+1).

Example 150: (S)-2-(tert-butoxy)-2-((M)-2-(5-fluoro-2-methoxybenzoyl)-6-(8-fluoro-5-methylchroman-6-yl)-4,7-dimethylisoindolin-5-yl)acetic acid

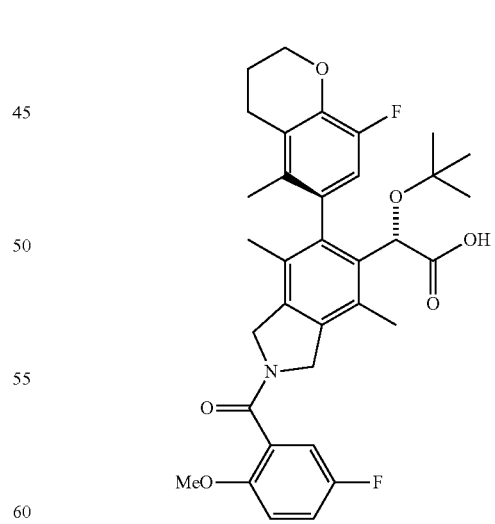

¹H NMR (400 MHz, CDCl₃) δ mixture of rotamers: 7.12-7.07 (m, 2H), 6.94 (m, 1H), 6.68 (m, 1H), 5.07 (s, 1H), 4.99 (m, 2H), 4.62-4.57 (m, 2H), 4.27 (m, 2H), 3.86 (m, 3H), 2.69 (m, 2H), 2.34-2.12 (m, 5H), 1.88-1.66 (m, 6H), 1.14 (m, 9H). LCMS (ES+) (m/z): 594.55 (M+1).

Example 151: (S)-2-((M)-2-(benzo[b]thiophene-4-carbonyl)-6-(8-fluoro-5-methylchroman-6-yl)-4,7-dimethylisoindolin-5-yl)-2-(tert-butoxy)acetic acid

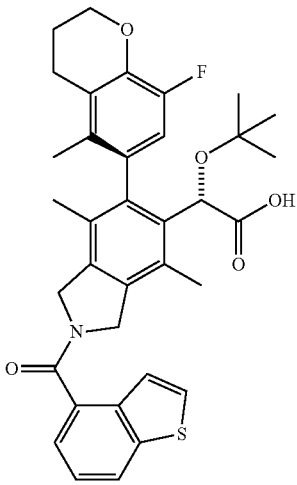

¹H NMR (400 MHz, CDCl₃) δ mixture of rotamers: 7.99 (m, 1H), 7.57 (m, 1H), 7.50-7.41 (m, 3H), 6.67 (m, 1H), 5.14-5.06 (m, 3H), 4.67-4.59 (m, 2H), 4.27 (m, 2H), 4.70 (m, 2H), 2.38-2.08 (m, 5H), 1.89-1.59 (m, 6H), 1.13 (m, 9H). LCMS (ES+) (m/z): 602.49 (M+1).

Example 152: (S)-2-(tert-butoxy)-2-((M)-2-(2,3-dihydrobenzofuran-7-carbonyl)-6-(8-fluoro-5-methylchroman-6-yl)-4,7-dimethylisoindolin-5-yl)acetic acid

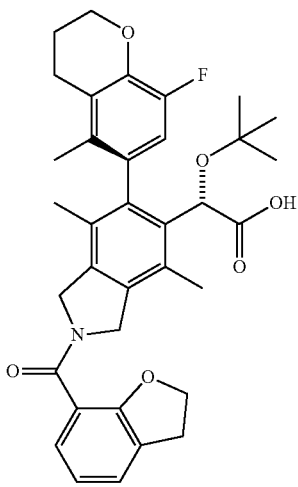

¹H NMR (400 MHz, CDCl₃) δ mixture of rotamers: 7.31-7.27 (m, 2H), 6.94 (m, 1H), 6.68 (m, 1H), 5.07-4.99 (m, 3H), 4.82-4.74 (m, 2H), 4.66 (m, 2H), 4.27 (m, 2H), 3.29 (m, 2H), 2.70 (m, 2H), 2.34-2.12 (m, 5H), 1.87-1.68 (m, 6H), 1.14 (m, 9H). LCMS (ES+) (m/z): 588.48 (M+1).

Example 153: (S)-2-(tert-butoxy)-2-((M)-2-(2,3-dihydrobenzo[b][1,4]dioxine-5-carbonyl)-6-(8-fluoro-5-methylchroman-6-yl)-4,7-dimethylisoindolin-5-yl)acetic acid ¹H NMR (400 MHz, CDCl₃) δ mixture of rotamers: 6.98-6.90 (m, 3H), 6.68 (m, 1H), 5.07 (s, 1H), 4.99 (m, 2H), 4.63 (m, 2H), 4.33-4.25 (m, 6H), 2.70 (m, 2H), 2.34-2.12 (m, 5H), 1.87-1.67 (m, 6H), 1.14 (m, 9H). LCMS (ES+) (m/z): 604.51 (M+1).

Example 154: (S)-2-(tert-butoxy)-2-((M)-6-(8-fluoro-5-methylchroman-6-yl)-4,7-dimethyl-2-(1-methyl-1H-indazole-5-carbonyl)isoindolin-5-yl)acetic acid ¹H NMR (400 MHz, CDCl₃) δ mixture of rotamers: 8.09 (m, 1H), 8.02 (m, 1H), 7.65 (m, 1H), 7.49 (m, 1H), 6.68 (m, 1H), 5.08-5.05 (m, 3H), 4.81 (m, 2H), 4.27 (m, 2H), 4.14 (m, 3H), 2.69 (m, 2H), 2.37-2.12 (m, 5H), 1.88-1.66 (m, 6H), 1.14 (m, 9H). LCMS (ES+) (m/z): 600.5 (M+1).

Example 155: (S)-2-(tert-butoxy)-2-(2-(2-(tert-butyl)benzoyl)-6-((M)-8-fluoro-5-methylchroman-6-yl)-4,7-dimethylisoindolin-5-yl)acetic acid

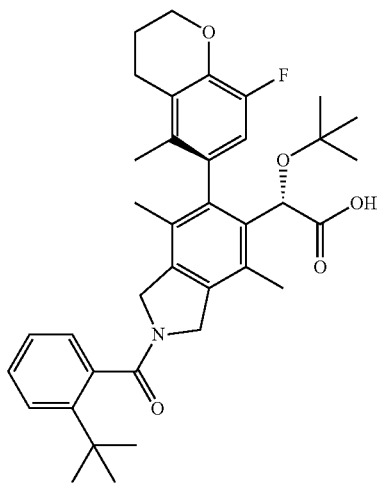

¹H NMR (400 MHz, CDCl₃) ∂ (mixture of rotamers) 7.59-7.11 (m, 4H), 6.66 (m, 1H), 5.10-4.34 (m, 5H), 4.25 (m, 2H), 2.68 (m, 2H), 2.37-2.07 (m, 6H), 1.91-1.21 (m, 17H) 1.12 (m, 9H). LCMS (ES+) (m/z): 602.48 (M+1).

Example 156: (S)-2-(tert-butoxy)-2-(6-((M)-8-fluoro-5-methylchroman-6-yl)-2-(3-methoxy-4-methylbenzoyl)-4,7-dimethylisoindolin-5-yl)acetic acid

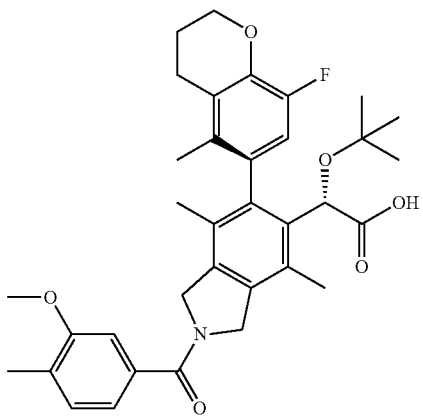

¹H NMR (400 MHz, CDCl₃) ∂ (mixture of rotamers) 7.19 (m, 1H), 7.05 (m, 2H), 6.66 (m, 1H), 5.01 (m, 3H), 4.77 (m, 2H), 4.25 (m, 2H), 3.86 (m, 3H), 2.67 (m, 2H), 2.37-2.14 (m, 6H), 2.10 (m, 2H), 1.90-1.63 (m, 6H) 1.12 (m, 9H). LCMS (ES+) (m/z): 590.40 (M+1); 1179.88 (2M+1).

Example 157: (S)-2-(tert-butoxy)-2-(2-(2,5-dimethylbenzoyl)-6-((M)-8-fluoro-5-methylchroman-6-yl)-4,7-dimethylisoindolin-5-yl)acetic acid

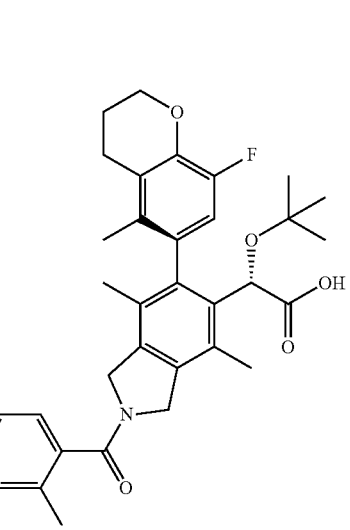

¹H NMR (400 MHz, CDCl₃) ∂ (mixture of rotamers) 7.19-7.04 (m, 3H), 6.66 (m, 1H), 5.01 (m, 3H), 4.48 (m, 2H), 4.25 (m, 2H), 2.0-2.05 (m, 11H), 1.89-1.59 (m, 6H) 1.12 (m, 9H). LCMS (ES+) (m/z): 574.40 (M+1); 1147.97 (2M+1).

Example 158: (S)-2-(2-benzoyl-6-((M)-8-fluoro-5-methylchroman-6-yl)-4,7-dimethylisoindolin-5-yl)-2-(tert-butoxy)acetic acid

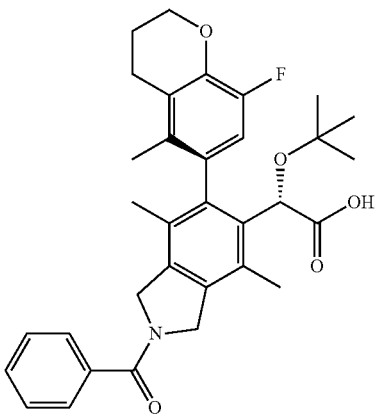

¹H NMR (400 MHz, CDCl₃) ∂ (mixture of rotamers) 7.58 (m, 2H), 7.49 (m, 3H), 6.68 (m, 1H), 5.04 (m, 3H), 4.75 (m, 2H), 4.27 (m, 2H), 2.69 (m, 2H), 2.40-2.04 (m, 5H), 1.91-1.63 (m, 6H), 1.13 (m, 9H). LCMS (ES+) (m/z): 546.52 (M+1); 1091.89 (2M+1).

Example 159: (S)-2-(tert-butoxy)-2-(6-((M)-8-fluoro-5-methylchroman-6-yl)-2-(3-methoxybenzoyl)-4,7-dimethylisoindolin-5-yl)acetic acid

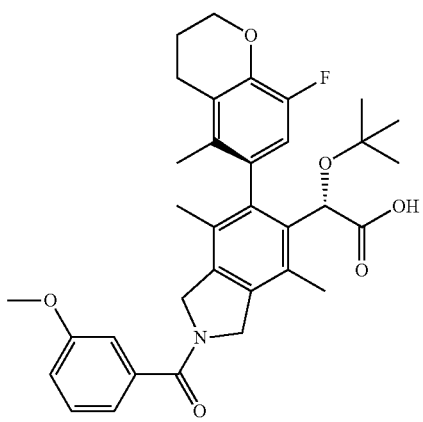

¹H NMR (400 MHz, CDCl₃) ∂ (mixture of rotamers) 7.36 (m, 1H), 7.17-6.95 (m, 3H), 6.65 (m, 1H), 5.01 (m, 3H), 4.73 (m, 2H), 4.25 (m, 2H), 3.84 (m, 3H), 2.67 (m, 2H), 2.38-2.01 (m, 5H), 1.88-1.59 (m, 6H) 1.10 (m, 9H). LCMS (ES+) (m/z): 576.54 (M+1); 1152.00 (2M+1).

Example 160: (S)-2-(tert-butoxy)-2-(6-((M)-8-fluoro-5-methylchroman-6-yl)-2-(5-methoxy-2-methylbenzoyl)-4,7-dimethylisoindolin-5-yl)acetic acid

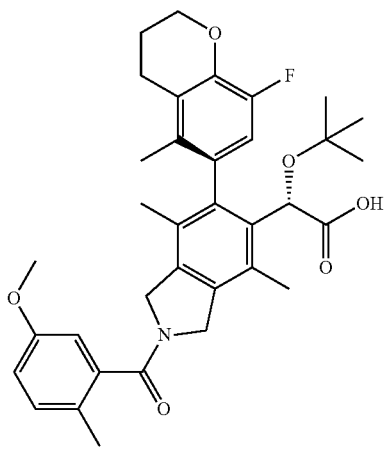

¹H NMR (400 MHz, CDCl₃) ∂ (mixture of rotamers) 7.20 (m, 1H), 6.95-6.79 (m, 2H), 6.68 (m, 1H), 5.03 (m, 3H), 4.50 (m, 2H), 4.28 (m, 2H), 3.82 (m, 3H), 2.69 (m, 2H), 2.41-2.04 (m, 8H), 1.93-1.59 (m, 6H) 1.13 (m, 9H). LCMS (ES+) (m/z): 590.58 (M+1); 1180.00 (2M+1).

Example 161: (S)-2-(tert-butoxy)-2-(2-(2,3-dihydro-1H-indene-4-carbonyl)-6-((M)-8-fluoro-5-methylchroman-6-yl)-4,7-dimethylisoindolin-5-yl)acetic acid

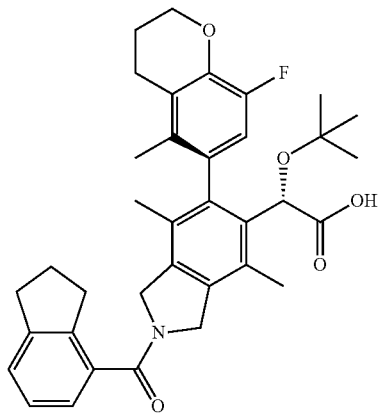

¹H NMR (400 MHz, CHLOROFORM-d) δ ppm 7.36-7.29 (m, 1H), 7.26-7.14 (m, 2H), 6.68 (t, J=12.8 Hz, 1H), 5.07 (br. s., 1H), 5.01 (d, J=15.7 Hz, 2H), 4.60 (d, J=14.7 Hz, 2H), 4.34-4.18 (m, 2H), 3.07-2.88 (m, 4H), 2.78-2.59 (m, 2H), 2.35 (s, 1.5H), 2.21-2.04 (m, 5.5H), 1.91-1.79 (m, 4.5H), 1.65 (s, 1.5H), 1.19-1.07 (m, 9H); LCMS (m/z) ES⁺=586.59 (M+1).

Example 162: (S)-2-(tert-butoxy)-2-((M)-2-(2,2-difluorobenzo[d][1,3]dioxole-4-carbonyl)-6-(8-fluoro-5-methylchroman-6-yl)-4,7-dimethylisoindolin-5-yl)acetic acid

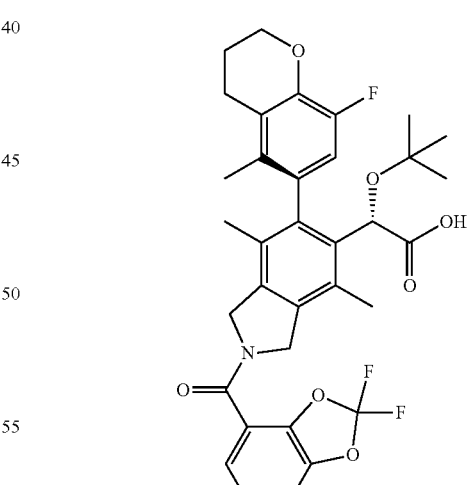

¹H NMR (400 MHz, CHLOROFORM-d) δ ppm 7.32-7.25 (m, 1H), 7.24-7.12 (m, 2H), 6.68 (t, J=10.6 Hz, 1H), 5.08 (br. s., 1H), 5.03 (d, J=15.0 Hz, 2H), 4.77 (d, J=15.5 Hz, 2H), 4.35-4.21 (m, 2H), 2.84-2.58 (m, 2H), 2.44-2.05 (m, 5H), 1.93-1.62 (m, 6H), 1.14 (d, J=6.6 Hz, 9H); LCMS (m/z) ES⁺=626.50 (M+1).

Examples 163-167 were made in a similar manner as Example 105.

Example 163: (S)-2-(tert-butoxy)-2-(2-(2-methoxybenzoyl)-4,7-dimethyl-6-(p-tolyl)isoindolin-5-yl)acetic acid

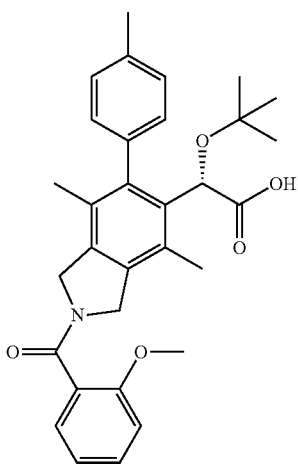 [SMILES: COc1ccccc1C(=O)N1Cc2c(C)c(-c3ccc(C)cc3)c([C@H](OC(C)(C)C)C(=O)O)c(C)c2C1]

¹H NMR (400 MHz, METHANOL-d₄) δ ppm 7.53-7.43 (m, 1H), 7.34 (td, J=1.9, 7.5 Hz, 1H), 7.31-7.21 (m, 3H), 7.20-7.03 (m, 3H), 5.04 (d, J=4.4 Hz, 1H), 4.91 (br. s., 2H), 4.60 (br. s, 2H), 3.89 (d, J=5.1 Hz, 3H), 2.41 (d, J=8.3 Hz, 3H), 2.38-2.10 (m, 3H), 1.97-1.68 (m, 3H), 0.93 (d, J=9.2 Hz, 9H); LCMS (m/z) ES⁺=502.52 (M+1).

Example 164: (S)-2-(tert-butoxy)-2-(2-(2,3-dihydrobenzofuran-7-carbonyl)-4,7-dimethyl-6-(p-tolyl)isoindolin-5-yl)acetic acid

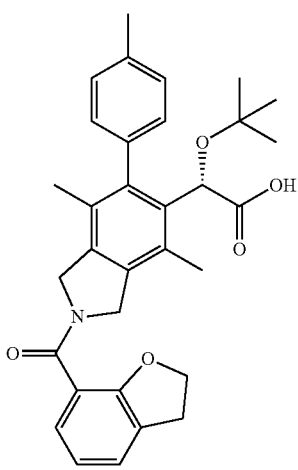

¹H NMR (400 MHz, METHANOL-d₄) δ ppm 7.36 (t, J=7.1 Hz, 1H), 7.32-7.18 (m, 4H), 7.09 (dd, J=7.7, 12.5 Hz, 1H), 6.96 (dt, J=5.7, 7.5 Hz, 1H), 5.05 (d, J=3.2 Hz, 1H), 4.91 (br. s., 2H), 4.77 (br. s., 2H), 4.66 (q, J=8.5 Hz, 2H), 3.37-3.22 (m, 2H), 2.42 (d, J=6.6 Hz, 3H), 2.38-2.13 (m, 3H), 1.97-1.71 (m, 3H), 0.93 (d, J=7.1 Hz, 9H); LCMS (m/z) ES⁺=514.54 (M+1).

Example 165: (S)-2-(tert-butoxy)-2-(4,7-dimethyl-2-(1-methyl-1H-indole-4-carbonyl)-6-(p-tolyl)isoindolin-5-yl)acetic acid

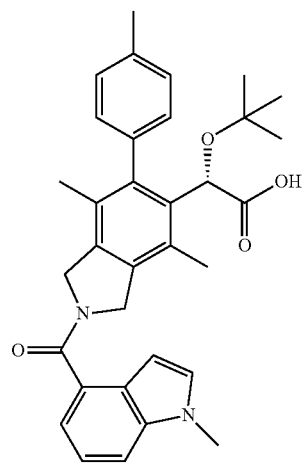

¹H NMR (400 MHz, METHANOL-d₄) δ ppm 7.55 (t, J=8.1 Hz, 1H), 7.37-7.19 (m, 6H), 7.16-6.98 (m, 1H), 6.48 (d, J=3.0 Hz, 1H), 5.10-4.97 (m, 3H), 4.67 (d, J=3.2 Hz, 2H), 3.87 (d, J=7.4 Hz, 3H), 2.49-2.32 (m, 4.5H), 2.06 (s, 1.5H), 1.96 (s, 1.5H), 1.63 (s, 1.5H), 0.94 (s, 4.5H), 0.90 (s, 4.5H); LCMS (m/z) ES⁺=525.57 (M+1).

Example 166: (S)-2-(2-(benzo[b]thiophene-4-carbonyl)-4,7-dimethyl-6-(p-tolyl)isoindolin-5-yl)-2-(tert-butoxy)acetic acid

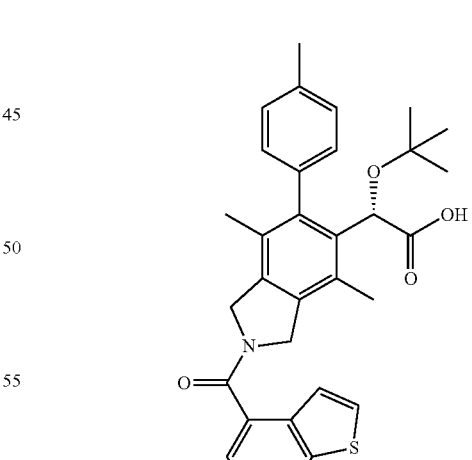

¹H NMR (400 MHz, METHANOL-d₄) δ ppm 8.08 (t, J=7.7 Hz, 1H), 7.73 (t, J=5.1 Hz, 1H), 7.61-7.40 (m, 3H), 7.34-7.19 (m, 3H), 7.15-6.98 (m, 1H), 5.12-4.99 (m, 3H), 4.63 (d, J=3.5 Hz, 2H), 2.46-2.35 (m, 4.5H), 2.08 (s, 1.5H), 1.97 (s, 1.5H), 1.65 (s, 1.5H), 0.94 (s, 4.5H), 0.90 (s, 4.5H); LCMS (m/z) ES⁺=528.50 (M+1).

Example 167: (S)-2-(2-(benzofuran-7-carbonyl)-4,7-dimethyl-6-(p-tolyl)isoindolin-5-yl)-2-(tert-butoxy)acetic acid

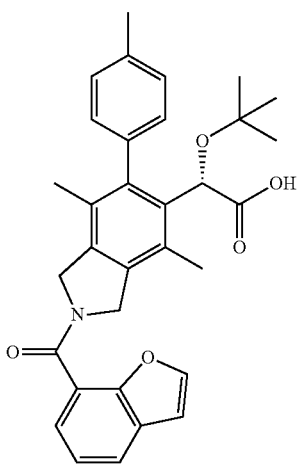 [SMILES: Cc1ccc(-c2c(C)c3c(c(C)c2[C@H](OC(C)(C)C)C(=O)O)CN(C(=O)c2cccc4c2OCC4)C3)cc1]

¹H NMR (400 MHz, METHANOL-d₄) δ ppm 7.87 (d, J=5.4 Hz, 1H), 7.80 (t, J=7.6 Hz, 1H), 7.49 (d, J=5.4 Hz, 1H), 7.43-7.35 (m, 1H), 7.34-7.19 (m, 3H), 7.15-7.02 (m, 1H), 7.02-6.93 (m, 1H), 5.12-4.98 (m, 3H), 4.75-4.63 (m, 2H), 2.49-2.33 (m, 4.5H), 2.09 (s, 1.5H), 1.96 (s, 1.5H), 1.66 (s, 1.5H), 0.93 (d, J=13.5 Hz, 9H) LCMS (m/z) ES⁺=512.51 (M+1).

Examples 168-200 were made in a similar manner as Example 103.

Example 168: (S)-2-((M)-2-(1-naphthoyl)-6-(8-fluoro-5-methylchroman-6-yl)-4,7-dimethylisoindolin-5-yl)-2-(tert-butoxy)acetic acid

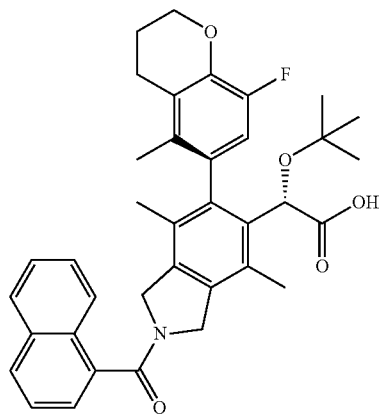

¹H NMR (400 MHz, CDCl₃) ∂ (mixture of rotamers) 7.92 (m, 3H), 7.54 (m, 4H), 6.65 (m, 1H), 5.21-4.99 (m, 3H), 4.57-4.41 (m, 2H), 4.24 (m, 2H), 2.65 (m, 2H), 2.42-1.95 (m, 5H), 1.90-1.46 (m, 6H), 1.11 (m, 9H). LCMS (ES+) (m/z): 596.55 (M+1); 1192.95 (2M+1).

Example 169: (S)-2-((M)-2-(benzofuran-7-carbonyl)-6-(8-fluoro-5-methylchroman-6-yl)-4,7-dimethylisoindolin-5-yl)-2-(tert-butoxy)acetic acid

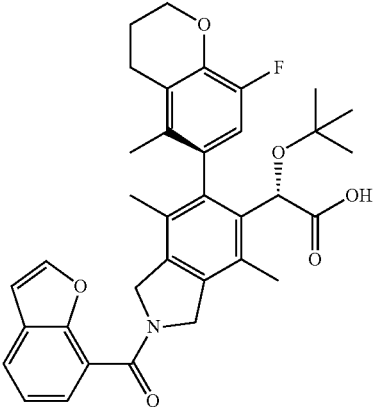

¹H NMR (400 MHz, CDCl₃) ∂ (mixture of rotamers) 7.69 (m, 2H), 7.46 (m, 1H), 7.33 (m, 1H), 6.86 (m, 1H), 6.65 (m, 1H), 5.07 (m, 3H), 4.69 (m, 2H), 4.25 (m, 2H), 2.66 (m, 2H), 2.40-2.00 (m, 5H), 1.92-1.53 (m, 6H), 1.11 (m, 9H). LCMS (ES+) (m/z): 586.38 (M+1); 1172.50 (2M+1).

Example 170: (S)-2-(tert-butoxy)-2-((M)-2-(3,5-difluorobenzoyl)-6-(8-fluoro-5-methylchroman-6-yl)-4,7-dimethylisoindolin-5-yl)acetic acid

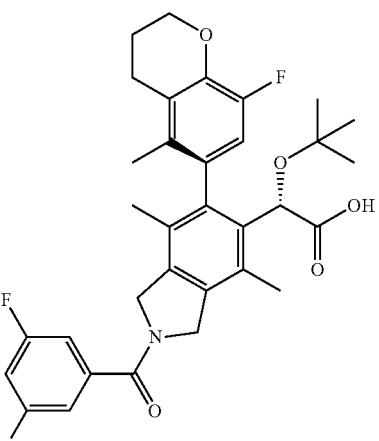

¹H NMR (400 MHz, CDCl₃) ∂ (mixture of rotamers) 7.10 (m, 2H), 6.93 (m, 1H), 6.66 (m, 1H), 5.10-4.91 (m, 3H), 4.72 (m, 2H), 4.26 (m, 2H), 2.68 (m, 2H), 2.37-2.05 (m, 5H), 1.89-1.65 (m, 6H), 1.12 (m, 9H). LCMS (ES+) (m/z): 582.51 (M+1); 1163.80 (2M+1).

Example 171: (S)-2-(tert-butoxy)-2-((M)-2-(3-chloro-4-fluorobenzoyl)-6-(8-fluoro-5-methylchroman-6-yl)-4,7-dimethylisoindolin-5-yl)acetic acid

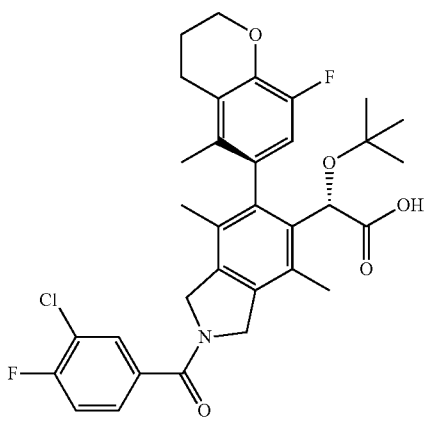

¹H NMR (400 MHz, CDCl₃) ∂ (mixture of rotamers) 7.66 (m, 1H), 7.48 (m, 1H), 7.24 (m, 1H), 6.66 (m, 1H), 5.00 (m, 3H), 4.73 (m, 2H), 4.26 (m, 2H), 2.67 (m, 2H), 2.37-2.04 (m, 5H), 1.89-1.64 (m, 6H), 1.12 (m, 9H). LCMS (ES+) (m/z): 598.34 (M+1); 1197.48 (2M+1).

Example 172: (S)-2-(tert-butoxy)-2-((M)-2-(3-chloro-2-methylbenzoyl)-6-(8-fluoro-5-methylchroman-6-yl)-4,7-dimethylisoindolin-5-yl)acetic acid

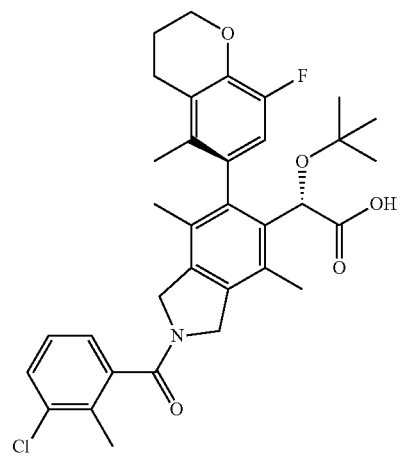

¹H NMR (400 MHz, CDCl₃) ∂ (mixture of rotamers) 7.43 (m, 1H), 7.21 (m, 2H), 6.65 (m, 1H), 5.01 (m, 3H), 4.46 (m, 2H), 4.25 (m, 2H), 2.67 (m, 2H), 2.43-2.04 (m, 8H), 1.90-1.60 (m, 6H), 1.12 (m, 9H). LCMS (ES+) (m/z): 598.35 (M+1); 1189.84 (2M+1).

Example 173: (S)-2-(tert-butoxy)-2-((M)-6-(8-fluoro-5-methylchroman-6-yl)-4,7-dimethyl-2-(3,4,5-trifluorobenzoyl)isoindolin-5-yl)acetic acid

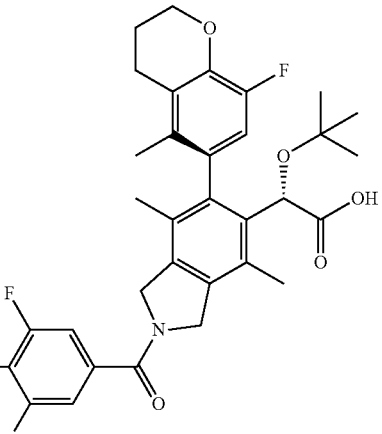

¹H NMR (400 MHz, CDCl₃) ∂ (mixture of rotamers) 7.25 (m, 2H), 6.66 (m, 1H), 5.12-4.91 (m, 3H), 4.74 (m, 2H), 4.25 (m, 2H), 2.68 (m, 2H), 2.36-2.05 (m, 5H), 1.89-1.65 (m, 6H), 1.12 (m, 9H). LCMS (ES+) (m/z): 600.52 (M+1).

Example 174: (S)-2-(tert-butoxy)-2-((M)-6-(8-fluoro-5-methylchroman-6-yl)-2-(4-fluorobenzoyl)-4,7-dimethylisoindolin-5-yl)acetic acid

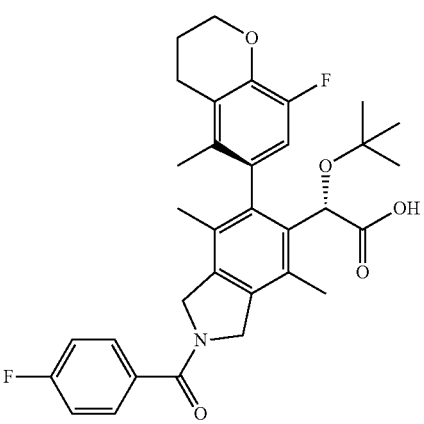

¹H NMR (400 MHz, CDCl₃) ∂ (mixture of rotamers) 7.59 (m, 2H), 7.16 (m, 2H), 6.66 (m, 1H), 5.03 (m, 3H), 4.74 (m, 2H), 4.26 (m, 2H), 2.68 (m, 2H), 2.38-2.04 (m, 5H), 1.90-1.62 (m, 6H), 1.11 (m, 9H). LCMS (ES+) (m/z): 564.53 (M+1); 1127.26 (2M+1).

Example 175: (S)-2-(tert-butoxy)-2-((M)-2-(4-chloro-3,5-difluorobenzoyl)-6-(8-fluoro-5-methylchroman-6-yl)-4,7-dimethylisoindolin-5-yl)acetic acid

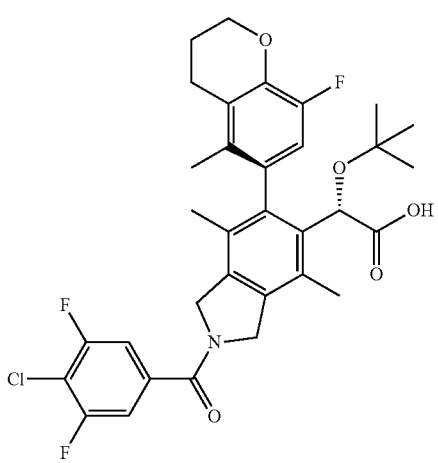

¹H NMR (400 MHz, CDCl₃) ∂ (mixture of rotamers) 7.22 (m, 2H), 6.66 (m, 1H), 5.03 (m, 3H), 4.72 (m, 2H), 4.26 (m, 2H), 2.68 (m, 2H), 2.38-2.05 (m, 5H), 1.90-1.66 (m, 6H), 1.12 (m, 9H). LCMS (ES+) (m/z): 616.31 (M+1).

Example 176: (S)-2-(tert-butoxy)-2-((M)-2-(2,3-difluorobenzoyl)-6-(8-fluoro-5-methylchroman-6-yl)-4,7-dimethylisoindolin-5-yl)acetic acid

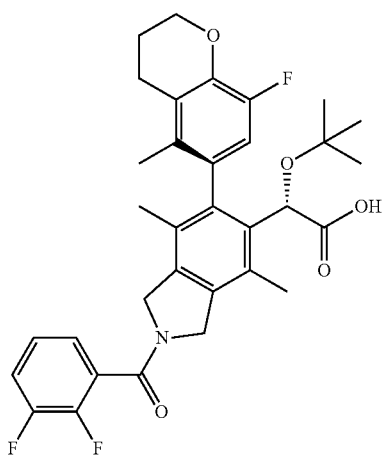

¹H NMR (400 MHz, CDCl₃) ∂ (mixture of rotamers) 7.23 (m, 3H), 6.65 (m, 1H), 5.01 (m, 3H), 4.66 (m, 2H), 4.26 (m, 2H), 2.68 (m, 2H), 2.39-2.03 (m, 5H), 1.90-1.63 (m, 6H), 1.12 (m, 9H). LCMS (ES+) (m/z): 582.35 (M+1); 1163.74 (2M+1).

Example 177: (S)-2-(tert-butoxy)-2-((M)-2-(5-fluoro-2-methylbenzoyl)-6-(8-fluoro-5-methylchroman-6-yl)-4,7-dimethylisoindolin-5-yl)acetic acid

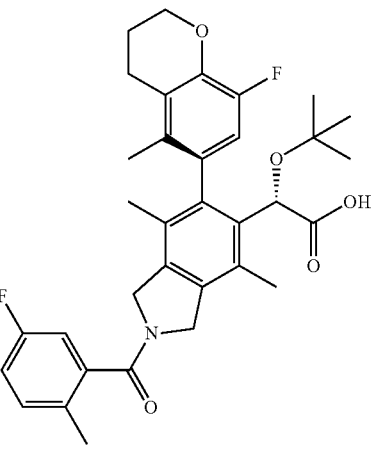

¹H NMR (400 MHz, CDCl₃) ∂ (mixture of rotamers) 7.26 (m, 1H), 7.01 (m, 2H), 6.66 (m, 1H), 5.02 (m, 3H), 4.48 (m, 2H), 4.26 (m, 2H), 2.68 (m, 2H), 2.38-2.04 (m, 8H), 1.90-1.60 (m, 6H), 1.12 (m, 9H). LCMS (ES+) (m/z): 578.38 (M+1); 1156.42 (2M+1).

Example 178: (S)-2-(tert-butoxy)-2-((M)-2-(3-fluoro-5-methylbenzoyl)-6-(8-fluoro-5-methylchroman-6-yl)-4,7-dimethylisoindolin-5-yl)acetic acid

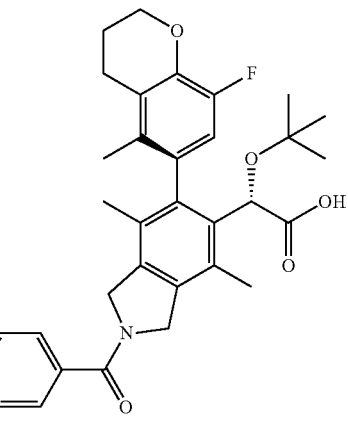

¹H NMR (400 MHz, CDCl₃) ∂ (mixture of rotamers) 7.15 (m, 1H), 7.10-6.93 (m, 2H), 6.66 (m, 1H), 5.01 (m, 3H), 4.71 (m, 2H), 4.25 (m, 2H), 2.68 (m, 2H), 2.45-2.04 (m, 8H), 1.91-1.63 (m, 6H), 1.12 (m, 9H). LCMS (ES+) (m/z): 578.45 (M+1); 1155.76 (2M+1).

Example 179: (S)-2-(tert-butoxy)-2-((M)-2-(2-fluoro-5-methoxybenzoyl)-6-(8-fluoro-5-methyl-chroman-6-yl)-4,7-dimethylisoindolin-5-yl)acetic acid

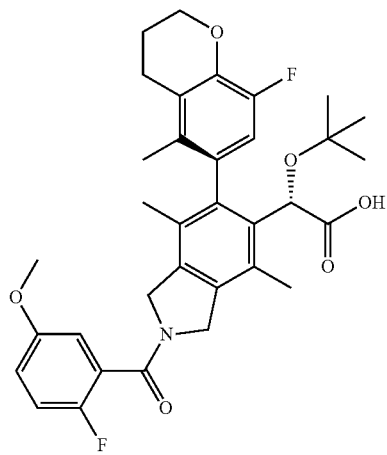

¹H NMR (400 MHz, CDCl₃) ∂ (mixture of rotamers) 7.08 (m, 1H), 6.94 (m, 2H), 6.66 (m, 1H), 5.02 (m, 3H), 4.68 (m, 2H), 4.26 (m, 2H), 3.81 (m, 3H), 2.68 (m, 2H), 2.38-2.03 (m, 5H), 1.91-1.63 (m, 6H), 1.12 (m, 9H). LCMS (ES+) (m/z): 594.49 (M+1); 1187.73 (2M+1).

Example 180: (S)-2-(tert-butoxy)-2-((M)-2-(4-fluoro-3-methoxybenzoyl)-6-(8-fluoro-5-methyl-chroman-6-yl)-4,7-dimethylisoindolin-5-yl)acetic acid

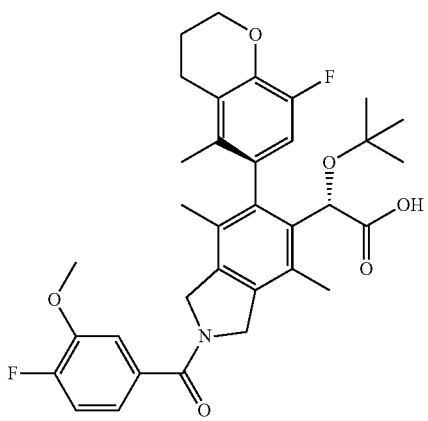

¹H NMR (400 MHz, CDCl₃) ∂ (mixture of rotamers) 7.21 (m, 1H), 7.13 (m, 2H), 6.66 (m, 1H), 5.01 (m, 3H), 4.75 (m, 2H), 4.25 (m, 2H), 3.92 (m, 3H), 2.67 (m, 2H), 2.38-2.02 (m, 5H), 1.92-1.64 (m, 6H), 1.12 (m, 9H). LCMS (ES+) (m/z): 594.48 (M+1); 1178.78 (2M+1).

Example 181: (S)-2-(tert-butoxy)-2-((M)-2-(3-chloro-5-fluorobenzoyl)-6-(8-fluoro-5-methylchroman-6-yl)-4,7-dimethylisoindolin-5-yl)acetic acid

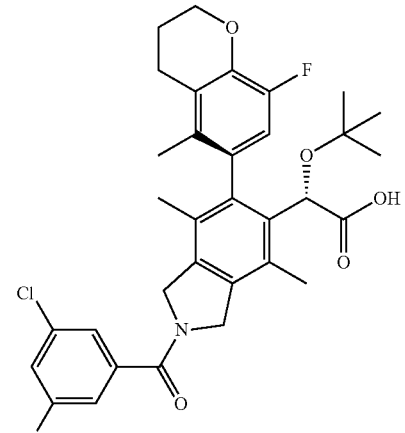

¹H NMR (400 MHz, CDCl₃) ∂ (mixture of rotamers) 7.36 (m, 1H), 7.19 (m, 2H), 6.66 (m, 1H), 5.02 (m, 3H), 4.71 (m, 2H), 4.25 (m, 2H), 2.68 (m, 2H), 2.37-2.04 (m, 5H), 1.90-1.65 (m, 6H), 1.12 (m, 9H). LCMS (ES+) (m/z): 598.35 (M+1); 1197.65 (2M+1).

Example 182: (S)-2-(tert-butoxy)-2-((M)-6-(8-fluoro-5-methylchroman-6-yl)-4,7-dimethyl-2-(5-methylnicotinoyl)isoindolin-5-yl)acetic acid

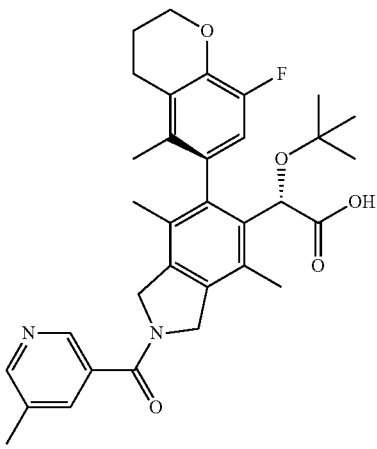

¹H NMR (400 MHz, CDCl₃) ∂ (mixture of rotamers) 8.92 (m, 1H), 8.74 (m, 1H), 8.23 (m, 1H), 6.66 (m, 1H), 5.04 (m, 3H), 4.81 (m, 2H), 4.26 (m, 2H), 2.76-2.53 (m, 5H), 2.39-2.04 (m, 5H), 1.92-1.64 (m, 6H), 1.12 (m, 9H). LCMS (ES+) (m/z): 561.37 (M+1); 1121.84 (2M+1).

Example 183: (S)-2-(tert-butoxy)-2-((M)-6-(8-fluoro-5-methylchroman-6-yl)-2-(2-methoxy-5-methylbenzoyl)-4,7-dimethylisoindolin-5-yl)acetic acid

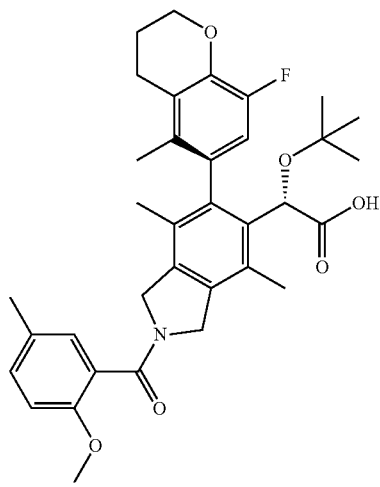

¹H NMR (400 MHz, CDCl₃) ∂ (mixture of rotamers) 7.19 (m, 1H), 7.12 (s, 1H), 6.87 (m, 1H), 6.66 (m, 1H), 5.00 (m, 3H), 4.59 (m, 2H), 4.25 (m, 2H), 3.83 (m, 3H), 2.68 (m, 2H), 2.38-2.04 (m, 8H), 1.91-1.60 (m, 6H), 1.11 (m, 9H). LCMS (ES+) (m/z): 590.40 (M+1); 1179.86 (2M+1).

Example 184: (S)-2-(tert-butoxy)-2-((M)-6-(8-fluoro-5-methylchroman-6-yl)-4,7-dimethyl-2-picolinoylisoindolin-5-yl)acetic acid

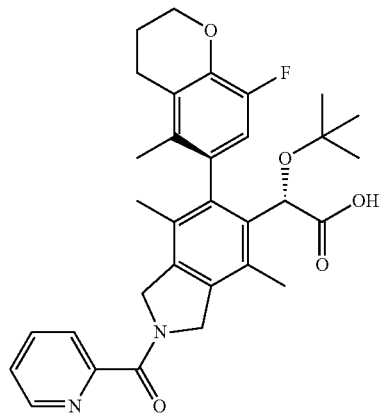

¹H NMR (400 MHz, CDCl₃) ∂ (mixture of rotamers) 8.69 (m, 1H), 7.92 (m, 2H), 7.43 (m, 1H), 6.69 (m, 1H), 5.15 (m, 5H), 4.26 (m, 2H), 2.68 (m, 2H), 2.38-2.05 (m, 5H), 1.89-1.70 (m, 6H), 1.12 (m, 9H). LCMS (ES+) (m/z): 547.34 (M+1); 1116.34 (2M+23).

Example 185: (S)-2-(tert-butoxy)-2-((M)-2-(5-chloro-2-methylbenzoyl)-6-(8-fluoro-5-methylchroman-6-yl)-4,7-dimethylisoindolin-5-yl)acetic acid

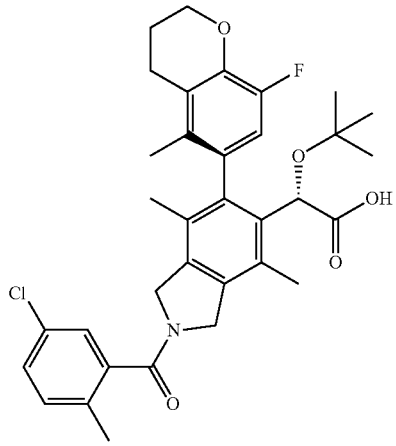

¹H NMR (400 MHz, CDCl₃) ∂ (mixture of rotamers) 7.26 (m, 3H), 6.66 (m, 1H), 5.00 (m, 3H), 4.48 (m, 2H), 4.25 (m, 2H), 2.67 (m, 2H), 2.39-2.04 (m, 8H), 1.91-1.60 (m, 6H), 1.12 (m, 9H). LCMS (ES+) (m/z): 594.34 (M+1); 1187.87 (2M+1).

Example 186: (S)-2-(tert-butoxy)-2-((M)-2-(3,4-difluorobenzoyl)-6-(8-fluoro-5-methylchroman-6-yl)-4,7-dimethylisoindolin-5-yl)acetic acid

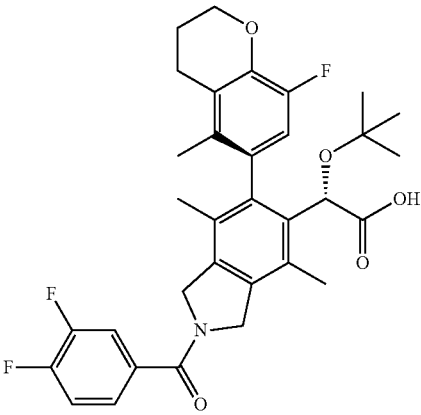

¹H NMR (400 MHz, CDCl₃) ∂ (mixture of rotamers) 7.49-7.20 (m, 3H), 6.66 (m, 1H), 5.01 (m, 3H), 4.74 (m, 2H), 4.26 (m, 2H), 2.68 (m, 2H), 2.38-2.04 (m, 5H), 1.91-1.64 (m, 6H), 1.12 (m, 9H). LCMS (ES+) (m/z): 582.35 (M+1); 1185.63 (2M+23).

Example 187: (S)-2-(tert-butoxy)-2-((M)-2-(3-fluoro-4-methoxybenzoyl)-6-(8-fluoro-5-methyl-chroman-6-yl)-4,7-dimethylisoindolin-5-yl)acetic acid

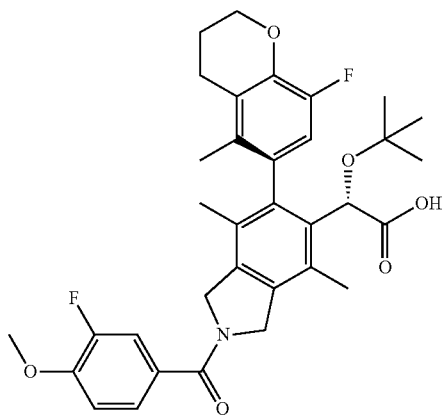

$^1$H NMR (400 MHz, CDCl$_3$) δ (mixture of rotamers) 7.37 (m, 2H), 7.03 (m, 1H), 6.67 (m, 1H), 5.01 (m, 3H), 4.78 (m, 2H), 4.25 (m, 2H), 3.94 (m, 3H), 2.68 (m, 2H), 2.36-2.05 (m, 5H), 1.88-1.65 (m, 6H) 1.12 (m, 9H). LCMS (ES+) (m/z): 594.39 (M+1), 1187.75 (M+23).

Example 188: (S)-2-(tert-butoxy)-2-((M)-2-(3,5-dichloro-4-fluorobenzoyl)-6-(8-fluoro-5-methylchroman-6-yl)-4,7-dimethylisoindolin-5-yl)acetic acid

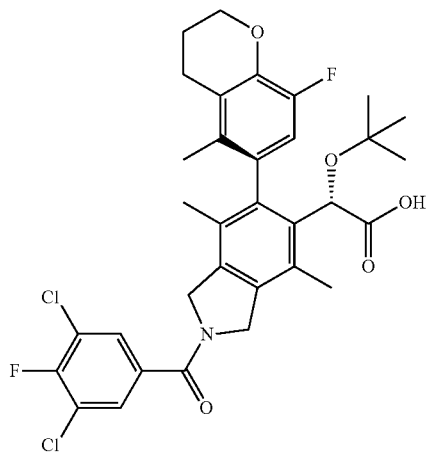

$^1$H NMR (400 MHz, CDCl$_3$) δ (mixture of rotamers) 7.55 (m, 2H), 6.66 (m, 1H), 5.01 (m, 3H), 4.73 (m, 2H), 4.25 (m, 2H), 2.68 (m, 2H), 2.36-2.04 (m, 5H), 1.89-1.66 (m, 6H) 1.11 (m, 9H). LCMS (ES+) (m/z): 632.33 (M+1).

Example 189: (S)-2-(tert-butoxy)-2-((M)-2-(2,4-dimethylbenzoyl)-6-(8-fluoro-5-methylchroman-6-yl)-4,7-dimethylisoindolin-5-yl)acetic acid

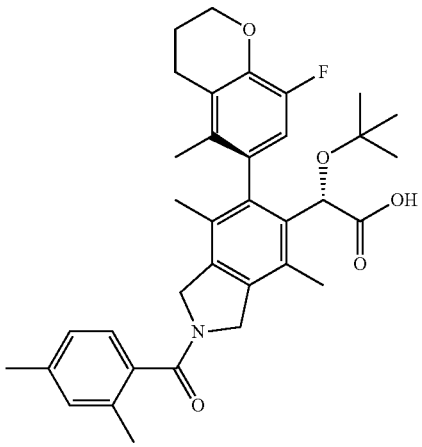

$^1$H NMR (400 MHz, CDCl$_3$) δ (mixture of rotamers) 7.17 (m, 1H), 7.08 (m, 2H), 6.66 (m, 1H), 5.02 (m, 3H), 4.48 (m, 2H), 4.25 (m, 2H), 2.71-2.05 (m, 13H), 1.90-1.58 (m, 6H) 1.12 (m, 9H). LCMS (ES+) (m/z): 574.58 (M+1), 1147.92 (2M+1).

Example 190: (S)-2-(tert-butoxy)-2-((M)-6-(8-fluoro-5-methylchroman-6-yl)-4,7-dimethyl-2-(4-methylbenzoyl)isoindolin-5-yl)acetic acid

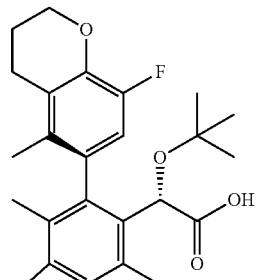

$^1$H NMR (400 MHz, CDCl$_3$) δ (mixture of rotamers) 7.48 (m, 2H), 7.26 (m, 2H), 6.66 (m, 1H), 5.02 (m, 3H), 4.75 (m, 2H), 4.26 (m, 2H), 2.67 (m, 2H), 2.46-2.04 (m, 8H), 1.88-1.62 (m, 6H) 1.11 (m, 9H). LCMS (ES+) (m/z): 560.35 (M+1), 1119.78 (2M+1).

Example 191: (S)-2-(tert-butoxy)-2-((M)-2-(3,5-dimethylbenzoyl)-6-(8-fluoro-5-methylchroman-6-yl)-4,7-dimethylisoindolin-5-yl)acetic acid

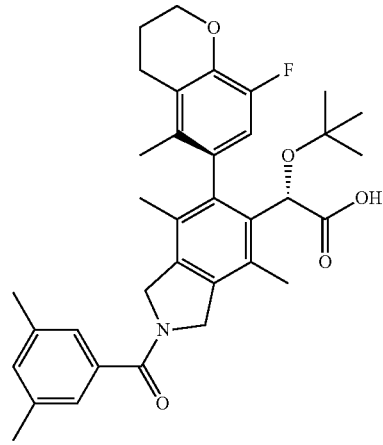

¹H NMR (400 MHz, CDCl₃) ∂ (mixture of rotamers) 7.15 (m, 2H), 7.09 (m, 1H), 6.66 (m, 1H), 5.01 (m, 3H), 4.71 (m, 2H), 4.25 (m, 2H), 2.68 (m, 2H), 2.40-2.05 (m, 11H), 1.89-1.62 (m, 6H) 1.11 (m, 9H). LCMS (ES+) (m/z): 574.38 (M+1), 1148.62 (2M+1).

Example 192: (S)-2-(tert-butoxy)-2-((M)-6-(8-fluoro-5-methylchroman-6-yl)-2-(4-methoxy-3-methylbenzoyl)-4,7-dimethylisoindolin-5-yl)acetic acid

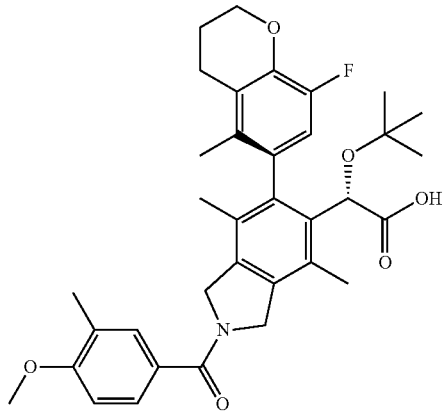

¹H NMR (400 MHz, CDCl₃) ∂ (mixture of rotamers) 7.42 (m, 2H), 6.86 (m, 1H), 6.67 (m, 1H), 5.01 (m, 3H), 4.79 (m, 2H), 4.25 (m, 2H), 3.87 (m, 3H), 2.68 (m, 2H), 2.36-2.05 (m, 8H), 1.89-1.64 (m, 6H) 1.12 (m, 9H). LCMS (ES+) (m/z): 590.53 (M+1), 1179.89 (2M+1).

Example 193: (S)-2-(tert-butoxy)-2-((M)-2-(2,3-dimethylbenzoyl)-6-(8-fluoro-5-methylchroman-6-yl)-4,7-dimethylisoindolin-5-yl)acetic acid

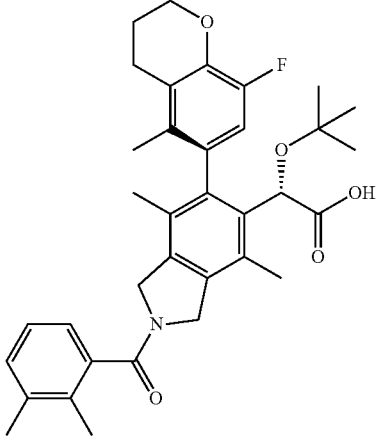

¹H NMR (400 MHz, CDCl₃) ∂ (mixture of rotamers) 7.23-7.09 (m, 3H), 6.66 (m, 1H), 5.02 (m, 3H), 4.47 (m, 2H), 4.25 (m, 2H), 2.67 (m, 2H), 2.38-2.04 (m, 11H), 1.90-1.58 (m, 6H) 1.12 (m, 9H). LCMS (ES+) (m/z): 574.54 (M+1), 1147.86 (2M+1).

Example 194: (S)-2-(tert-butoxy)-2-((M)-2-(3-chloro-4,5-difluorobenzoyl)-6-(8-fluoro-5-methylchroman-6-yl)-4,7-dimethylisoindolin-5-yl)acetic acid

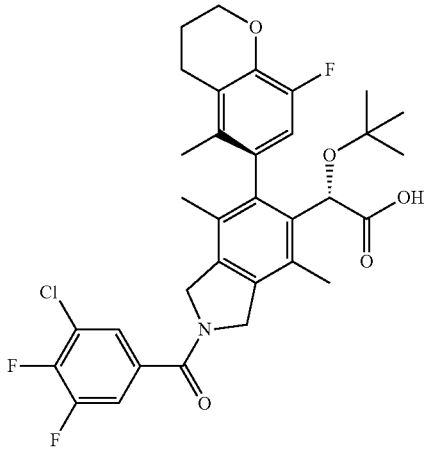

¹H NMR (400 MHz, CDCl₃) ∂ (mixture of rotamers) 7.48-7.31 (m, 2H), 6.66 (m, 1H), 5.01 (m, 3H), 4.73 (m, 2H), 4.25 (m, 2H), 2.68 (m, 2H), 2.36-2.05 (m, 5H), 1.88-1.65 (m, 6H) 1.12 (m, 9H). LCMS (ES+) (m/z): 616.46 (M+1).

Example 195: (S)-2-(tert-butoxy)-2-((M)-2-(3-fluoro-2-methoxybenzoyl)-6-(8-fluoro-5-methyl-chroman-6-yl)-4,7-dimethylisoindolin-5-yl)acetic acid

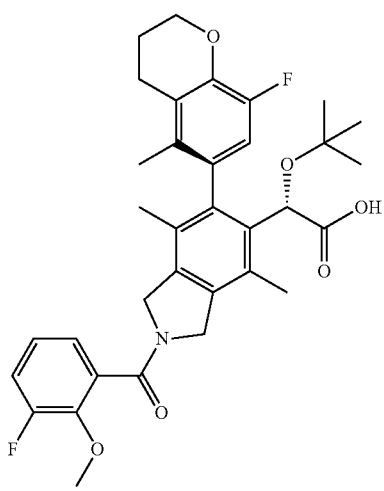

¹H NMR (400 MHz, CDCl₃) ∂ (mixture of rotamers) 7.22-7.06 (m, 3H), 6.66 (m, 1H), 5.10-4.93 (m, 3H), 4.58 (m, 2H), 4.25 (m, 2H), 3.98 (m, 3H), 2.67 (m, 2H), 2.37-2.04 (m, 5H), 1.89-1.60 (m, 6H) 1.12 (m, 9H). LCMS (ES+) (m/z): 594.60 (M+1), 1187.90 (2M+1).

Example 196: (S)-2-(tert-butoxy)-2-((M)-6-(8-fluoro-5-methylchroman-6-yl)-2-(4-methoxybenzoyl)-4,7-dimethylisoindolin-5-yl)acetic acid

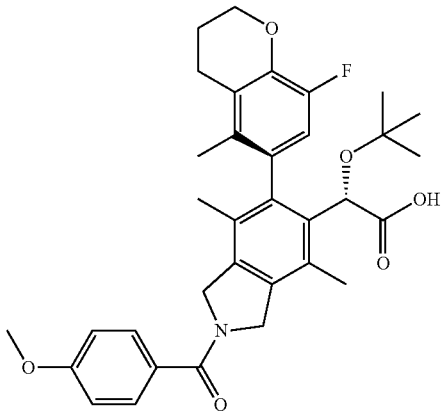

¹H NMR (400 MHz, CDCl₃) ∂ (mixture of rotamers) 7.57 (m, 2H), 6.96 (m, 2H), 6.67 (m, 1H), 5.03 (m, 3H), 4.79 (m, 2H), 4.25 (m, 2H), 3.86 (m, 3H), 2.67 (m, 2H), 2.37-2.05 (m, 5H), 1.89-1.64 (m, 6H) 1.12 (m, 9H). LCMS (ES+) (m/z): 576.34 (M+1), 1152.61 (2M+1).

Example 197: (S)-2-(tert-butoxy)-2-((M)-6-(8-fluoro-5-methylchroman-6-yl)-2-(2-fluoro-6-methyl-benzoyl)-4,7-dimethylisoindolin-5-yl)acetic acid

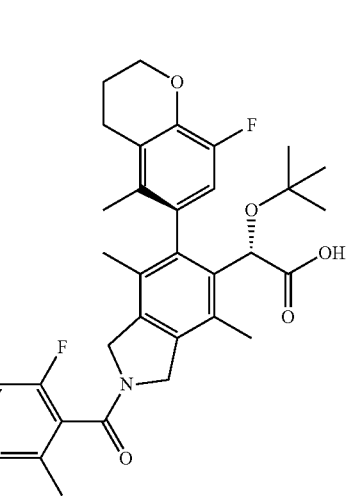

¹H NMR (400 MHz, CDCl3) ∂ (mixture of rotamers) 7.29 (m, 1H), 7.11-6.94 (m, 2H), 6.66 (m, 1H), 5.02 (m, 3H), 4.63 (m, 1H), 4.41 (m, 1H), 4.25 (m, 2H), 2.67 (m, 2H), 2.40-2.05 (m, 8H), 1.90-1.60 (m, 6H) 1.12 (m, 9H). LCMS (ES+) (m/z): 578.36 (M+1), 1155.65 (2M+1).

Example 198: (S)-2-(tert-butoxy)-2-((M)-2-(4-chlorobenzoyl)-6-(8-fluoro-5-methylchroman-6-yl)-4,7-dimethylisoindolin-5-yl)acetic acid

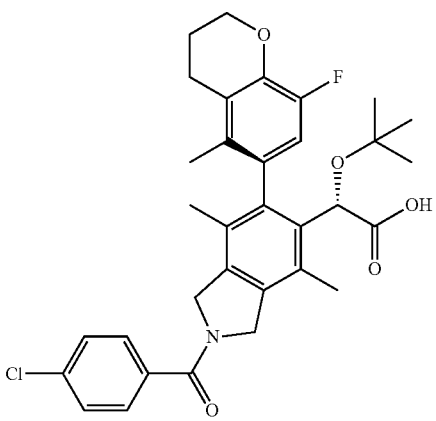

¹H NMR (400 MHz, CDCl₃) ∂ (mixture of rotamers) 7.53 (m, 2H), 7.45 (m, 2H), 6.66 (m, 1H), 5.02 (m, 3H), 4.72 (m, 2H), 4.25 (m, 2H), 2.67 (m, 2H), 2.36-2.05 (m, 5H), 1.89-1.63 (m, 6H) 1.12 (m, 9H). LCMS (ES+) (m/z): 580.32 (M+1).

Example 199: (S)-2-(tert-butoxy)-2-((M)-6-(8-fluoro-5-methylchroman-6-yl)-2-(2-methoxybenzoyl)-4,7-dimethylisoindolin-5-yl)acetic acid

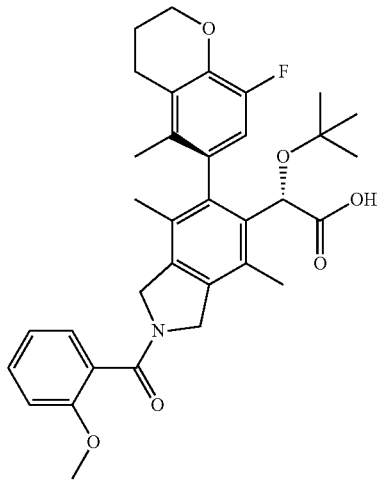

¹H NMR (400 MHz, CDCl₃) δ (mixture of rotamers) 7.41 (m, 1H), 7.32 (m, 1H), 7.01 (m, 2H), 6.66 (m, 1H), 5.02 (m, 3H), 4.57 (m, 2H), 4.26 (m, 2H), 3.86 (m, 3H), 2.68 (m, 2H), 2.38-2.05 (m, 5H), 1.90-1.58 (m, 6H) 1.12 (m, 9H). LCMS (ES+) (m/z): 576.36 (M+1), 1173.75 (2M+23).

Example 200: (S)-2-(tert-butoxy)-2-((M)-6-(8-fluoro-5-methylchroman-6-yl)-2-(2-methoxy-4-methylbenzoyl)-4,7-dimethylisoindolin-5-yl)acetic acid

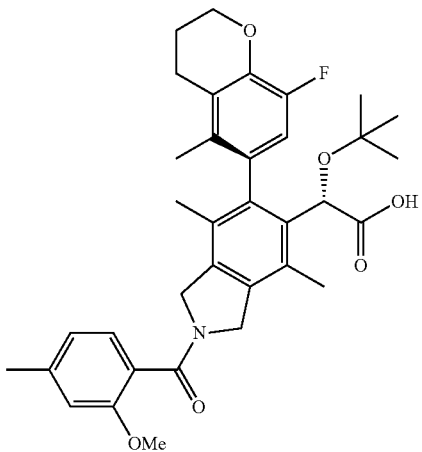

¹H NMR (CDCl3) δ: 7.20 (m, 1H), 6.89-6.74 (m, 2H), 6.66 (m, 1H), 5.01 (m, 3H), 4.59 (m, 2H), 4.25 (m, 2H), 3.84 (m, 3H), 2.67 (m, 2H), 2.45-2.02 (m, 8H), 1.90-1.59 (m, 6H), 1.12 (m, 9H). LCMS ES+(m/z): 590.52 (M+1); 1179.82 (2M+1).

Example 201: (S)-2-(tert-butoxy)-2-((M)-6-(8-fluoro-5-methylchroman-6-yl)-2-(5-(3-fluorophenyl)-1,3,4-oxadiazol-2-yl)-4,7-dimethylisoindolin-5-yl)acetic acid

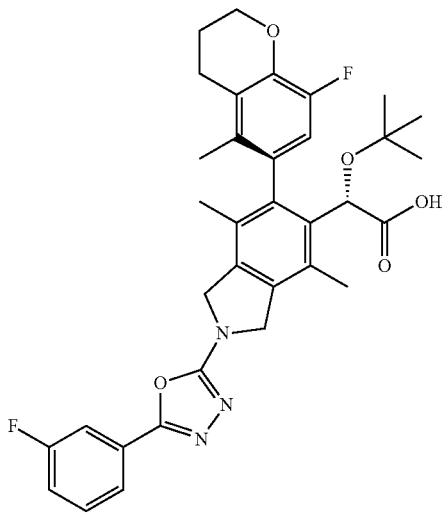

Step 1: (S)-methyl 2-(tert-butoxy)-2-((M)-6-(8-fluoro-5-methylchroman-6-yl)-2-(2-(3-fluorobenzoyl)hydrazinecarbonyl)-4,7-dimethylisoindolin-5-yl)acetate

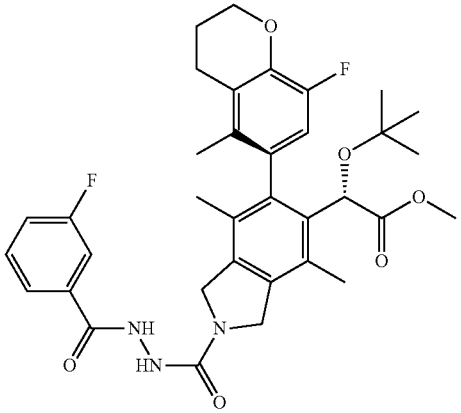

A solution of (S)-methyl 2-(tert-butoxy)-2-((M)-6-(8-fluoro-5-methylchroman-6-yl)-4,7-dimethylisoindolin-5-yl)acetate (20 mg, 0.044 mmol) in 2 mL THF was added dropwise to phosgene (0.058 mL, 0.110 mmol) in 1 mL THF at 0° C. The reaction was warmed slowly to room temperature and stirred for 1 hour, then concentrated to a brown oil and redissolved in 2 mL THF. The solution was cooled to 0° C. and pyridine (3.91 µl, 0.048 mmol) was added dropwise followed by a solution of 3-fluorobenzohydrazide (33.8 mg, 0.220 mmol) dissolved in 2 mL THF. The solution was warmed slowly to room temperature and stirred for 2 hours. The solvent was removed to leave a brown oil. The oil was dissolved in EtOAc, washed with 1M HCl, brine and dried over Na2SO4. The oil was purified by HPLC to yield the title compound as a white solid (9.6 mg, 0.015 mmol, 34.4% yield). LCMS (ES+) (m/z): 636.41 (M+1).

Step 2: (S)-methyl 2-(tert-butoxy)-2-((M)-6-(8-fluoro-5-methylchroman-6-yl)-2-(5-(3-fluorophenyl)-1,3,4-oxadiazol-2-yl)-4,7-dimethylisoindolin-5-yl)acetate

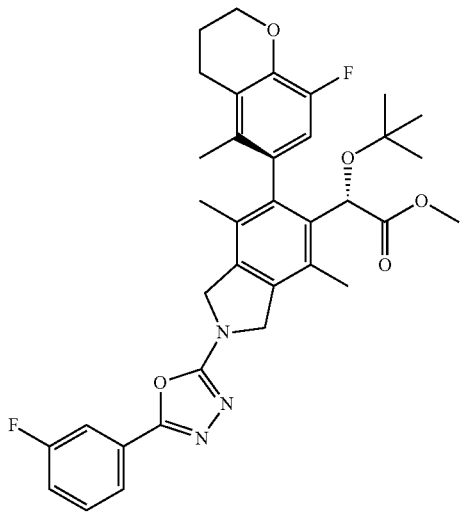

A solution of (S)-methyl 2-(tert-butoxy)-2-((M)-6-(8-fluoro-5-methylchroman-6-yl)-2-(2-(3-fluorobenzoyl)hydrazinecarbonyl)-4,7-dimethylisoindolin-5-yl)acetate (9.6 mg, 0.015 mmol) and burgess reagent (10.80 mg, 0.045 mmol) in 2 mL DCM was heated in a sealed microwave vial at 70° C. for 30 minutes. The solution was diluted with DCM and washed with water. The organic layer was dried over sodium sulfate and purified by silica gel chromatography (0-100% ethyl acetate/hexanes gradient elution) to give the title compound as a purple oil (9.33 mg). LCMS (ES+) (m/z): 618.53 (M+1).

Step 3: (S)-2-(tert-butoxy)-2-((M)-6-(8-fluoro-5-methylchroman-6-yl)-2-(5-(3-fluorophenyl)-1,3,4-oxadiazol-2-yl)-4,7-dimethylisoindolin-5-yl)acetic acid To a solution of (S)-methyl 2-(tert-butoxy)-2-((M)-6-(8-fluoro-5-methylchroman-6-yl)-2-(5-(3-fluorophenyl)-1,3,4-oxadiazol-2-yl)-4,7-dimethylisoindolin-5-yl)acetate (9.33 mg, 0.015 mmol) in 2 mL Dioxane was added LiOH (0.227 mL, 0.227 mmol). The solution was heated to 70° C. and stirred overnight. SM remains by LCMS, another 10 eq LiOH was added and heated to 80° C. for 1 hour. Solution concentrated and redissolved in EtoAC, washed with 1 M HCl, brine and solvent removed. The resulting oil was purified by HPLC to yield the title compound as a white powder (1.8 mg, 2.98 μmol, 19.74% yield).

$^1$H NMR (400 MHz, CDCl$_3$) ∂ (mixture of rotamers) 7.78 (m, 1H), 7.67 (m, 1H), 7.46 (m, 1H), 7.17 (m, 1H), 6.70 (m, 1H), 5.10 (m, 1H), 4.96 (m, 4H), 4.26 (m, 2H), 2.69 (m, 2H), 2.34 (m, 3H), 2.12 (m, 2H), 1.85 (m, 6H), 1.13 (m, 9H). LCMS (ES+) (m/z): 604.39 (M+1).

Example 202: (S)-2-((M)-2-(benzo[d]oxazol-2-yl)-6-(8-fluoro-5-methylchroman-6-yl)-4,7-dimethylisoindolin-5-yl)-2-(tert-butoxy)acetic acid

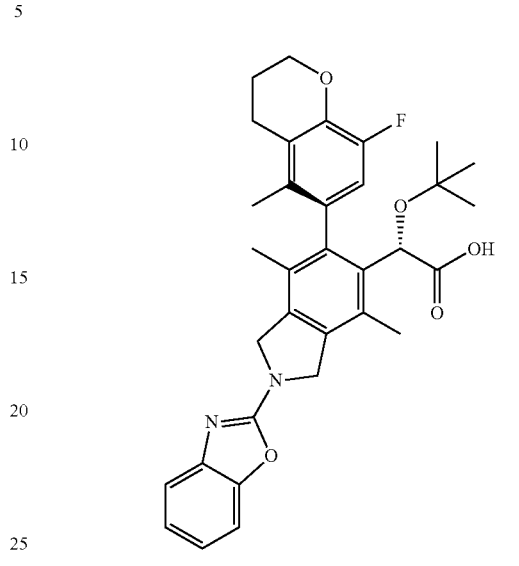

Step 1 (S)-methyl 2-((M)-2-(benzo[d]oxazol-2-yl)-6-(8-fluoro-5-methylchroman-6-yl)-4,7-dimethylisoindolin-5-yl)-2-(tert-butoxy)acetate

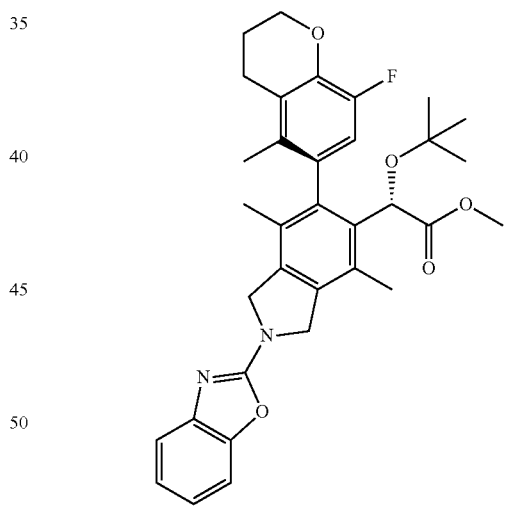

A solution of (S)-methyl 2-(tert-butoxy)-2-((M)-6-(8-fluoro-5-methylchroman-6-yl)-4,7-dimethylisoindolin-5-yl)acetate (10 mg, 0.022 mmol), 2-chlorobenzo[d]oxazole (5.01 μl, 0.044 mmol), and K$_2$CO$_3$ (6.07 mg, 0.044 mmol) in 2 mL DMF were heated in a sealed microwave vial for 30 minutes at 150° C. The solution was diluted with diethyl ether and washed with water x2, brine, dried over sodium sulfate and purified by silica gel chromatography (0-100% ethyl acetate/hexanes gradient elution) to give the title compound as a colorless oil (10 mg). LCMS (ES+) (m/z): 573.42

Step 2 (S)-2-((M)-2-(benzo[d]oxazol-2-yl)-6-(8-fluoro-5-methylchroman-6-yl)-4,7-dimethylisoindolin-5-yl)-2-(tert-butoxy)acetic acid To a solution of (S)-methyl 2-((M)-2-(benzo[d]oxazol-2-yl)-6-(8-fluoro-5-methylchroman-6-yl)-4,7-dimethylisoindolin-5-yl)-2-(tert-butoxy)acetate (10 mg, 0.017 mmol) in 2 mL Dioxane was added LiOH (0.262 mL, 0.262 mmol). The solution was heated to 70° C. and stirred overnight. SM remains by LCMS, another 10 eq LiOH was added and heated to 80° C. for 1 hour. The solution was concentrated and redissolved in EtoAC, washed with 1 M HCl, brine and solvent removed. The resulting oil was purified by HPLC to yield the title compound as a white powder (2.5 mg, 4.48 µmol, 25.6% yield).

$^1$H NMR (400 MHz, CDCl$_3$) ∂ (mixture of rotamers) 7.51 (m, 1H), 7.36 (m, 1H), 7.25 (m, 1H), 7.12 (m, 1H), 6.70 (m, 1H), 5.06 (m, 5H), 4.26 (m, 2H), 2.69 (m, 2H), 2.34 (m, 3H), 2.12 (m, 2H), 1.85 (m, 6H), 1.14 (m, 9H). LCMS (ES+) (m/z): 559.36 (M+1); 581.37 (M+23).

Example 203: (S)-2-(tert-butoxy)-2-((M)-2-(5-(3,4-difluorobenzyl)-1,3,4-oxadiazol-2-yl)-6-(8-fluoro-5-methylchroman-6-yl)-4,7-dimethylisoindolin-5-yl)acetic acid The title compound was made in a similar manner to that described in Example 201.

$^1$H NMR (400 MHz, CDCl$_3$) ∂ (mixture of rotamers) 7.20-7.01 (m, 3H), 6.67 (m, 1H), 5.07 (m, 1H), 4.82 (m, 4H), 4.26 (m, 2H), 4.07 (m, 3H), 2.68 (m, 2H), 2.29 (m, 3H), 2.11 (m, 2H), 1.87-1.75 (m, 6H) 1.12 (m, 9H). LCMS (ES+) (m/z): 636.54 (M+1), 658.54 (M+23).

Example 204: (S)-2-(tert-butoxy)-2-((M)-6-(8-fluoro-5-methylchroman-6-yl)-2-(5-fluorobenzo[d]oxazol-2-yl)-4,7-dimethylisoindolin-5-yl)acetic acid

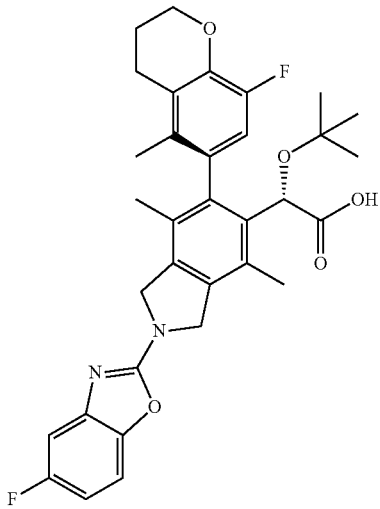

The title compound was made in a similar manner to that described in Example 202.

$^1$H NMR (400 MHz, CDCl$_3$) ∂ (mixture of rotamers) 7.21 (m, 1H), 7.10 (m, 1H), 6.73 (m, 2H), 5.13-4.93 (m, 5H), 4.26 (m, 2H), 2.68 (m, 2H), 2.34 (m, 3H), 2.12 (m, 2H), 1.85 (m, 6H), 1.14 (m, 9H). LCMS (ES+) (m/z): 577.34 (M+1); 600.42 (2M+1).

Example 205: (S)-2-(tert-butoxy)-2-((M)-6-(8-fluoro-5-methylchroman-6-yl)-4,7-dimethyl-2-((M)-2-methylpiperidine-1-carbonyl)isoindolin-5-yl)acetic acid The title compound was made in a similar manner to example 100.

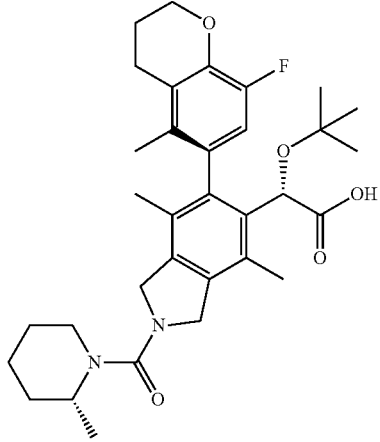

$^1$H NMR (400 MHz, CDCl$_3$) ∂ (mixture of rotamers) 6.67 (m, 1H), 5.05 (m, 1H), 4.74 (m, 4H), 4.25 (m, 2H), 3.15 (m, 1H), 3.07 (m, 1H), 2.68 (m, 2H), 2.26 (m, 3H), 2.11 (m, 2H), 1.88-1.46 (m, 9H), 1.30-1.07 (m, 16H). LCMS (ES+) (m/z): 667.43 (M+1); 1134.06 (2M+1).

Example 206: (S)-2-(tert-butoxy)-2-((M)-2-(4,4-dimethylazepane-1-carbonyl)-6-(8-fluoro-5-methylchroman-6-yl)-4,7-dimethylisoindolin-5-yl)acetic acid The title compound was made in a similar manner to example 100.

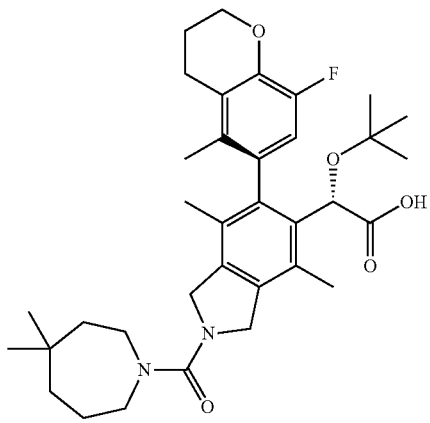

$^1$H NMR (400 MHz, CDCl$_3$) ∂ (mixture of rotamers) 6.67 (m, 1H), 5.06 (m, 1H), 4.75 (m, 4H), 4.25 (m, 2H), 3.41 (m, 4H), 2.68 (m, 2H), 2.32-2.04 (m, 5H), 1.90-1.70 (m, 8H), 1.64 (m, 2H), 1.44 (m, 2H), 1.11 (m, 9H), 0.96 (m, 6H). LCMS (ES+) (m/z): 595.46 (M+1); 1189.97 (2M+1).

Example 207: (S)-2-(tert-butoxy)-2-((M)-6-(8-fluoro-5-methylchroman-6-yl)-4,7-dimethyl-2-(neopentylcarbamoyl)isoindolin-5-yl)acetic acid The title compound was made in a similar manner to example 100.

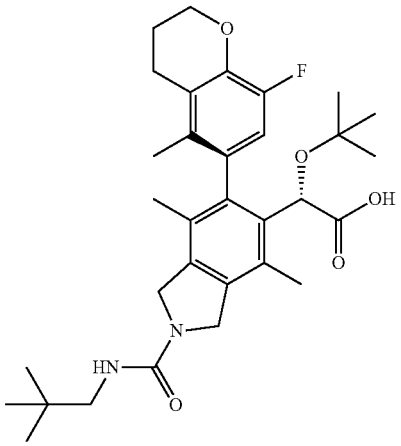

$^1$H NMR (400 MHz, CDCl$_3$) ∂ (mixture of rotamers) 6.67 (m, 1H), 5.06 (m, 1H), 4.69 (m, 4H), 4.40 (m, 1H), 4.26 (m, 2H), 3.14 (m, 2H), 2.68 (m, 2H), 2.28 (m, 3H), 2.11 (m, 2H), 1.85 (m, 3H), 1.78 (m, 3H), 1.12 (m, 9H), 0.94 (m, 9H). LCMS (ES+) (m/z): 555.41 (M+1); 1109.97 (2M+1).

Example 208: (S)-2-(tert-butoxy)-2-((M)-6-(8-fluoro-5-methylchroman-6-yl)-4,7-dimethyl-2-(pyrrolidine-1-carbon yl)isoindolin-5-yl)acetic acid The title compound was made in a similar manner to example 100.

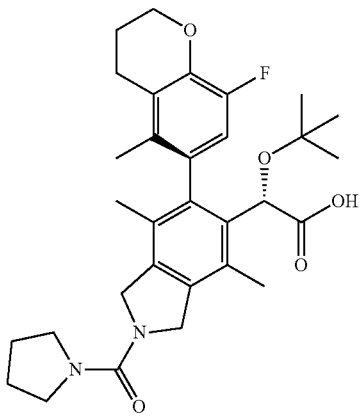

$^1$H NMR (400 MHz, CDCl$_3$) ∂ (mixture of rotamers) 6.68 (m, 1H), 5.05 (m, 1H), 4.77 (m, 4H), 4.25 (m, 2H), 3.48 (m, 4H), 2.68 (m, 2H), 2.27 (m, 3H), 2.11 (m, 2H), 1.96-1.72 (m, 10H), 1.11 (m, 9H). LCMS (ES+) (m/z): 539.37 (M+1); 1077.80 (2M+1).

Example 209: (S)-2-(tert-butoxy)-2-((M)-6-(8-fluoro-5-methylchroman-6-yl)-4,7-dimethyl-2-((S)-3-methylmorpholine-4-carbonyl)isoindolin-5-yl) acetic acid The title compound was made in a similar manner to example 100.

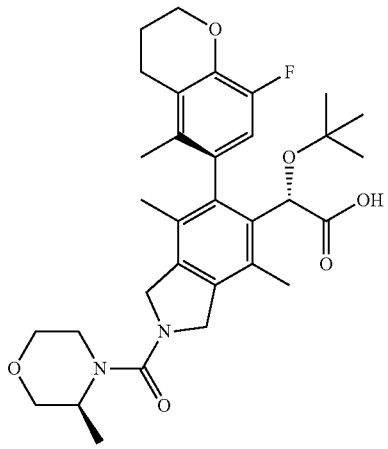

$^1$H NMR (400 MHz, CDCl$_3$) ∂ (mixture of rotamers) 6.67 (m, 1H), 5.05 (m, 1H), 4.76 (m, 4H), 4.26 (m, 2H), 3.93-3.56 (m, 5H), 3.38 (m, 2H), 2.68 (m, 2H), 2.27 (m, 3H), 2.11 (m, 2H), 1.85 (m, 3H), 1.77 (m, 3H), 1.35 (m, 3H), 1.12 (m, 9H). LCMS (ES+) (m/z): 569.38 (M+1); 1137.83 (2M+1).

Example 210: (S)-2-(tert-butoxy)-2-((M)-6-(8-fluoro-5-methylchroman-6-yl)-2-((3-fluorophenyl)carbamoyl)-4,7-dimethylisoindolin-5-yl)acetic acid

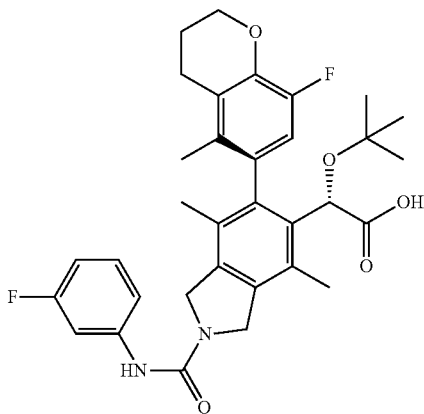

Step 1: (S)-methyl 2-(tert-butoxy)-2-((M)-6-(8-fluoro-5-methylchroman-6-yl)-2-((3-fluorophenyl)carbamoyl)-4,7-dimethylisoindolin-5-yl)acetate

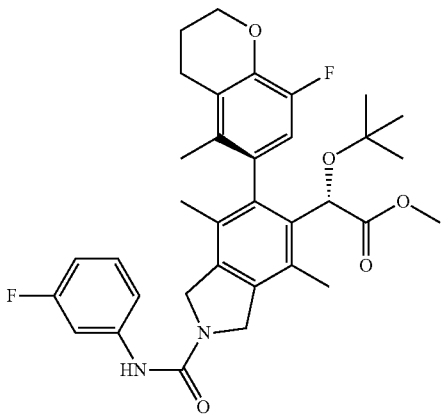

To a solution of phosgene (0.464 mL, 0.878 mmol) in 2 mL THF at 0° C. was added a solution of 3-fluoroaniline (0.042 mL, 0.439 mmol) in 3 mL THF dropwise. The solution was stirred for 30 minutes then warmed slowly to room temperature and solvent removed. The oil was redissolved in 2 mL THF and cooled to 0° C. A solution of (S)-methyl 2-(tert-butoxy)-2-((M)-6-(8-fluoro-5-methylchroman-6-yl)-4,7-dimethylisoindolin-5-yl)acetate (40 mg, 0.088 mmol) in 3 mL THF was added dropwise. The solution was stirred for 30 minutes then warmed to room temperature and solvent removed. The purple oil was dissolved in EtOAc was washed with 1M HCl, brine, dried over sodium sulfate and solvent removed. The oil was purified by HPLC to yield the tittle compound as a white solid (6.9 mg). LCMS (ES+) (m/z): 593.43 (M+1); 1185.77 (2M+1).

Step 2: (S)-2-(tert-butoxy)-2-((M)-6-(8-fluoro-5-methylchroman-6-yl)-2-((3-fluorophenyl)carbamoyl)-4,7-dimethylisoindolin-5-yl)acetic acid To a solution of (S)-methyl 2-(tert-butoxy)-2-((M)-6-(8-fluoro-5-methylchroman-6-yl)-2-((3-fluorophenyl)carbamoyl)-4,7-dimethylisoindolin-5-yl)acetate (6.9 mg, 0.012 mmol) in 2 mL Dioxane was added LiOH (0.175 mL, 0.175 mmol). The solution was heated to 70° C. and stirred overnight. The solution was concentrated and dissolved in EtoAc, washed with 1 M HCl, brine and solvent removed. The resulting oil was purified by HPLC to yield the title compound as a white powder (1.2 mg, 2.074 μmol, 17.81% yield).

$^1$H NMR (400 MHz, CDCl$_3$) ∂ (mixture of rotamers) 7.45 (m, 1H), 7.30-7.09 (m, 2H), 6.72 (m, 2H), 6.35 (s, 1H), 5.08 (s, 1H), 4.81 (m, 4H), 4.26 (m, 2H), 2.69 (m, 2H), 2.31 (s, 3H), 2.12 (m, 2H), 1.89-1.77 (m, 6H) 1.13 (m, 9H). LCMS (ES+) (m/z): 579.55 (M+1), 1180.53 (2M+23).

Example 211: (S)-2-(tert-butoxy)-2-((M)-2-(4,4-dimethylpiperidine-1-carbonyl)-6-(8-fluoro-5-methylchroman-6-yl)-4,7-dimethylisoindolin-5-yl)acetic acid The title compound was made in a similar manner to example 100.

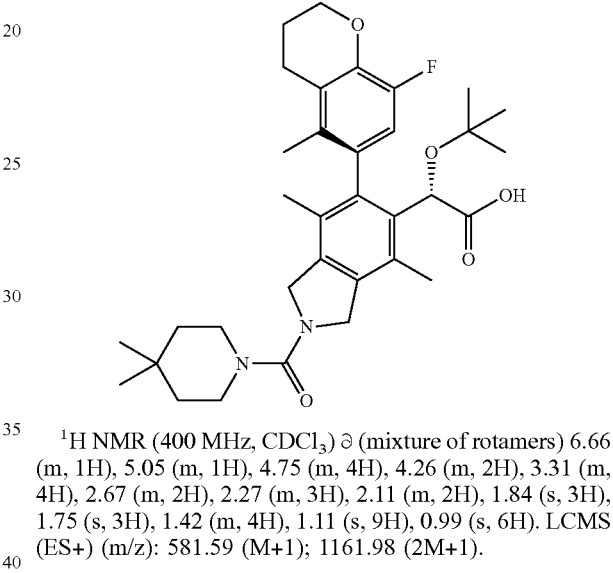

$^1$H NMR (400 MHz, CDCl$_3$) ∂ (mixture of rotamers) 6.66 (m, 1H), 5.05 (m, 1H), 4.75 (m, 4H), 4.26 (m, 2H), 3.31 (m, 4H), 2.67 (m, 2H), 2.27 (m, 3H), 2.11 (m, 2H), 1.84 (s, 3H), 1.75 (s, 3H), 1.42 (m, 4H), 1.11 (s, 9H), 0.99 (s, 6H). LCMS (ES+) (m/z): 581.59 (M+1); 1161.98 (2M+1).

Example 212: (S)-2-(tert-butoxy)-2-((M)-6-(8-fluoro-5-methylchroman-6-yl)-4,7-dimethyl-2-((S)-2-methylpyrrolidine-1-carbonyl)isoindolin-5-yl)acetic acid The title compound was made in a similar manner to example 100.

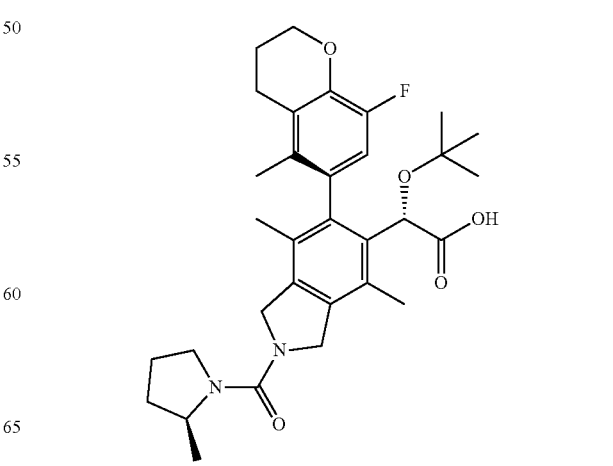

¹H NMR (400 MHz, CDCl₃) ∂ (mixture of rotamers) 6.67 (m, 1H), 5.02 (m, 3H), 4.54 (m, 2H), 4.24 (m, 2H), 4.09 (m, 1H), 3.59-3.39 (m, 2H), 2.68 (m, 2H), 2.28 (s, 3H), 2.11 (m, 2H), 1.98-1.71 (m, 8H), 1.49 (m, 1H), 1.21 (m, 3H), 1.12 (s, 9H). LCMS (ES+) (m/z): 553.41 (M+1); 1105.94 (2M+1).

Example 213: (S)-2-(tert-butoxy)-2-((M)-2-(4,4-difluoropiperidine-1-carbonyl)-6-(8-fluoro-5-methylchroman-6-yl)-4,7-dimethylisoindolin-5-yl)acetic acid The title compound was made in a similar manner to example 100.

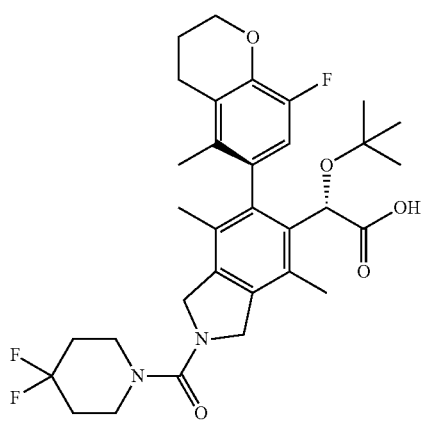

¹H NMR (400 MHz, CDCl₃) ∂ (mixture of rotamers) 6.66 (m, 1H), 5.06 (s, 1H), 4.78 (m, 4H), 4.25 (m, 2H), 3.48 (m, 4H), 2.67 (m, 2H), 2.27 (s, 3H), 2.16-1.98 (m, 6H), 1.85 (3, 3H), 1.77 (s, 3H), 1.12 (s, 9H). LCMS (ES+) (m/z): 589.42 (M+1); 1177.87 (2M+1).

Example 214: (S)-2-(tert-butoxy)-2-((M)-2-(3,3-dimethylpyrrolidine-1-carbonyl)-6-(8-fluoro-5-methylchroman-6-yl)-4,7-dimethylisoindolin-5-yl)acetic acid The title compound was made in a similar manner to example 100.

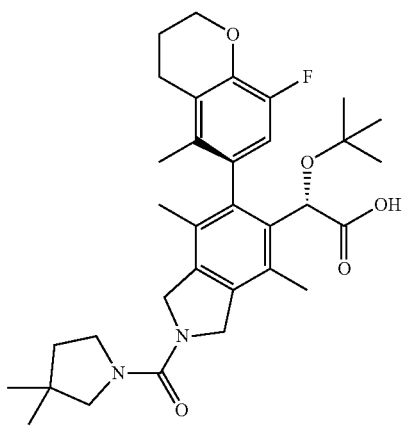

¹H NMR (400 MHz, CDCl₃) ∂ (mixture of rotamers) 6.67 (m, 1H), 5.05 (m, 1H), 4.77 (m, 4H), 4.26 (m, 2H), 3.58 (m, 2H), 3.23 (s, 2H), 2.68 (m, 2H), 2.27 (m, 3H), 2.11 (m, 2H), 1.88-1.64 (m, 8H), 1.11 (m, 15H). LCMS (ES+) (m/z): 567.60 (M+1); 1134.06 (2M+1).

Example 215: ((S)-2-(tert-butoxy)-2-((M)-6-(8-fluoro-5-methylchroman-6-yl)-4,7-dimethyl-2-(2-oxo-2-(piperidin-1-yl)acetyl)isoindolin-5-yl)acetic acid The title compound was made in a similar manner to example 129 except using (2S)(M)-Methyl 2-(tert-butoxy)-2-(-6-(8-fluoro-5-methylchroman-6-yl)-4,7-dimethylisoindolin-5-yl)acetate in step 1.

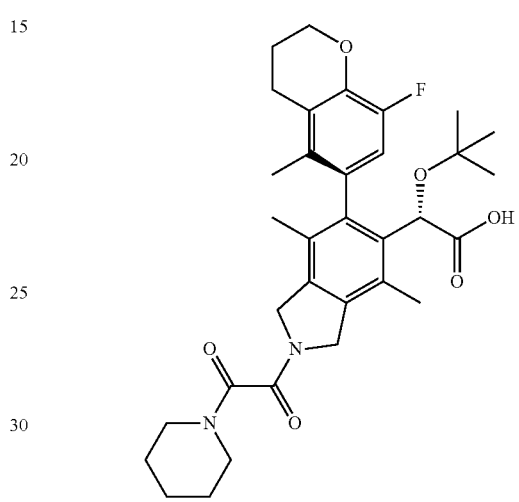

¹H NMR (400 MHz, CDCl3) δ (mixture of rotamers) 6.69 (m, 1H), 5.08 (s, 1H), 4.86 (m, 4H), 4.27 (m, 2H), 3.65 (m, 2H), 3.45 (m, 2H), 2.69 (m, 2H), 2.28 (m, 3H), 2.13 (m, 2H), 1.78 (m, 3H), 1.74-1.59 (br. m, 9H), 1.14 (m, 9H); LCMS (ES+) (m/z): 525.52

Example 216: (S)-2-((M)-2-(benzo[d][1,3]dioxol-4-ylmethyl)-6-(8-fluoro-5-methylchroman-6-yl)-4,7-dimethylisoindolin-5-yl)-2-(tert-butoxy)acetic acid

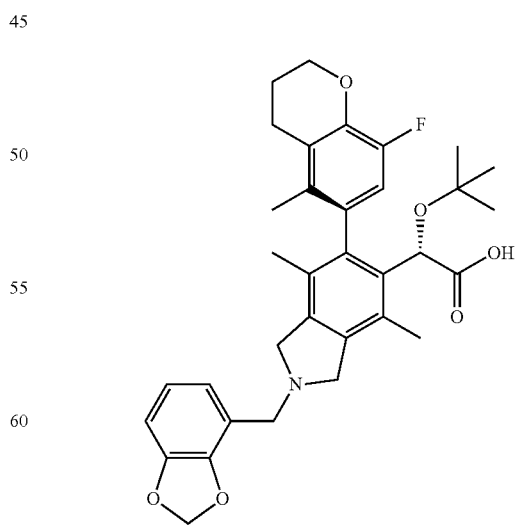

The title compound was made in a similar manner to example 8.

1H NMR (400 MHz, CHLOROFORM-d) δ 6.94-6.87 (m, 3H), 6.65 (m, 1H), 5.97 (m, 2H), 5.05-4.90 (m, 3H), 4.53-4.08 (m, 6H), 2.67 (m, 2H), 2.37-2.01 (m, 5H), 1.75 (m, 6H), 1.10 (s, 9H); LCMS (ES+) (m/z): 576.4 (M+1).

Example 217: (S)-2-(tert-butoxy)-2-((M)-6-(8-fluoro-5-methylchroman-6-yl)-4,7-dimethyl-2-(phenoxycarbonyl)isoindolin-5-yl)acetic acid

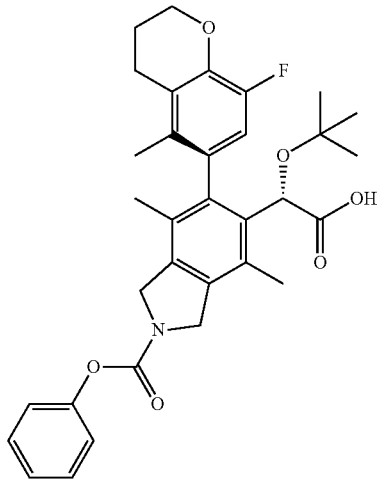

Step 1

Phenyl 5-((S)-1-(tert-butoxy)-2-methoxy-2-oxoethyl)-6-((M)-8-fluoro-5-methylchroman-6-yl)-4,7-dimethylisoindoline-2-carboxylate

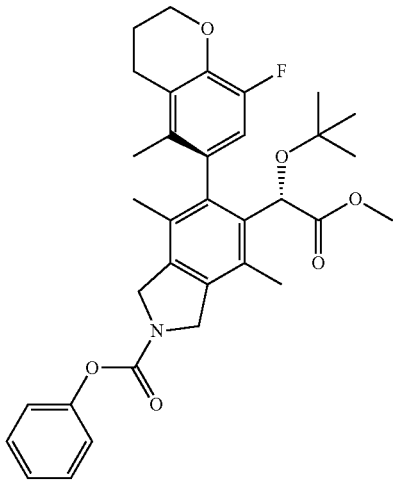

To a solution of phenyl carbonochloridate (0.022 mL, 0.176 mmol) in 2 mL THF at 0° C. was added a solution of (S)-methyl 2-(tert-butoxy)-2-(6-((M)-8-fluoro-5-methylchroman-6-yl)-4,7-dimethylisoindolin-5-yl)acetate (40 mg, 0.088 mmol) in 2 mL THF. The solution was slowly warmed to room temperature and stirred for 2 h. The solution was concentrated in vacuo, dissolved in etoac, washed with 1M HCl, brine, dried over sodium sulfate and solvent removed to afford the title compound as a green oil (50.5 mg). LCMS (ES+) (m/z): 598.42 (M+23).

Step 2

(S)-2-(tert-butoxy)-2-((M)-6-(8-fluoro-5-methylchroman-6-yl)-4,7-dimethyl-2-(phenoxycarbonyl)isoindolin-5-yl)acetic acid

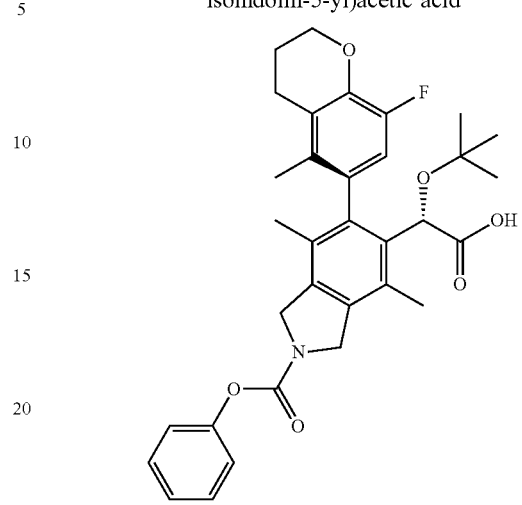

To a solution of phenyl (M)-phenyl 5-((S)-1-(tert-butoxy)-2-methoxy-2-oxoethyl)-6-(8-fluoro-5-methylchroman-6-yl)-4,7-dimethylisoindoline-2-carboxylate (50.5 mg, 0.088 mmol) in 6 mL Dioxane was added LiOH (1.316 mL, 1.316 mmol). The solution was heated to 70° C. and stirred overnight. SM remains by LCMS, another 10 eq LiOH was added and heated to 80° C. for 1 hour. The solution was concentrated and redissolved in EtoAC, washed with 1 M HCl, brine and solvent removed. The resulting oil was purified by HPLC to yield the title compound as a white powder (5.5 mg, 9.79 µmol, 11.16% yield).

$^1$H NMR (400 MHz, CDCl$_3$) ∂ (mixture of rotamers) 7.38 (m, 2H), 7.20 (m, 3H), 6.69 (m, 1H), 5.08 (m, 1H), 4.97-4.76 (m, 4H), 4.27 (m, 2H), 2.68 (m, 2H), 2.30 (m, 3H), 2.12 (m, 2H), 1.92-1.74 (m, 6H), 1.14 (m, 9H). LCMS (ES+) (m/z): 562.33 (M+1); 1145.74 (2M+23).

Example 218: (S)-2-(tert-butoxy)-2-((M)-6-(8-fluoro-5-methylchroman-6-yl)-2-((3-fluorophenyl)sulfonyl)-4,7-dimethylisoindolin-5-yl)acetic acid The title compound was made in a similar manner to example 5 except using (2S)(M)-Methyl 2-(tert-butoxy)-2-(-6-(8-fluoro-5-methylchroman-6-yl)-4,7-dimethylisoindolin-5-yl)acetate in step 1.

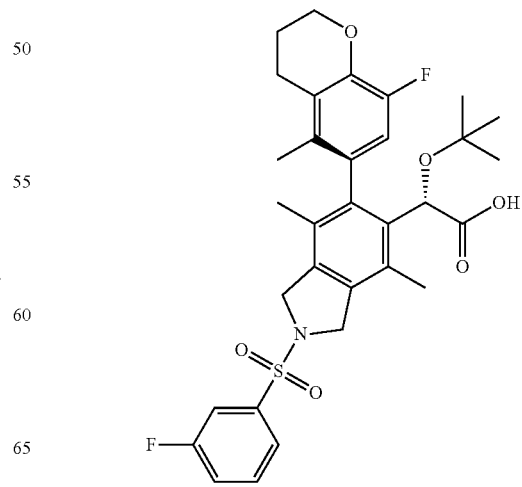

¹H NMR (400 MHz, CDCl₃) ∂ (mixture of rotamers) 7.71 (m, 1H), 7.62 (m, 1H), 7.54 (m, 1H), 7.31 (m, 1H), 6.62 (m, 1H), 5.02 (s, 1H), 4.63 (m, 4H), 4.25 (m, 2H), 2.66 (m, 2H), 2.21 (s, 3H), 2.10 (m, 2H), 1.83-1.68 (m, 6H), 1.10 (s, 9H). LCMS (ES+) (m/z): 600.49 (M+1).

The following compounds were made in a manner using the procedures outlined above unless otherwise noted.

Example 219: (S)-2-(tert-butoxy)-2-(4,7-dimethyl-2-(2-methylbenzoyl)-6-(p-tolyl)isoindolin-5-yl)acetic acid

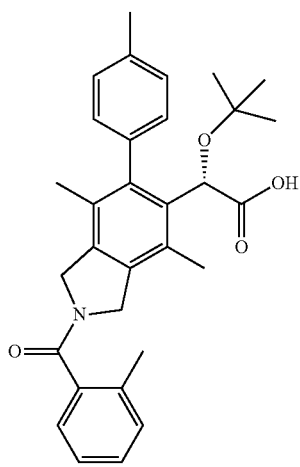 [SMILES: Cc1ccc(-c2c(C)c3c(c(C)c2[C@H](OC(C)(C)C)C(=O)O)CN(C(=O)c2ccccc2C)C3)cc1]

¹H NMR (400 MHz, CDCl₃) δ 7.32-7.41 (m, 3H), 7.31 (d, 3H), 7.24 (d, 1H), 7.02-7.13 (m, 1H), 5.18 (s, 1H), 4.99-5.10 (m, 2H), 4.43-4.55 (m, 2H), 2.44 (d, 3H), 2.40 (d, 3H), 2.34 (s, 1.5H), 2.13 (s, 1.5H), 1.97 (s, 1.5H), 1.76 (s, 1.5H), 1.00 (m, 9H). LCMS (ES+) (m/z): 486.48 (M+1), 508.40 (M+23), 971.69 (2M+1), 993.71 (2M+23).

Example 220: (S)-2-(tert-butoxy)-2-(2-(3-chlorobenzoyl)-4,7-dimethyl-6-(p-tolyl)isoindolin-5-yl)acetic acid

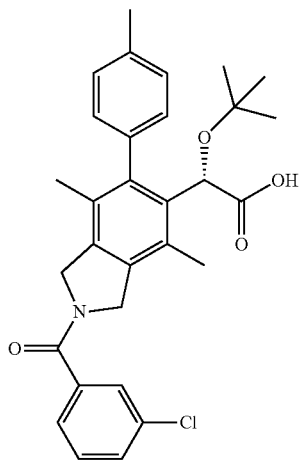

¹H NMR (400 MHz, CDCl₃) δ 7.57 (br. s., 1H), 7.41-7.52 (m, 3H), 7.33-7.40 (m, 1H), 7.23 (s, 2H), 7.01-7.12 (m, 1H), 5.16 (s, 1H), 4.96 (s, 2H), 4.72 (d, 2H), 2.42 (d, 3H), 2.32 (s, 1.5H), 2.16 (s, 1.5H), 1.95 (s, 1.5H), 1.80 (s, 1.5H), 0.99 (d, J=8.53 Hz, 9H). LCMS (ES+) (m/z): 506.50 (M+1), 528.45 (M+23), 1011.75 (2M+1), 1033.69 (2M+23).

Example 221: (S)-2-(tert-butoxy)-2-(2-(3-fluoro-2-methylbenzoyl)-4,7-dimethyl-6-(p-tolyl)isoindolin-5-yl)acetic acid

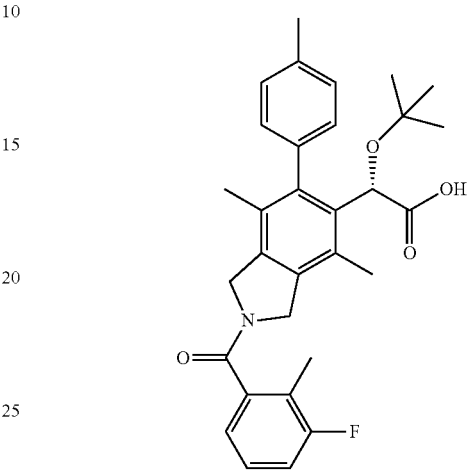

¹H NMR (400 MHz, CDCl₃) δ 7.36 (br. s, 1H), 7.25 (br. S, 4H), 7.04-7.15 (m, 2H), 5.18 (s, 1H), 4.97-5.11 (m, 2H), 4.46-4.56 (m, 2H), 2.44 (d, 3H), 2.25-2.37 (m, 4.5H), 2.14 (s, 1.5H), 1.97 (s, 1.5H), 1.78 (s, 1.5H), 1.00-1.03 (s, 9H). LCMS (ES+) (m/z): 504.45 (M+1), 526.47 (M+23), 1007.75 (2M+1), 1029.72 (2M+23).

Example 222: (S)-2-(tert-butoxy)-2-(2-(3-methoxy-4-methylbenzoyl)-4,7-dimethyl-6-(p-tolyl)isoindolin-5-yl)acetic acid

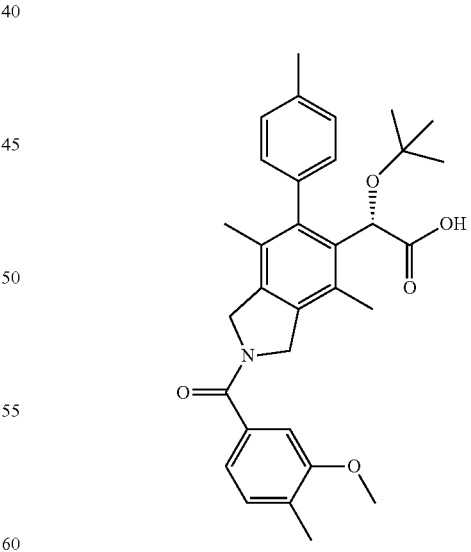

¹H NMR (400 MHz, CDCl₃) δ 7.35 (d, 1H), 7.16-7.25 (m, 3H), 6.97-7.11 (m, 3H), 5.15 (s, 1H), 4.89-5.10 (m, 2H), 4.76 (d, 2H), 3.87 (d, 3H), 2.41 (d, 3H), 2.31 (s, 1.5H), 2.27 (d, 3H), 2.14 (s, 1.5H), 1.94 (s, 1.5H), 1.78 (s, 1.5H), 0.98 (d, 9H). LCMS (ES+) (m/z): 516.49 (M+1), 538.52 (M+23), 1031.81 (2M+1).

Example 223: (S)-2-(tert-butoxy)-2-(4,7-dimethyl-2-(1-methyl-1H-pyrazole-5-carbonyl)-6-(p-tolyl)isoindolin-5-yl)acetic acid

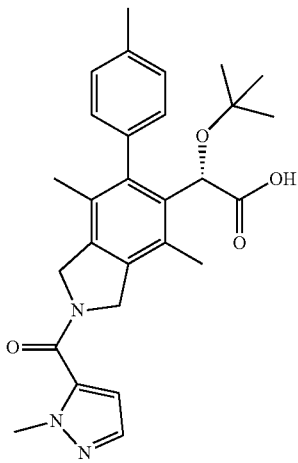 [SMILES: Cc1ccc(-c2c(C)c3c(c(C)c2[C@H](OC(C)(C)C)C(=O)O)CN(C(=O)c2ccnn2C)C3)cc1]

¹H NMR (400 MHz, CDCl₃) δ 7.62 (dd, 1H), 7.37 (d, 1H), 7.23-7.30 (m, 2H), 7.09 (t, 1H), 6.67 (dd, 1H), 5.19 (s, 1H), 4.86-5.12 (m, 4H), 4.09-4.19 (m, 3H), 2.39-2.52 (m, 3H), 2.34 (s, 1.5H), 2.25 (s, 1.5H), 1.97 (s, 1.5H), 1.88 (s, 1.5H), 0.94-1.10 (m, 9H). LCMS (ES+) (m/z): 476.45 (M+1), 973.94 (2M+23).

Example 224: (S)-2-(tert-butoxy)-2-(2-(4-(tert-butyl)benzoyl)-4,7-dimethyl-6-(p-tolyl)isoindolin-5-yl)acetic acid

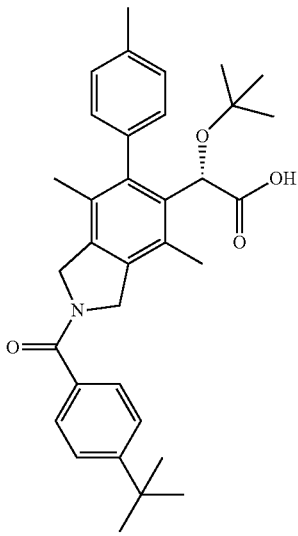 [SMILES: Cc1ccc(-c2c(C)c3c(c(C)c2[C@H](OC(C)(C)C)C(=O)O)CN(C(=O)c2ccc(C(C)(C)C)cc2)C3)cc1]

¹H NMR (400 MHz, CDCl₃) δ 7.45-7.61 (m, 3H), 7.38 (d, 1H), 7.22-7.29 (m, 3H), 7.08 (dd, 1H), 5.18 (s, 1H), 5.08 (d, 1H), 5.00 (d, 1H), 4.82 (d, 2H), 2.44 (d, 3H), 2.34 (s, 1.5H), 2.19 (s, 1.5H), 1.97 (s, 1.5H), 1.83 (s, 1.5H), 1.38 (d, 9H), 1.00 (s, 9H). LCMS (ES+) (m/z): 528.52 (M+1), 1055.74 (2M+1), 1077.86 (2M+23).

Example 225: (S)-2-(tert-butoxy)-2-(4,7-dimethyl-2-(3-methylbenzoyl)-6-(p-tolyl)isoindolin-5-yl)acetic acid

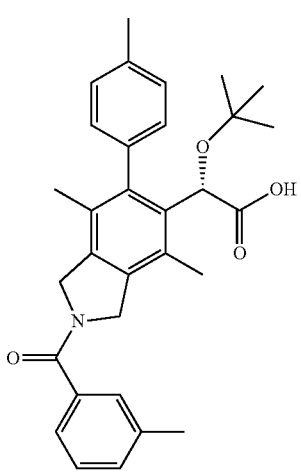 [SMILES: Cc1ccc(-c2c(C)c3c(c(C)c2[C@H](OC(C)(C)C)C(=O)O)CN(C(=O)c2cccc(C)c2)C3)cc1]

¹H NMR (400 MHz, CDCl₃) δ 7.35-7.47 (m, 4H), 7.21-7.32 (m, 3H), 7.08 (dd, 1H), 5.18 (s, 1H), 4.91-5.13 (m, 2H), 4.75 (d, 2H), 2.38-2.50 (m, 6H), 2.34 (s, 1.5H), 2.17 (s, 1.5H), 1.97 (s, 1.5H), 1.80 (s, 1.5H), 1.01 (d, 9H). LCMS (ES+) (m/z): 486.50 (M+1), 508.51 (M+23), 971.67 (2M+1), 993.73 (2M+23).

Example 226: (S)-2-(tert-butoxy)-2-(2-(3-chloro-5-fluorobenzoyl)-4,7-dimethyl-6-(p-tolyl)isoindolin-5-yl)acetic acid

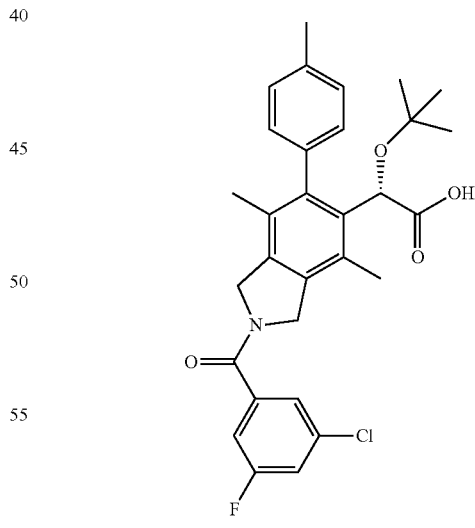

¹H NMR (400 MHz, CDCl₃) δ 7.39 (br. s., 2H), 7.16-7.34 (m, 4H), 6.99-7.16 (m, 1H), 5.18 (br. s., 1H), 4.90-5.13 (m, 2H), 4.76 (s, 2H), 2.39-2.62 (m, 3H), 1.5H), 2.20 (br. s., 1.5H), 1.97 (br. s., 1.5H), 1.83 (br. s., 1.5H), 1.01 (d, 9H). LCMS (ES+) (m/z): 524.39 (M+1), 546.33 (M+23), 1046.69 (2M+1), 1069.35 (2M+23).

Example 227: (S)-2-(tert-butoxy)-2-(4,7-dimethyl-6-(p-tolyl)-2-(4-(trifluoromethyl)benzoyl)isoindolin-5-yl)acetic acid

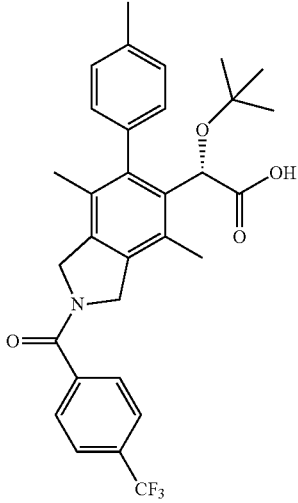 [SMILES: Cc1ccc(-c2c(C)c3c(c(C)c2[C@H](OC(C)(C)C)C(=O)O)CN(C(=O)c2ccc(C(F)(F)F)cc2)C3)cc1]

¹H NMR (400 MHz, CDCl₃) δ 7.66-7.90 (m, 4H), 7.18-7.32 (m, 3H), 7.06 (d, 1H), 5.18 (br. s., 1H), 4.90-5.14 (m, 2H), 4.75 (s, 1H), 4.71 (s, 1H), 2.44 (d, 3H), 2.35 (br. s., 1.5H), 2.17 (br. s, 1.5H), 1.98 (s, 1.5H), 1.81 (s, 1.5H), 1.01 (d, 9H). LCMS (ES+) (m/z): 540.44 (M+1), 562.39 (M+23), 1079.60 (2M+1).

Example 228: (S)-2-(tert-butoxy)-2-(2-(cyclobutanecarbonyl)-4,7-dimethyl-6-(p-tolyl)isoindolin-5-yl)acetic acid

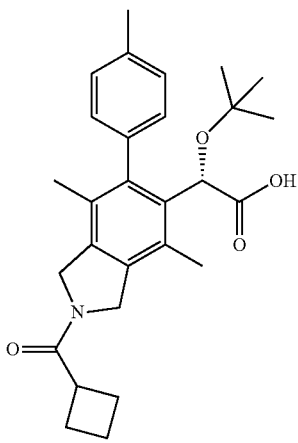 [SMILES: Cc1ccc(-c2c(C)c3c(c(C)c2[C@H](OC(C)(C)C)C(=O)O)CN(C(=O)C2CCC2)C3)cc1]

¹H NMR (400 MHz, CDCl₃) δ 7.37 (d, 1H), 7.22-7.31 (m, 2H), 7.09 (br. s, 1H), 5.19 (d, 1H), 4.65-4.88 (m, 4H), 3.31-3.43 (m, 1H), 2.39-2.53 (m, 6H), 2.22-2.35 (m, 5H), 2.02-2.12 (m, 2H), 1.90-2.02 (m, 4H), 1.02 (s, 9H). LCMS (ES+) (m/z): 450.55 (M+1), 472.56 (M+23), 899.84 (2M+1), 921.82 (2M+23).

Example 229: (S)-2-(2-benzoyl-4,7-dimethyl-6-(p-tolyl)isoindolin-5-yl)-2-(tert-butoxy)acetic acid

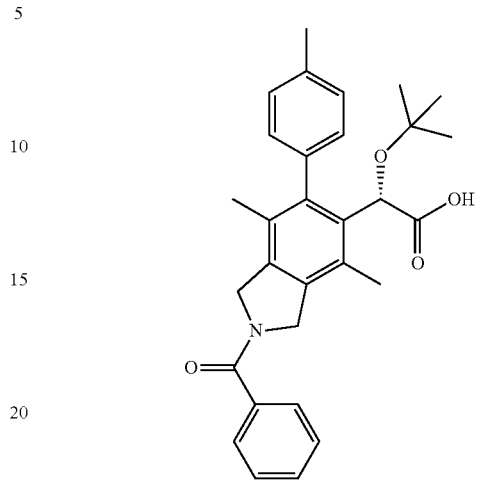

¹H NMR (400 MHz, CDCl₃) δ 7.57-7.67 (m, 2H), 7.46-7.57 (m, 3H), 7.38 (d, J=7.03 Hz, 1H), 7.21-7.27 (m, 2H), 7.08 (dd, J=19.70, 7.15 Hz, 1H), 5.18 (s, 1H), 4.92-5.14 (m, 2H), 4.92-5.14 (m, 2H), 4.76 (d, J=13.30 Hz, 2H), 2.44 (d, J=6.27 Hz, 3H), 2.35 (s, 1.5H), 2.17 (s, 1.5H), 1.98 (s, 1.5H), 1.80 (s, 1.5H), 1.00 (s, 9H). LCMS (ES+) (m/z): 472.55 (M+1), 943.92 (2M+1), 965.62 (2M+23).

Example 230: (S)-2-(tert-butoxy)-2-(2-(3-(tert-butyl)benzoyl)-4,7-dimethyl-6-(p-tolyl)isoindolin-5-yl)acetic acid

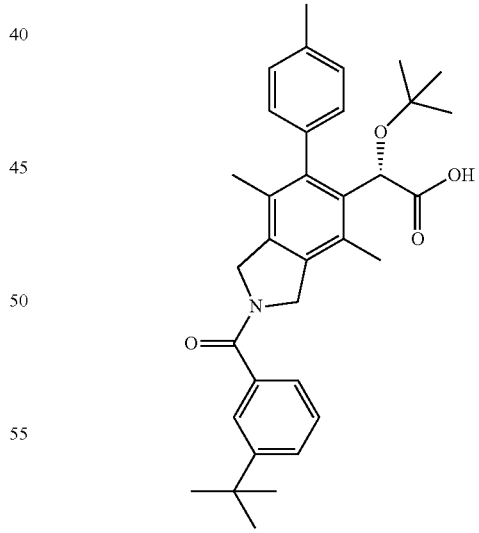

¹H NMR (400 MHz, CDCl₃) δ 7.57-7.62 (m, 1H), 7.47-7.54 (m, 1H), 7.31-7.44 (m, 3H), 7.18-7.25 (m, 2H), 7.04 (br. s, 1H), 5.15 (s, 1H), 4.91-5.12 (m, 2H), 4.75 (s, 1H), 4.71 (s, 1H), 2.41 (d, 3H), 2.32 (s, 1.5H), 2.13 (s, 1.5H), 1.95 (s, 1.5H), 1.77 (s, 1.5H), 1.35 (d, 9H), 0.98 (d, 9H). LCMS (ES+) (m/z): 528.61 (M+1), 550.55 (M+23), 1055.95 (2M+1), 1078.00 (2M+23).

Example 231: (S)-2-(tert-butoxy)-2-(4,7-dimethyl-2-((S)-tetrahydrofuran-3-carbonyl)-6-(p-tolyl)isoindolin-5-yl)acetic acid

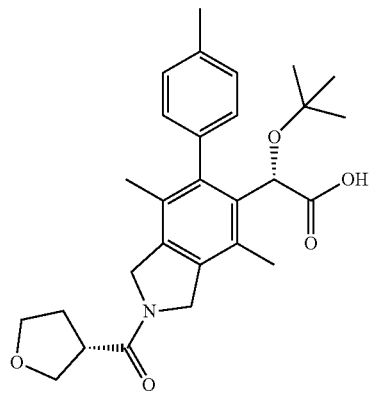 [SMILES: Cc1ccc(-c2c(C)c3c(c(C)c2[C@H](OC(C)(C)C)C(=O)O)CN(C(=O)[C@H]2CCOC2)C3)cc1]

The title compound was isolated as a white solid after reverse phase hplc.

¹H NMR (400 MHz, CDCl₃) δ 7.25 (m, 3H), 7.1 (m, 1H), 5.05 (s, 1H), 4.9 (m, 2H), 4.7 (m, 2H), 4.05 (m, 1H), 3.9 (m, 2H), 3.8 (m, 1H), 3.5 (m, 1H), 2.4 (s, 3H), 2.8 (s, 3H), 2.15 (m, 2H), 1.85 (s, 3H), 0.9 (s, 9H). LCMS (ES+) (m/z): 466.48 (M+1); 931.80 (2M+1).

Example 232: (S)-2-(tert-butoxy)-2-(2-(3-ethoxypropanoyl)-4,7-dimethyl-6-(p-tolyl)isoindolin-5-yl)acetic acid

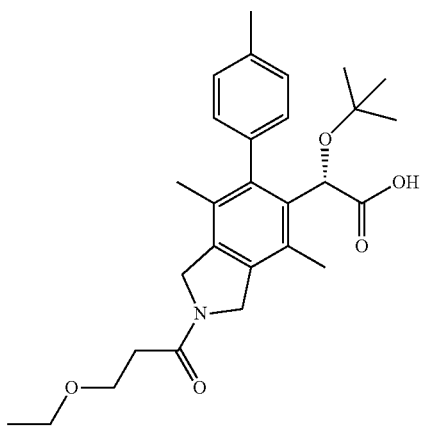 [SMILES: CCOCCC(=O)N1Cc2c(C)c(-c3ccc(C)cc3)c([C@H](OC(C)(C)C)C(=O)O)c(C)c2C1]

The title compound was isolated as a white solid after reverse phase hplc.

¹H NMR (400 MHz, CDCl₃) δ 7.35 (m, 1H), 7.21 (m, 2H), 7.06 (m, 1H), 5.15 (s, 1H), 4.90-4.67 (m, 4H), 3.82 (m, 2H), 3.54 (m, 2H), 2.69 (m, 2H), 2.40 (s, 3H), 2.24 (s, 3H), 1.87 (s, 3H), 1.19 (m, 3H), 0.98 (s, 9H). LCMS (ES+) (m/z): 468.45 (M+1); 957.84 (2M+23).

Example 233: (S)-2-(tert-butoxy)-2-(2-(2-(3-fluorophenyl)acetyl)-4,7-dimethyl-6-(p-tolyl)isoindolin-5-yl)acetic acid

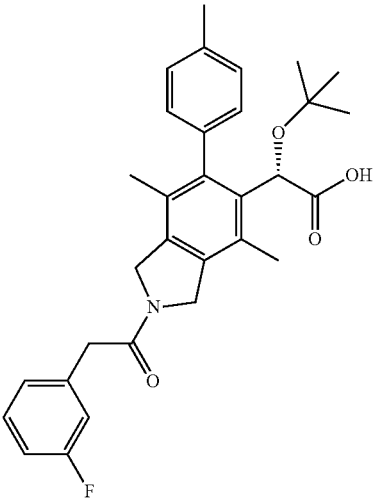 [SMILES: Cc1ccc(-c2c(C)c3c(c(C)c2[C@H](OC(C)(C)C)C(=O)O)CN(C(=O)Cc2cccc(F)c2)C3)cc1]

The title compound was isolated as a white solid after reverse phase hplc.

¹H NMR (400 MHz, CDCl₃) δ 7.37-6.91 (m, 8H), 5.14 (s, 1H), 4.90-4.70 (m, 4H), 3.79 (m, 2H), 2.40 (s, 3H), 2.23 (d, 3H), 1.87 (d, 3H), 0.97 (s, 9H). LCMS (ES+) (m/z): 504.42 (M+1); 1007.97 (2M+1).

Example 234: (S)-2-(tert-butoxy)-2-(2-(3-isopropoxybenzoyl)-4,7-dimethyl-6-(p-tolyl)isoindolin-5-yl)acetic acid

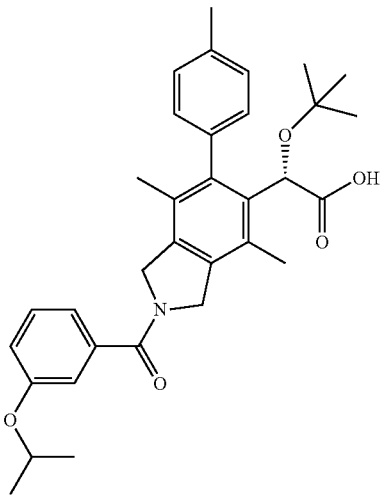 [SMILES: Cc1ccc(-c2c(C)c3c(c(C)c2[C@H](OC(C)(C)C)C(=O)O)CN(C(=O)c2cccc(OC(C)C)c2)C3)cc1]

The title compound was isolated as a white solid after reverse phase hplc.

¹H NMR (400 MHz, CDCl₃) δ 7.39-6.93 (m, 8H), 5.14 (s, 1H), 5.09-4.52 (m, 5H), 2.40 (d, 3H), 2.33-2.09 (m, 3H), 1.96-1.73 (m, 3H), 1.34 (m, 6H), 0.97 (d, 9H). LCMS (ES+) (m/z): 530.40 (M+1); 1059.85 (2M+1).

Example 235: (S)-2-(tert-butoxy)-2-(2-(5-methoxynicotinoyl)-4,7-dimethyl-6-(p-tolyl)isoindolin-5-yl)acetic acid

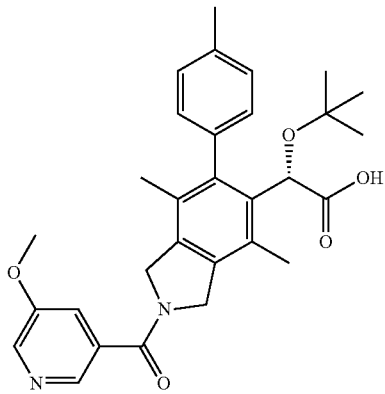 [SMILES: COc1cncc(C(=O)N2Cc3c(C)c(-c4ccc(C)cc4)c([C@H](OC(C)(C)C)C(=O)O)c(C)c3C2)c1]

The title compound was isolated as a white solid after reverse phase hplc.

$^1$H NMR (400 MHz, CDCl$_3$) δ (mix of rotamers) 8.61 (m, 1H), 8.53 (m, 1H), 8.76 (m, 1H), 7.35 (m, 1H), 7.24 (m, 2H), 7.07 (m, 1H), 5.16 (m, 1H), 5.11-4.67 (m, 4H), 4.00 (d, 3H), 2.42 (d, 3H), 2.36-2.12 (m, 3H), 2.00-1.77 (m, 3H), 0.99 (d, 9H). LCMS (ES+) (m/z): 503.43 (M+1); 1005.73 (2M+1).

Example 236: (S)-2-(tert-butoxy)-2-(4,7-dimethyl-2-(5-methylnicotinoyl)-6-(p-tolyl)isoindolin-5-yl)acetic acid

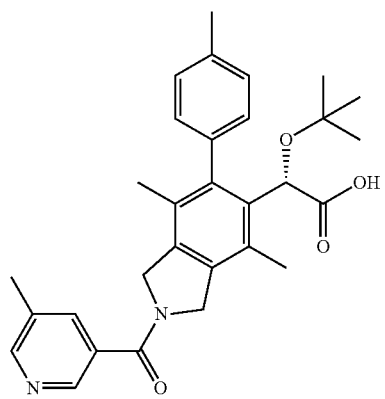 [SMILES: Cc1ccc(-c2c(C)c3c(c(C)c2[C@H](OC(C)(C)C)C(=O)O)CN(C(=O)c2cncc(C)c2)C3)cc1]

The title compound was isolated as a white solid after reverse phase hplc.

$^1$H NMR (400 MHz, CDCl$_3$) δ (mixture of rotamers) 8.92 (m, 1H), 8.75 (m, 1H), 8.23 (m, 1H), 7.35 (m, 1H), 7.24 (m, 2H), 7.07 (m, 1H), 5.16 (m, 1H), 5.11-4.67 (m, 4H), 2.60 (d, 3H), 2.42 (d, 3H), 2.36-2.12 (m, 3H), 2.00-1.77 (m, 3H), 1.00 (d, 9H). LCMS (ES+) (m/z): 487.45 (M+1); 973.72 (2M+1).

Example 237: (S)-2-(tert-butoxy)-2-(4,7-dimethyl-2-(1-methyl-1H-imidazole-4-carbonyl)-6-(p-tolyl)isoindolin-5-yl)acetic acid

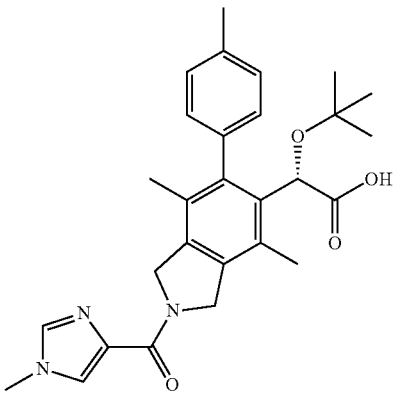 [SMILES: Cc1ccc(-c2c(C)c3c(c(C)c2[C@H](OC(C)(C)C)C(=O)O)CN(C(=O)c2cn(C)cn2)C3)cc1]

The title compound was isolated as a white solid after reverse phase hplc.

$^1$H NMR (400 MHz, CDCl$_3$) δ 8.14 (m, 1H), 7.78 (m, 1H), 7.34 (m, 1H), 7.23 (m, 2H), 7.06 (m, 1H), 5.38-4.84 (m, 5H), 3.86 (m, 3H), 2.41 (s, 3H), 2.26 (s, 3H), 1.91 (m, 3H), 0.97 (s, 9H). LCMS (ES+) (m/z): 476.42 (M+1); 951.88 (2M+1).

Example 238: (S)-2-(tert-butoxy)-2-(4,7-dimethyl-2-(1-methyl-1H-imidazole-2-carbonyl)-6-(p-tolyl)isoindolin-5-yl)acetic acid

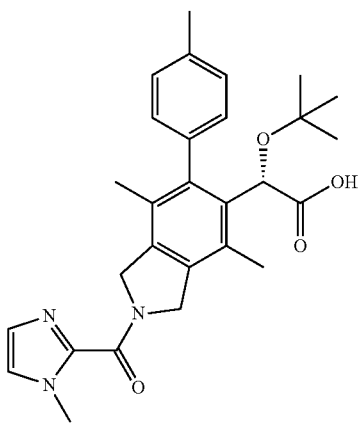 [SMILES: Cc1ccc(-c2c(C)c3c(c(C)c2[C@H](OC(C)(C)C)C(=O)O)CN(C(=O)c2nccn2C)C3)cc1]

The title compound was isolated as a white solid after reverse phase hplc.

$^1$H NMR (400 MHz, CDCl$_3$) δ 8.46 (m, 1H), 7.83 (m, 1H), 7.34 (m, 1H), 7.23 (m, 2H), 7.05 (m, 1H), 5.17 (m, 1H), 4.98 (m, 4H), 4.09 (s, 3H), 2.41 (s, 3H), 2.28 (m, 3H), 1.92 (m, 3H), 0.99 (s, 9H). LCMS (ES+) (m/z): 476.42 (M+1); 951.82 (2M+1).

Example 239: (S)-2-(tert-butoxy)-2-(4,7-dimethyl-2-(1-methyl-1H-imidazole-2-carbonyl)-6-(p-tolyl)isoindolin-5-yl)acetic acid

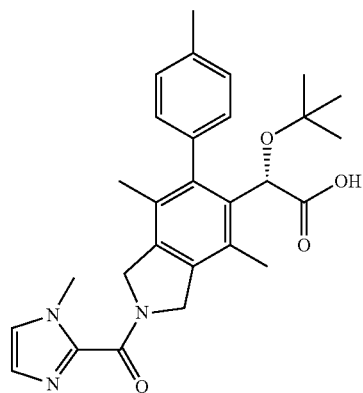 [SMILES: Cc1ccc(-c2c(C)c3c(c(C)c2[C@H](OC(C)(C)C)C(=O)O)CN(C(=O)c2nccn2C)C3)cc1]

The title compound was isolated as a white solid after reverse phase hplc.

$^1$H NMR (400 MHz, CDCl$_3$) δ 7.45-7.02 (m, 6H), 5.22-4.89 (m, 5H), 4.00 (s, 3H), 2.40 (m, 3H), 2.34-2.18 (m, 3H), 1.95-1.80 (m, 3H), 0.98 (m, 9H). LCMS (ES+) (m/z): 476.49 (M+1); 951.68 (2M+1).

Example 240: (S)-2-(tert-butoxy)-2-(4,7-dimethyl-2-(1-methyl-1H-pyrazole-3-carbonyl)-6-(p-tolyl)isoindolin-5-yl)acetic acid

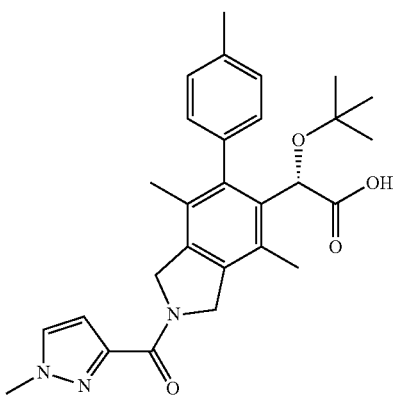 [SMILES: Cc1ccc(-c2c(C)c3c(c(C)c2[C@H](OC(C)(C)C)C(=O)O)CN(C(=O)c2ccn(C)n2)C3)cc1]

The title compound was isolated as a white solid after reverse phase hplc.

$^1$H NMR (400 MHz, CDCl$_3$) δ 7.44-6.85 (m, 6H), 5.40-4.86 (m, 5H), 3.98 (m, 3H), 2.40 (m, 3H), 2.30 (m, 3H), 1.93 (m, 3H), 0.98 (m, 9H). LCMS (ES+) (m/z): 476.41 (M+1); 951.80 (2M+1).

Example 241: (S)-2-(tert-butoxy)-2-(4,7-dimethyl-6-(p-tolyl)-2-(3,3,3-trifluoro-2,2-dimethylpropanoyl)isoindolin-5-yl)acetic acid

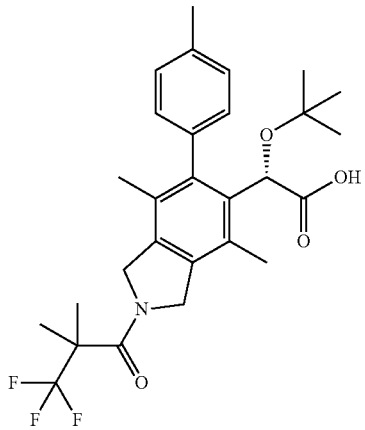 [SMILES: Cc1ccc(-c2c(C)c3c(c(C)c2[C@H](OC(C)(C)C)C(=O)O)CN(C(=O)C(C)(C)C(F)(F)F)C3)cc1]

The title compound was isolated as a white solid after reverse phase hplc.

$^1$H NMR (400 MHz, CDCl$_3$) δ 7.38-7.02 (m, 4H), 5.40-4.86 (m, 5H), 2.40 (s, 3H), 2.25 (s, 3H), 1.88 (s, 3H), 1.60 (s, 6H), 0.98 (s, 9H). LCMS (ES+) (m/z): 506.40 (M+1); 1033.82 (2M+23).

Example 242: (S)-2-(tert-butoxy)-2-(2-(2-(tert-butyl)benzoyl)-4,7-dimethyl-6-(p-tolyl)isoindolin-5-yl)acetic acid

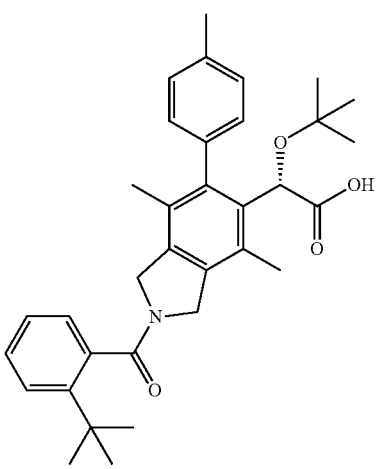 [SMILES: Cc1ccc(-c2c(C)c3c(c(C)c2[C@H](OC(C)(C)C)C(=O)O)CN(C(=O)c2ccccc2C(C)(C)C)C3)cc1]

The title compound was isolated as a white solid after reverse phase hplc.

$^1$H NMR (400 MHz, CDCl$_3$) δ 7.58-6.96 (m, 8H), 5.15 (s, 1H), 5.06-4.32 (m, 4H), 2.40 (s, 3H), 2.14-1.87 (m, 3H), 1.42 (m, 9H), 1.24 (m, 3H), 0.95 (m, 9H). LCMS (ES+) (m/z): 528.49 (M+1); 1056.01 (2M+1).

Example 243: (S)-2-(tert-butoxy)-2-(4,7-dimethyl-2-(1-methylcyclohexanecarbonyl)-6-(p-tolyl)isoindolin-5-yl)acetic acid

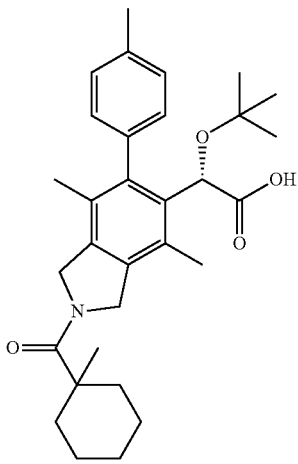 [SMILES: Cc1ccc(-c2c(C)c3c(c(C)c2[C@H](OC(C)(C)C)C(=O)O)CN(C(=O)C2(C)CCCCC2)C3)cc1]

¹H NMR (400 MHz, METHANOL-d₄) δ ppm 7.33-7.24 (m, 3H), 7.10 (d, J=8.1 Hz, 1H), 5.10-4.94 (m, 3H), 4.93-4.71 (m, 2H), 2.42 (s, 3H), 2.37-2.22 (m, 5H), 1.90 (s, 3H), 1.73-1.25 (m, 11H), 0.99-0.84 (m, 9H); LCMS (m/z) ES⁺=492 (M+1).

Example 244: (2S)-2-(tert-butoxy)-2-(2-(3-methoxycyclohexanecarbonyl)-4,7-dimethyl-6-(p-tolyl)isoindolin-5-yl)acetic acid—Diastereomer Mixture 1

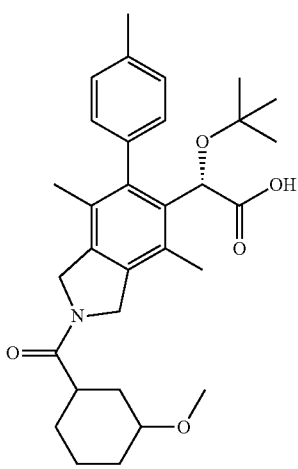 [SMILES: COC1CCCC(C(=O)N2Cc3c(C)c(-c4ccc(C)cc4)c([C@H](OC(C)(C)C)C(=O)O)c(C)c3C2)C1]

¹H NMR (400 MHz, CHLOROFORM-d) δ ppm 7.36 (d, J=6.5 Hz, 1H), 7.29-7.19 (m, 2H), 7.07 (d, J=7.0 Hz, 1H), 5.17 (d, J=3.7 Hz, 1H), 4.96-4.68 (m, 4H), 3.71-3.62 (m, 1H), 3.37 (d, J=7.7 Hz, 3H), 3.00-2.85 (m, 1H), 2.42 (s, 3H), 2.28 (s, 3H), 2.05-1.88 (m, 5H), 1.87-1.73 (m, 2H), 1.73-1.52 (m, 3H), 1.50-1.37 (m, 1H), 1.00 (s, 9H); LCMS (m/z) ES+=508 (M+1).

Example 245: (2S)-2-(tert-butoxy)-2-(2-(3-methoxycyclohexanecarbonyl)-4,7-dimethyl-6-(p-tolyl)isoindolin-5-yl)acetic acid—Diastereomer Mixture 2

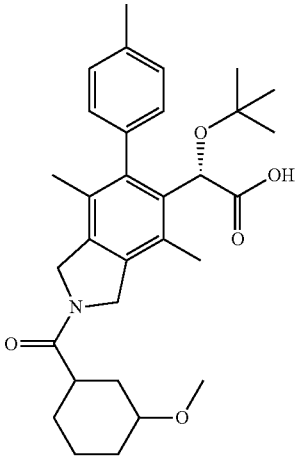 [SMILES: COC1CCCC(C(=O)N2Cc3c(C)c(-c4ccc(C)cc4)c([C@H](OC(C)(C)C)C(=O)O)c(C)c3C2)C1]

¹H NMR (400 MHz, CHLOROFORM-d) δ ppm 7.35 (d, J=7.1 Hz, 1H), 7.30-7.17 (m, 2H), 7.07 (d, J=6.1 Hz, 1H), 5.17 (d, J=6.8 Hz, 1H), 4.96-4.72 (m, 4H), 3.68 (br. s., 0.4H), 3.46-3.35 (m, 3H), 3.34-3.22 (m, 0.6H), 2.96 (br. s., 0.4H), 2.65-2.52 (m, 0.6H), 2.43 (s, 3H), 2.28 (d, J=2.9 Hz, 3H), 2.23-2.07 (m, 1H), 2.05-1.86 (m, 4H), 1.80 (d, J=11.8 Hz, 1H), 1.71-1.48 (m, 2H), 1.47-1.19 (m, 3H), 1.09-0.93 (m, 9H); LCMS (m/z) ES+=508 (M+1).

Example 246: (S)-2-(tert-butoxy)-2-(2-(4-fluoro-3-methylbenzoyl)-4,7-dimethyl-6-(p-tolyl)isoindolin-5-yl)acetic acid

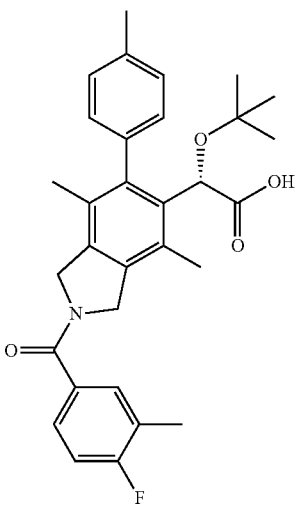 [SMILES: Cc1ccc(-c2c(C)c3c(c(C)c2[C@H](OC(C)(C)C)C(=O)O)CN(C(=O)c2ccc(F)c(C)c2)C3)cc1]

¹H NMR (400 MHz, CHLOROFORM-d) (mixture of rotamers) δ ppm 7.49-7.32 (m, 3H), 7.30-7.19 (m, 2H), 7.15-6.98 (m, 2H), 5.16 (s, 1H), 5.10-4.88 (m, 2H), 4.80-4.67 (m, 2H), 2.47-2.38 (m, 3H), 2.37-2.12 (m, 6H), 1.99-1.74 (m, 3H), 1.06-0.91 (m, 9H); LCMS (m/z) ES+=504 (M+1).

Example 247: (S)-2-(tert-butoxy)-2-(2-(2,4-difluorobenzol)-4,7-dimethyl-6-(p-tolyl)isoindolin-5-yl)acetic acid

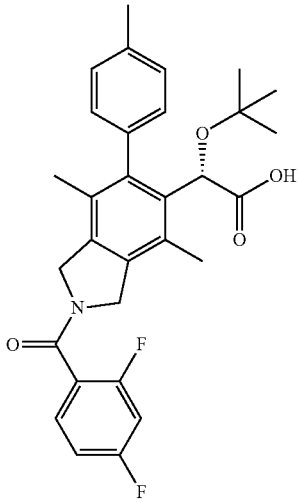 [SMILES: Cc1ccc(-c2c(C)c3c(c(C)c2[C@H](OC(C)(C)C)C(=O)O)CN(C(=O)c2ccc(F)cc2F)C3)cc1]

¹H NMR (400 MHz, CHLOROFORM-d) (mixture of rotamers) δ ppm 7.55-7.44 (m, 1H), 7.35 (d, J=7.6 Hz, 1H), 7.30-7.19 (m, 2H), 7.13-6.89 (m, 3H), 5.16 (s, 1H), 5.10-4.90 (m, 2H), 4.73-4.57 (m, 2H), 2.47-2.38 (m, 3H), 2.36-2.09 (m, 3H), 1.99-1.74 (m, 3H), 1.06-0.91 (m, 9H); LCMS (m/z) ES⁺=508 (M+1).

Example 248: (S)-2-(tert-butoxy)-2-(2-(2-fluoro-5-methoxybenzoyl)-4,7-dimethyl-6-(p-tolyl)isoindolin-5-yl)acetic acid

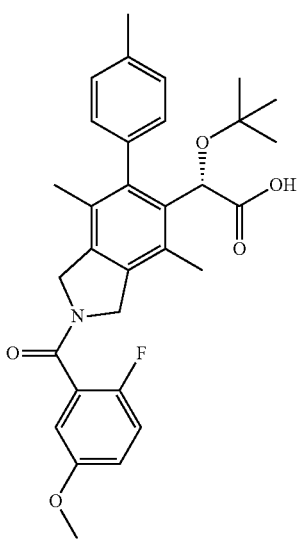 [SMILES: COc1ccc(C)c(C(=O)N2Cc3c(C)c(-c4ccc(C)cc4)c([C@H](OC(C)(C)C)C(=O)O)c(C)c3C2)c1]

¹H NMR (400 MHz, METHANOL-d₄) δ ppm (mixture of rotamers) 7.36-7.15 (m, 4H), 7.13-6.98 (m, 3H), 5.09-5.00 (m, 1H), 4.94 (br. s., 2H), 4.70 (br. s., 2H), 3.89-3.74 (m, 3H), 2.47-2.11 (m, 6H), 2.01-1.67 (m, 3H), 1.02-0.80 (m, 9H); LCMS (m/z) ES⁺=520 (M+1).

Example 249: (S)-2-(tert-butoxy)-2-(2-(5-methoxy-2-methylbenzoyl)-4,7-dimethyl-6-(p-tolyl)isoindolin-5-yl)acetic acid

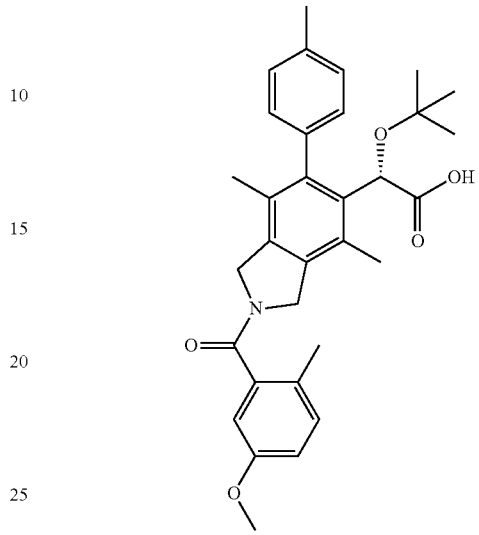

¹H NMR (400 MHz, METHANOL-d₄) δ ppm (mixture of rotamers) 7.32-7.18 (m, 4H), 7.14-7.03 (m, 1H), 6.99-6.86 (m, 2H), 5.08-5.01 (m, 1H), 4.97-4.91 (m, 2H), 4.58-4.51 (m, 2H), 3.85-3.76 (m, 3H), 2.47-2.39 (m, 3H), 2.37 (s, 1.5H), 2.26 (s, 3H), 2.15 (s, 1.5H), 1.98-1.66 (m, 3H), 0.99-0.86 (m, 9H); LCMS (m/z) ES⁺=516 (M+1).

Example 250: (S)-2-(tert-butoxy)-2-(2-(2-methoxy-5-methylbenzoyl)-4,7-dimethyl-6-(p-tolyl)isoindolin-5-yl)acetic acid

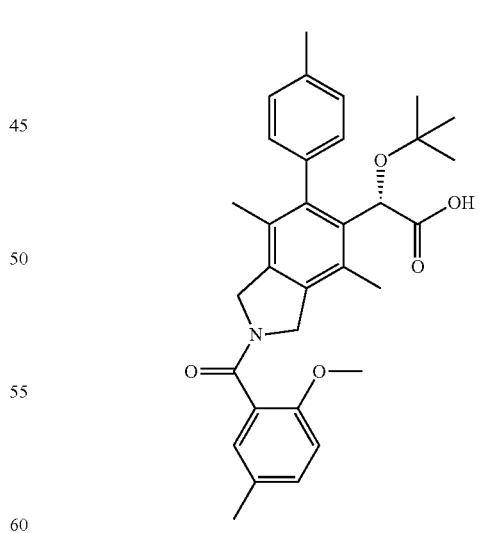

¹H NMR (400 MHz, METHANOL-d₄) δ ppm (mixture of rotamers) 7.34-7.22 (m, 4H), 7.18-7.13 (m, 1H), 7.13-6.99 (m, 2H), 5.09-4.99 (m, 1H), 4.92-4.88 (m, 2H), 4.60 (br. s, 2H), 3.89-3.81 (m, 3H), 2.45-2.39 (m, 3H), 2.38-2.30 (m, 4.5H), 2.15 (s, 1.5H), 1.93 (s, 1.5H), 1.72 (s, 1.5H), 0.98-0.87 (m, 9H); LCMS (m/z) ES⁺=516 (M+1).

Example 251: (S)-2-(tert-butoxy)-2-(2-(4-fluoro-3-methoxybenzoyl)-4,7-dimethyl-6-(p-tolyl)isoindolin-5-yl)acetic acid

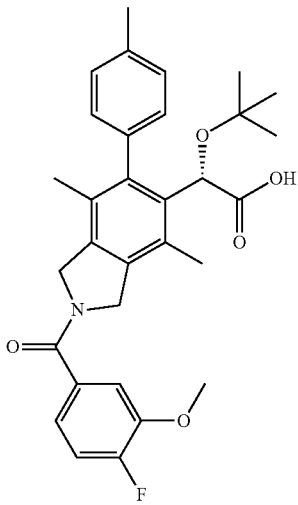 [SMILES: COc1cc(C(=O)N2Cc3c(C)c(-c4ccc(C)cc4)c([C@H](OC(C)(C)C)C(=O)O)c(C)c3C2)ccc1F]

¹H NMR (400 MHz, METHANOL-d₄) δ ppm (mixture of rotamers) 7.42-7.34 (m, 1H), 7.32-7.18 (m, 5H), 7.15-7.03 (m, 1H), 5.08-5.03 (m, 1H), 4.98-4.93 (m, 2H), 4.85-4.80 (m, 2H), 3.98-3.89 (m, 3H), 2.46-2.39 (m, 3H), 2.39-2.17 (m, 3H), 1.97-1.73 (m, 3H), 0.98-0.86 (m, 9H); LCMS (m/z) ES⁺=520 (M+1).

Example 252: (S)-2-(tert-butoxy)-2-(2-(3-chloro-4-fluorobenzoyl)-4,7-dimethyl-6-(p-tolyl)isoindolin-5-yl)acetic acid

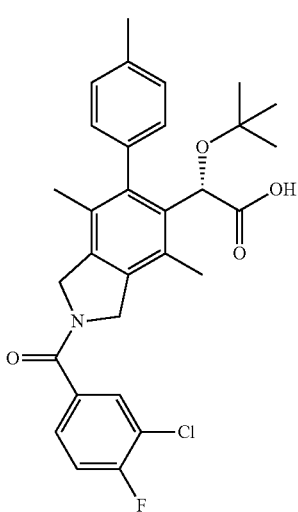 [SMILES: Cc1ccc(-c2c(C)c3c(c(C)c2[C@H](OC(C)(C)C)C(=O)O)CN(C(=O)c2ccc(F)c(Cl)c2)C3)cc1]

¹H NMR (400 MHz, METHANOL-d₄) (mixture of rotamers) δ ppm 7.88-7.78 (m, 1H), 7.71-7.59 (m, 1H), 7.44-7.36 (m, 1H), 7.32-7.21 (m, 3H), 7.13-7.01 (m, 1H), 5.06-5.02 (m, 1H), 4.98-4.93 (m, 2H), 4.85-4.78 (m, 2H), 2.46-2.39 (m, 3H), 2.38-2.18 (m, 3H), 1.96-1.74 (m, 3H), 0.97-0.88 (m, 9H); LCMS (m/z) ES+=524 (M+1).

Example 253: (S)-2-(tert-butoxy)-2-(2-(2-fluoro-3-methoxybenzoyl)-4,7-dimethyl-6-(p-tolyl)isoindolin-5-yl)acetic acid

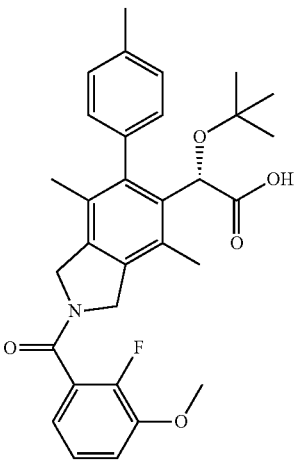 [SMILES: COc1cccc(C(=O)N2Cc3c(C)c(-c4ccc(C)cc4)c([C@H](OC(C)(C)C)C(=O)O)c(C)c3C2)c1F]

¹H NMR (400 MHz, METHANOL-d₄) (mixture of rotamers) δ ppm 7.37-7.21 (m, 5H), 7.17-6.99 (m, 2H), 5.12-5.03 (m, 1H), 4.96 (br. s., 2H), 4.69 (br. s., 2H), 4.02-3.89 (m, 3H), 2.50-2.12 (m, 6H), 2.02-1.69 (m, 3H), 1.02-0.84 (m, 9H); LCMS (m/z) ES⁺=520 (M+1).

Example 254: (S)-2-(tert-butoxy)-2-(2-(4-fluorobenzoyl)-4,7-dimethyl-6-(p-tolyl)isoindolin-5-yl)acetic acid

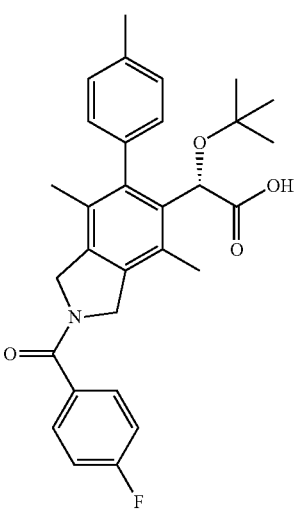 [SMILES: Cc1ccc(-c2c(C)c3c(c(C)c2[C@H](OC(C)(C)C)C(=O)O)CN(C(=O)c2ccc(F)cc2)C3)cc1]

¹H NMR (400 MHz, METHANOL-d₄) (mixture of rotamers) δ ppm 7.79-7.64 (m, 2H), 7.37-7.20 (m, 5H), 7.18-7.01 (m, 1H), 5.09-5.04 (m, 1H), 5.01-4.94 (m, 2H), 4.86-4.81 (m, 2H), 2.48-2.40 (m, 3H), 2.40-2.17 (m, 3H), 1.99-1.74 (m, 3H), 0.99-0.87 (m, 9H); LCMS (m/z) ES+=490 (M+1).

Example 255: (S)-2-(tert-butoxy)-2-(2-(2,3-dihydrobenzo[b][1,4]dioxine-6-carbonyl)-4,7-dimethyl-6-(p-tolyl)isoindolin-5-yl)acetic acid

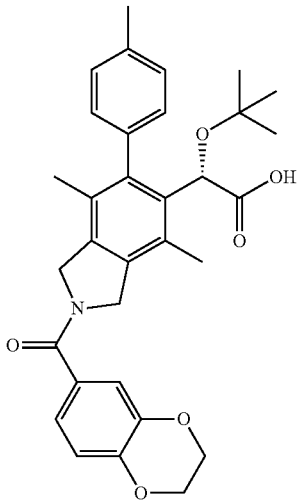 [SMILES: Cc1ccc(-c2c(C)c3c(c(C)c2[C@H](OC(C)(C)C)C(=O)O)CN(C(=O)c2ccc4c(c2)OCCO4)C3)cc1]

$^1$H NMR (400 MHz, METHANOL-d$_4$) (mixture of rotamers) δ ppm 7.37-7.25 (m, 3H), 7.23-7.05 (m, 3H), 7.02-6.92 (m, 1H), 5.10-5.04 (m, 1H), 5.00-4.93 (m, 2H), 4.92-4.84 (m, 2H), 4.38-4.27 (m, 4H), 2.49-2.41 (m, 3H), 2.40-2.20 (m, 3H), 1.99-1.76 (m, 3H), 1.02-0.88 (m, 9H); LCMS (m/z) ES$^+$=530.44 (M+1).

Example 256: (S)-2-(tert-butoxy)-2-(2-(1-hydroxy-1,3-dihydrobenzo[c][1,2]oxaborole-6-carbonyl)-4,7-dimethyl-6-(p-tolyl)isoindolin-5-yl)acetic acid

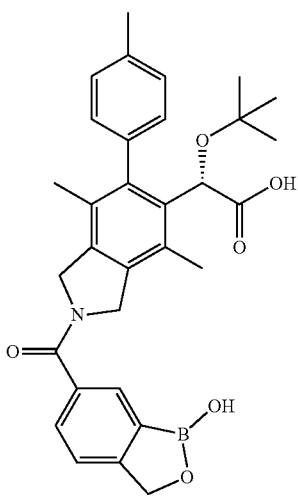 [SMILES: Cc1ccc(-c2c(C)c3c(c(C)c2[C@H](OC(C)(C)C)C(=O)O)CN(C(=O)c2ccc4c(c2)B(O)OC4)C3)cc1]

$^1$H NMR (400 MHz, METHANOL-d$_4$) (mixture of rotamers) δ ppm 7.94 (br. s., 1H), 7.82-7.70 (m, 1H), 7.64-7.52 (m, 1H), 7.39-7.22 (m, 3H), 7.19-7.02 (m, 1H), 5.22-5.14 (m, 2H), 5.10-5.05 (m, 1H), 5.04-4.97 (m, 2H), 4.84-4.76 (m, 2H), 2.49-2.16 (m, 6H), 2.00-1.72 (m, 3H), 1.00-0.89 (m, 9H); LCMS (m/z) ES$^+$=528 (M+1).

Example 257: (S)-2-(2-(3-boronobenzoyl)-4,7-dimethyl-6-(p-tolyl)isoindolin-5-yl)-2-(tert-butoxy)acetic acid

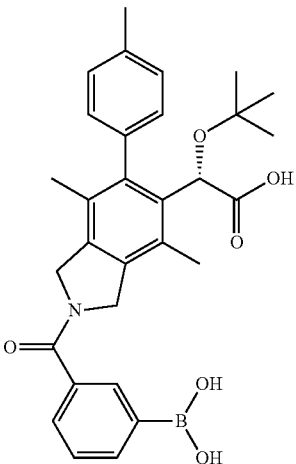 [SMILES: Cc1ccc(-c2c(C)c3c(c(C)c2[C@H](OC(C)(C)C)C(=O)O)CN(C(=O)c2cccc(B(O)O)c2)C3)cc1]

$^1$H NMR (400 MHz, METHANOL-d$_4$) (mixture of rotamers) δ ppm 8.15-7.43 (m, 4H), 7.39-7.22 (m, 3H), 7.16-7.02 (m, 1H), 5.10-5.05 (m, 1H), 5.04-4.95 (m, 2H), 4.85-4.78 (m, 2H), 2.48-2.19 (m, 6H), 2.00-1.73 (m, 3H), 1.01-0.90 (m, 9H); LCMS (m/z) ES$^+$=516 (M+1).

Example 258: (S)-2-(tert-butoxy)-2-(2-(3-methoxy-2-methylbenzoyl)-4,7-dimethyl-6-(p-tolyl)isoindolin-5-yl)acetic acid

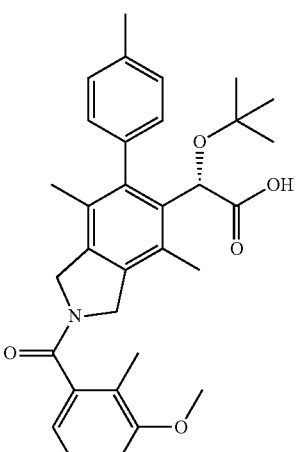

$^1$H NMR (400 MHz, METHANOL-d$_4$) (mixture of rotamers) δ ppm 7.40-7.21 (m, 4H), 7.17-7.00 (m, 2H), 7.00-6.88 (m, 1H), 5.10-5.04 (m, 1H), 4.99-4.94 (m, 2H), 4.56-4.48 (m, 2H), 3.95-3.85 (m, 3H), 2.47-2.36 (m, 5H), 2.24-2.19 (m, 3H), 2.16 (s, 1H), 1.99-1.69 (m, 3H), 1.01-0.87 (m, 9H); LCMS (m/z) ES$^+$=516.48 (M+1).

Example 259: (S)-2-(tert-butoxy)-2-(4,7-dimethyl-2-(2-methylnicotinoyl)-6-(p-tolyl)isoindolin-5-yl)acetic acid

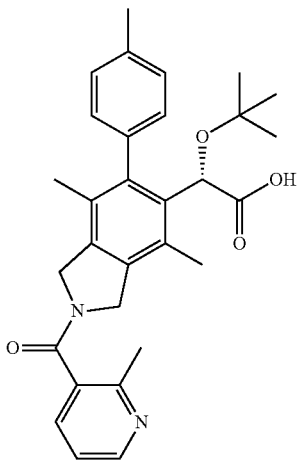 [SMILES: Cc1ccc(-c2c(C)c3c(c(C)c2[C@H](OC(C)(C)C)C(=O)O)CN(C(=O)c2cccnc2C)C3)cc1]

¹H NMR (400 MHz, METHANOL-d₄) (mixture of rotamers) δ ppm 8.78 (br. s., 1H), 8.60-8.38 (m, 1H), 7.98-7.77 (m, 1H), 7.42-7.22 (m, 3H), 7.20-6.99 (m, 1H), 5.15-5.00 (m, 3H), 4.77-4.62 (m, 2H), 2.77 (br. s., 3H), 2.55-2.14 (m, 6H), 2.06-1.74 (m, 3H), 1.02-0.82 (m, 9H); LCMS (m/z) ES⁺=487 (M+1).

Example 260: (S)-2-(tert-butoxy)-2-(4,7-dimethyl-2-(4-methylnicotinoyl)-6-(p-tolyl)isoindolin-5-yl)acetic acid

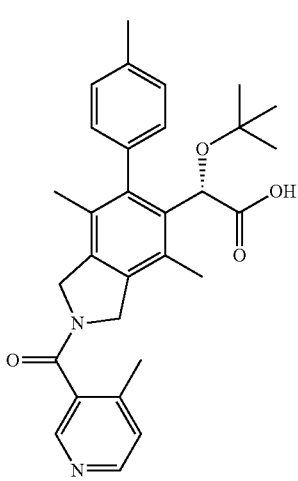 [SMILES: Cc1ccc(-c2c(C)c3c(c(C)c2[C@H](OC(C)(C)C)C(=O)O)CN(C(=O)c2cnccc2C)C3)cc1]

¹H NMR (400 MHz, METHANOL-d₄) (mixture of rotamers) δ ppm 8.85 (d, J=6.7 Hz, 1H), 8.70 (dd, J=5.9, 8.4 Hz, 1H), 7.84 (dd, J=5.8, 9.8 Hz, 1H), 7.34-7.21 (m, 3H), 7.14-7.00 (m, 1H), 5.10-4.97 (m, 3H), 4.72-4.57 (m, 2H), 2.64-2.54 (m, 3H), 2.47-2.13 (m, 6H), 2.00-1.70 (m, 3H), 1.00-0.85 (m, 9H); LCMS (m/z) ES⁺=487 (M+1).

Example 261: (S)-2-(tert-butoxy)-2-(2-(3,4-difluorobenzol)-4,7-dimethyl-6-(p-tolyl)isoindolin-5-yl) acetic acid

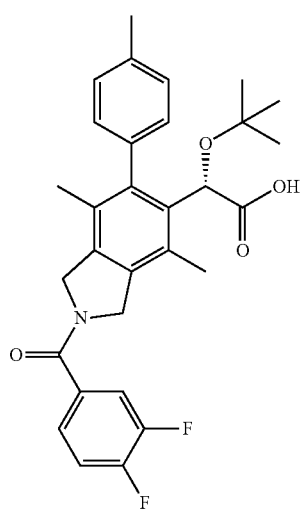 [SMILES: Cc1ccc(-c2c(C)c3c(c(C)c2[C@H](OC(C)(C)C)C(=O)O)CN(C(=O)c2ccc(F)c(F)c2)C3)cc1]

¹H NMR (400 MHz, METHANOL-d₄) (mixture of rotamers) δ ppm 7.68-7.58 (m, 1H), 7.55-7.47 (m, 1H), 7.46-7.36 (m, 1H), 7.33-7.21 (m, 3H), 7.14-7.02 (m, 1H), 5.08-5.03 (m, 1H), 4.99-4.93 (m, 2H), 4.85-4.79 (m, 2H), 2.47-2.39 (m, 3H), 2.38-2.18 (m, 3H), 1.96-1.75 (m, 3H), 0.98-0.87 (m, 9H); LCMS (m/z) ES⁺=508 (M+1).

Example 262: (S)-2-(tert-butoxy)-2-(2-(2,5-difluorobenzoyl)-4,7-dimethyl-6-(p-tolyl)isoindolin-5-yl) acetic acid

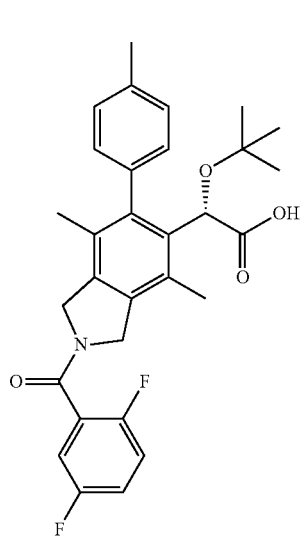 [SMILES: Cc1ccc(-c2c(C)c3c(c(C)c2[C@H](OC(C)(C)C)C(=O)O)CN(C(=O)c2cc(F)ccc2F)C3)cc1]

¹H NMR (400 MHz, METHANOL-d₄) (mixture of rotamers) δ ppm 7.39-7.21 (m, 6H), 7.15-7.03 (m, 1H), 5.08-5.03 (m, 1H), 4.97-4.91 (m, 2H), 4.74-4.68 (m, 2H), 2.47-2.39 (m, 3H), 2.38-2.15 (m, 3H), 1.98-1.74 (m, 3H), 0.97-0.88 (m, 9H); LCMS (m/z) ES⁺=508 (M+1).

Example 263: (S)-2-(tert-butoxy)-2-(2-(5-chloro-2-methylbenzoyl)-4,7-dimethyl-6-(p-tolyl)isoindolin-5-yl)acetic acid

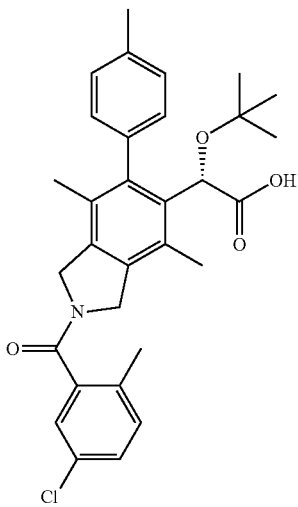 [SMILES: Cc1ccc(-c2c(C)c3c(c(C)c2[C@H](OC(C)(C)C)C(=O)O)CN(C(=O)c2cc(Cl)ccc2C)C3)cc1]

¹H NMR (400 MHz, METHANOL-d₄) (mixture of rotamers) δ ppm 7.48-7.18 (m, 6H), 7.15-7.00 (m, 1H), 5.09-5.02 (m, 1H), 4.95 (br. s., 2H), 4.55 (br. s., 2H), 2.48-2.35 (m, 4.5H), 2.32 (s, 3H), 2.16 (s, 1.5H), 1.98-1.69 (m, 3H), 0.99-0.84 (m, 9H); LCMS (m/z) ES+=520 (M+1).

Example 264: (S)-2-(tert-butoxy)-2-(2-(4-chloro-3-fluorobenzoyl)-4,7-dimethyl-6-(p-tolyl)isoindolin-5-yl)acetic acid

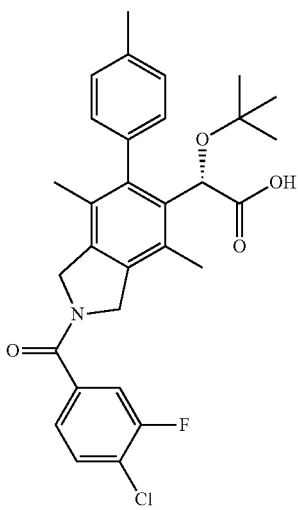 [SMILES: Cc1ccc(-c2c(C)c3c(c(C)c2[C@H](OC(C)(C)C)C(=O)O)CN(C(=O)c2ccc(Cl)c(F)c2)C3)cc1]

¹H NMR (400 MHz, METHANOL-d4) (mixture of rotamers) δ ppm 7.71-7.53 (m, 2H), 7.52-7.44 (m, 1H), 7.34-7.19 (m, 3H), 7.14-7.01 (m, 1H), 5.07-5.03 (m, 1H), 4.98-4.93 (m, 2H), 4.85-4.80 (m, 2H), 2.47-2.39 (m, 3H), 2.38-2.18 (m, 3H), 1.98-1.75 (m, 3H), 0.95-0.86 (m, 9H); LCMS (m/z) ES+=524 (M+1).

Example 265: (S)-2-(2-(benzo[d][1,3]dioxole-5-carbonyl)-4,7-dimethyl-6-(p-tolyl)isoindolin-5-yl)-2-(tert-butoxy)acetic acid

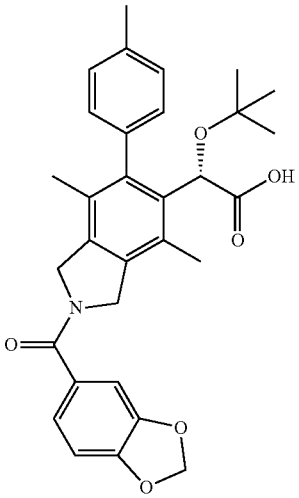 [SMILES: Cc1ccc(-c2c(C)c3c(c(C)c2[C@H](OC(C)(C)C)C(=O)O)CN(C(=O)c2ccc4c(c2)OCO4)C3)cc1]

¹H NMR (400 MHz, METHANOL-d₄) (mixture of rotamers) δ ppm 7.36-7.23 (m, 3H), 7.23-7.17 (m, 1H), 7.14 (br. s, 1H), 7.12-7.03 (m, 1H), 6.99-6.88 (m, 1H), 6.12-5.96 (m, 2H), 5.09-5.02 (m, 1H), 4.98-4.92 (m, 2H), 4.91-4.79 (m, 2H), 2.49-2.39 (m, 3H), 2.39-2.17 (m, 3H), 1.98-1.76 (m, 3H), 1.01-0.86 (m, 9H); LCMS (m/z) ES⁺=516.47 (M+1).

Example 266: (S)-2-(tert-butoxy)-2-(2-(3-carbamoyl-5-fluorobenzoyl)-4,7-dimethyl-6-(p-tolyl)isoindolin-5-yl)acetic acid

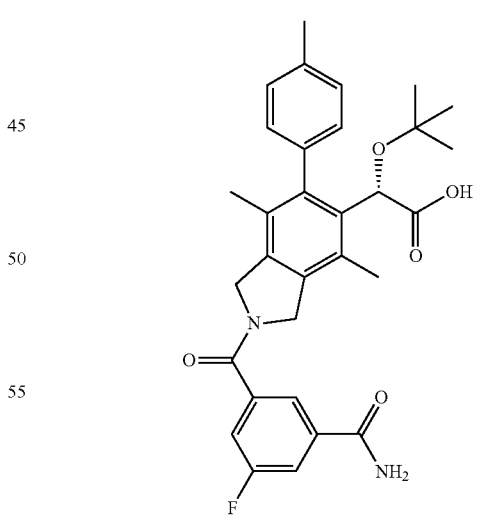

¹H NMR (400 MHz, METHANOL-d₄) (mixture of rotamers) δ ppm 8.01-7.91 (m, 1H), 7.84-7.74 (m, 1H), 7.65-7.57 (m, 1H), 7.33-7.19 (m, 3H), 7.15-7.01 (m, 1H), 5.08-5.04 (m, 1H), 5.01-4.95 (m, 2H), 4.85-4.81 (m, 2H), 2.46-2.40 (m, 3H), 2.39-2.19 (m, 3H), 1.98-1.75 (m, 3H), 0.96-0.87 (m, 9H); LCMS (m/z) ES⁺=533.49 (M+1).

Example 267: (S)-3-(5-(tert-butoxy(carboxy) methyl)-4,7-dimethyl-6-(p-tolyl)isoindoline-2-carbonyl)-5-fluorobenzoic acid

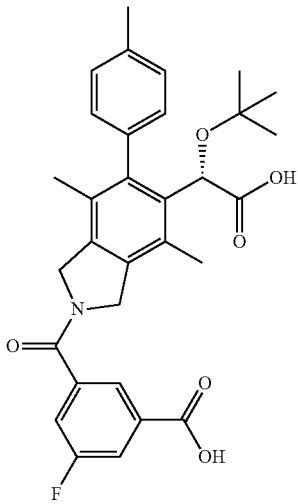 [SMILES: Cc1ccc(-c2c(C)c3c(c(C)c2[C@H](OC(C)(C)C)C(=O)O)CN(C(=O)c2cc(F)cc(C(=O)O)c2)C3)cc1]

¹H NMR (400 MHz, METHANOL-d₄) (mixture of rotamers) δ ppm 8.16-8.03 (m, 1H), 7.91-7.80 (m, 1H), 7.74-7.64 (m, 1H), 7.32-7.20 (m, 3H), 7.15-7.00 (m, 1H), 5.07-5.03 (m, 1H), 4.99-4.94 (m, 2H), 4.84-4.81 (m, 2H), 2.45-2.39 (m, 3H), 2.38-2.17 (m, 3H), 1.97-1.72 (m, 3H), 0.96-0.87 (m, 9H); LCMS (m/z) ES+=534.51 (M+1).

Example 268: (S)-2-(tert-butoxy)-2-(4,7-dimethyl-2-nicotinoyl-6-(p-tolyl)isoindolin-5-yl)acetic acid

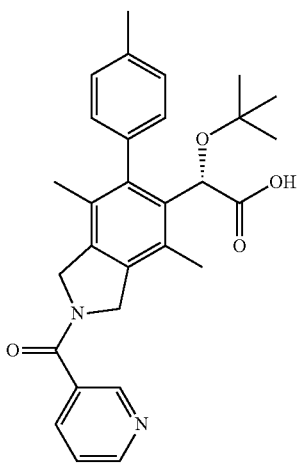 [SMILES: Cc1ccc(-c2c(C)c3c(c(C)c2[C@H](OC(C)(C)C)C(=O)O)CN(C(=O)c2cccnc2)C3)cc1]

¹H NMR (400 MHz, METHANOL-d₄) (mixture of rotamers) δ ppm 8.99-8.87 (m, 1H), 8.82-8.70 (m, 1H), 8.31 (tt, J=1.8, 8.0 Hz, 1H), 7.73 (dt, J=5.3, 8.2 Hz, 1H), 7.34-7.20 (m, 3H), 7.08 (dd, J=7.9, 15.6 Hz, 1H), 5.09-5.03 (m, 1H), 5.01-4.96 (m, 2H), 4.94-4.74 (m, 2H), 2.48-2.39 (m, 3H), 2.39-2.17 (m, 3H), 1.99-1.74 (m, 3H), 0.98-0.87 (m, 9H); LCMS (m/z) ES+=473.51 (M+1).

Example 269: (S)-2-(tert-butoxy)-2-(4,7-dimethyl-2-(thiazole-5-carbonyl)-6-(p-tolyl)isoindolin-5-yl)acetic acid

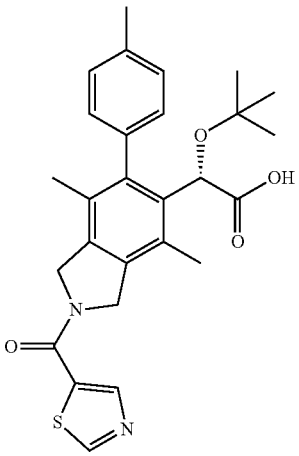 [SMILES: Cc1ccc(-c2c(C)c3c(c(C)c2[C@H](OC(C)(C)C)C(=O)O)CN(C(=O)c2cncs2)C3)cc1]

¹H NMR (400 MHz, METHANOL-d₄) δ ppm 9.23 (d, J=3.8 Hz, 1H), 8.58 (d, J=7.8 Hz, 1H), 7.38-7.23 (m, 3H), 7.13 (d, J=7.8 Hz, 1H), 5.24 (br. s., 2H), 5.09 (s, 1H), 5.00 (br. s., 2H), 2.45 (s, 3H), 2.39 (s, 3H), 1.96 (d, J=1.8 Hz, 3H), 0.96 (s, 9H); LCMS (m/z) ES+=479.45 (M+1).

Example 270: (S)-2-(tert-butoxy)-2-(2-(4-chlorobenzoyl)-4,7-dimethyl-6-(p-tolyl)isoindolin-5-yl)acetic acid

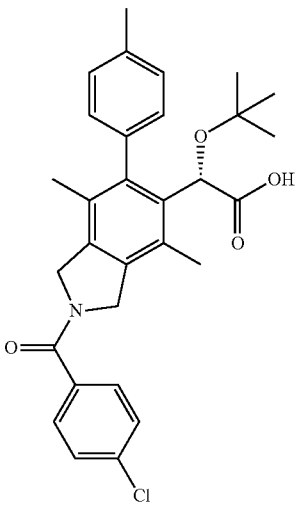 [SMILES: Cc1ccc(-c2c(C)c3c(c(C)c2[C@H](OC(C)(C)C)C(=O)O)CN(C(=O)c2ccc(Cl)cc2)C3)cc1]

¹H NMR (400 MHz, METHANOL-d₄) (mixture of rotamers) δ ppm 7.74-7.62 (m, 2H), 7.60-7.47 (m, 2H), 7.37-7.19 (m, 3H), 7.18-7.01 (m, 1H), 5.10-5.04 (m, 1H), 5.02-4.94 (m, 2H), 4.85-4.78 (m, 2H), 2.49-2.41 (m, 3H), 2.40-2.17 (m, 3H), 2.01-1.74 (m, 3H), 1.02-0.85 (m, 9H); LCMS (m/z) ES+=506.44 (M+1).

Example 271: (S)-2-(tert-butoxy)-2-(2-(3,5-dichlorobenzoyl)-4,7-dimethyl-6-(p-tolyl)isoindolin-5-yl)acetic acid

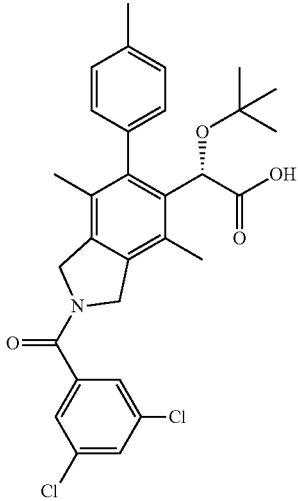 [SMILES: Cc1ccc(-c2c(C)c3c(c(C)c2[C@H](OC(C)(C)C)C(=O)O)CN(C(=O)c2cc(Cl)cc(Cl)c2)C3)cc1]

¹H NMR (400 MHz, METHANOL-d₄) (mixture of rotamers) δ ppm 7.65 (br. s., 3H), 7.42-7.21 (m, 3H), 7.18-6.97 (m, 1H), 5.06 (br. s., 1H), 4.96 (br. s., 2H), 4.82 (br. s., 2H), 2.56-2.20 (m, 6H), 2.03-1.74 (m, 3H), 1.08-0.83 (m, 9H); LCMS (m/z) ES+=540.42 (M+1).

Example 272: (S)-2-(tert-butoxy)-2-(4,7-dimethyl-2-(oxazole-4-carbonyl)-6-(p-tolyl)isoindolin-5-yl)acetic acid

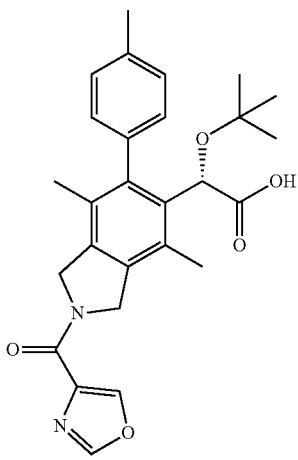 [SMILES: Cc1ccc(-c2c(C)c3c(c(C)c2[C@H](OC(C)(C)C)C(=O)O)CN(C(=O)c2cocn2)C3)cc1]

¹H NMR (400 MHz, METHANOL-d₄) (mixture of rotamers) δ ppm 8.61-8.51 (m, 1H), 8.37-8.24 (m, 1H), 7.40-7.23 (m, 3H), 7.20-7.04 (m, 1H), 5.39-5.25 (m, 2H), 5.08 (s, 1H), 5.02-4.94 (m, 2H), 2.44 (s, 3H), 2.40-2.30 (m, 3H), 2.00-1.88 (m, 3H), 0.96 (s, 9H); LCMS (m/z) ES⁺=463.49 (M+1).

Example 273: (S)-2-(tert-butoxy)-2-(4,7-dimethyl-2-picolinoyl-6-(p-tolyl)isoindolin-5-yl)acetic acid

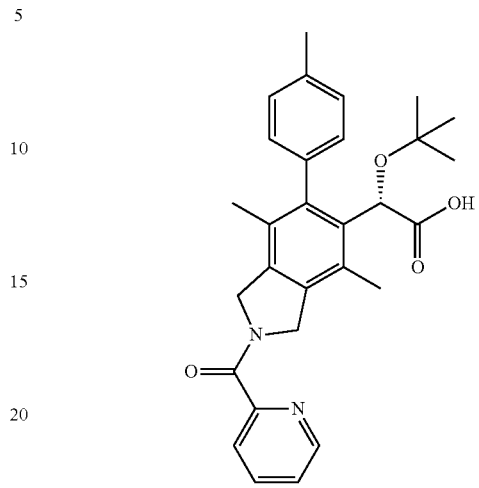

¹H NMR (400 MHz, METHANOL-d₄) (mixture of rotamers) δ ppm 8.71 (br. s., 1H), 8.11-7.99 (m, 1H), 7.98-7.83 (m, 1H), 7.68-7.52 (m, 1H), 7.39-7.21 (m, 3H), 7.20-7.03 (m, 1H), 5.17-5.10 (m, 2H), 5.10-5.05 (m, 1H), 5.04-4.98 (m, 2H), 2.52-2.21 (m, 6H), 2.02-1.78 (m, 3H), 1.06-0.82 (m, 9H); LCMS (m/z) ES+=473.53 (M+1).

Example 274: (S)-2-(tert-butoxy)-2-(4,7-dimethyl-2-(2-phenyloxazole-5-carbonyl)-6-(p-tolyl)isoindolin-5-yl)acetic acid

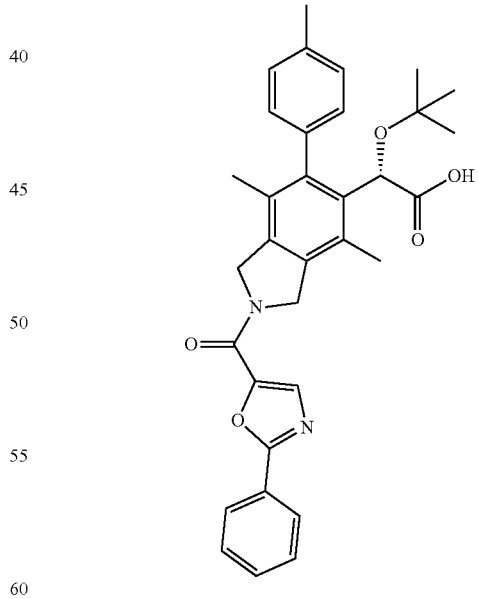

¹H NMR (400 MHz, METHANOL-d₄) (mixture of rotamers) δ ppm 8.26-8.12 (m, 2H), 8.02 (d, J=4.3 Hz, 1H), 7.67-7.50 (m, 3H), 7.42-7.24 (m, 3H), 7.14 (d, J=7.8 Hz, 1H), 5.41-5.23 (m, 2H), 5.10 (s, 1H), 5.05-4.95 (m, 2H), 2.51-2.35 (m, 6H), 2.06-1.91 (m, 3H), 0.97 (s, 9H); LCMS (m/z) ES⁺=539.52 (M+1).

Example 275: (S)-2-(2-(benzo[d][1,3]dioxole-4-carbonyl)-4,7-dimethyl-6-(p-tolyl)isoindolin-5-yl)-2-(tert-butoxy)acetic acid

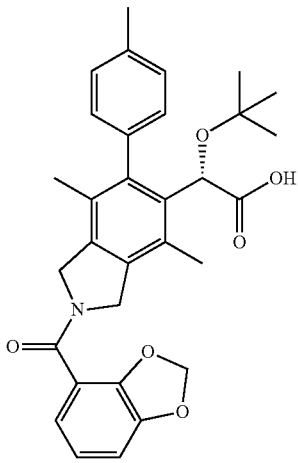 [SMILES: Cc1ccc(-c2c(C)c3c(c(C)c2[C@H](OC(C)(C)C)C(=O)O)CN(C(=O)c2cccc4c2OCO4)C3)cc1]

$^1$H NMR (400 MHz, CHLOROFORM-d) (mixture of rotamers) δ ppm 7.45-7.32 (m, 1H), 7.31-7.18 (m, 2H), 7.15-6.86 (m, 4H), 6.15-5.97 (m, 2H), 5.17 (s, 1H), 5.10-4.86 (m, 2H), 4.85-4.69 (m, 2H), 2.49-2.36 (m, 3H), 2.35-2.10 (m, 3H), 1.98-1.76 (m, 3H), 1.08-0.91 (m, 9H); LCMS (m/z) ES$^+$=516.50 (M+1).

Example 276: (S)-2-(tert-butoxy)-2-(2-(3,4-dichlorobenzoyl)-4,7-dimethyl-6-(p-tolyl)isoindolin-5-yl)acetic acid

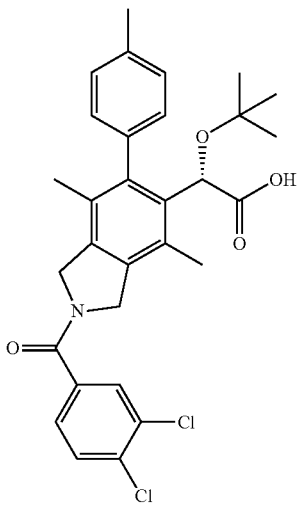 [SMILES: Cc1ccc(-c2c(C)c3c(c(C)c2[C@H](OC(C)(C)C)C(=O)O)CN(C(=O)c2ccc(Cl)c(Cl)c2)C3)cc1]

$^1$H NMR (400 MHz, CHLOROFORM-d) (mixture of rotamers) δ ppm 7.74-7.66 (m, 1H), 7.63-7.51 (m, 1H), 7.48-7.40 (m, 1H), 7.39-7.31 (m, 1H), 7.31-7.18 (m, 2H), 7.13-6.95 (m, 1H), 5.16 (s, 1H), 5.10-4.87 (m, 2H), 4.79-4.64 (m, 2H), 2.47-2.37 (m, 3H), 2.37-2.11 (m, 3H), 1.99-1.76 (m, 3H), 1.05-0.91 (m, 9H); LCMS (m/z) ES$^+$=540.43 (M+1).

Example 277: (S)-2-(tert-butoxy)-2-(2-(3,4-dichloro-5-fluorobenzoyl)-4,7-dimethyl-6-(p-tolyl)isoindolin-5-yl)acetic acid

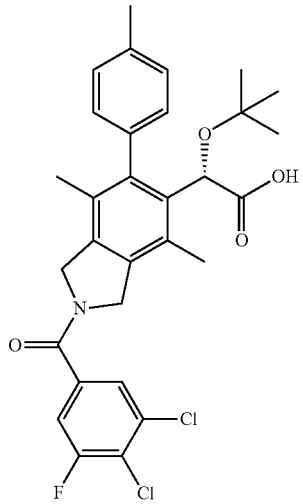 [SMILES: Cc1ccc(-c2c(C)c3c(c(C)c2[C@H](OC(C)(C)C)C(=O)O)CN(C(=O)c2cc(F)c(Cl)c(Cl)c2)C3)cc1]

$^1$H NMR (400 MHz, METHANOL-d$_4$) (mixture of rotamers) δ ppm 7.77-7.69 (m, 1H), 7.64-7.54 (m, 1H), 7.36-7.23 (m, 3H), 7.16-7.03 (m, 1H), 5.09-5.03 (m, 1H), 5.01-4.93 (m, 2H), 4.87-4.83 (m, 2H), 2.50-2.41 (m, 3H), 2.40-2.21 (m, 3H), 1.99-1.77 (m, 3H), 1.00-0.90 (m, 9H); LCMS (m/z) ES$^+$=558.43 (M+1).

Example 278: (S)-2-(tert-butoxy)-2-(2-(3,4-difluoro-5-methylbenzoyl)-4,7-dimethyl-6-(p-tolyl)isoindolin-5-yl)acetic acid

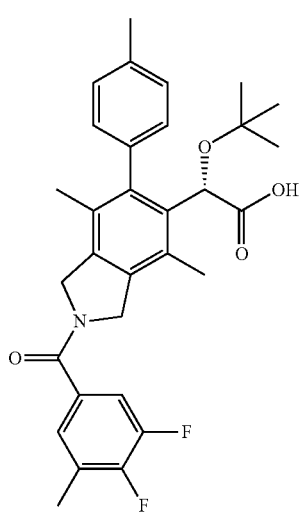 [SMILES: Cc1ccc(-c2c(C)c3c(c(C)c2[C@H](OC(C)(C)C)C(=O)O)CN(C(=O)c2cc(C)c(F)c(F)c2)C3)cc1]

$^1$H NMR (400 MHz, CHLOROFORM-d) (mixture of rotamers) δ ppm 7.41-7.32 (m, 1H), 7.31-7.17 (m, 4H), 7.12-6.98 (m, 1H), 5.16 (s, 1H), 5.09-4.88 (m, 2H), 4.80-4.65 (m, 2H), 2.45-2.40 (m, 3H), 2.40-2.35 (m, 3H), 2.34-2.14 (m, 3H), 1.98-1.79 (m, 3H), 1.04-0.94 (m, 9H); LCMS (m/z) ES$^+$=522.51 (M+1).

Example 279: (S)-2-(tert-butoxy)-2-(4,7-dimethyl-6-(p-tolyl)-2-(3,4,5-trifluorobenzoyl)isoindolin-5-yl)acetic acid

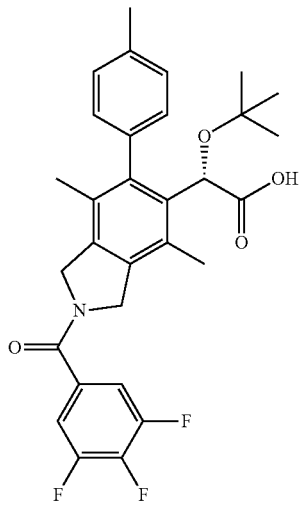 [SMILES: Cc1ccc(-c2c(C)c3c(c(C)c2[C@H](OC(C)(C)C)C(=O)O)CN(C(=O)c2cc(F)c(F)c(F)c2)C3)cc1]

¹H NMR (400 MHz, METHANOL-d₄ (mixture of rotamers) δ ppm 7.67-7.43 (m, 2H), 7.42-7.21 (m, 3H), 7.19-7.00 (m, 1H), 5.06 (br. s., 1H), 5.01-4.68 (m, 4H), 2.49-2.19 (m, 6H), 2.05-1.69 (m, 3H), 1.06-0.83 (m, 9H); LCMS (m/z) ES⁺=526.36 (M+1).

Example 280: (S)-2-(tert-butoxy)-2-(2-(3-chloro-4,5-difluorobenzoyl)-4,7-dimethyl-6-(p-tolyl)isoindolin-5-yl)acetic acid

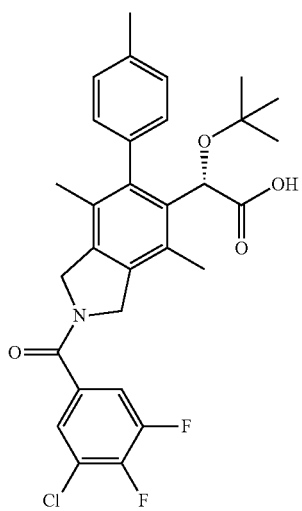 [SMILES: Cc1ccc(-c2c(C)c3c(c(C)c2[C@H](OC(C)(C)C)C(=O)O)CN(C(=O)c2cc(F)c(F)c(Cl)c2)C3)cc1]

¹H NMR (400 MHz, CHLOROFORM-d) (mixture of rotamers) δ ppm 7.52-7.42 (m, 1H), 7.40-7.32 (m, 2H), 7.31-7.17 (m, 2H), 7.12-6.97 (m, 1H), 5.17 (s, 1H), 5.10-4.85 (m, 2H), 4.82-4.63 (m, 2H), 2.49-2.37 (m, 3H), 2.36-2.12 (m, 3H), 2.01-1.76 (m, 3H), 1.12-0.93 (m, 9H); LCMS (m/z) ES⁺=542.44 (M+1).

Example 281: (S)-2-(tert-butoxy)-2-(2-(3,5-dichloro-4-fluorobenzoyl)-4,7-dimethyl-6-(p-tolyl)isoindolin-5-yl)acetic acid

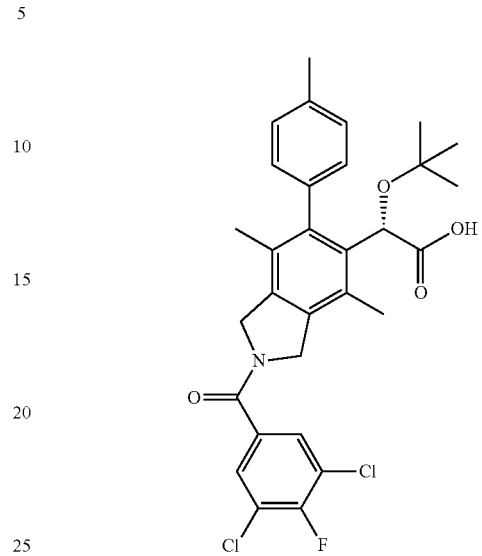

¹H NMR (400 MHz, CHLOROFORM-d) (mixture of rotamers) δ ppm 7.63-7.51 (m, 2H), 7.41-7.31 (m, 1H), 7.30-7.18 (m, 2H), 7.14-6.99 (m, 1H), 5.16 (s, 1H), 5.10-4.87 (m, 2H), 4.82-4.63 (m, 2H), 2.48-2.39 (m, 3H), 2.36-2.15 (m, 3H), 1.98-1.78 (m, 3H), 1.07-0.94 (m, 9H); LCMS (m/z) ES⁺=558.37 (M+1).

Example 282: (S)-2-(tert-butoxy)-2-(2-(4-chloro-3,5-difluorobenzoyl)-4,7-dimethyl-6-(p-tolyl)isoindolin-5-yl)acetic acid

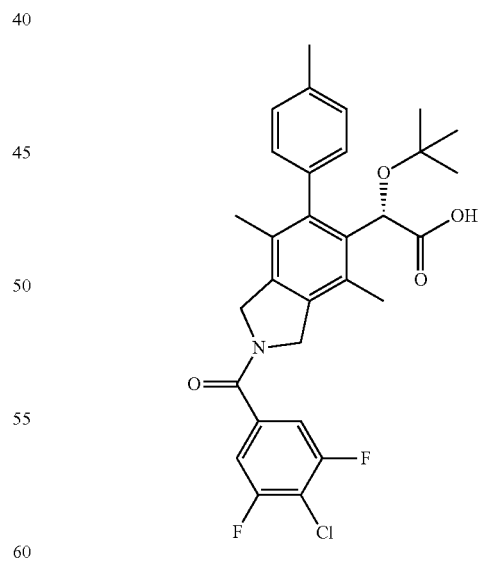

¹H NMR (400 MHz, CHLOROFORM-d) (mixture of rotamers) δ ppm 7.40-7.31 (m, 1H), 7.30-7.18 (m, 4H), 7.13-6.97 (m, 1H), 5.16 (s, 1H), 5.09-4.88 (m, 2H), 4.82-4.61 (m, 2H), 2.48-2.38 (m, 3H), 2.37-2.11 (m, 3H), 1.99-1.76 (m, 3H), 1.07-0.90 (m, 9H); LCMS (m/z) ES⁺=542.43 (M+1).

Example 283: (S)-2-(tert-butoxy)-2-(4,7-dimethyl-2-(6-methylnicotinoyl)-6-(p-tolyl)isoindolin-5-yl)acetic acid

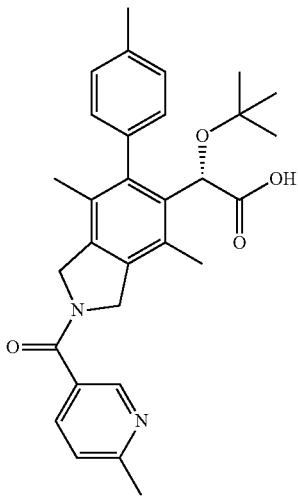 [SMILES: Cc1ccc(-c2c(C)c3c(c(C)c2[C@H](OC(C)(C)C)C(=O)O)CN(C(=O)c2ccc(C)nc2)C3)cc1]

¹H NMR (400 MHz, METHANOL-$d_4$) (mixture of rotamers) δ ppm 9.09-8.91 (m, 1H), 8.58 (t, J=7.8 Hz, 1H), 7.91 (t, J=8.5 Hz, 1H), 7.40-7.22 (m, 3H), 7.19-7.00 (m, 1H), 5.15-5.06 (m, 1H), 5.05-4.99 (m, 2H), 4.98-4.80 (m, 2H), 2.91-2.75 (m, 3H), 2.53-2.17 (m, 6H), 2.03-1.76 (m, 3H), 1.04-0.85 (m, 9H); LCMS (m/z) ES⁺=487.49 (M+1).

Example 284: (S)-2-(tert-butoxy)-2-(2-(2,3-dimethoxybenzoyl)-4,7-dimethyl-6-(p-tolyl)isoindolin-5-yl)acetic acid

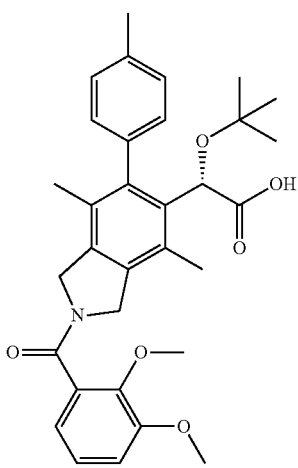 [SMILES: COc1cccc(C(=O)N2Cc3c(C)c(-c4ccc(C)cc4)c([C@H](OC(C)(C)C)C(=O)O)c(C)c3C2)c1OC]

¹H NMR (400 MHz, CHLOROFORM-d) (mixture of rotamers) δ ppm 7.40-7.30 (m, 1H), 7.26-7.11 (m, 3H), 7.10-6.96 (m, 2H), 6.96-6.88 (m, 1H), 5.21-5.10 (m, 1H), 5.09-4.89 (m, 2H), 4.74-4.49 (m, 2H), 3.96-3.91 (m, 3H), 3.90 (s, 3H), 2.46-2.37 (m, 3H), 2.36-2.06 (m, 3H), 1.99-1.69 (m, 3H), 1.06-0.91 (m, 9H); LCMS (m/z) ES⁺=532.54 (M+1).

Example 285: (S)-2-(tert-butoxy)-2-((M)-2-(2,5-difluorobenzoyl)-6-(8-fluoro-5-methylchroman-6-yl)-4,7-dimethylisoindolin-5-yl)acetic acid

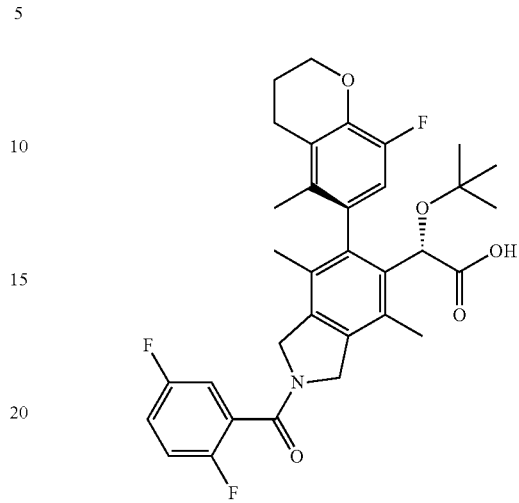

The title compound was isolated as a white solid after reverse phase hplc.

¹H NMR (400 MHz, CDCl₃) ∂ (mixture of rotamers) 7.14 (m, 3H), 6.66 (m, 1H), 5.02 (m, 3H), 4.66 (m, 2H), 4.26 (m, 2H), 2.68 (m, 2H), 2.37-2.05 (m, 5H), 1.89-1.63 (m, 6H), 1.12 (m, 9H). LCMS (ES+) (m/z): 582.35 (M+1); 1163.63 (2M+1).

Example 286: (S)-2-(tert-butoxy)-2-((M)-6-(8-fluoro-5-methylchroman-6-yl)-2-(4-methoxy-2-methylbenzoyl)-4,7-dimethylisoindolin-5-yl)acetic acid

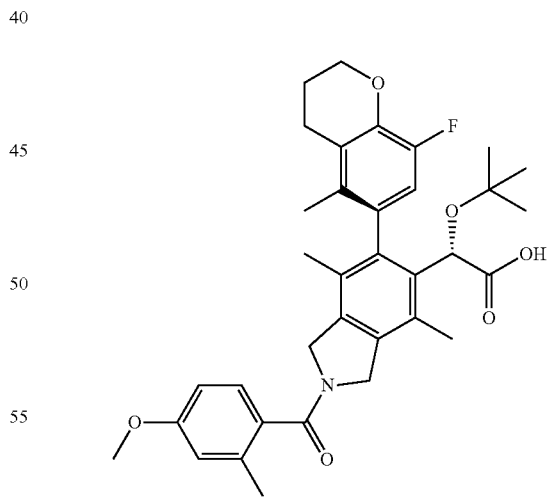

The title compound was isolated as a white solid after reverse phase hplc.

¹H NMR (400 MHz, CDCl₃) ∂ (mixture of rotamers) 7.21 (m, 1H), 6.79 (m, 2H), 6.65 (m, 1H), 5.02 (m, 3H), 4.50 (m, 2H), 4.25 (m, 2H), 3.83 (m, 3H), 2.67 (m, 2H), 2.41-2.02 (m, 8H), 1.91-1.60 (m, 6H), 1.12 (m, 9H). LCMS (ES+) (m/z): 590.49 (M+1); 1179.86 (2M+1).

Example 287: (S)-2-(tert-butoxy)-2-(4,7-dimethyl-2-((neopentyloxy)carbonyl)-6-(p-tolyl)isoindolin-5-yl)acetic acid

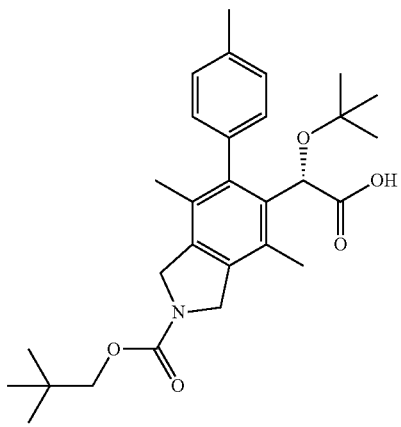 [SMILES: Cc1ccc(-c2c(C)c3c(c(C)c2[C@H](OC(C)(C)C)C(=O)O)CN(C(=O)OCC(C)(C)C)C3)cc1]

The title compound was isolated as a white solid after reverse phase hplc.

¹H NMR (400 MHz, CDCl₃) δ 7.34 (m, 1H), 7.22 (m, 2H), 7.06 (m, 1H), 5.14 (s, 1H), 4.71 (m, 4H), 3.88 (s, 2H), 2.40 (s, 3H), 2.24 (s, 3H), 1.87 (s, 3H), 0.99 (m, 18H). LCMS (ES+) (m/z): 482.49 (M+1); 963.88 (2M+1).

Example 288: (S)-2-(tert-butoxy)-2-(2-(3-fluorophenylcarbonothioyl)-4,7-dimethyl-6-(p-tolyl)isoindolin-5-yl)acetic acid

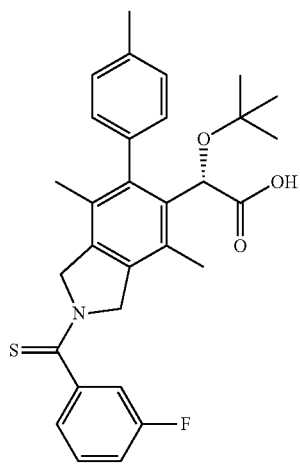 [SMILES: Cc1ccc(-c2c(C)c3c(c(C)c2[C@H](OC(C)(C)C)C(=O)O)CN(C(=S)c2cccc(F)c2)C3)cc1]

Step 1

(S)-ethyl 2-(tert-butoxy)-2-(2-(3-fluorophenylcarbonothioyl)-4,7-dimethyl-6-(p-tolyl)isoindolin-5-yl)acetate A mixture of 3-fluorobenzaldehyde (12.55 mg, 0.101 mmol), (S)-ethyl 2-(tert-butoxy)-2-(4,7-dimethyl-6-(p-tolyl)isoindolin-5-yl)acetate (40 mg, 0.101 mmol), and sulfur (3.89 mg, 0.121 mmol) in N,N-Dimethylformamide (DMF) (1 mL) was heated at 100° C. for 1 h. The reaction was cooled to ambient temperature, diluted with ice water, extracted with EtOAc, washed with brine, dried over Na₂SO₄, filtered, and concentrated in vacuo. Purification with column chromatography (0-50% EtOAc/Hexane) afforded the title compound (12.3 mg, 0.023 mmol, 22.79% yield) as yellow oil. LCMS (m/z) ES+=534.51 (M+1).

Step 2

(S)-2-(tert-butoxy)-2-(2-(3-fluorophenylcarbonothioyl)-4,7-dimethyl-6-(p-tolyl)isoindolin-5-yl)acetic acid A solution of (S)-ethyl 2-(tert-butoxy)-2-(2-(3-fluorophenylcarbonothioyl)-4,7-dimethyl-6-(p-tolyl)isoindolin-5-yl)acetate (12.3 mg, 0.023 mmol) in ethanol (0.5 mL) and Tetrahydrofuran (THF) (0.5 mL) was treated with 2M LiOH (0.115 mL, 0.23 mmol) and stirred at 70° C. for 5 hours. The reaction was cooled to ambient temperature and concentrated in vacuo. The residue was purified by reverse phase HPLC (35-95% MeCN/H2O-0.1% TFA) to afford the title compound (2.2 mg, 4.26 µmol, 18.54% yield) as an off-white solid. NMR showed rotamers.

¹H NMR (400 MHz, METHANOL-d4) d ppm 7.52-7.39 (m, 1H), 7.33-6.99 (m, 7H), 5.31-5.14 (m, 2H), 5.03 (d, J=6.4 Hz, 1H), 4.79 (d, J=3.8 Hz, 2H), 2.45-2.10 (m, 6H), 1.98-1.67 (m, 3H), 0.91 (d, J=9.9 Hz, 9H); LCMS (m/z) ES+=506.49 (M+1).

Example 289: (S)-2-(tert-butoxy)-2-(2-((3,3-difluoropyrrolidin-1-yl)sulfonyl)-4,7-dimethyl-6-(p-tolyl)isoindolin-5-yl)acetic acid

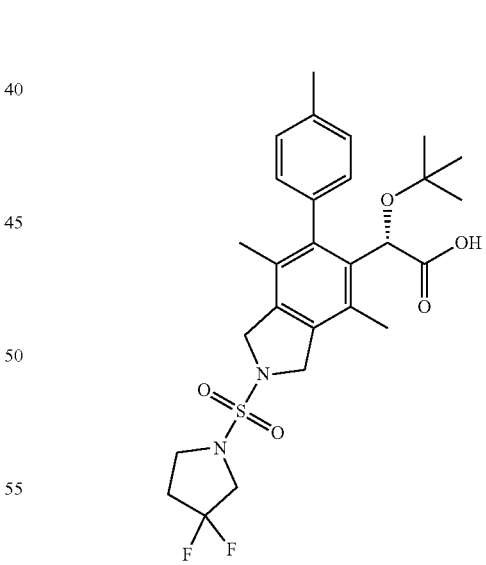

The title compound was isolated as a white solid after reverse phase hplc.

¹H NMR (400 MHz, CDCl₃) δ 7.33 (m, 1H), 7.22 (m, 2H), 7.05 (m, 1H), 5.14 (s, 1H), 4.78-4.56 (m, 4H), 3.77-3.52 (m, 4H), 2.40 (s, 6H), 2.22 (s, 3H), 1.85 (s, 3H), 0.99 (s, 9H). LCMS (ES+) (m/z): 537.51 (M+1).

Example 290: (S)-2-(tert-butoxy)-2-(4,7-dimethyl-2-((pyrimidin-2-ylmethyl)carbamoyl)-6-(p-tolyl)isoindolin-5-yl)acetic acid Example 292: (S)-2-(tert-butoxy)-2-(4,7-dimethyl-2-((R)-2-methylpyrrolidine-1-carbonyl)-6-(p-tolyl)isoindolin-5-yl)acetic acid

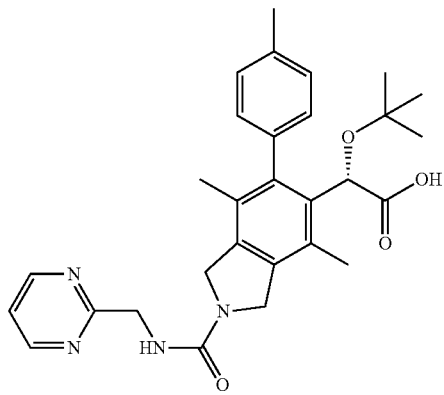 [SMILES: Cc1ccc(-c2c(C)c3c(c(C)c2[C@H](OC(C)(C)C)C(=O)O)CN(C(=O)NCc2ncccn2)C3)cc1]

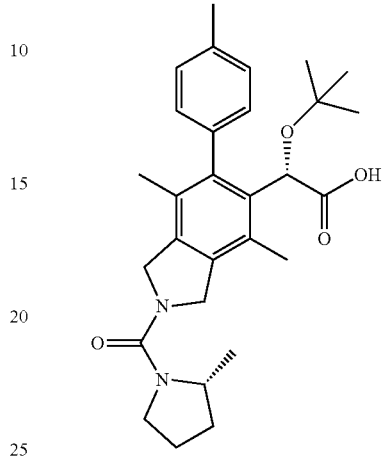

The title compound was isolated as a white solid after reverse phase hplc.

$^1$H NMR (400 MHz, CDCl$_3$) δ 8.80 (m, 2H), 7.35 (m, 1H), 7.20 (m, 2H), 7.05 (m, 1H), 5.15 (s, 1H), 4.75 (m, 5H), 2.40 (s, 3H), 2.25 (s, 3H), 1.90 (s, 3H), 1.25 (s, 1H), 0.95 (s, 9H). LCMS (ES+) (m/z): 503.45 (M+1); 1005.85 (2M+1).

$^1$H NMR (400 MHz, CDCl$_3$) δ 7.36 (d, 1H), 7.18-7.27 (m, 2H), 7.07 (d, 1H), 5.15 (s, 1H), 5.06 (d, 1H), 4.90 (d, 1H), 4.48-4.60 (m, 2H), 4.06-4.15 (m, 1H), 3.39-3.59 (m, 2H), 2.41 (s, 3H), 2.26 (s, 3H), 2.13 (td, 1H), 1.92 (dt, 1H), 1.89 (s, 3H), 1.81 (br. s, 1H), 1.50 (br. s, 1H), 1.21 (d, 3H), 0.98 (s, 9H). LCMS (ES+) (m/z): 479.61 (M+1), 501.60 (M+23), 957.93 (2M+1), 979.85 (2M+23).

Example 291: (S)-2-(tert-butoxy)-2-(2-(3,3-dimethylpyrrolidine-1-carbonyl)-4,7-dimethyl-6-(p-tolyl)isoindolin-5-yl)acetic acid Example 293: (S)-2-(tert-butoxy)-2-(4,7-dimethyl-2-((S)-2-methylpiperidine-1-carbonyl)-6-(p-tolyl)isoindolin-5-yl)acetic acid

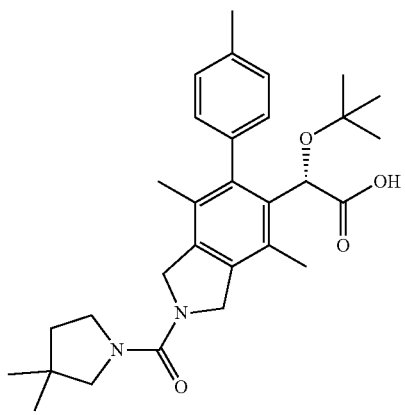 [SMILES: Cc1ccc(-c2c(C)c3c(c(C)c2[C@H](OC(C)(C)C)C(=O)O)CN(C(=O)N2CCC(C)(C)C2)C3)cc1]

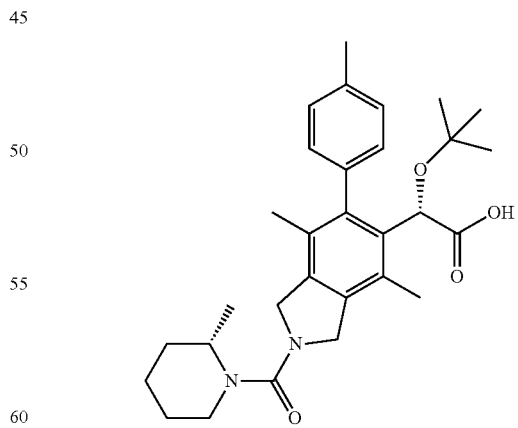

The title compound was isolated as a white solid after reverse phase hplc.

$^1$H NMR (400 MHz, CDCl$_3$) δ 7.35 (m, 1H), 7.21 (m, 2H), 7.06 (m, 1H), 5.14 (s, 1H), 4.90-4.64 (m, 4H), 3.58 (m, 2H), 3.23 (s, 2H), 2.39 (s, 3H), 2.23 (s, 3H), 1.87 (s, 3H), 1.69 (m, 2H), 1.11 (s, 6H), 0.96 (s, 9H). LCMS (ES+) (m/z): 493.53 (M+1); 985.89 (2M+1).

$^1$H NMR (Chloroform-d) δ: 7.36 (d, 1H), 7.18-7.25 (m, 1H), 7.06 (d, 1H), 5.14 (s, 1H), 4.74-4.89 (m, 2H), 4.60-4.74 (m, 2H), 4.08 (d, 1H), 3.51 (d, 1H), 3.08 (m, 1H), 2.41 (s, 3H), 2.25 (s, 3H), 1.88 (s, 3H), 1.50-1.80 (m, 6H), 1.22-1.30 (m, 3H), 0.97 (s, 9H).). LCMS (ES+) (m/z): 493.6 (M+1).

Example 294: (S)-2-(tert-butoxy)-2-(2-((S)-3-fluoro-pyrrolidine-1-carbonyl)-4,7-dimethyl-6-(p-tolyl)isoindolin-5-yl)acetic acid
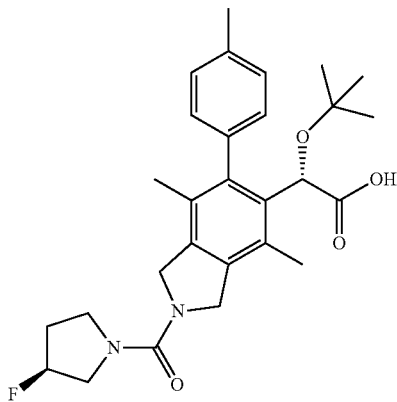 [SMILES: Cc1ccc(-c2c(C)c3c(c(C)c2[C@H](OC(C)(C)C)C(=O)O)CN(C(=O)N2CC[C@H](F)C2)C3)cc1]
¹H NMR (400 MHz, METHANOL-d₄) δ ppm 7.35-7.19 (m, 3H), 7.09 (d, J=8.3 Hz, 1H), 5.40-5.18 (m, 1H), 5.05 (s, 1H), 5.01-4.91 (m, 2H), 4.75-4.61 (m, 2H), 3.91-3.61 (m, 4H), 2.42 (s, 3H), 2.35-1.95 (m, 5H), 1.88 (s, 3H), 0.93 (s, 9H); LCMS (m/z) ES+=483.56 (M+1).
Scheme 3
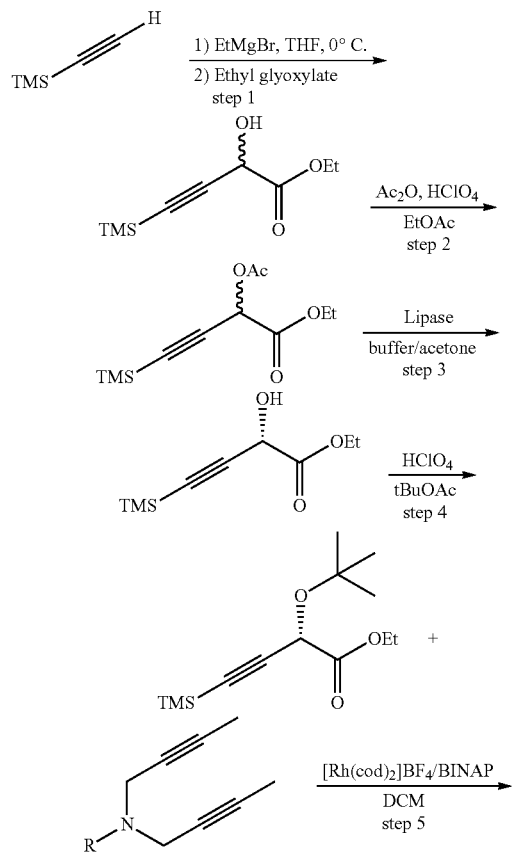
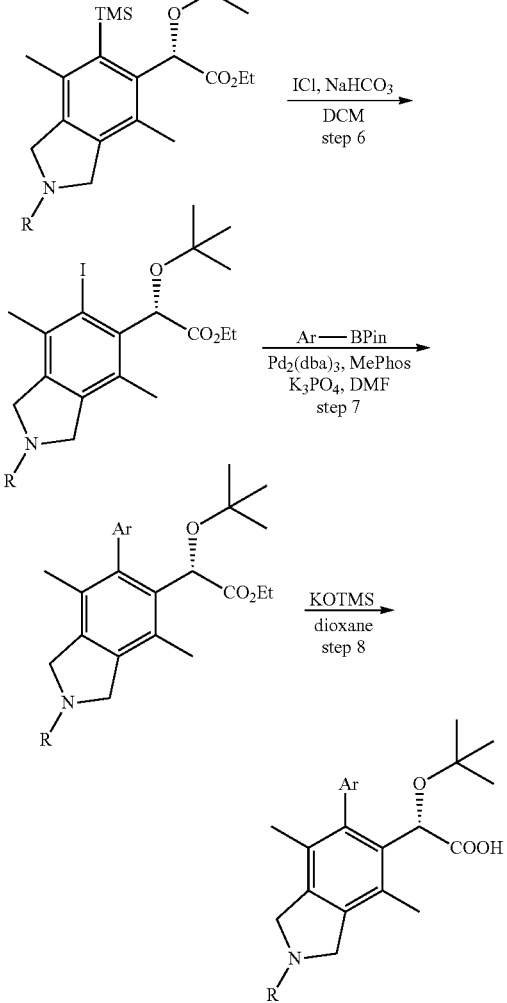
Example 295: (S)-2-(tert-butoxy)-2-((M)-6-(8-chloro-5-methylchroman-6-yl)-2-(3-fluorobenzoyl)-4,7-dimethylisoindolin-5-yl)acetic acid
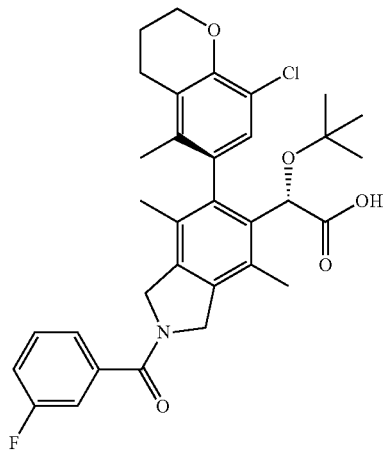

187

N,N-di(but-2-yn-1-yl)-3-fluorobenzamide

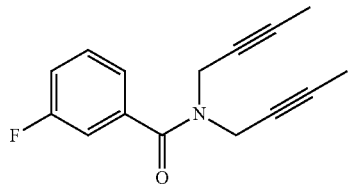 [SMILES: CC#CCN(CC#CC)C(=O)c1cccc(F)c1]

To an ice cold solution of 1-bromobut-2-yne (7.15 g, 53.8 mmol) in anhydrous DMF (45 mL) was added NaH (60%, 2.44 g, 61.1 mmol). After stirring at 0° C. for 15 min, a solution of 3-fluorobenzamide (3.4 g, 24.4 mmol) in anhydrous DMF (5 mL) was added dropwise over 1 hr. The resulting mixture was warmed up to RT and stirred for 1 hr before being quenched with water (100 mL) and extracted with ether (2×200 mL). The combined ether solutions were were washed with brine, dried over $Na_2SO_4$ and concentrated under reduced pressure to give the crude product which was purified by column chromatography (silica gel, 0-15% EtOAc/petroleum ether) to afford N,N-di(but-2-yn-1-yl)-3-fluorobenzamide (4.78 g, 80% yield) as a yellow oil.

Step 1

Ethyl 2-hydroxy-4-(trimethylsilyl)but-3-ynoate

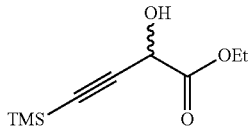 [SMILES: CCOC(=O)C(O)C#C[Si](C)(C)C]

To a solution of TMS-acetylene (250 g, 2.55 mol) in anhydrous THF (2.5 L) at 0° C. was added 3M EtMgBr/ether (933 mL, 2.80 mol) dropwise under an $N_2$ atmosphere while maintaining the inner temperature below 5° C. After stirring at 0° C. for 30 min, the suspension was added to an ice cold solution of 50% ethyl glyoxylate/toluene (624 g, 3.05 mol) in anhydrous THF (5 L) via cannula. After stirring at 0° C. for 1 h, the mixture was quenched with saturated aqueous $NH_4Cl$ solution (3 L) and extracted with EtOAc (2×1 L). The combined EtOAc solutions were concentrated at reduced pressure. The residue was diluted with EtOAc (3 L). The solution was washed with water (2×1 L) and brine (2×1 L), dried over $Na_2SO_4$ and concentrated under reduced pressure. The crude material was purified by flash chromatography (silica gel, 0-10% EtOAc/petroleum ether) to give the title compound (285 g, 56%) as a yellow oil. $^1$H NMR (400 MHz, CHLOROFORM-d) δ=4.83 (d, J=7.3 Hz, 1H), 4.34 (qq, J=7.2, 10.8 Hz, 2H), 3.02 (d, J=7.3 Hz, 1H), 1.34 (t, J=7.2 Hz, 3H), 0.22-0.16 (m, 9H).

Step 2

Ethyl 2-acetoxy-4-(trimethylsilyl)but-3-ynoate

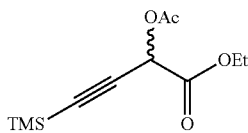 [SMILES: CCOC(=O)C(C#C[Si](C)(C)C)OC(C)=O]

188

To a 10 L flask was added EtOAc (7.5 L) followed by $Ac_2O$ (400 mL). After stirring at RT for 30 minutes the mixture was cooled to 0° C. and treated with another portion of $Ac_2O$ (2.1 L). After 1 hour at 0° C., the solution was allowed to warm to RT. To the solution was added ethyl 2-hydroxy-4-(trimethylsilyl)but-3-ynoate (520 g, 2.60 mol). After stirring at RT for 1 hour the solution was washed with 1N aqueous NaOH (3×, 20 L total). The solution was then washed with brine (5 L), dried over $Na_2SO_4$ and concentrated to dryness at reduced pressure. The crude product was purified by flash chromatography (silica gel, 0-5% EtOAc/petroleum ether) to give the title compound (590 g, 94%) as a yellow oil. $^1$H NMR (400 MHz, CHLOROFORM-d) δ=5.69 (s, 1H), 4.36-4.21 (m, 2H), 2.19 (s, 3H), 1.32 (t, J=7.2 Hz, 3H), 0.25-0.15 (m, 9H).

Step 3

(S)-Ethyl 2-hydroxy-4-(trimethylsilyl)but-3-ynoate

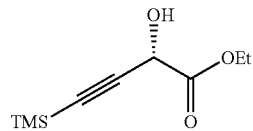

To a solution of ethyl 2-acetoxy-4-(trimethylsilyl)but-3-ynoate (150 g, 0.620 mol) in acetone (1.88 L) and phosphate buffer solution (pH 7.2, 7.5 L) was added Amano Lipase PS (75 g). After stirring at 20° C. overnight, the reaction mixture was diluted with water (2.5 L) and extracted with EtOAc (3 L). The layers were separated and the organic layer was washed with brine (3×, 10 L total volume), dried over $Na_2SO_4$, filtered and concentrated under reduced pressure to give the crude product. This material was purified by flash chromatography (silica gel, 0-10% EtOAc/petroleum ether) to afford the title compound (55 g, 44%) as a yellow oil. $^1$H NMR (400 MHz, CHLOROFORM-d) δ=4.83 (d, J=7.3 Hz, 1H), 4.34 (qq, J=7.2, 10.8 Hz, 2H), 3.02 (d, J=7.3 Hz, 1H), 1.34 (t, J=7.2 Hz, 3H), 0.22-0.16 (m, 9H).

Step 4

(S)-Ethyl 2-(tert-butoxy)-4-(trimethylsilyl)but-3-ynoate

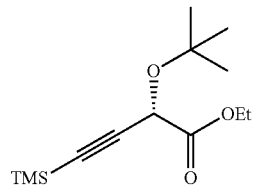 [SMILES: CCOC(=O)[C@H](C#C[Si](C)(C)C)OC(C)(C)C]

To a solution of (S)-ethyl 2-hydroxy-4-(trimethylsilyl) but-3-ynoate (100 g, 0.500 mol) in t-BuOAc (2.5 L) was added $HClO_4$ (41 mL, 0.500 mol) dropwise at RT. After stirring for 40 minutes, the mixture was quenched with $NaHCO_3$ powder, diluted with water (2 L) and extracted with EtOAc (2 L). The EtOAc solution was washed with brine, dried over $Na_2SO_4$, filtered and concentrated under reduced pressure to give the crude product. This material was was purified by flash chromatography (silica gel, 0-5% EtOAc/petroleum ether) to afford the title compound (103 g, 81%) as a yellow oil. $^1$H NMR (400 MHz, CHLOROFORM-d) b=4.72 (s, 1H), 4.33-4.20 (m, 2H), 1.31 (t, J=7.2 Hz, 3H), 1.28 (s, 9H), 0.17 (s, 9H).

Step 5

(S)-Ethyl 2-(tert-butoxy)-2-(2-(3-fluorobenzoyl)-4,7-dimethyl-6-(trimethylsilyl)isoindolin-5-yl)acetate

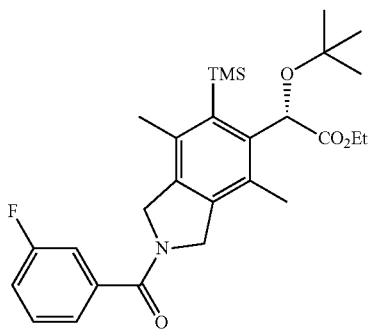 [SMILES: CCOC(=O)[C@@H](OC(C)(C)C)c1c(C)c2c(c(C)c1[Si](C)(C)C)CN(C(=O)c1cccc(F)c1)C2]

A suspension of [Rh(cod)$_2$]BF$_4$ (0.317 g, 0.780 mmol) and (+/−)-BINAP (0.486 g, 0.780 mmol) in anhydrous DCM (26 mL) was sparged with H$_2$ for 5 minutes and stirred under 1 atm (balloon) of H$_2$. After 1 hour the solution was concentrated at reduced pressure. The solution was redissolved in 10 mL of DCM and the solution added to a flask containing a solution of (S)-ethyl 2-(tert-butoxy)-4-(trimethylsilyl)but-3-ynoate (1.00 g, 3.90 mmol) in 10 mL of DCM. This solution was heated to 40° C. and treated with a solution of N,N-di(but-2-yn-1-yl)-3-fluorobenzamide (2.85 g, 11.7 mmol, 3.00 equiv) in 28 mL of DCM (syringe pump) over 3 hours. TLC (silica gel, 7:3 hexanes/EtOAc) at this point indicated partial conversion of (S)-ethyl 2-(tert-butoxy)-4-(trimethylsilyl)but-3-ynoate to the desired product (vs authentic TLC standard). The solution was then treated with an additional 0.10 equiv portion of catalyst solution in 10 mL of DCM followed by slow addition of 2.00 equiv of N,N-di(but-2-yn-1-yl)-3-fluorobenzamide in 12 mL of DCM over 3 hours. The solution was then cooled to RT and stirred overnight. TLC at this point showed about 85% conversion. The solution was concentrated to dryness at reduced pressure and the residue subjected to flash chromatography (silica gel, 0-50% EtOAc/hexanes) to afford the title compound (1.53 g, 79%) as a tan foam.

Step 6

(S)-Ethyl 2-(tert-butoxy)-2-(2-(3-fluorobenzoyl)-6-iodo-4,7-dimethylisoindolin-5-yl)acetate

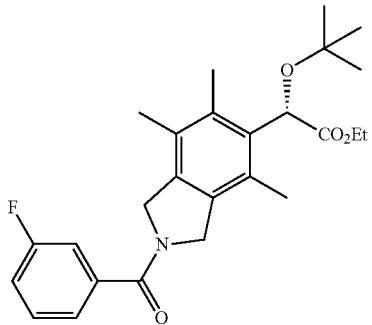

To a stirred solution of (S)-ethyl 2-(tert-butoxy)-2-(2-(3-fluorobenzoyl)-4,7-dimethyl-6-(trimethylsilyl)isoindolin-5-yl)acetate (3.15 g, 6.30 mmol) in anhydrous DCM (52 mL) at 0° C. was added NaHCO$_3$ (10.6 g, 126 mmol). The mixture was then treated with 1M ICl/DCM (6.93 mL, 6.93 mmol) by dropwise addition. After 12 minutes LCMS indicated complete reaction. The solution was partitioned between EtOAc and 5% aqueous sodium thiosulfate and the phases separated. The aqueous phase was extracted once with EtOAc. The combined EtOAc solutions were washed with water (1×), brine (1×), dried over Na$_2$SO$_4$ and concentrated at reduced pressure to give 3.67 g of a pale yellow foam. This material was subjected to flash chromatography (silica gel, 0-100% EtOAc/hexanes) to give the title compound (3.20 g, 92%) as a white foam.

Step 7

(S)-ethyl 2-(tert-butoxy)-2-((M)-6-(8-chloro-5-methylchroman-6-yl)-2-(3-fluorobenzoyl)-4,7-dimethylisoindolin-5-yl)acetate

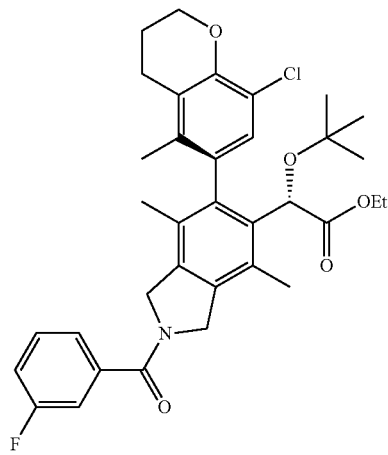

In a sealable vial, a degassed mixture of (S)-ethyl 2-(tert-butoxy)-2-(2-(3-fluorobenzoyl)-6-iodo-4,7-dimethylisoindolin-5-yl)acetate (73.0 mg, 0.132 mmol), 2-(8-chloro-5-methylchroman-6-yl)-4,4,5,5-tetramethyl-1,3,2-dioxaborolane (65.1 mg, 0.211 mmol), K$_3$PO$_4$ (84 mg, 0.396 mmol) and MePhos (9.62 mg, 0.026 mmol) in N,N-Dimethylformamide (DMF) (1.0 mL) was treated with Pd(dba)$_2$ (24.16 mg, 0.026 mmol) and the flask containing the mixture was sealed, then immersed into a 80° C. oil bath and stirred for 50 minutes. The mixture was cooled, diluted with EtOAc, washed with water, then brine, dried over Na$_2$SO$_4$, filtered and concentrated. The residue was purified on silica gel (4 g gold column, 0-20% hexanes/EtOAc) to afford an off-white residue (38 mg, 48%). LC/MS (m/z) ES+=608 (M+1).

Step 8

(S)-2-(tert-butoxy)-2-((M)-6-(8-chloro-5-methyl-chroman-6-yl)-2-(3-fluorobenzoyl)-4,7-dimethyl-isoindolin-5-yl)acetic acid A mixture of (S)-ethyl 2-(tert-butoxy)-2-((M)-6-(8-chloro-5-methylchroman-6-yl)-2-(3-fluorobenzoyl)-4,7-dimethylisoindolin-5-yl)acetate (38.0 mg, 0.062 mmol) in 1,4-Dioxane (1.5 mL) was treated with 2M LiOH (0.312 mL, 0.625 mmol) and the mixture was heated to 60° C. and stirred for 3 hours. The temperature was increased to 70° C. and stirring was continued overnight. Additional 2M LiOH (0.312 mL, 0.625 mmol) was added and stirring at 70° C. was continued overnight. The mixture was concentrated, 1N HCl added and the mixture was extracted with EtOAc. The extracts were washed with brine, dried over $Na_2SO_4$, filtered and concentrated in vacuo. The residue was purified by RP-HPLC to afford a colorless residue (7.4 mg, 20%). $^1$H NMR (400 MHz, $CDCl_3$) δ ppm 7.51-7.42 (m, 1H), 7.39-7.36 (m, 1H), 7.33-7.25 (m, 1H), 7.24-7.15 (m, 1H), 6.95 (d, J=12.3 Hz, 1H), 5.02 (d, J=15.3 Hz, 3H), 4.74 (d, J=15.3 Hz, 2H), 4.31 (q, J=5.3 Hz, 2H), 2.75-2.66 (m, 2H), 2.35 (s, 1.5H), 2.19 (s, 1.5H), 2.16-2.07 (m, 2H), 1.94-1.66 (m, 6H), 1.19-1.07 (m, 9H); LC/MS (m/z) ES+=580 (M+1). LC/MS (m/z) ES+=580 (M+1).

Compounds 296-306 were prepared in a manner similar to the procedures described for Example 295.

Example 296: (2S)-2-(tert-butoxy)-2-(6-(4-chloro-2-methylphenyl)-2-(3-fluorobenzoyl)-4,7-dimethyl-isoindolin-5-yl)acetic acid

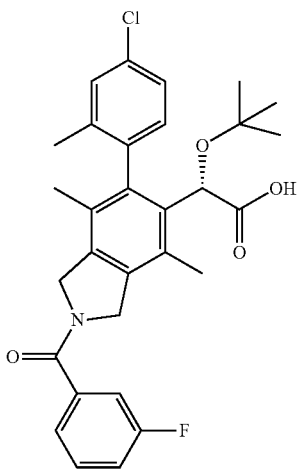 [SMILES: Cc1cc(Cl)ccc1-c1c(C)c2c(c(C)c1[C@H](OC(C)(C)C)C(=O)O)CN(C(=O)c1cccc(F)c1)C2]

$^1$H NMR (CHLOROFORM-d) δ: 7.41-7.52 (m, 1H), 7.33-7.40 (m, 1H), 7.29 (br. s., 2H), 7.14-7.25 (m, 2H), 6.96 (br. s., 1H), 4.90-5.14 (m, 3H), 4.67-4.81 (m, 2H), 2.18-2.44 (m, 3H), 2.01-2.11 (m, 3H), 1.63-1.88 (m, 3H), 0.99-1.16 (m, 9H). LCMS (ES+) (m/z): 524.3 (M+1).

Example 297: (2S)-2-(tert-butoxy)-2-(2-(3-fluorobenzoyl)-6-(2-hydroxy-4-methylphenyl)-4,7-dimethylisoindolin-5-yl)acetic acid

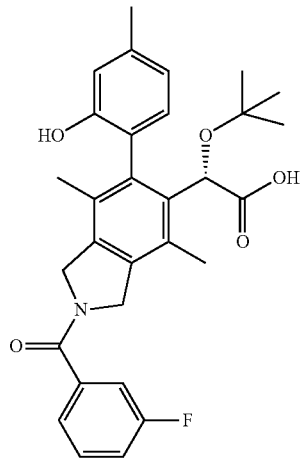 [SMILES: Cc1ccc(-c2c(C)c3c(c(C)c2[C@H](OC(C)(C)C)C(=O)O)CN(C(=O)c2cccc(F)c2)C3)c(O)c1]

$^1$H NMR (CHLOROFORM-d) δ: 7.45-7.53 (m, 1H), 7.37-7.43 (m, 1H), 7.32 (d, 1H), 7.21 (d, 1H), 6.81-6.99 (m, 3H), 5.28 (d, 1H), 4.95-5.14 (m, 2H), 4.77 (d, 2H), 2.39 (d, 3H), 2.16-2.37 (m, 3H), 1.74-1.90 (m, 3H), 1.13 (d, 9H) LCMS (ES+) (m/z): 506.38 (M+1).

Example 298: (2S)-2-(tert-butoxy)-2-(2-(3-fluorobenzoyl)-6-(4-methoxy-2-methylphenyl)-4,7-dimethylisoindolin-5-yl)acetic acid

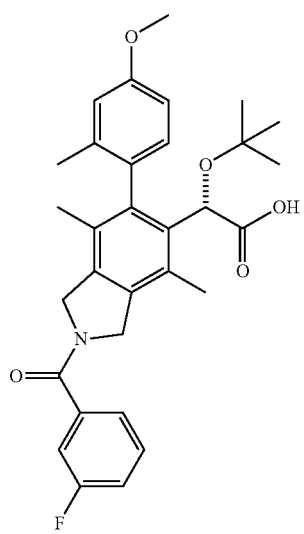 [SMILES: COc1ccc(-c2c(C)c3c(c(C)c2[C@H](OC(C)(C)C)C(=O)O)CN(C(=O)c2cccc(F)c2)C3)c(C)c1]

The title compound was isolated as a white solid after reverse phase HPLC. $^1$H NMR (400 MHz, $CDCl_3$) δ mixture of rotamers, 4:1 mixture of atropisomers: 7.50-7.42 (m, 1H), 7.37-7.35 (m, 1H), 7.33-7.27 (m, 1H), 7.22-7.16 (m, 1H), 6.96-6.91 (m, 1H), 6.84-6.75 (m, 2H), 5.17-4.91 (m, 3H), 4.76-4.72 (m, 2H), 3.85-3.83 (m, 3H), 2.38-2.20 (m, 3H), 2.07-1.97 (m, 3H), 1.89-1.67 (m, 3H), 1.13-1.00 (m, 9H). LCMS (ES+) (m/z): 520.39 (M+1).

Example 299: (2S)-2-(tert-butoxy)-2-(6-(2,3-dihydropyrano[4,3,2-de]quinolin-7-yl)-2-(3-fluorobenzoyl)-4,7-dimethylisoindolin-5-yl)acetic acid

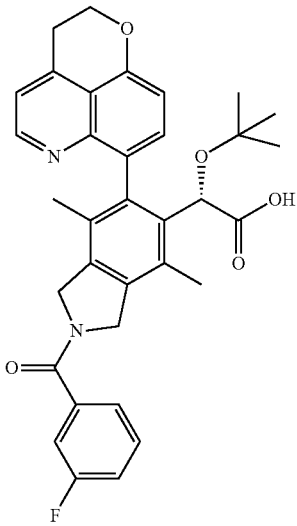 [SMILES: Cc1c2c(c(C)c([C@H](OC(C)(C)C)C(=O)O)c1-c1ccc3c4c(ccnc14)CCO3)CN(C(=O)c1cccc(F)c1)C2]

¹H NMR (CHLOROFORM-d) δ: 8.95-9.12 (m, 1H), 7.89 (d, 1H), 7.62-7.80 (m, 3H), 7.44-7.52 (m, 2H), 7.35-7.42 (m, 3H), 7.16-7.27 (m, 2H), 4.62-5.15 (m, 7H), 3.58 (br. s., 2H), 2.28-2.52 (m, 3H), 1.57-1.78 (m, 3H), 0.90-1.05 (m, 9H). LCMS (ES+) (m/z): 569.3 (M+1).

Example 300: (2S)-2-(tert-butoxy)-2-(6-(5-chloroquinolin-8-yl)-2-(3-fluorobenzoyl)-4,7-dimethylisoindolin-5-yl)acetic acid

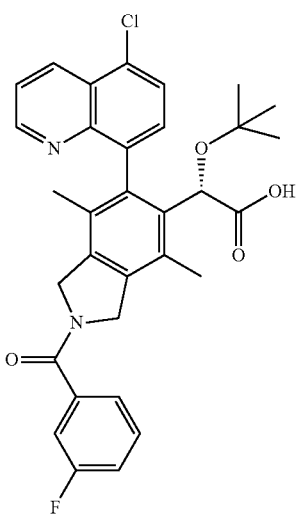 [SMILES: Cc1c2c(c(C)c([C@H](OC(C)(C)C)C(=O)O)c1-c1ccc(Cl)c3cccnc13)CN(C(=O)c1cccc(F)c1)C2]

¹H NMR (CHLOROFORM-d) δ: 8.93 (m, 2H), 7.92 (d, 1H), 7.81 (m, 1H), 7.64 (br. s., 1H), 7.41-7.52 (m, 1H), 7.36 (m, 1H), 7.27-7.31 (m, 1H), 7.13-7.24 (m, 1H), 4.65-5.12 (m, 5H), 2.91-3.02 (m, 2H), 2.19-2.42 (m, 3H), 1.52-1.74 (m, 3H), 0.84 (br. s., 9H). LCMS (ES+) (m/z): 561.2/563.2 (M+1).

Example 301: (S)-2-(tert-butoxy)-2-(6-((M)-8-fluoro-5-methyl-3,4-dihydro-2H-benzo[b][1,4]oxazin-6-yl)-2-(3-fluorobenzoyl)-4,7-dimethylisoindolin-5-yl)acetic acid

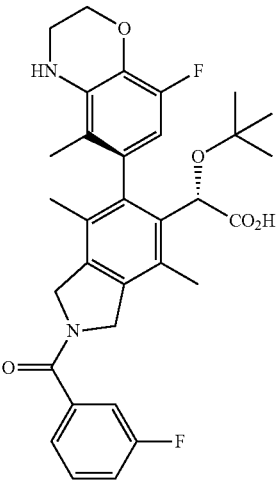

¹H NMR (CHLOROFORM-d) δ: 7.42-7.53 (m, 1H), 7.36 (m, 1H), 7.29 (d, 1H), 7.15-7.24 (m, 1H), 6.27 (m, 1H), 5.09 (s, 1H), 5.01 (d, 2H), 4.74 (d, 2H), 4.34 (m, 2H), 3.55-3.59 (m, 2H), 2.13-2.35 (m, 3H), 1.69-1.87 (m, 6H), 1.13 (d, 9H).). LCMS (ES+) (m/z): 565.3 (M+1).

Example 302: (S)-2-(tert-butoxy)-2-(6-(4,4-dimethylcyclohex-1-en-1-yl)-2-(3-fluorobenzoyl)-4,7-dimethylisoindolin-5-yl)acetic acid

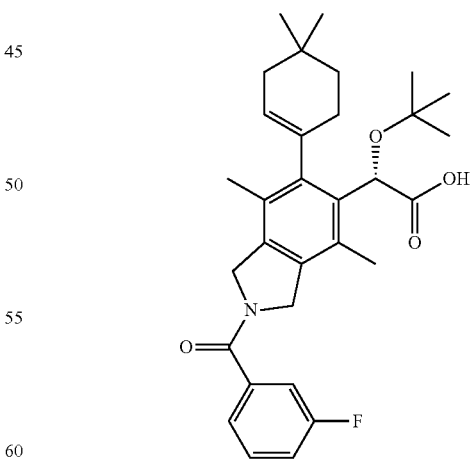

¹H NMR (CHLOROFORM-d) b: 7.41-7.49 (m, 1H), 7.34 (d, 1H), 7.27 (br. s., 1H), 7.18 (m, 1H), 5.44 (br. s., 1H), 4.63-5.05 (m, 4H), 2.25-2.52 (m, 3H), 2.11-2.19 (m, 3H), 1.93-2.04 (m, 4H), 1.49 (m, 2H), 1.17-1.26 (m, 9H), 0.99-1.07 (m, 6H). LCMS (ES+) (m/z): 508.9 (M+1).

Example 303: (2S)-2-(tert-butoxy)-2-(2-(3-fluorobenzoyl)-4,7-dimethyl-6-(5-methyl-3,4-dihydro-2H-benzo[b][1,4]oxazin-6-yl)isoindolin-5-yl)acetic acid

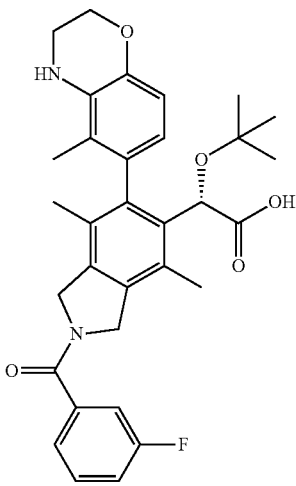 [SMILES: Cc1c(-c2c(C)c3c(c(C)c2[C@H](OC(C)(C)C)C(=O)O)CN(C(=O)c2cccc(F)c2)C3)ccc2c1NCCO2]

¹H NMR (400 MHz, METHANOL-d₄) (mixture of rotamers) δ ppm 7.64-7.53 (m, 1H), 7.52-7.46 (m, 1H), 7.46-7.38 (m, 1H), 7.35-7.22 (m, 1H), 6.81-6.68 (m, 1H), 6.58-6.45 (m, 1H), 5.10-5.03 (m, 1H), 5.02-4.95 (m, 2H), 4.85-4.79 (m, 2H), 4.36-4.23 (m, 2H), 3.60-3.50 (m, 2H), 2.51-2.25 (m, 3H), 1.89-1.65 (m, 6H), 1.14-1.04 (m, 9H); LCMS (m/z) ES+=547.48 (M+1).

Example 304: (S)-2-(tert-butoxy)-2-(6-(chroman-6-yl)-2-(3-fluorobenzoyl)-4,7-dimethylisoindolin-5-yl)acetic acid

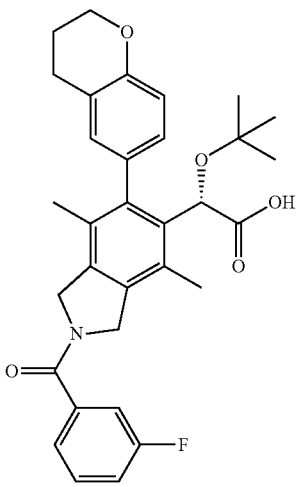 [SMILES: Cc1c2c(c(C)c([C@H](OC(C)(C)C)C(=O)O)c1-c1ccc3c(c1)CCCO3)CN(C(=O)c1cccc(F)c1)C2]

¹H NMR (400 MHz, METHANOL-d₄) (mixture of rotamers and atropisomers) δ ppm 7.64-7.53 (m, 1H), 7.52-7.46 (m, 1H), 7.43 (d, J=9.5 Hz, 1H), 7.36-7.26 (m, 1H), 7.15-7.04 (m, 1H), 6.96-6.75 (m, 2H), 5.17-5.08 (m, 1H), 5.04-4.94 (m, 2H), 4.85-4.76 (m, 2H), 4.30-4.16 (m, 2H), 2.94-2.67 (m, 2H), 2.44-2.15 (m, 3H), 2.14-2.01 (m, 2H), 2.00-1.79 (m, 3H), 1.03-0.91 (m, 9H); LCMS (m/z) ES+=532.48 (M+1).

Example 305: (2S)-2-(tert-butoxy)-2-(2-(3-fluorobenzoyl)-4,7-dimethyl-6-(5-methylchroman-6-yl)isoindolin-5-yl)acetic acid

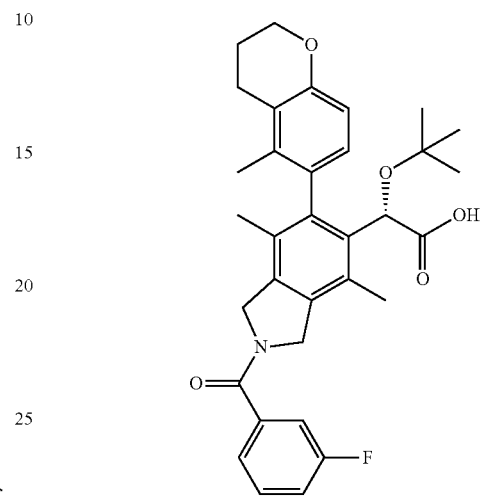

¹H NMR (400 MHz, METHANOL-d₄) (mixture of rotamers and atropisomers) δ ppm 7.61-7.50 (m, 1H), 7.50-7.36 (m, 2H), 7.32-7.22 (m, 1H), 7.10-6.61 (m, 2H), 5.08-4.99 (m, 1H), 4.99-4.92 (m, 2H), 4.83-4.77 (m, 2H), 4.28-4.02 (m, 2H), 2.82-2.57 (m, 2H), 2.51-2.18 (m, 3H), 2.15-1.96 (m, 2H), 1.92-1.59 (m, 6H), 1.14-0.90 (m, 9H); LCMS (m/z) ES+=546.53 (M+1).

Example 306: (2S)-2-(tert-butoxy)-2-(6-(2-chloro-4-methylphenyl)-2-(3-fluorobenzoyl)-4,7-dimethylisoindolin-5-yl)acetic acid

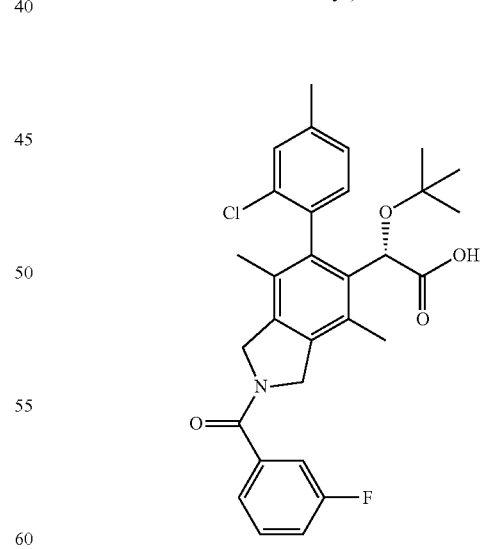

¹H NMR (400 MHz, CHLOROFORM-d) (mixture of rotamers) δ ppm 7.56-7.42 (m, 1H), 7.40-7.34 (m, 1H), 7.33-7.24 (m, 2H), 7.24-7.15 (m, 1H), 7.14-7.04 (m, 1H), 6.98-6.80 (m, 1H), 5.35-5.19 (m, 1H), 5.18-4.90 (m, 2H), 4.85-4.67 (m, 2H), 2.50-2.28 (m, 6H), 1.92-1.67 (m, 3H), 1.22-1.09 (m, 9H); LCMS (m/z) ES+=524 (M+1).

Scheme 4

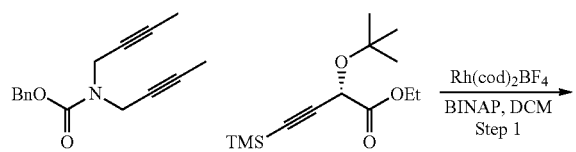

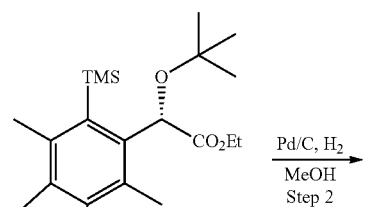

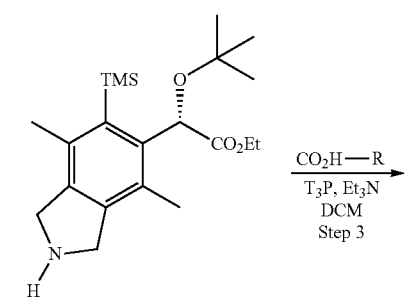

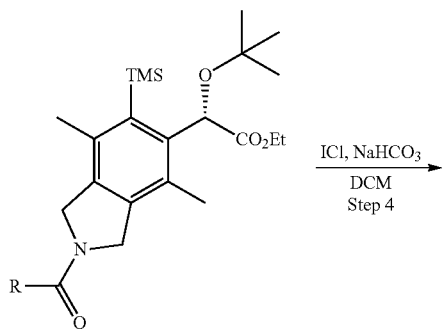

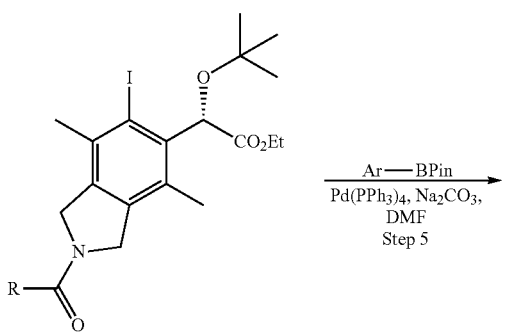

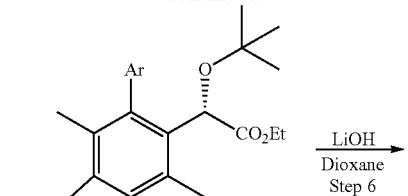

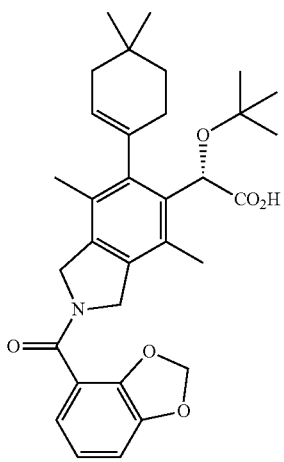 [SMILES: Cc1c2c(c(C)c([C@H](OC(C)(C)C)C(=O)O)c1C1=CCC(C)(C)CC1)CN(C(=O)c1cccc3c1OCO3)C2]

Example 307: (S)-2-(2-(benzo[d][1,3]dioxole-4-carbonyl)-6-(4,4-dimethylcyclohex-1-en-1-yl)-4,7-dimethylisoindolin-5-yl)-2-(tert-butoxy)acetic acid

Step 1

(S)-Benzyl 5-(1-(tert-butoxy)-2-ethoxy-2-oxoethyl)-4,7-dimethyl-6-(trimethylsilyl)isoindoline-2-carboxylate A mixture of [Rh(cod)$_2$]BF$_4$ (5.00 g, 12.3 mmol) and (R)-BINAP (7.67 g, 12.3 mmol) in DCM (50 mL) was stirred at RT under H$_2$ (1 atm) until the solution turned to dark red color (4 hours). The resulting mixture was placed under N$_2$ and treated with a solution of (S)-ethyl 2-(tert-butoxy)-4-(trimethylsilyl)but-3-ynoate (50.0 g, 195 mmol) in DCM (100 mL). After heating to 40° C., a solution of benzyl di(but-2-yn-1-yl)carbamate (99.6 g, 390 mmol) in DCM (400 mL) was added dropwise over 2.5 hours and the reaction mixture was stirred at 40° C. for an additional 30 minutes. The resulting mixture was concentrated in vacuo to give the crude product which was purified by column chromatography (silica gel, 0-10% EtOAc/petroleum ether) to afford the title compound (84 g, 84%) as a yellow oil.

Step 2

(S)-Ethyl 2-(tert-butoxy)-2-(4,7-dimethyl-6-(trimethylsilyl)isoindolin-5-yl)acetate A solution of benzyl 5-(1-(tert-butoxy)-2-ethoxy-2-oxoethyl)-4,7-dimethyl-6-(trimethylsilyl)isoindoline-2-carboxylate (280 mg, 0.547 mmol) in Methanol (4.885 mL) was charged with Pd/C (58.2 mg, 0.055 mmol) and stirred under an atmosphere of $H_2$. After 1 h, the reaction mixture was filtered through a pad of celite, and the filter cake was rinsed with DCM. The filtrate was concentrated in vacuo to afford (S)-ethyl 2-(tert-butoxy)-2-(4,7-dimethyl-6-(trimethylsilyl)isoindolin-5-yl)acetate (207 mg, 0.547 mmol, 100% yield). LC/MS (m/z) ES+=378.5 (M+1).

Step 3

(S)-Ethyl 2-(2-(benzo[d][1,3]dioxole-4-carbonyl)-4,7-dimethyl-6-(trimethylsilyl)isoindolin-5-yl)-2-(tert-butoxy)acetate A solution of crude (S)-ethyl 2-(tert-butoxy)-2-(4,7-dimethyl-6-(trimethylsilyl)isoindolin-5-yl)acetate (207 mg, 0.547 mmol, 100% yield) was dissolved in EtOAc (5 mL) and treated with benzo[d][1,3]dioxole-4-carboxylic acid (182 mg, 1.094 mmol), followed by $NEt_3$ (0.229 mL, 1.642 mmol), and then $T_3P$ (0.977 mL, 1.642 mmol). The reaction was stirred for 1.5 h, poured over sat. $NaHCO_3$, and extracted with EtOAc. The organic extracts were washed with brine, dried over $Na_2SO_4$, and concentrated in vacuo to give (S)-ethyl 2-(2-(benzo[d][1,3]dioxole-4-carbonyl)-4,7-dimethyl-6-(trimethylsilyl)isoindolin-5-yl)-2-(tert-butoxy)acetate (288 mg, 0.547 mmol, 100% yield). LC/MS (m/z) ES+=526.3 (M+1).

Step 4

(S)-Ethyl 2-(2-(benzo[d][1,3]dioxole-4-carbonyl)-6-iodo-4,7-dimethylisoindolin-5-yl)-2-(tert-butoxy)acetate A solution of (S)-ethyl 2-(2-(benzo[d][1,3]dioxole-4-carbonyl)-4,7-dimethyl-6-(trimethylsilyl)isoindolin-5-yl)-2-(tert-butoxy)acetate (288 mg, 0.547 mmol, 100% yield) was dissolved in DCM (5 mL) and cooled to 0° C. and treated dropwise with iodine chloride (1M in DCM) (0.657 mL, 0.657 mmol). After 20 min, the reaction mixture was diluted with DCM and washed with a 50% sat. solution of $Na_2S_2O_4$. The organic layer was washed with brine, dried over $Na_2SO_4$, then concentrated in vacuo. The residue was purified by silica gel chromatography (24 g SiO2, 0-60% EtOAc-Hexanes) to afford the title compound (245 mg, 0.423 mmol, 77%). $^1$H NMR (400 MHz, CHLOROFORM-d) b=7.03-6.98 (m, 1H), 6.96-6.92 (m, 2H), 6.06 (d, J=2.5 Hz, 2H), 5.89 (s, 1H), 5.03-4.90 (m, 2H), 4.82-4.70 (m, 2H), 4.25-4.08 (m, 3H), 2.46-2.35 (m, 3H), 2.32-2.21 (m, 3H), 1.31-1.20 (m, 12H). LC/MS (m/z) ES+=580.4 (M+1).

Step 5

(S)-ethyl 2-(2-(benzo[d][1,3]dioxole-4-carbonyl)-6-(4,4-dimethylcyclohex-1-en-1-yl)-4,7-dimethylisoindolin-5-yl)-2-(tert-butoxy)acetate A solution of (S)-ethyl 2-(2-(benzo[d][1,3]dioxole-4-carbonyl)-6-iodo-4,7-dimethylisoindolin-5-yl)-2-(tert-butoxy)acetate (76 mg, 0.131 mmol), 2-(4,4-dimethylcyclohex-1-en-1-yl)-4,4,5,5-tetramethyl-1,3,2-dioxaborolane (46.5 mg, 0.197 mmol) and $Na_2CO_3$ (2.0 M) (0.202 mL, 0.403 mmol) in DMF were degassed with $N_2$ for 10 min. $Pd(PPh_3)_4$ (15.16 mg, 0.013 mmol) was added, and reaction was heated in microwave reactor for 20 min. Mixture was then poured over sat. aq. $NaHCO_3$ and extracted with EtOAc. The organic layers were washed with brine, dried over $Na_2SO_4$, filtered and concentrated in vacuo. LC/MS (m/z) ES+=562.3 (M+1).

Step 6

(S)-2-(2-(benzo[d][1,3]dioxole-4-carbonyl)-6-(4,4-dimethylcyclohex-1-en-1-yl)-4,7-dimethylisoindolin-5-yl)-2-(tert-butoxy)acetic acid A solution of (S)-ethyl 2-(2-(benzo[d][1,3]dioxole-4-carbonyl)-6-(4,4-dimethylcyclohex-1-en-1-yl)-4,7-dimethylisoindolin-5-yl)-2-(tert-butoxy)acetate (73.7 mg, 0.131 mmol, 100% yield) in 1,4-dioxane (1.312 mL) was treated with lithium hydroxide (0.650 mL, 1.3 mmol) and heated to 80° C. After 18 h, the reaction mixture was concentrated in vacuo, taken up in DCM, washed with 1 M HCl, brine, and dried over $Na_2SO_4$. The solvent was removed in vacuo, and the crude product was purified by reverse phase HPLC (30-100% ACN—H2O) to afford (S)-2-(2-(benzo[d][1,3]dioxole-4-carbonyl)-6-(4,4-dimethylcyclohex-1-en-1-yl)-4,7-dimethylisoindolin-5-yl)-2-(tert-butoxy)acetic acid (26 mg, 0.049 mmol, 37.1% yield). $^1$H NMR (CHLOROFORM-d) δ: 6.87-7.11 (m, 3H), 6.06 (s, 2H), 5.35-5.89 (m, 2H), 4.68-5.04 (m, 4H), 1.89-2.58 (m, 11H), 1.52 (d, 2H), 1.24 (d, 9H), 1.05 (br. s., 6H). LCMS (ES+) (m/z): 534.4 (M+1).

Examples 308-311 were prepared in a manner similar to the procedures described above for Example 307.

Example 308: (S)-2-(2-(benzo[d][1,3]dioxole-4-carbonyl)-6-(4-chlorophenyl)-4,7-dimethylisoindolin-5-yl)-2-(tert-butoxy)acetic acid

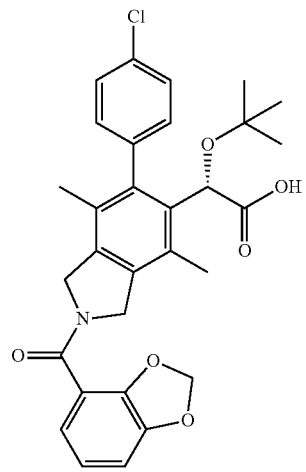 [SMILES: Cc1c2c(c(C)c([C@H](OC(C)(C)C)C(=O)O)c1-c1ccc(Cl)cc1)CN(C(=O)c1cccc3c1OCO3)C2]

¹H NMR (CHLOROFORM-d) δ: 7.44 (br. s., 3H), 7.07-7.18 (m, 1H), 6.97-7.04 (m, 1H), 6.93 (m, 2H), 6.04 (d, 2H), 4.77 (s, 5H), 2.14-2.36 (m, 3H), 1.78-1.94 (m, 3H), 1.01 (d, 9H). LCMS (ES+) (m/z): 536.3/538.3 (M+1).

Example 309: (2S)-2-(2-(benzo[d][1,3]dioxole-4-carbonyl)-6-(2-chloro-4-methylphenyl)-4,7-dimethylisoindolin-5-yl)-2-(tert-butoxy)acetic acid

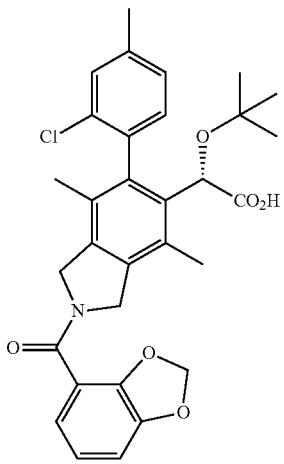 [SMILES: Cc1ccc(-c2c(C)c3c(c(C)c2[C@H](OC(C)(C)C)C(=O)O)CN(C(=O)c2cccc4c2OCO4)C3)c(Cl)c1]

¹H NMR (CHLOROFORM-d) δ: 7.26-7.50 (m, 2H), 7.04-7.18 (m, 1H), 6.81-7.03 (m, 3H), 5.99-6.10 (m, 2H), 4.72-5.27 (m, 5H), 1.99-2.47 (m, 7H), 1.70-1.97 (m, 3H), 0.96-1.18 (m, 9H). LCMS (ES+) (m/z): 550.3/552.3 (M+1).

Example 310: (2S)-2-(2-(benzo[d][1,3]dioxole-4-carbonyl)-6-(8-fluoro-5-methyl-3,4-dihydro-2H-benzo[b][1,4]oxazin-6-yl)-4,7-dimethylisoindolin-5-yl)-2-(tert-butoxy)acetic acid

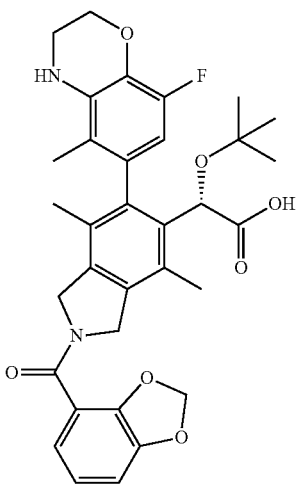 [SMILES: Cc1c(-c2c(C)c3c(c(C)c2[C@H](OC(C)(C)C)C(=O)O)CN(C(=O)c2cccc4c2OCO4)C3)cc(F)c2c1NCCO2]

¹H NMR (CHLOROFORM-d) δ: 6.20-7.08 (m, 4H), 6.05 (d, 2H), 4.72-5.16 (m, 5H), 4.34 (br. s., 2H), 3.57 (br. s., 2H), 2.16-2.34 (m, 3H), 1.69-1.89 (m, 6H), 1.13 (d, 9H). LCMS (ES+) (m/z): 591.52 (M+1).

Example 311: (2S)-2-(tert-butoxy)-2-(2-(3-fluorobenzoyl)-4,7-dimethyl-6-(5-methyl-3,4-dihydro-2H-benzo[b][1,4]oxazin-6-yl)isoindolin-5-yl)acetic acid

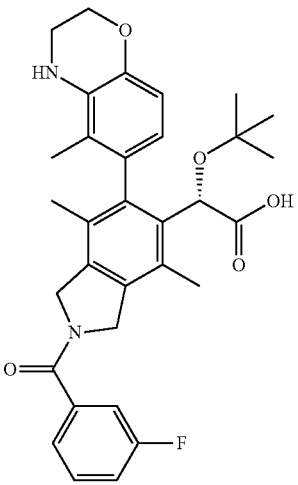 [SMILES: Cc1c(-c2c(C)c3c(c(C)c2[C@H](OC(C)(C)C)C(=O)O)CN(C(=O)c2cccc(F)c2)C3)ccc2c1NCCO2]

¹H NMR (CHLOROFORM-d) δ: 7.42-7.53 (m, 1H), 7.36 (m, 1H), 7.29 (d, 1H), 7.15-7.24 (m, 1H), 6.27 (m, 1H), 5.09 (s, 1H), 5.01 (d, 2H), 4.74 (d, 2H), 4.34 (m, 2H), 3.55-3.59 (m, 2H), 2.13-2.35 (m, 3H), 1.69-1.87 (m, 6H), 1.13 (d, 9H). LCMS (ES+) (m/z): 565.3 (M+1).

Scheme 5

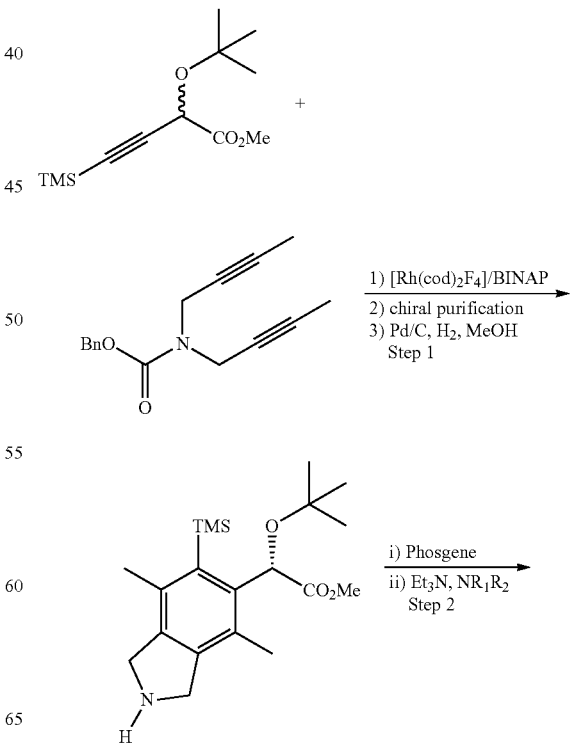

-continued

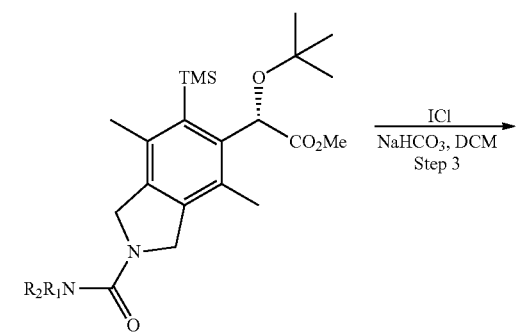

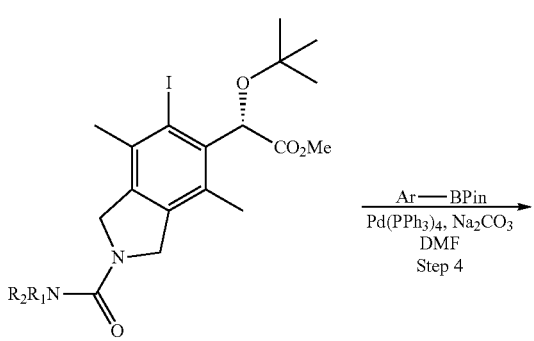

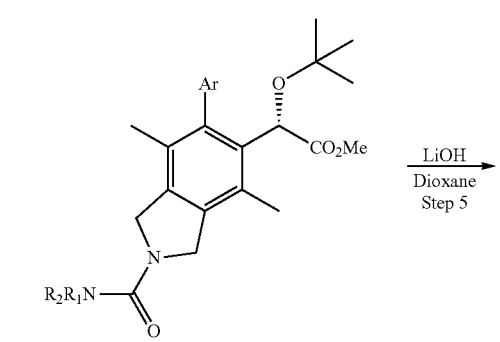

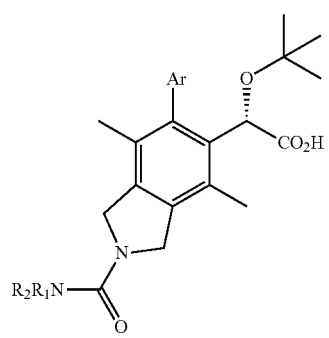

Example 312: (S)-2-(tert-butoxy)-2-((M)-2-(3,3-difluoropyrrolidine-1-carbonyl)-4,7-dimethyl-6-(5-methyl-3,4-dihydro-2H-benzo[b][1,4]oxazin-6-yl)isoindolin-5-yl)acetic acid

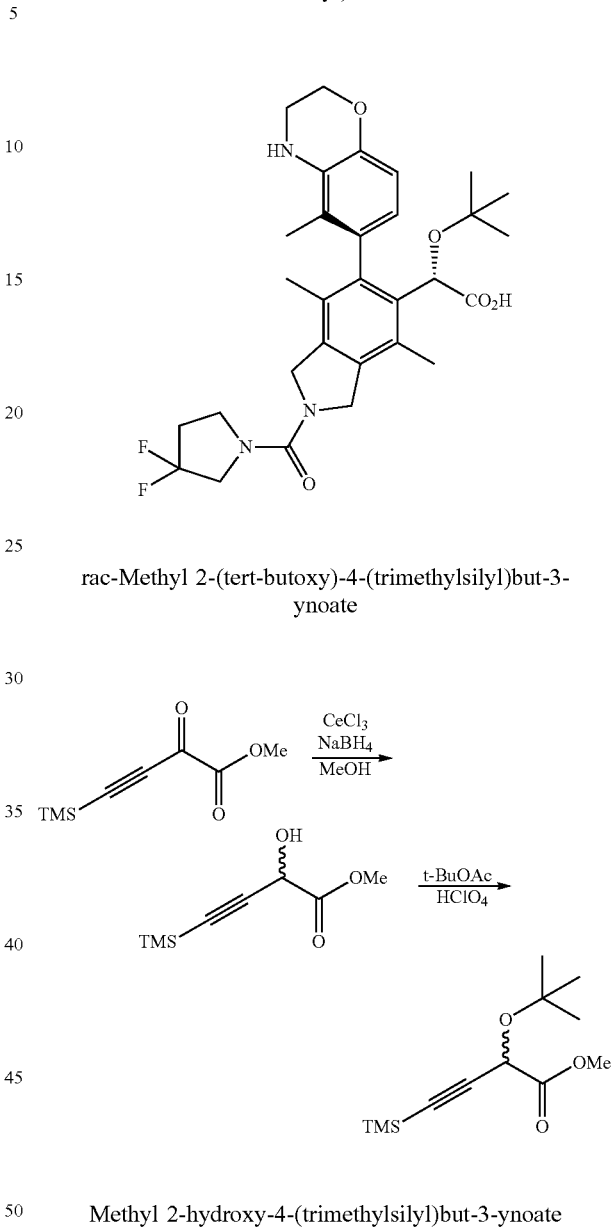

rac-Methyl 2-(tert-butoxy)-4-(trimethylsilyl)but-3-ynoate

Methyl 2-hydroxy-4-(trimethylsilyl)but-3-ynoate

A solution of methyl 2-oxo-4-(trimethylsilyl)but-3-ynoate (485 mg, 2.63 mmol) in Methanol (20 mL) was treated with cerium(III) chloride heptahydrate (1226 mg, 3.29 mmol), followed by portion-wise addition of sodium borohydride (49.8 mg, 1.316 mmol) and the mixture was stirred at ambient temperature for 30 minutes. Additional NaBH$_4$ (25 mg) was added (3:05 pm) and then another portion (20 mg, 3:25 pm). After 10-15 minutes stirring at ambient temperature, the mixture was concentrated. 1N HCl was added and the mixture was extracted with DCM. The extracts were dried over MgSO$_4$, filtered and concentrated. The residue was purified on silica (24 g column, 0-20% hexanes/EtOAc) to afford a pale yellow oil. $^1$H NMR (400 MHz, CHLOROFORM-d) δ=4.86 (d, J=7.3 Hz, 1H), 3.88 (s, 3H), 3.00 (d, J=7.3 Hz, 1H), 0.19 (s, 9H).

Methyl 2-(tert-butoxy)-4-(trimethylsilyl)but-3-ynoate

A solution of methyl 2-hydroxy-4-(trimethylsilyl)but-3-ynoate (92 mg, 0.494 mmol) in t-Butyl acetate (15 mL) was treated with perchloric acid (0.119 mL, 1.976 mmol). A ground glass stopper was placed on the flask and the mixture was stirred at ambient temperature for 30 minutes. The mixture was diluted with EtOAc, washed with 1N NaOH, then brine, dried over $Na_2SO_4$, filtered, and concentrated in vacuo to a pink tinged oil. The residue was used crude in the next step. $^1$H NMR (400 MHz, CHLOROFORM-d) δ=4.75 (s, 1H), 3.81 (s, 3H), 1.28 (s, 9H), 0.17 (s, 9H).

Step 1

(S)-Benzyl 5-(1-(tert-butoxy)-2-methoxy-2-oxoethyl)-4,7-dimethyl-6-(trimethylsilyl)isoindoline-2-carboxylate

[Rh(cod)$_2$]BF$_3$ (0.335 g, 0.825 mmol) and (+/−) BINAP (0.514 g, 0.825 mmol) were suspended in Dichloromethane (36 ml) and stirred for 5 min. The mixture was then purged with $H_2$ for 1 min, and stirred under 1 atm $H_2$. After 1 h, methyl 2-(tert-butoxy)-4-(trimethylsilyl)but-3-ynoate (1 g, 4.13 mmol) in DCM (2 mL) was added, followed by the dropwise addition of 2 eq. diyne over 90 min. The reaction was stirred 90 min at ambient temperature, followed by the dropwise addition of an additional 2 eq diyne over a period of 90 min. After 30 min, the reaction mixture was concentrated in vacuo, and purified by silica gel chromatography (80 g SiO$_2$, 0-30% EtOAc-cyclohexane) to afford the title compound (4.2 g, 79%). The racemic mixture was purified by preparative HPLC chromatography (20% MeOH modified CO$_2$ on either Cell2 or CC4, 140 bar, 40 C, 2 ml/min. The material was dissolved in 3:1 mixture of MeOH/CHCl$_3$ at 75 mg/ml and prepped (15 mg/200 ul injection on 21.20×150 mm CC4) to afford (S)-benzyl 5-(1-(tert-butoxy)-2-methoxy-2-oxoethyl)-4,7-dimethyl-6-(trimethylsilyl)isoindoline-2-carboxylate (>99% ee). $^1$H NMR (400 MHz, CHLOROFORM-d) b=7.49-7.32 (m, 5H), 5.66 (br. s., 1H), 5.33-5.19 (m, 2H), 4.80-4.62 (m, 4H), 3.73 (s, 3H), 2.37 (d, J=13.1 Hz, 3H), 2.23 (d, J=10.8 Hz, 3H), 1.19 (s, 9H), 0.50 (br. s., 9H). LCMS (ES+) (m/z): 498.4 (M+1).

(S)-Methyl 2-(tert-butoxy)-2-(4,7-dimethyl-6-(trimethylsilyl)isoindolin-5-yl)acetate A solution of (S)-benzyl 5-(1-(tert-butoxy)-2-methoxy-2-oxoethyl)-4,7-dimethyl-6-(trimethylsilyl)isoindoline-2-carboxylate (150 mg, 0.301 mmol) in Methanol (3 mL) was treated with Pd/C (32.1 mg, 0.030 mmol). The suspension was stirred under an atmosphere of $H_2$ for 40 min, then filtered through celite. Filter cake was washed with DCM, and filtrate was concentrated in vacuo to give title compound (110 mg, 0.303 mmol, 100% yield). $^1$H NMR (400 MHz, CHLOROFORM-d) δ ppm 5.65 (br. s., 1H), 4.21 (d, J=5.1 Hz, 4H), 3.71 (s, 3H), 2.35 (s, 3H), 2.21 (s, 3H), 1.18 (s, 9H), 0.48 (br. s., 9H); LCMS (m/z) ES+=364 (M+1).

Step 2

(S)-methyl 2-(tert-butoxy)-2-(2-(3,3-difluoropyrrolidine-1-carbonyl)-4,7-dimethyl-6-(trimethylsilyl)isoindolin-5-yl)acetate An ice cold solution of phosgene (20% in toluene) (1.353 mL, 2.5575 mmol) in Tetrahydrofuran (5 mL) was treated dropwise with a solution of (S)-methyl 2-(tert-butoxy)-2-(4,7-dimethyl-6-(trimethylsilyl)isoindolin-5-yl)acetate (372 mg, 1.023 mmol) in Tetrahydrofuran (7.5 mL). The resulting purple solution was stirred in ice bath for 20 min, and then warmed to ambient temperature. After 50 min, the reaction mixture was concentrated in vacuo to give the carbamoyl chloride as green oil. The residue was dissolved in tetrahydrofuran (10 mL), cooled to 0° C., and treated with pyridine (0.091 mL, 1.125 mmol), Et$_3$N (1.069 mL, 7.6725 mmol), and 3,3-difluoropyrrolidine, Hydrochloride (0.734 g, 5.115 mmol). The reaction was stirred at 0° C. for 45 min, and then at ambient temperature. After 18 h the reaction was diluted with ice water, extracted with EtOAc, washed with 1M HCl, brine, dried over Na$_2$SO$_4$, filtered, and concentrated in vacuo to give crude (S)-methyl 2-(tert-butoxy)-2-(2-(3,3-difluoropyrrolidine-1-carbonyl)-4,7-dimethyl-6-(trimethylsilyl)isoindolin-5-yl)acetate (479.6 mg, 0.966 mmol, 94% yield) as a brown foam. 1H NMR (400 MHz, CHLOROFORM-d) δ ppm 5.64 (br. s., 1H), 4.83-4.60 (m, 4H), 3.83 (t, J=13.2 Hz, 2H), 3.78-3.69 (m, 5H), 2.46-2.30 (m, 5H), 2.22 (s, 3H), 1.17 (s, 9H), 0.49 (s, 9H); LCMS (m/z) ES+=497.52 (M+1

Step 3

(S)-methyl 2-(tert-butoxy)-2-(2-(3,3-difluoropyrrolidine-1-carbonyl)-6-iodo-4,7-dimethylisoindolin-5-yl)acetate An ice cold mixture of (S)-methyl 2-(tert-butoxy)-2-(2-(3,3-difluoropyrrolidine-1-carbonyl)-4,7-dimethyl-6-(trimethylsilyl)isoindolin-5-yl)acetate (479.6 mg, 0.966 mmol, 94% yield) and sodium bicarbonate (0.859 g, 10.23 mmol) in Dichloromethane (10 mL) was treated dropwise with ICl (1M in DCM) (1.030 mL, 1.03 mmol) over 20 min, and stirred at 0° C. After 1 h, the reaction was quenched with aq. Na$_2$S$_2$O$_3$, extracted with EtOAc, washed with brine, dried over Na$_2$SO$_4$, filtered, and concentrated in vacuo. Purification with column chromatography (0-70% EtOAc/Hexane) afforded (S)-methyl 2-(tert-butoxy)-2-(2-(3,3-difluoropyrrolidine-1-carbonyl)-6-iodo-4,7-dimethylisoindolin-5-yl)acetate (413.1 mg, 0.751 mmol, 73.4% yield) (N35491-7-3) as brown solid. 1H NMR (400 MHz, CHLOROFORM-d) d ppm 5.91 (s, 1H), 4.87-4.58 (m, 4H), 3.83 (t, J=13.1 Hz, 2H), 3.77-3.65 (m, 5H), 2.47-2.33 (m, 5H), 2.30 (s, 3H), 1.23 (s, 9H); LCMS (m/z) ES+=551.37 (M+1).

Step 4

(S)-Methyl 2-(tert-butoxy)-2-((M)-2-(3,3-difluoropyrrolidine-1-carbonyl)-4,7-dimethyl-6-(5-methyl-3,4-dihydro-2H-benzo[b][1,4]oxazin-6-yl)isoindolin-5-yl)acetate A solution of (S)-methyl 2-(tert-butoxy)-2-(2-(3,3-difluoropyrrolidine-1-carbonyl)-6-iodo-4,7-dimethylisoindolin-5-yl)acetate (70 mg, 0.127 mmol) and 5-methyl-6-(4,4,5,5-tetramethyl-1,3,2-dioxaborolan-2-yl)-3,4-dihydro-2H-benzo[b][1,4]oxazine (52.5 mg, 0.191 mmol) in N,N-Dimethylformamide (DMF) (1.3 mL) was degassed with N$_2$ for 10 min, treated with 2M Na$_2$CO$_3$ (0.191 mL, 0.382 mmol), Pd(Ph$_3$P)$_4$ (14.70 mg, 0.013 mmol), and irradiated in the microwave at 120° C. for 20 min. The reaction was poured into aq. sat. NaHCO$_3$, extracted with EtOAc, washed with brine, dried over Na$_2$SO$_4$, filtered, and concentrated. Purification with column chromatography (0-100% EtOAc/

Hexane) afforded the title compound (38.9 mg, 0.068 mmol, 53.5% yield) as light brown oil. LCMS (m/z) ES+=594.47 (M+Na).

Step 5

(S)-2-(tert-butoxy)-2-((M)-2-(3,3-difluoropyrrolidine-1-carbonyl)-4,7-dimethyl-6-(5-methyl-3,4-dihydro-2H-benzo[b][1,4]oxazin-6-yl)isoindolin-5-yl) acetic acid (S)-methyl 2-(tert-butoxy)-2-((M)-2-(3,3-difluoropyrrolidine-1-carbonyl)-4,7-dimethyl-6-(5-methyl-3,4-dihydro-2H-benzo[b][1,4]oxazin-6-yl)isoindolin-5-yl)acetate (38.9 mg, 0.068 mmol, 53.5% yield) (N35491-10-2) in 1,4-Dioxane (1 mL) was treated with 2M LiOH (0.340 mL, 0.68 mmol), stirred at 70° C. for 9 hours, and then concentrated. Purification with reverse phase HPLC (20-85% MeCN/H2O-0.1% TFA) afforded (2S)-2-(tert-butoxy)-2-(2-(3,3-difluoropyrrolidine-1-carbonyl)-4,7-dimethyl-6-(5-methyl-3,4-dihydro-2H-benzo[b][1,4]oxazin-6-yl)isoindolin-5-yl) acetic acid (25 mg, 0.044 mmol, 65.3% yield) as white solid. ¹H NMR (400 MHz, METHANOL-d4) δ ppm 6.79 (d, J=8.3 Hz, 1H), 6.60 (d, J=8.3 Hz, 1H), 5.05 (s, 1H), 4.83 (d, J=5.5 Hz, 4H), 4.33 (t, J=4.4 Hz, 2H), 3.92 (t, J=13.1 Hz, 2H), 3.80 (t, J=7.3 Hz, 2H), 3.65-3.55 (m, 2H), 2.51-2.35 (m, 5H), 1.87 (s, 3H), 1.81 (s, 3H), 1.11 (s, 9H); LCMS (m/z) ES⁺=556.52 (M−1).

Examples 313-322 were made in a similar manner as Example 312.

Example 313: (S)-2-(tert-butoxy)-2-(6-(chroman-6-yl)-2-(3,3-difluoropyrrolidine-1-carbonyl)-4,7-dimethylisoindolin-5-yl)acetic acid

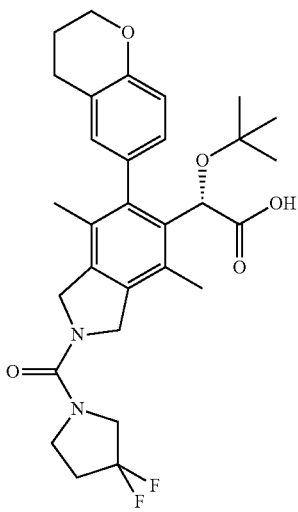 [SMILES: Cc1c2c(c(C)c([C@H](OC(C)(C)C)C(=O)O)c1-c1ccc3c(c1)CCCO3)CN(C(=O)N1CCC(F)(F)C1)C2]

¹H NMR (400 MHz, METHANOL-d₄) (mixture of atropisomers) δ ppm 7.16-7.05 (m, 1H), 6.95-6.76 (m, 2H), 5.15-5.08 (m, 1H), 4.86-4.74 (m, 4H), 4.31-4.17 (m, 2H), 3.92 (t, J=13.2 Hz, 2H), 3.79 (t, J=7.4 Hz, 2H), 2.92-2.70 (m, 2H), 2.52-2.38 (m, 2H), 2.37-2.29 (m, 3H), 2.13-1.99 (m, 2H), 1.97-1.89 (m, 3H), 1.05-0.91 (m, 9H); LCMS (m/z) ES⁺=1085.88 (2M+1).

Example 314: (2S)-2-(tert-butoxy)-2-(6-(2-chloro-4-methylphenyl)-2-(3,3-difluoropyrrolidine-1-carbonyl)-4,7-dimethylisoindolin-5-yl)acetic acid

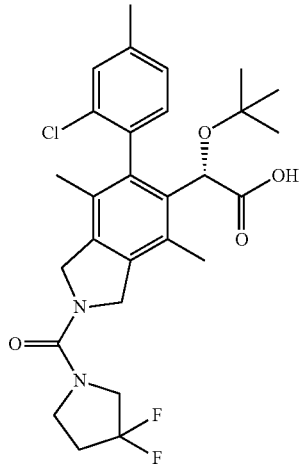 [SMILES: Cc1ccc(-c2c(C)c3c(c(C)c2[C@H](OC(C)(C)C)C(=O)O)CN(C(=O)N2CCC(F)(F)C2)C3)c(Cl)c1]

¹H NMR (400 MHz, METHANOL-d₄) δ ppm 7.46-7.34 (m, 2H), 7.26 (d, J=7.8 Hz, 1H), 4.97 (s, 1H), 4.86-4.76 (m, 4H), 3.92 (t, J=13.1 Hz, 2H), 3.80 (t, J=7.4 Hz, 2H), 2.53-2.40 (m, 5H), 2.38 (s, 3H), 1.91 (s, 3H), 1.02 (s, 9H); LCMS (m/z) ES⁺=535.47 (M+1).

Example 315: (2S)-2-(tert-butoxy)-2-(2-(3,3-difluoropyrrolidine-1-carbonyl)-6-(8-fluoro-5-methyl-3,4-dihydro-2H-benzo[b][1,4]oxazin-6-yl)-4,7-dimethyl-isoindolin-5-yl) acetic acid

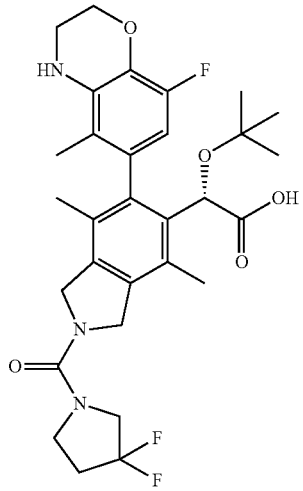 [SMILES: Cc1c(-c2c(C)c3c(c(C)c2[C@H](OC(C)(C)C)C(=O)O)CN(C(=O)N2CCC(F)(F)C2)C3)cc(F)c2c1NCCO2]

¹H NMR (CHLOROFORM-d) δ: 6.29 (d, 1H), 5.09 (s, 1H), 4.78 (d, 4H), 4.35 (m, 2H), 3.85 (m, 2H), 3.74-3.79 (m, 2H), 3.57 (m, 2H), 2.33-2.45 (m, 2H), 2.26 (s, 3H), 1.80 (s, 3H), 1.75 (s, 3H), 1.13 (s, 9H). LCMS (ES+) (m/z): 576.3 (M+1).

Example 316: (2S)-2-(tert-butoxy)-2-(6-(2-chloro-4-methylphenyl)-4,7-dimethyl-2-(piperidine-1-carbonyl)isoindolin-5-yl)acetic acid

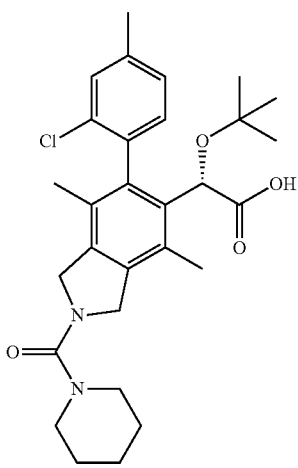 [SMILES: Cc1ccc(-c2c(C)c3c(c(C)c2[C@H](OC(C)(C)C)C(=O)O)CN(C(=O)N2CCCCC2)C3)c(Cl)c1]

$^1$H NMR (400 MHz, METHANOL-d$_4$) δ ppm 7.36 (s, 1H), 7.20 (d, J=7.5 Hz, 1H), 7.04 (d, J=7.8 Hz, 1H), 5.05 (s, 1H), 4.81 (d, J=11.5 Hz, 4H), 3.42-3.36 (m, 4H), 2.45 (s, 3H), 2.43 (s, 3H), 1.84 (s, 3H), 1.76-1.62 (m, 6H), 1.11 (s, 9H); LCMS (m/z) ES$^+$=513.50 (M+1).

Example 317: (S)-2-(tert-butoxy)-2-(6-(chroman-6-yl)-4,7-dimethyl-2-(piperidine-1-carbonyl)isoindolin-5-yl)acetic acid

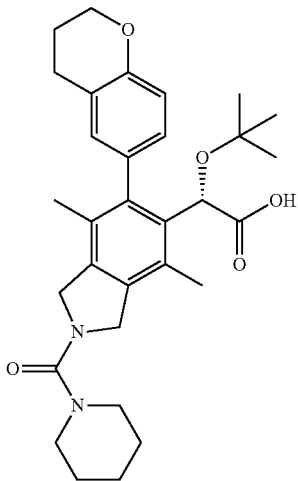 [SMILES: Cc1c2c(c(C)c([C@H](OC(C)(C)C)C(=O)O)c1-c1ccc3c(c1)CCCO3)CN(C(=O)N1CCCCC1)C2]

$^1$H NMR (400 MHz, METHANOL-d$_4$) (mixture of atropisomers) δ ppm 7.13-7.06 (m, 1H), 6.94-6.77 (m, 2H), 5.16-5.08 (m, 1H), 4.84-4.71 (m, 4H), 4.29-4.19 (m, 2H), 3.42-3.35 (m, 4H), 2.96-2.70 (m, 2H), 2.33 (s, 3H), 2.14-1.99 (m, 2H), 1.97-1.86 (m, 3H), 1.78-1.58 (m, 6H), 1.03-0.93 (m, 9H); LCMS (m/z) ES$^+$=521.56 (M+1).

Example 318: (2S)-2-(tert-butoxy)-2-(6-(8-fluoro-5-methyl-3,4-dihydro-2H-benzo[b][1,4]oxazin-6-yl)-4,7-dimethyl-2-(piperidine-1-carbonyl)isoindolin-5-yl)acetic acid

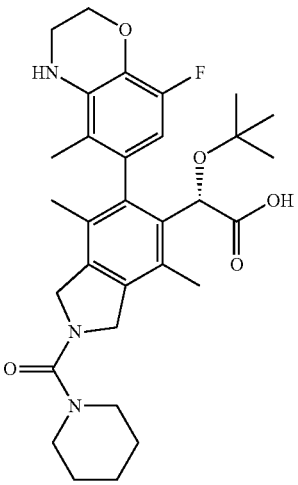 [SMILES: Cc1c(-c2c(C)c3c(c(C)c2[C@H](OC(C)(C)C)C(=O)O)CN(C(=O)N2CCCCC2)C3)cc(F)c2c1NCCO2]

$^1$H NMR (CHLOROFORM-d) δ: 6.28 (d, 1H), 5.07 (s, 1H), 4.69-4.83 (m, 4H), 4.34 (m, 2H), 3.56 (m, 2H), 3.31 (br. s., 4H), 2.26 (s, 3H), 1.79 (s, 3H), 1.73 (s, 3H), 1.64 (br. s., 6H), 1.12 (s, 9H). LCMS (ES+) (m/z): 554.3 (M+1).

Example 319: (2S)-2-(tert-butoxy)-2-(4,7-dimethyl-6-(5-methyl-3,4-dihydro-2H-benzo[b][1,4]oxazin-6-yl)-2-(piperidine-1-carbonyl)isoindolin-5-yl)acetic acid

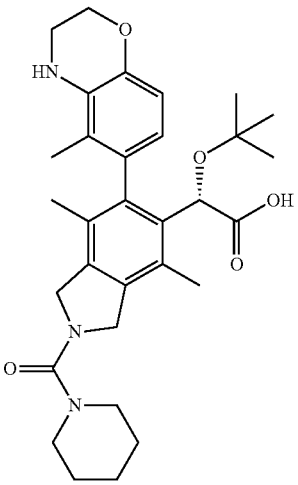 [SMILES: Cc1c(-c2c(C)c3c(c(C)c2[C@H](OC(C)(C)C)C(=O)O)CN(C(=O)N2CCCCC2)C3)ccc2c1NCCO2]

$^1$H NMR (400 MHz, METHANOL-d$_4$) δ ppm 6.75 (d, J=8.3 Hz, 1H), 6.57 (d, J=8.3 Hz, 1H), 5.03 (s, 1H), 4.77 (d, J=4.6 Hz, 4H), 4.30 (t, J=4.4 Hz, 2H), 3.64-3.50 (m, 2H), 3.41-3.33 (m, 4H), 2.38 (s, 3H), 1.84 (s, 3H), 1.78 (s, 3H), 1.67 (br. s., 6H), 1.08 (s, 9H); LCMS (m/z) ES$^+$=536.56 (M+1).

Example 320: (2S)-2-(tert-butoxy)-2-(2-(3,3-difluoropyrrolidine-1-carbonyl)-4,7-dimethyl-6-(5-methylchroman-6-yl)isoindolin-5-yl)acetic acid

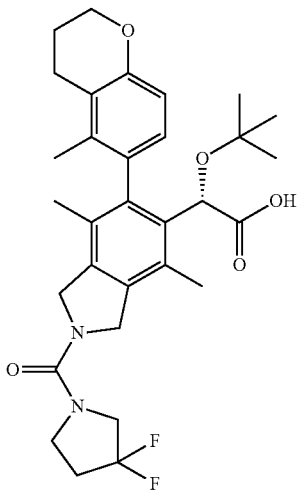 [SMILES: Cc1c(-c2c(C)c3c(c(C)c2[C@H](OC(C)(C)C)C(=O)O)CN(C(=O)N2CCC(F)(F)C2)C3)ccc2c1CCCO2]

¹H NMR (400 MHz, METHANOL-d₄) (3:1 mixture of atropisomers) δ ppm 7.15-6.76 (m, 1H), 6.75-6.65 (m, 1H), 5.08 (s, 0.25H), 5.04 (s, 0.75H), 4.86-4.75 (m, 4H), 4.19 (t, J=5.0 Hz, 2H), 3.92 (t, J=13.1 Hz, 2H), 3.80 (t, J=7.4 Hz, 2H), 2.79-2.63 (m, 2H), 2.54-2.29 (m, 5H), 2.20-2.03 (m, 2H), 1.90-1.75 (m, 6H), 1.15-0.93 (m, 9H); LCMS (m/z) ES⁺=557.53 (M+1).

Example 321: (2S)-2-(tert-butoxy)-2-(4,7-dimethyl-6-(5-methylchroman-6-yl)-2-(piperidine-1-carbonyl)isoindolin-5-yl)acetic acid

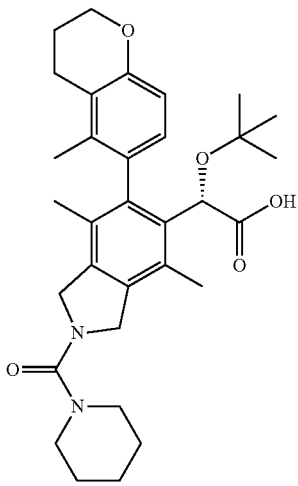 [SMILES: Cc1c(-c2c(C)c3c(c(C)c2[C@H](OC(C)(C)C)C(=O)O)CN(C(=O)N2CCCCC2)C3)ccc2c1CCCO2]

¹H NMR (400 MHz, METHANOL-d₄) (3:1 mixture of atropisomers) δ ppm 7.13-6.76 (m, 1H), 6.75-6.63 (m, 1H), 5.10-5.01 (m, 1H), 4.85-4.73 (m, 4H), 4.28-4.09 (m, 2H), 3.41-3.36 (m, 4H), 2.78-2.62 (m, 2H), 2.45-2.33 (m, 3H), 2.17-2.03 (m, 2H), 1.90-1.76 (m, 6H), 1.75-1.62 (m, 6H), 1.15-0.94 (m, 9H); LCMS (m/z) ES⁺=535.55 (M+1).

Example 322: (2S)-2-(tert-butoxy)-2-(6-(2-chloro-4-methylphenyl)-4,7-dimethyl-2-(piperidine-1-carbonyl)isoindolin-5-yl)acetic acid

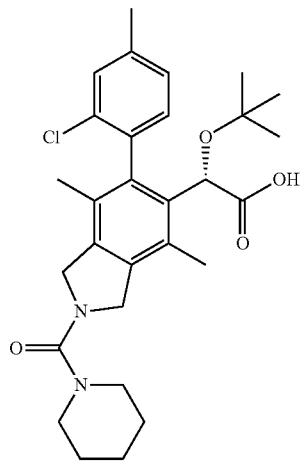 [SMILES: Cc1ccc(-c2c(C)c3c(c(C)c2[C@H](OC(C)(C)C)C(=O)O)CN(C(=O)N2CCCCC2)C3)c(Cl)c1]

¹H NMR (400 MHz, METHANOL-d₄) δ ppm 7.47-7.32 (m, 1.4H), 7.30-7.15 (m, 1H), 7.04 (d, J=7.5 Hz, 0.6H), 5.12-4.96 (m, 1H), 4.84-4.74 (m, 4H), 3.37 (br. s., 4H), 2.50-2.32 (m, 6H), 1.90 (s, 1H), 1.84 (s, 2H), 1.69 (br. s., 6H), 1.11 (s, 6H), 1.02 (s, 3H); LCMS (m/z) ES⁺=513.48 (M+1).

Example 323: 2-(tert-butoxy)-2-(6-(4-chloro-2-methylphenyl)-2-(3,3-difluoropyrrolidine-1-carbonyl)-4,7-dimethylisoindolin-5-yl)acetic acid The title compound was made in a similar manner to Example 100.

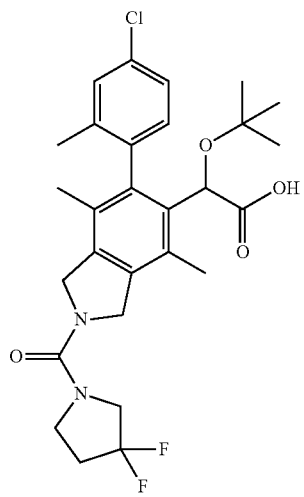 [SMILES: Cc1cc(Cl)ccc1-c1c(C)c2c(c(C)c1C(OC(C)(C)C)C(=O)O)CN(C(=O)N1CCC(F)(F)C1)C2]

¹H NMR (CHLOROFORM-d) δ: 7.29 (s, 1H), 7.21 (d, 2H), 4.95-5.17 (m, 1H), 4.78 (d, 4H), 3.84 (m, 2H), 3.75 (m, 2H), 2.28-2.45 (m, 5H), 1.96-2.10 (m, 3H), 1.70-1.83 (m, 3H), 1.02-1.15 (m, 9H). LCMS (ES+) (m/z): 557.64/559.38 (M+23).

Example 324: (2S)-2-(tert-butoxy)-2-(6-(4-chloro-2-methylphenyl)-2-(cyclohexanecarbonyl)-4,7-dimethylisoindolin-5-yl)acetic acid The title compound was made in a similar manner to Example 103.

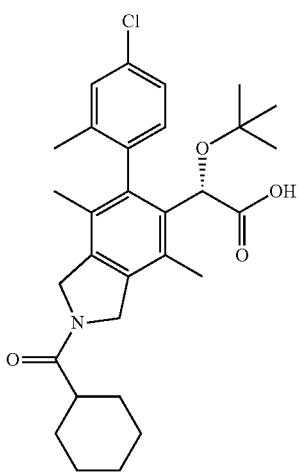 [SMILES: Cc1cc(Cl)ccc1-c1c(C)c2c(c(C)c1[C@H](OC(C)(C)C)C(=O)O)CN(C(=O)C1CCCCC1)C2]

$^1$H NMR (400 MHz, CHLOROFORM-d) δ 7.38-7.52 (m, 3H), 7.13 (d, J=7.18 Hz, 1H), 5.06 (br. s., 1H), 2.43-2.57 (m, 1H), 4.68-4.91 (m, 4H), 2.28 (d, 3H), 1.89 (d, 3H), 1.82 (d, 4H), 1.73 (br. s., 1H), 1.61 (d, 2H), 1.30-1.46 (m, 3H), 1.01 (s, 9H). LCMS (ES+) (m/z): 498.5 (M+1).

Example 325: (2S)-2-(tert-butoxy)-2-(6-(4-chloro-2-methylphenyl)-2-(3,3-dimethylbutanoyl)-4,7-dimethylisoindolin-5-yl)acetic acid The title compound was made in a similar manner to Example 103.

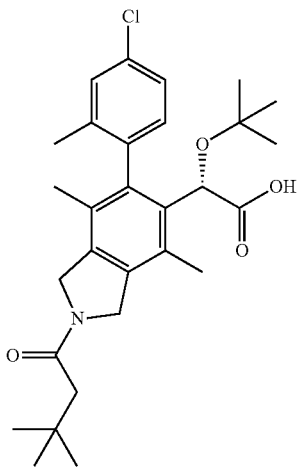 [SMILES: Cc1cc(Cl)ccc1-c1c(C)c2c(c(C)c1[C@H](OC(C)(C)C)C(=O)O)CN(C(=O)CC(C)(C)C)C2]

$^1$H NMR (400 MHz, CDCl$_3$) δ ppm 7.49-7.39 (m, 3H), 7.13 (br. s., 1H), 5.06 (br. s., 1H), 4.88-4.72 (m, 4H), 2.36-2.30 (m, 2H), 2.27 (s, 3H), 1.88 (s, 3H), 1.13 (d, 9H), 1.01 (s, 9H). LCMS (ES+) (m/z): 486.46/488.39 (M+1)

Example 326: (2S)-2-(tert-butoxy)-2-(6-(2-chloro-4-methylphenyl)-2-(3-fluorobenzoyl)-4,7-dimethylisoindolin-5-yl)acetic acid The title compound was made in a similar manner to Example 103.

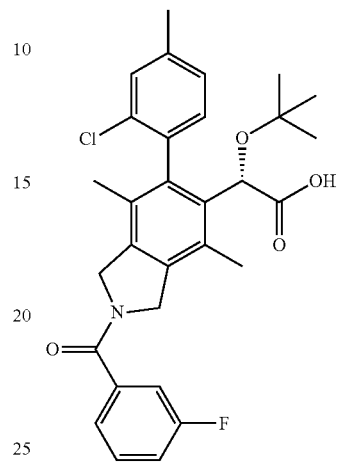

$^1$H NMR (400 MHz, CHLOROFORM-d) (mixture of rotamers and atropisomer) δ ppm 7.54-7.42 (m, 1H), 7.41-7.34 (m, 1H), 7.34-7.24 (m, 2H), 7.24-7.13 (m, 1H), 7.13-7.04 (m, 1H), 6.96-6.80 (m, 1H), 5.35-4.88 (m, 3H), 4.84-4.65 (m, 2H), 2.53-2.26 (m, 6H), 2.00-1.67 (m, 3H), 1.20-1.03 (m, 9H); LCMS (m/z) ES+=524 (M+1).

Anti-HIV Activity

MT4 Assay

Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", Antimicrob. Agents Chemother. 2007, 51: 3147-3154; and Pauwels et al., "Sensitive and rapid assay on MT-4 cells for the detection of antiviral compounds against the AIDS virus", J. of Virological Methods 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer Glo™ (Promega, Madison, Wis.). IC$_{50}$s were determined from a 10 point dose response curve using 3-4-fold serial dilution for each compound, which spans a concentration range >1000 fold.

These values are plotted against the molar compound concentrations using the standard four parameter logistic equation:

$$y=((V\text{max}*x^n)/(K^n+x^n))+Y2$$

where:
Y2=minimum y n=slope factor
Vmax=maximum y x=compound concentration [M]
K=$EC_{50}$ When tested in the MT4 assay compounds were found to have $IC_{50}$ values listed in Table 1.

TABLE 1

| Example | $IC_{50}$ (uM) |
|---|---|
| 1 | 0.035 |
| 2 | 0.036 |
| 3 | 0.04 |
| 4 | 0.033 |
| 5 | 0.042 |
| 6 | 2977 |
| 7 | 0.004 |
| 8 | 0.005 |
| 9 | 0.098 |
| 10 | 0.071 |
| 11 | 0.174 |
| 12 | 0.82 |
| 13 | 0.044 |
| 14 | 0.118 |
| 15 | 2.133 |
| 16 | 0.062 |
| 17 | 1.28 |
| 18 | 0.075 |
| 19 | 0.34 |
| 20 | 0.115 |
| 21 | 0.04 |
| 22 | 0.02 |
| 23 | 0.203 |
| 24 | 0.012 |
| 25 | 0.946 |
| 26 | 0.054 |
| 27 | 0.932 |
| 28 | 0.094 |
| 29 | 0.184 |
| 30 | 0.047 |
| 31 | 0.203 |
| 32 | 0.723 |
| 33 | 0.616 |
| 34 | 0.086 |
| 35 | 0.012 |
| 36 | 0.037 |
| 37 | 0.723 |
| 38 | 1.230 |
| 39 | 0.872 |
| 40 | 3.427 |
| 41 | 0.050 |
| 42 | 0.025 |
| 43 | 0.937 |
| 44 | 3.350 |
| 45 | 0.043 |
| 46 | 4.077 |
| 47 | 0.044 |
| 48 | 0.573 |
| 49 | 0.100 |
| 50 | 0.029 |
| 51 | 0.044 |
| 52 | 0.018 |
| 53 | 0.051 |
| 54 | 0.288 |
| 55 | 0.086 |
| 56 | 0.012 |
| 57 | 0.044 |
| 58 | 0.350 |
| 59 | 0.279 |
| 60 | 0.014 |
| 61 | 0.038 |
| 62 | 0.044 |
| 63 | 0.015 |
| 64 | 0.106 |
| 65 | 0.010 |
| 66 | 0.006 |
| 67 | 0.055 |
| 68 | 0.008 |
| 69 | 0.014 |
| 70 | 0.034 |
| 71 | 0.276 |
| 72 | 0.016 |
| 73 | 0.026 |
| 74 | 0.021 |
| 75 | 0.034 |
| 76 | 0.012 |
| 77 | 0.160 |
| 78 | 0.126 |
| 79 | 0.231 |
| 80 | 0.381 |
| 81 | 0.016 |
| 82 | 0.014 |
| 83 | 0.006 |
| 84 | 0.011 |
| 85 | 0.120 |
| 86 | 1.163 |
| 87 | 0.005 |
| 88 | 0.018 |
| 89 | 0.011 |
| 90 | 0.267 |
| 91 | 0.013 |
| 92 | 0.016 |
| 93 | 0.007 |
| 94 | 0.044 |
| 95 | 0.778 |
| 96 | 0.014 |
| 97 | 0.144 |
| 98 | 2.296 |
| 99 | 0.045 |
| 100 | 0.005 |
| 101 | 0.003 |
| 102 | 0.002 |
| 103 | 0.002 |
| 104 | 0.002 |
| 105 | 0.014 |
| 106 | 0.143 |
| 107 | 0.007 |
| 108 | 0.006 |
| 109 | 0.036 |
| 110 | 0.006 |
| 111 | 0.016 |
| 112 | 0.029 |
| 113 | 0.010 |
| 114 | 0.005 |
| 115 | 0.006 |
| 116 | 0.031 |
| 117 | 0.017 |
| 118 | 0.014 |
| 119 | 0.003 |
| 120 | 0.003 |
| 121 | 0.004 |
| 122 | 0.003 |
| 123 | 0.004 |
| 124 | 1.090 |
| 125 | 0.015 |
| 126 | 0.013 |
| 127 | 0.318 |
| 128 | 8.539 |
| 129 | 0.014 |
| 130 | 0.041 |
| 131 | 0.019 |
| 132 | 0.021 |
| 133 | 0.005 |
| 134 | 0.006 |
| 135 | 0.023 |
| 136 | 0.002 |
| 137 | 0.002 |
| 138 | 0.002 |
| 139 | 0.037 |
| 140 | 0.002 |
| 141 | 0.004 |
| 142 | 0.031 |
| 143 | 0.004 |
| 144 | 0.005 |
| 145 | 0.002 |
| 146 | 0.003 |
| 147 | 0.013 |

TABLE 1-continued

| Example | IC$_{50}$ (uM) |
| --- | --- |
| 148 | 0.009 |
| 149 | 0.002 |
| 150 | 0.004 |
| 151 | 0.005 |
| 152 | 0.002 |
| 153 | 0.004 |
| 154 | 0.008 |
| 155 | 0.048 |
| 156 | 0.003 |
| 157 | 0.003 |
| 158 | 0.002 |
| 159 | 0.002 |
| 160 | 0.004 |
| 161 | 0.003 |
| 162 | 0.002 |
| 163 | 0.004 |
| 164 | 0.004 |
| 165 | 0.108 |
| 166 | 0.027 |
| 167 | 0.004 |
| 168 | 0.011 |
| 169 | 0.002 |
| 170 | 0.002 |
| 171 | 0.002 |
| 172 | 0.007 |
| 173 | 0.003 |
| 174 | 0.004 |
| 175 | 0.005 |
| 176 | 0.004 |
| 177 | 0.002 |
| 178 | 0.002 |
| 179 | 0.004 |
| 180 | 0.004 |
| 181 | 0.005 |
| 182 | 0.005 |
| 183 | 0.004 |
| 184 | 0.002 |
| 185 | 0.004 |
| 186 | 0.002 |
| 187 | 0.003 |
| 188 | 0.004 |
| 189 | 0.004 |
| 190 | 0.005 |
| 191 | 0.002 |
| 192 | 0.005 |
| 193 | 0.005 |
| 194 | 0.011 |
| 195 | 0.003 |
| 196 | 0.002 |
| 197 | 0.004 |
| 198 | 0.005 |
| 199 | 0.004 |
| 200 | 0.011 |
| 201 | 0.387 |
| 202 | 0.124 |
| 203 | 0.063 |
| 204 | 0.665 |
| 205 | 0.004 |
| 206 | 0.005 |
| 207 | 0.004 |
| 208 | 0.004 |
| 209 | 0.023 |
| 210 | 0.014 |
| 211 | 0.005 |
| 212 | 0.002 |
| 213 | 0.003 |
| 214 | 0.003 |
| 215 | 0.010 |
| 216 | 0.004 |
| 217 | 0.012 |
| 218 | 0.011 |
| 219 | 0.004 |
| 220 | 0.004 |
| 221 | 0.004 |
| 222 | 0.004 |
| 223 | 0.013 |
| 224 | 0.044 |
| 225 | 0.005 |

TABLE 1-continued

| Example | IC$_{50}$ (uM) |
| --- | --- |
| 226 | 0.005 |
| 227 | 0.014 |
| 228 | 0.013 |
| 229 | 0.005 |
| 230 | 0.111 |
| 231 | 0.037 |
| 232 | 0.148 |
| 233 | 0.012 |
| 234 | 0.026 |
| 235 | 0.005 |
| 236 | 0.005 |
| 237 | 0.067 |
| 238 | 0.940 |
| 239 | 0.016 |
| 240 | 0.121 |
| 241 | 0.025 |
| 242 | 0.013 |
| 243 | 0.018 |
| 244 | 0.014 |
| 245 | 0.026 |
| 246 | 0.005 |
| 247 | 0.005 |
| 248 | 0.005 |
| 249 | 0.005 |
| 250 | 0.004 |
| 251 | 0.003 |
| 252 | 0.004 |
| 253 | 0.012 |
| 254 | 0.004 |
| 255 | 0.013 |
| 256 | 0.740 |
| 257 | 0.134 |
| 258 | 0.015 |
| 259 | 0.020 |
| 260 | 0.015 |
| 261 | 0.004 |
| 262 | 0.005 |
| 263 | 0.006 |
| 264 | 0.009 |
| 265 | 0.004 |
| 266 | 0.126 |
| 267 | 3.463 |
| 268 | 0.014 |
| 269 | 0.116 |
| 270 | 0.004 |
| 271 | 0.008 |
| 272 | 0.086 |
| 273 | 0.004 |
| 274 | 0.297 |
| 275 | 0.005 |
| 276 | 0.016 |
| 277 | 0.014 |
| 278 | 0.005 |
| 279 | 0.004 |
| 280 | 0.008 |
| 281 | 0.017 |
| 282 | 0.007 |
| 283 | 0.013 |
| 284 | 0.048 |
| 285 | 0.002 |
| 286 | 0.011 |
| 287 | 0.005 |
| 288 | 0.015 |
| 289 | 0.014 |
| 290 | 2.558 |
| 291 | 0.005 |
| 292 | 0.005 |
| 293 | 0.004 |
| 294 | 0.004 |
| 295 | 0.009 |
| 296 | 0.005 |
| 297 | 0.042 |
| 298 | 0.024 |
| 299 | 0.014 |
| 300 | 0.040 |
| 301 | 0.005 |
| 302 | 0.004 |
| 303 | 0.005 |

TABLE 1-continued

| Example | IC$_{50}$ (uM) |
|---|---|
| 304 | 0.004 |
| 305 | 0.002 |
| 306 | 0.038 |
| 307 | 0.004 |
| 308 | 0.004 |
| 309 | 0.004 |
| 310 | 0.018 |
| 311 | 0.015 |
| 312 | 0.006 |
| 313 | 0.004 |
| 314 | 0.004 |
| 315 | 0.015 |
| 316 | 0.041 |
| 317 | 0.003 |
| 318 | 0.005 |
| 319 | 0.004 |
| 320 | 0.003 |
| 321 | 0.002 |
| 322 | 0.005 |
| 323 | 0.013 |
| 324 | 0.013 |
| 325 | 0.013 |
| 326 | 0.005 |

What is claimed is:

1. A compound of Formula I:

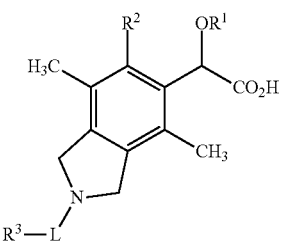

Formula I or a pharmaceutically acceptable salt thereof, wherein:
$R^1$ is $C_{1-6}$alkyl;
$R^2$ is $C_{5-14}$aryl, $C_{3-7}$cycloalkyl, $C_{3-7}$cycloalkenyl, $C_{2-9}$heterocycle, or $C_{2-9}$heteroaryl, wherein each $R^2$ group is optionally substituted by one to four substituents selected from halo, $C_{1-6}$alkyl, $C_{1-6}$hetereoalkyl, or $C_{1-6}$alkylene or $C_{1-6}$hetereoalklylene wherein said $C_{1-6}$alkylene or $C_{1-6}$hetereoalklylene are bonded to adjacent carbon atoms on said $C_{5-14}$aryl, $C_{3-7}$cycloalkyl, $C_{3-7}$cycloalkenyl, $C_{3-9}$heterocycle, or $C_{5-9}$heteroaryl to form a fused ring;
L is a bond, —CH$_2$(CO)—, —C$_{1-3}$alkylene-, —SO$_2$-, —C(O)—, —C(S)—, —C(NH)—, —C(O)NH—, —C(O)NHCH$_2$—, —C(O)OCH$_2$—, —C(O)O—, —C(O)C(O)—, —SO$_2$—NH—, or —CH$_2$C(O)—;
$R^3$ is H, CN, $C_{1-6}$alkyl, $C_{5-14}$aryl, CH$_2$C$_{5-14}$aryl, CH$_2$C$_{3-7}$cycloalkyl, $C_{3-7}$cycloalkyl, $C_{3-7}$spirocycloalkyl, $C_{3-7}$cycloalkenyl, $C_{2-9}$heterocycle, or $C_{2-9}$heteroaryl, wherein each $R^3$ group is optionally substituted by one to four substituents selected from halo, $C_{1-6}$alkyl, $C_{2-8}$bridgedheterocycle, $C_{3-7}$cycloalkyl, $C_{1-3}$fluoroalkyl, —OC$_{1-6}$alkyl, —C(O)R$^4$, —C(O)NR$^4$, —C(O)NHR$^4$, $C_{5-14}$aryl, $C_{1-6}$hetereoalkyl, —B(OH)$_2$, $C_{2-9}$heterocycle, $C_{1-6}$heteroaryl, —C(O)OC$_{1-6}$alkyl, or two substituents bonded to adjacent atoms may bond together to form a fused ring and that fused ring may optionally be substituted with R$^4$;

$R^4$ is CN, halo, —OC$_{1-6}$alkyl, $C_{1-6}$alkyl, $C_{3-7}$cycloalkyl, $C_{2-9}$heterocycle, or $C_{5-14}$aryl;
and wherein each heterocycle, heteroaryl, heteroalkyl, and heteroalkylene comprises
one to three heteroatoms selected from S, N, B, or O.

2. A compound or salt according to claim 1 wherein $R^1$ is t-butyl.

3. A compound or salt according to claim 1 wherein $R^2$ is optionally substituted phenyl.

4. A compound or salt according to claim 3 wherein $R^2$ is phenyl substituted by one to four substituents selected from fluorine, methyl, —CH$_2$CH$_2$CH$_2$O— wherein said —CH$_2$CH$_2$CH$_2$O— is bonded to adjacent carbon atoms on said phenyl to form a bicyclic ring, or —NHCH$_2$CH$_2$O— wherein said —NHCH$_2$CH$_2$O— is bonded to adjacent carbon atoms on said phenyl to form a bicyclic ring.

5. A compound or salt according to claim 1 wherein $R^3$ is $C_{1-6}$alkyl, phenyl, naphthyl, cyclopentyl, cyclohexyl, pyridyl, or tetrahydropyranyl, each of which is optionally substituted by 1-3 substituents selected from halogen, $C_{1-6}$alkyl, —OC$_{1-6}$alky, $C_{1-3}$fluoroalkyl, or phenyl.

6. A compound or salt according to claim 1 wherein the stereochemistry on the carbon to which OR$^1$ is bound is as depicted below

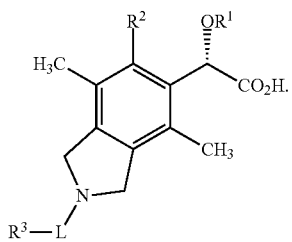

7. A compound or salt according to claim 1 wherein the compound or salt is

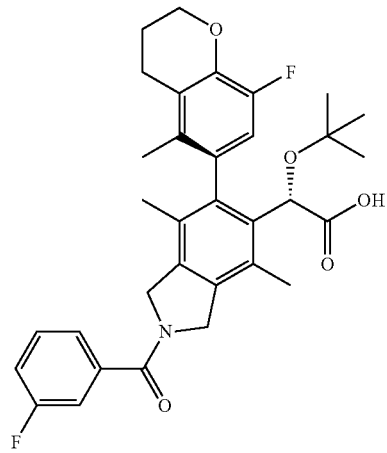

or a pharmaceutically acceptable salt therof.

8. A compound or salt according to claim 1 wherein the compound or salt is

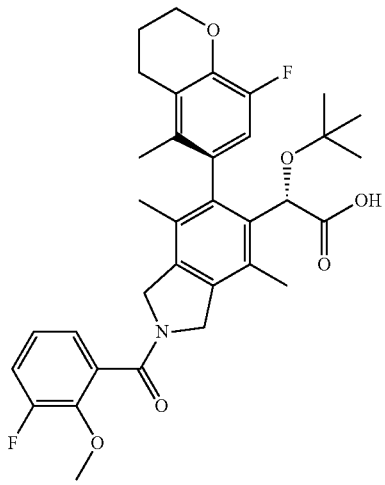

or a pharmaceutically acceptable salt thereof.

9. A compound according or salt to claim 1 wherein the compound or salt is

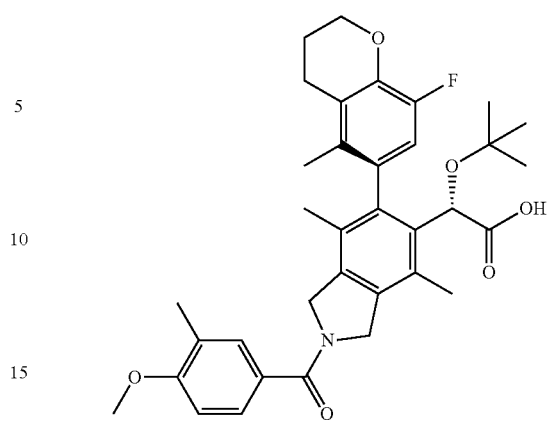

or a pharmaceutically acceptable salt thereof.

10. A pharmaceutically acceptable salt according to claim 1.

11. A pharmaceutical composition comprising a compound according to claim 1 or a pharmaceutically acceptable salt thereof.

12. A method for treating a viral infection in a patient mediated at least in part by a virus in the retrovirus family of viruses, comprising administering to said patient a composition according to claim 11.

13. The method of claim 12 wherein said viral infection is mediated by the HIV virus.

* * * * *